(12) United States Patent
Finn

(10) Patent No.: US 9,943,574 B2
(45) Date of Patent: Apr. 17, 2018

(54) COMBINATION FOR TREATING AN INFLAMMATORY DISORDER

(71) Applicant: Arthrogen B.V., Amsterdam (NL)

(72) Inventor: Jonathan D. Finn, Amsterdam (NL)

(73) Assignee: Arthrogen B.V., Amsterdam (NL)

( * ) Notice: Subject to any disclaimer, the term of this patent is extended or adjusted under 35 U.S.C. 154(b) by 240 days.

(21) Appl. No.: 14/411,047

(22) PCT Filed: Jun. 26, 2013

(86) PCT No.: PCT/NL2013/050455
§ 371 (c)(1),
(2) Date: Dec. 23, 2014

(87) PCT Pub. No.: WO2014/003553
PCT Pub. Date: Jan. 3, 2014

(65) Prior Publication Data
US 2015/0190481 A1    Jul. 9, 2015

Related U.S. Application Data

(60) Provisional application No. 61/664,818, filed on Jun. 27, 2012.

(30) Foreign Application Priority Data

Jun. 27, 2012   (EP) ..................... 12173853

(51) Int. Cl.
*A61K 45/06* (2006.01)
*A61K 38/46* (2006.01)
*A61K 9/127* (2006.01)
*C12N 9/16* (2006.01)
*C12N 9/14* (2006.01)
*A61K 38/00* (2006.01)
*C07K 14/705* (2006.01)

(52) U.S. Cl.
CPC ............ *A61K 38/465* (2013.01); *A61K 9/127* (2013.01); *A61K 38/46* (2013.01); *C12N 9/14* (2013.01); *C12N 9/16* (2013.01); *C12Y 301/03005* (2013.01); *C12Y 306/01006* (2013.01); *A61K 38/00* (2013.01); *C07K 14/70596* (2013.01); *C07K 2319/00* (2013.01); *C12Y 306/01005* (2013.01)

(58) Field of Classification Search
None
See application file for complete search history.

(56) References Cited

PUBLICATIONS

Fausther et al. (Dec. 2011, Am J. of Physiology Gastrointestinal Liver Physiol. 302, 447-459) in IDS on Dec. 23, 2014.*
Finn et al. (Molecular Therapy, May 2014, vol. 22, p. S265).*
Deaglio, Silvia et al., "Adenosine generation catalyzed by CD39 and CD73 expressed on regulatory T cells mediates immune suppression", The Journal of Experimental Medicine, Rockefeller University Press, US, vol. 204, No. 5, Jun. 1, 2007, pp. 1257-1265.

(Continued)

*Primary Examiner* — Agnieszka Boesen
(74) *Attorney, Agent, or Firm* — Gilberto M. Villacorta; Sunit Talapatra; Foley & Lardner LLP

(57) ABSTRACT

The invention provides a combination of a source of a CD39 and of a source of a CD73.

12 Claims, 18 Drawing Sheets

(56) References Cited

PUBLICATIONS

Fausther, Michel et al., "Coexpression of ecto-5'-nucleotidase/CD73 with specific NTPDases differentially regulates adenosine formation in the rat liver", American Journal of Physiology—Gastrointestinal and Liver Physiology, vol. 302, No. 4, Feb. 15, 2012, pp. G447-G459.

International Search Report of PCT/NL2013/050455 dated Sep. 16, 2013.

Jimenez, Paula A et al., "ATPase and ADPase activities in synovial membrane of equine metacarpophalangeal joint", Life Sciences, vol. 70, No. 20, Apr. 5, 2002, pp. 2445-2455.

Reutershan, J. et al., "Adenosine and inflammation: CD39 and CD73 are critical mediators in LPS-induced PMN trafficking into the lungs", FASEB Journal, Fed. of American Soc. For Biology, US, vol. 23, No. 2, Feb. 1, 2009, pp. 473-482.

\* cited by examiner

Fig. 3
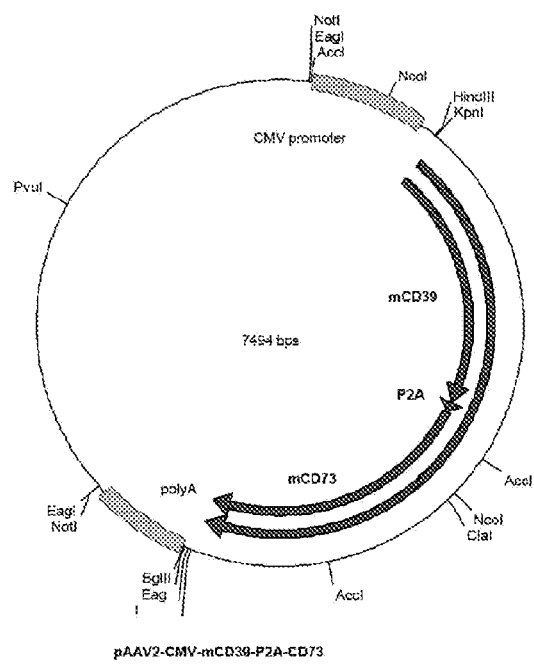
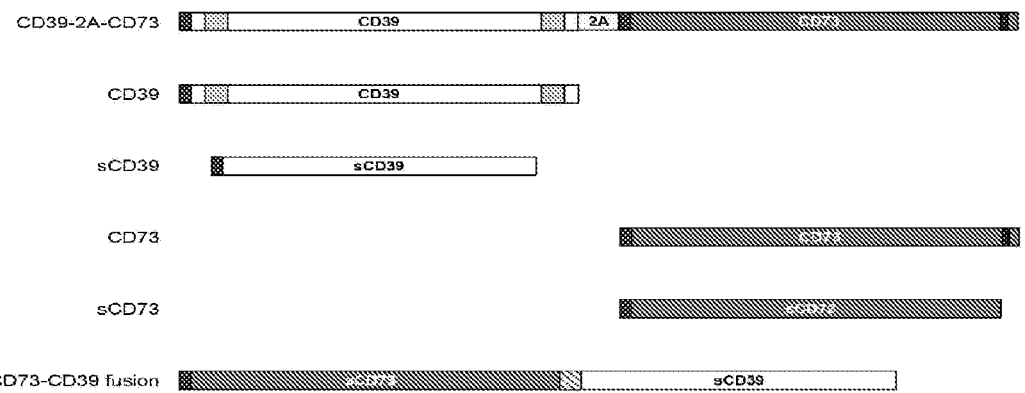

Fig 10 A
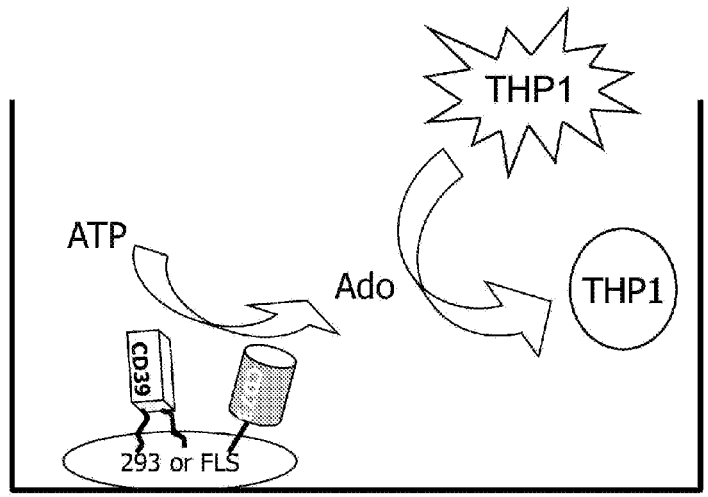
B 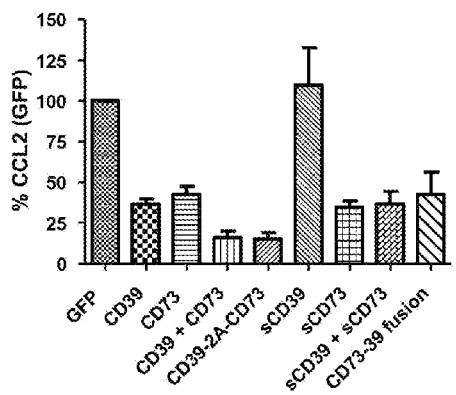
C 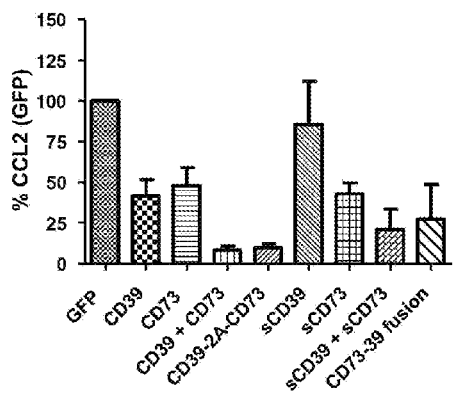
D 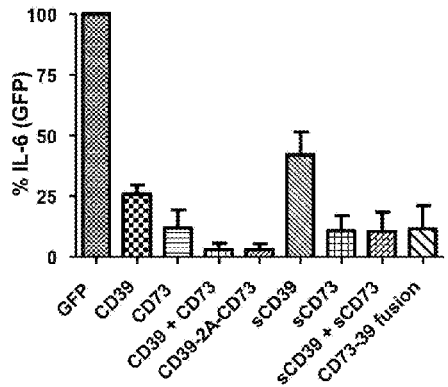
E 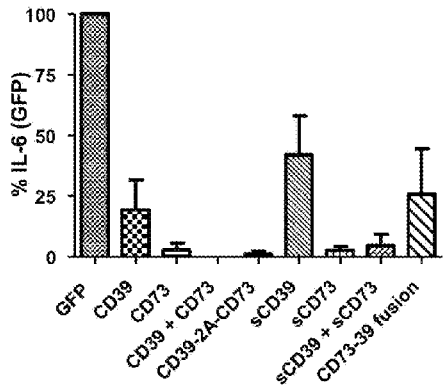

Fig. 13
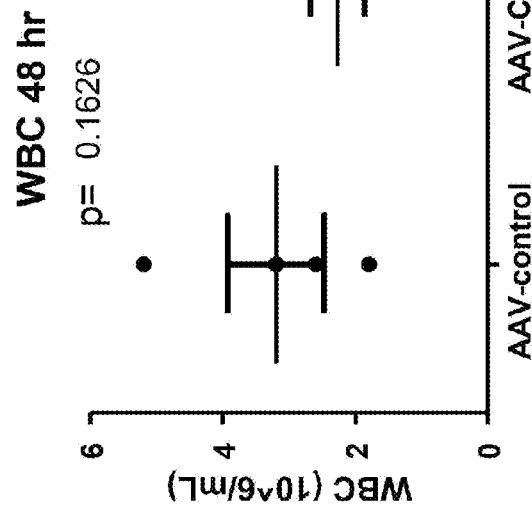
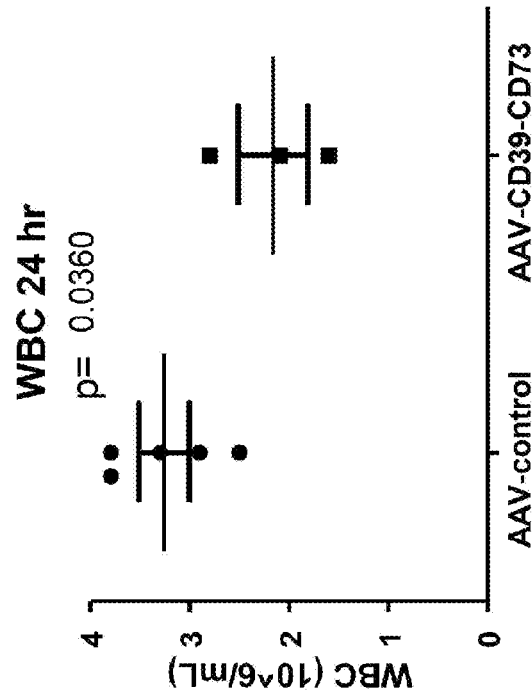

COMBINATION FOR TREATING AN INFLAMMATORY DISORDER

CROSS REFERENCE TO RELATED APPLICATIONS

The present application is a National Stage of International Application No. PCT/NL2013/050455, filed Jun. 26, 2013, which claims priority to European Application No. 12173853.8 and U.S. Provisional Application No. 61/664,818, both filed Jun. 27, 2012. The contents of these applications are herein incorporated by reference in their entirety.

FIELD OF THE INVENTION

The invention provides a combination for treating an inflammatory disorder.

BACKGROUND OF THE INVENTION

Rheumatoid arthritis (RA) is a chronic inflammatory disease that affects ~1% of the population. It is a complicated auto-immune disease and its etiology is unclear, however there are a number of factors (genetic, environmental, etc) that can contribute to the pathology[1]. Several treatments are already known to treat an inflammatory disease such as RA. However, each of these treatments has drawbacks. In the case of confirmed diagnosis the recommended gold standard is to initiate methotrexate (MTX) treatment. Methotrexate is the most commonly prescribed drug for rheumatoid arthritis. It acts by inhibiting the enzyme dihydrofolate reductase, thus interfering with the folate processing machinery of the cell and affecting cell division[2]. MTX is often used in combination with other conventional disease modifying anti-rheumatic drugs (DMARDs) and/or corticosteroids. MTX side effects include gastrointestinal effects and an increased chance of liver damage, leading to 16-18% of patients withdrawing from treatment'. If disease activity cannot be controlled by conventional treatment, biological treatment is considered. Biologicals like anti-TNF therapies (infliximab, etanercept), CTLA4-Ig (abatacept), anti-CD20 (rituximab), and anti-interleukin 6 (IL6) receptor (tocilizumab), have the potential to reduce toxic side effects due to their specificity[4], however these treatments come with their own side effects, including increased risk of infection and increased risk of heart disease. It is now possible to reach 20% improvement in about 60% of the RA patients using this approach. However, biologicals have limited effects in many patients and the need for repetitive therapy remains.

Therefore there is still a need for designing new treatments for inflammatory diseases such as RA which do not have all the drawbacks of existing treatments.

DESCRIPTION OF THE INVENTION

The inventors designed a combination of a source of a CD39 and a source of a CD73 that could attractively be used for treating an inflammatory disorder.

Combination

In a first aspect, there is provided a combination of a source of a CD39 and a source of a CD73, preferably a combination of a source of a CD39 protein and a source of a CD73 protein.

CD39 (ENTPD1, Ectonucleoside triphosphate diphosphohydrolase 1) is a membrane protein that is highly expressed on functional regulatory T cells (Tregs). It has or exhibits nucleoside triphosphate diphosphohydrolase (NTPDase) activity and is responsible for the conversion of adenosine triphosphate (ATP) to adenosine diphosphate (ADP) and/or adenosine monophosphate (AMP). The inventors investigated the ATPase activity of synovial fluid isolated from patients with rheumatoid arthritis (high inflammation) and compared it to the ATPase activity of synovial fluid from patients with osteoarthritis (low inflammation). Surprisingly it was found that the RA patients demonstrated significantly less ATPase activity than osteoarthritis (OA) patients, indicating that restoration of ATPase activity by CD39 expression may be beneficial (see FIG. 1). The invention primarily relates to a source of a CD39 as defined herein. However, the invention is not limited thereto. Other NTPDase proteins are known to the skilled person, such as CD39L1 and NTPDase8. A CD39 source could be replaced herein by another source of NTPDase, such as a source of a CD39L1 or a source of a NTPDase8. Tregs also express another membrane anchored protein, CD73 (5NTE, Ecto-5-prime-nucleotidase) which is an ecto-nucleotidase that converts AMP to adenosine.

The inventors investigated gene expression profiles from synovial tissue isolated from RA patients and surprisingly found that when comparing high v.s. low inflammation tissue, there are many differences in expression of genes involved in the ATP:adenosine pathway. Specifically, it was found that while CD39 expression levels were not significantly different, there was a large decrease in CD73 expression when comparing high inflammation tissue with low inflammation tissue, indicating that this gene pathway might be a worthwhile target for intervention (see FIG. 2B).

Surprisingly, the inventors demonstrated that the use of a combination of a source of a CD39 and of a source of a CD73 is critical for improving the ATP:adenosine balance or ratio at the site of inflammation. The inventors demonstrated that a combination of a source of a CD39 and of a source of a CD73 exhibits a synergistic effect on the ATP:adenosine balance or ratio, contributing to a therapeutic effect in inflammatory disorders.

The term "a source of a CD39 and a CD73" may be replaced by "a source of a CD39 and a source of a CD73" or by "a source of a CD39 protein and a source of a CD73 protein". A source of a CD39 preferably comprises a CD39 protein, a CD39 polypeptide, a CD39 peptide, a CD39 derived peptide or a CD39 protein fragment and/or a nucleic acid molecule encoding a CD39 protein or polypeptide or peptide or derived peptide or protein fragment. A CD39 protein as encompassed by the present invention may be a membrane bound CD39 protein or a soluble protein as identified herein. A nucleic acid molecule encoding a CD39 protein as encompassed the present invention may be a nucleic acid molecule encoding for a membrane bound CD39 protein or a nucleic acid molecule encoding for soluble protein as defined herein. A preferred CD39 protein is a mammalian NTPDase protein. A further preferred CD39 protein is a human NTPDase protein. A more preferred CD39 protein is represented by SEQ ID NO: 1 or SEQ ID NO: 5 or SEQ ID NO: 49 or SEQ ID NO: 51. This first preferred CD39 protein (i.e. SEQ ID NO: 1) is derived from the human protein and is preferably encoded by SEQ ID NO: 2 and/or SEQ ID NO: 55. This second preferred CD39 protein (i.e. SEQ ID NO: 5) is derived from the murine protein and is preferably encoded by SEQ ID NO: 6. This third preferred source of a CD39 protein is a NTPDase protein (i.e. SEQ ID NO: 49) and is the *homo sapiens* CD39L1 preferably encoded by SEQ ID NO: 48. This fourth preferred source of a CD39 protein is a NTPDase protein (i.e. SEQ ID NO: 51) and is the *homo sapiens* NTPDase 8 preferably encoded by SEQ ID NO: 50. A source of a CD73 preferably comprises a CD73 protein, a CD73 polypeptide, a CD73 peptide, a CD73 derived peptide or a CD73 protein fragment and/or a nucleic acid molecule encoding a CD73 protein or polypeptide or peptide or derived peptide or protein fragment. A CD73 protein as encompassed the present invention may be a membrane bound CD73 protein or a soluble protein as identified herein. A nucleic acid molecule encoding a CD73 protein as encompassed the present invention may be a nucleic acid molecule encoding for a membrane bound CD73 protein or a nucleic acid molecule encoding for soluble protein as defined herein. A preferred CD73 protein is a mammalian ecto-nucleotidase protein. A further preferred CD39 protein is a human ecto-nucleotidase protein. A more preferred CD73 protein is represented by SEQ ID NO: 3 or SEQ ID NO: 7. This first preferred CD73 protein (i.e. SEQ ID NO: 3) is derived from the human protein and is preferably encoded by SEQ ID NO: 4 and/or SEQ ID NO: 56. This second preferred CD73 protein (i.e. SEQ ID NO: 7) is derived from the murine protein and is preferably encoded by SEQ ID NO: 8.

Below we defined preferred sources of CD39 and of CD73 that are encompassed by the invention. Since the invention relates to a combination of a source of a CD39 and of a source of a CD73, each of the sources of a CD39 defined herein may be combined with each of the sources of a CD73 defined herein. It is also encompassed by the present invention to use a combination of a source of a CD39 being protein-based (i.e. protein, protein fragment, peptide, derived peptide or polypeptide as identified herein) with a source of a CD73 being not protein-based (i.e. nucleic acid molecule), and vice versa.

Within the context of the invention, the word "combination" means that a source of a CD39 and a source of a CD73 are contemplated and encompassed. Each source may be together or present together or combined together or physically in contact with the other source forming one single composition. Each source may alternatively be comprised within one distinct composition. However the invention provides the insight that both sources are needed or are used in order to get an optimal or maximum effect as defined later on. If each source is not present in a same composition, each source may be used sequentially or simultaneously.

In an embodiment, a combination is provided wherein a source of a CD39 and a source of a CD73 are present in one single composition or wherein a source of a CD39 is present in one composition and a source of a CD73 is present in a distinct composition. Composition will be defined later herein.

A source of a CD39 protein may be obtained from any organism as long as it could provide a polypeptide comprising an amino acid sequence that has at least 60% sequence identity or similarity with the amino acid sequence of a mammalian NTPDase protein and/or a human NTPDase protein, and/or with SEQ ID NO: 1 and/or SEQ ID NO: 5 and/or SEQ ID NO: 49 and/or SEQ ID NO: 51 or a part thereof and/or it has or exhibits a nucleoside triphosphate diphosphohydrolase activity. Identity or similarity with a SEQ ID NO: 1 and/or SEQ ID NO: 5 and/or SEQ ID NO: 49 and/or SEQ ID NO: 51 means identity or similarity with a SEQ ID NO: 1 and/or SEQ ID NO: 5 and/or SEQ ID NO: 49 and/or SEQ ID NO: 51 over its whole length or as a whole. The same holds for any sequence identified herein. Identity or similarity with a mammalian NTPDase protein and/or a human NTPDase protein and/or with amino acid sequence SEQ ID NO: 1 and/or SEQ ID NO: 5 and/or SEQ ID NO: 49 and/or SEQ ID NO: 51 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 20%, 30%, 40%, 50%, 60%, 70%, 80%, 80%, 90% or 100% of the length of SEQ ID NO: 1 and/or SEQ ID NO: 5 and/or SEQ ID NO: 49 and/or SEQ ID NO: 51. Having or exhibiting a nucleoside triphosphate diphosphohydrolase activity means it is able to convert ATP into ADP. Additionally a source of CD39 may also convert ADP into AMP. Therefore a way of assessing such activity is to determine the concentration of ATP in a sample. In an embodiment, said concentration is assessed over time. Having or exhibiting a nucleoside triphosphate diphosphohydrolase activity or having or exhibiting a detectable nucleoside triphosphate diphosphohydrolase activity or having or exhibiting an induction or an increase of triphosphate diphosphohydrolase activity means that the concentration of ATP is reduced by comparison to the ATP concentration detected in a similar sample wherein no CD39 source is present. Reduced in this context may mean a reduction of 1%, 5%, 10%, 20%, 25%, 30%, 35%, 40%, 45%, 50%, 55%, 60%, 65%, 70%, 75%, 80%, 85%, 90%, 95%, 100%. In an embodiment, said reduction is detected over time. A sample may be a sample from a subject. Said sample may be or may comprise a cell, a cell supernatant, a tissue from said subject. Said sample may be an in vitro tissue culture of cells from human or animal origin. Such activity may be assessed using the assay described in the experimental part.

A source of a CD39 protein may also be a nucleic acid molecule as follows:
 i. a nucleotide sequence comprising a nucleotide sequence that has at least 60% sequence identity or similarity with a nucleotide sequence encoding a mammalian NTPDase protein and/or with a human NTPDase protein and/or with SEQ ID NO: 2 and/or SEQ ID NO: 55 and/or SEQ ID NO: 6 and/or SEQ ID NO: 48 and/or SEQ ID NO: 50 or a part thereof
 ii. a nucleotide sequences the complementary strand of which hybridizes to a nucleic acid molecule of sequence of (i);
 iii. a nucleotide sequence the sequence of which differs from the sequence of a nucleic acid molecule of (iii) due to the degeneracy of the genetic code or
 iv. a nucleotide sequence that encodes an amino acid sequence that has at least 60% amino acid identity or similarity with a mammalian NTPDase protein and/or a human NTPDase protein and/or with an amino acid sequence encoded by a nucleotide sequence SEQ ID NO:2 and/or SEQ ID NO: 55 and/or SEQ ID NO: 6 and/or SEQ ID NO: 48 and/or SEQ ID NO: 50 or a part thereof.

Preferably said amino acid sequence being a CD39 source represents a polypeptide that exhibits a nucleoside triphosphate diphosphohydrolase activity. Assessing a nucleoside triphosphate diphosphohydrolase activity has already been defined herein.

Identity or similarity with SEQ ID NO: 2 and/or SEQ ID NO: 55 and/or SEQ ID NO: 6 and/or SEQ ID NO: 48 and/or SEQ ID NO: 50 means identity or similarity over the whole length of SEQ ID NO: 2 and/or SEQ ID NO: 55 and/or SEQ ID NO: 6 and/or SEQ ID NO: 48 and/or SEQ ID NO: 50. Identity or similarity with a nucleotide sequence encoding a mammalian NTPDase protein and/or a human NTPDase protein and/or with SEQ ID NO: 2 and/or SEQ ID NO: 55 and/or SEQ ID NO: 6 and/or SEQ ID NO: 48 and/or SEQ ID NO: 50 or a part thereof and/or with an amino acid sequence of a mammalian NTPDase protein and/or a human NTPDase protein and/or with an amino acid sequence encoded by a nucleotide sequence SEQ ID NO:2 and/or SEQ ID NO: 55 and/or SEQ ID NO: 6 and/or SEQ ID NO: 48 and/or SEQ ID NO: 50 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

"A part thereof" in this context means at least 10%, 20%, 30%, 40%, 50%, 60%, 70%, 80%, 80%, 90% or 100% of the length of SEQ ID NO: 1 or SEQ ID NO: 6 or SEQ ID NO:2 or SEQ ID NO: 55 or SEQ ID NO: 5 and/or SEQ ID NO:48 and/or SEQ ID NO: 50 and/or SEQ ID NO: 49 and/or SEQ ID NO: 51.

A source of a CD39 may be a CD39 protein, CD39 peptide, CD39 derived peptide or CD39 protein fragment or CD39 polypeptide and/or a nucleic acid molecule encoding a CD39 protein or peptide or derived peptide or protein fragment or polypeptide. A CD39 protein as encompassed by the present invention may be a membrane bound CD39 protein or a soluble protein as identified herein. A nucleic acid molecule encoding a CD39 protein as encompassed the present invention may be a nucleic acid molecule encoding for a membrane bound CD39 protein or a nucleic acid molecule encoding for soluble protein as defined herein. A preferred source of a CD39 is a soluble CD39 protein and/or a nucleic acid molecule encoding a soluble CD39 protein. A preferred soluble CD39 protein is a soluble NTPDase protein derived from a soluble mammalian NTPDase protein and/or a soluble human NTPDase protein. A more preferred soluble CD39 protein is represented by SEQ ID NO: 9 (derived from the murine soluble CD39 protein and/or derived from murine CD39 represented by SEQ ID NO: 5) or 11 (derived from the human soluble CD39 protein and/or derived from human CD39 represented by SEQ ID NO: 1) and/or is encoded by SEQ ID NO: 10 and/or 12. Preferably said protein, peptide, or derived peptide or protein fragment or polypeptide exhibits a nucleoside triphosphate diphosphohydrolase activity. Preferably said nucleic acid molecule encoding said protein, peptide, derived peptide or protein fragment or polypeptide codes for a protein or peptide or derived peptide or protein fragment or polypeptide that exhibits a nucleoside triphosphate diphosphohydrolase activity. Assessing a nucleoside triphosphate diphosphohydrolase activity has already been defined herein.

A protein, polypeptide, protein fragment or peptide or derived peptide as a source of a CD39 encompassed by the present invention may comprise 1, 2, 3, 4, 5, 6, 7, 8, 9, 10, 11, 12, 13, 14, 15, 16, 17, 18, 19, 20 or more substitutions and/or insertions and/or deletions and/or additional N- or C-terminal amino acids or chemical moieties compared to a mammalian NTPDase protein and/or a human NTPDase protein and/or soluble CD39 protein derived from the mammalian NTPDase protein and/or human NTPDase protein and/or SEQ ID NO:1 or SEQ ID NO: 5 or SEQ ID NO: 49 or SEQ ID NO: 51 or SEQ ID NO: 9 or SEQ ID NO: 11 to increase stability, solubility, and/or activity by comparison to the stability, solubility, and/or activity of the mammalian NTPDase protein and/or human NTPDase protein and/or soluble CD39 protein derived from the mammalian NTPDase protein and/or human NTPDase protein and/or SEQ ID NO:1 or SEQ ID NO: 5 or SEQ ID NO: 49 or SEQ ID NO: 51 or SEQ ID NO: 9 or SEQ ID NO: 11.

A protein fragment or peptide or derived peptide or polypeptide as a source of a CD39 encompassed by the present invention may comprise a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more contiguous amino acids of a corresponding CD39 protein and/or soluble CD39 protein, preferably a mammalian NTPDase protein and/or a human NTPDase protein and/or soluble CD39 protein derived from the mammalian NTPDase protein and/or human NTPDase protein and/or SEQ ID NO: 1 or SEQ ID NO: 5 or SEQ ID NO: 49 or SEQ ID NO: 51 or SEQ ID NO: 9 or SEQ ID NO: 11.

A CD39 source may be said functional when a CD39 protein, protein fragment, peptide, derived peptide, polypeptide or encoded CD39 protein, protein fragment, polypeptide or peptide or derived peptide exhibits a detectable nucleoside triphosphate diphosphohydrolase activity preferably as assessed in the experimental part or exhibits at least the nucleoside triphosphate diphosphohydrolase activity of a mammalian NTPDase protein and/or of a human NTPDase protein and/or of soluble CD39 protein derived from the mammalian NTPDase protein and/or of human NTPDase protein and/or of SEQ ID NO:1 or SEQ ID NO: 5 or SEQ ID NO: 49 or SEQ ID NO: 51 or SEQ ID NO: 9 or SEQ ID NO: 11 to at least some extent. "To at least some extent" preferably means that at least 5%, 10%, 20%, 30%, 40%, 50%, 60%, 70%, 80%, at least 90% or 100%. Assessing a nucleoside triphosphate diphosphohydrolase activity has already been defined herein.

Accordingly, a preferred source of a CD39 protein comprises an amino acid sequence that has at least 60% sequence identity or similarity with amino acid sequence of a soluble CD39 derived from the mammalian NTPDase protein and/or human NTPDase protein and/or SEQ ID NO:9 and/or SEQ ID NO: 11 or a part thereof and/or it has or exhibits a nucleoside triphosphate diphosphohydrolase activity. Identity or similarity with SEQ ID NO: 9 and/or SEQ ID NO: 11 means identity or similarity with SEQ ID NO: 9 and/or SEQ ID NO: 11 over its whole length or as a whole. Identity or similarity with amino acid sequence of a soluble CD39 derived from the mammalian NTPDase protein and/or human NTPDase protein and/or SEQ ID NO: 9 and/or SEQ ID NO: 11 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 20%, 30%, 40%, 50%, 60%, 70%, 80%, 80%, 90% or 100% of the length of SEQ ID NO: 9 and/or SEQ ID NO: 11.

Accordingly a source of a CD39 protein may also be a nucleic acid molecule as follows:
 i. a nucleotide sequence comprising a nucleotide sequence that has at least 60% sequence identity or similarity with a nucleotide sequence encoding a soluble CD39 protein derived from a mammalian NTPDase protein and/or with a human NTPDase protein, preferably with SEQ ID NO: 10 and/or SEQ ID NO: 12 or a part thereof
 ii. a nucleotide sequences the complementary strand of which hybridizes to a nucleic acid molecule of sequence of (i);
 iii. a nucleotide sequence the sequence of which differs from the sequence of a nucleic acid molecule of (iii) due to the degeneracy of the genetic code or
 iv. a nucleotide sequence that encodes an amino acid sequence that has at least 60% amino acid identity or similarity with a soluble CD39 protein derived from a mammalian NTPDase protein and/or with a human NTPDase protein, preferably with an amino acid sequence encoded by a nucleotide sequence SEQ ID NO: 10 and/or SEQ ID NO: 12 or a part thereof.

Preferably said amino acid sequence being a CD39 source represents a polypeptide that exhibits a nucleoside triphosphate diphosphohydrolase activity. Assessing a nucleoside triphosphate diphosphohydrolase activity has already been defined herein.

Identity or similarity with a nucleotide sequence encoding a soluble CD39 protein derived from a mammalian NTPDase protein and/or a human NTPDase protein, preferably with SEQ ID NO: 10 and/or SEQ ID NO: 12 or a part thereof and/or with an amino acid sequence of a soluble mammalian CD39 protein derived NTPDase protein and/or a human NTPDase protein, preferably an amino acid sequence encoded by nucleotide sequence SEQ ID NO: 10 and/or SEQ ID NO: 12 or a part thereof is preferably at least 65%, 70%, 75%, 80%, 85%, 90%, 95%, 97%, 98%, 99% or 100% sequence identity. Identity or similarity with SEQ ID NO: 10 and/or SEQ ID NO: 12 means identity or similarity with SEQ ID NO: 9 and/or SEQ ID NO: 11 over its whole length or as a whole. The assessment of sequence identity may be carried out as explained in the general part dedicated to "general definitions".

"A part thereof" in this context means at least 10%, 20%, 30%, 40%, 50%, 60%, 70%, 80%, 80%, 90% or 100% of the length of SEQ ID NO:9 or SEQ ID NO:11 or SEQ ID NO: 10 or SEQ ID NO: 12.

A source of a CD73 protein may be obtained from any organism as long as it could provide a polypeptide comprising an amino acid sequence that has at least 60% sequence identity or similarity with the amino acid sequence of a mammalian ecto-nucleotidase protein and/or a human ecto-nucleotidase protein, and/or with SEQ ID NO: 3 or SEQ ID NO: 7 or a part thereof and/or it has or exhibits an ecto-nucleotidase activity. Identity or similarity with SEQ ID NO: 3 or SEQ ID NO: 7 means identity or similarity with SEQ ID NO:3 or SEQ ID NO:7 over its whole length or as a whole. "A part thereof" in this context means at least 10%, 20%, 30%, 40%, 50%, 60%, 70%, 80%, 80%, 90% or 100% of the length of SEQ ID NO: 3 or SEQ ID NO: 7.

Identity or similarity with a mammalian ecto-nucleotidase protein and/or a human ecto-nucleotidase protein and/or with amino acid sequence SEQ ID NO: 3 or SEQ ID NO: 7 or as part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

Having or exhibiting an ecto-nucleotidase activity means it is able to convert adenosine monophosphate (AMP) and/or adenosine diphosphate (ADP) to adenosine. Therefore a way of assessing such activity is to determine the concentration of adenosine in a sample. In an embodiment, said concentration is assessed over time. Having or exhibiting or inducing or promoting an ecto-nucleotidase activity means that the concentration of adenosine is increased by comparison to the adenosine concentration detected in a similar sample wherein no CD73 source is present. In an embodiment, AMP is added in the sample tested. Subsequently, the concentration of adenosine is determined or assessed. Increased in this context may mean an increase of 1%, 5%, 10%, 20%, 25%, 30%, 35%, 40%, 45%, 50%, 55%, 60%, 65%, 70%, 75%, 80%, 85%, 90%, 95%, 100%, 120%, 150%, 200%, 500%, 1000% or more. In an embodiment, said increase is detected over time. A sample may be a sample from a subject. Said sample may be or may comprise a cell, a cell supernatant, a tissue from said subject. Said sample may be an in vitro tissue culture on cells of human or animal origin. Such activity may be assessed using the assay described in the experimental part.

A source of a CD73 protein may also be a nucleic acid molecule as follows:
  i. a nucleotide sequence comprising a nucleotide sequence that has at least 60% sequence identity or similarity with a nucleotide sequence encoding a mammalian ecto-nucleotidase protein and/or with a human ecto-nucleotidase protein and/or with SEQ ID NO: 4 or SEQ ID NO: 56 or SEQ ID NO: 8 or a part thereof,
  ii. a nucleotide sequences the complementary strand of which hybridizes to a nucleic acid molecule of sequence of (i);
  iii. a nucleotide sequence the sequence of which differs from the sequence of a nucleic acid molecule of (iii) due to the degeneracy of the genetic code or
  iv. a nucleotide sequence that encodes an amino acid sequence that has at least 60% amino acid identity or similarity with a mammalian ecto-nucleotidase and/or a with human ecto-nucleotidase protein and/or with an amino acid sequence encoded by a nucleotide sequence SEQ ID NO: 4 or SEQ ID NO: 56 or SEQ ID NO: 8 or a part thereof. Preferably said amino acid sequence represents a polypeptide that exhibits an ecto-nucleotidase activity.

Identity or similarity with SEQ ID NO: 4 and/or SEQ ID NO: 56 and/or SEQ ID NO: 8 means identity or similarity with SEQ ID NO:4 and/or SEQ ID NO: 56 and/or SEQ ID NO:8 over its whole length or as a whole. Identity or similarity with a nucleotide sequence encoding a mammalian ecto-nucleotidase protein and/or a human ecto-nucleotidase protein and/or with SEQ ID NO: 4 and/or SEQ ID NO: 56 and/or SEQ ID NO: 8 or a part thereof and/or with an amino acid sequence of a mammalian ecto-nucleotidase protein and/or a human ecto-nucleotidase protein and/or an amino acid sequence encoded by a nucleotide sequence SEQ ID NO: 4 and/or SEQ ID NO: 56 and/or SEQ ID NO: 8 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

"A part thereof" in this context means at least 10%, 20%, 30%, 40%, 50%, 60%, 70%, 80%, 80%, 90% or 100% of the length of SEQ ID NO: 4 or SEQ ID NO:56 or SEQ ID NO: 8.

A source of a CD73 protein may also be a CD73 derived peptide or peptide or protein fragment or polypeptide and/or a nucleic acid molecule encoding a CD73 protein or derived peptide or peptide or protein fragment or polypeptide. A CD73 protein as encompassed by the present invention may be a membrane bound CD73 protein or a soluble protein as identified herein. A nucleic acid molecule encoding a CD73 protein as encompassed by the present invention may be a nucleic acid molecule encoding for a membrane bound CD73 protein or a nucleic acid molecule encoding for soluble protein as defined herein. A preferred source of a CD73 protein is a soluble CD73 protein and/or a nucleic acid molecule encoding a soluble CD73 protein. A preferred soluble CD73 protein is a soluble ecto-nucleotidase protein derived from a soluble mammalian ecto-nucleotidase protein and/or a soluble human ecto-nucleotidase protein. A more preferred soluble CD73 protein is represented by SEQ ID NO: 13 (derived from a murine soluble CD73 protein and/or derived from murine CD73 represented by SEQ ID NO: 7) or SEQ ID NO: 15 (derived from a human soluble CD73 protein and/or derived from human CD73 represented by SEQ ID NO: 3). SEQ ID NO: 13 is preferably encoded by SEQ ID NO: 14. SEQ ID NO: 15 is preferably encoded by SEQ ID NO: 16. Preferably said peptide or derived peptide or protein fragment or polypeptide exhibits an ecto-nucleotidase activity. Preferably said nucleic acid molecule encoding said peptide or derived peptide or protein fragment or polypeptide codes for a derived peptide or protein fragment or polypeptide that exhibits an ecto-nucleotidase activity. Exhibiting an ecto-nucleotidase activity has already been defined herein.

A protein fragment or derived peptide or peptide or polypeptide as a source of a CD73 encompassed by the present invention may comprise 1, 2, 3, 4, 5, 6, 7, 8, 9, 10, 11, 12, 13, 14, 15, 16, 17, 18, 19, 20 or more substitutions and/or insertions and/or deletions and/or additional N- or C-terminal amino acids or chemical moieties to a mammalian ecto-nucleotidase protein and/or to a human ecto-nucleotidase protein and/or to soluble CD73 protein derived from the mammalian ecto-nucleotidase protein and/or to human ecto-nucleotidase protein and/or to SEQ ID NO: 3 or SEQ ID NO: 7 or SEQ ID NO: 13 or SEQ ID NO: 15 to increase stability, solubility and/or activity by comparison to the stability, solubility and/or activity of a mammalian ecto-nucleotidase protein and/or of a human ecto-nucleotidase protein and/or of a soluble CD73 protein derived from the mammalian ecto-nucleotidase protein and/or of a human ecto-nucleotidase protein and/or of SEQ ID NO: 3 or SEQ ID NO: 7 or SEQ ID NO: 13 or SEQ ID NO: 15.

A protein fragment or peptide or derived peptide or polypeptide as a source of a CD73 encompassed by the present invention may comprise a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more contiguous amino acids of a corresponding CD73 protein and/or soluble CD73 protein, preferably a mammalian ecto-nucleotidase protein and/or a human ecto-nucleotidase protein and/or soluble CD73 protein derived from the mammalian ecto-nucleotidase protein and/or human ecto-nucleotidase protein and/or SEQ ID NO: 3 or SEQ ID NO: 7 or SEQ ID NO: 13 or SEQ ID NO: 15.

A CD73 source may be said functional when a CD73 protein, protein fragment, polypeptide or peptide or derived peptide or encoded CD73 protein, protein fragment, polypeptide or peptide or derived peptide exhibits an ecto-nucleotidase activity preferably as assessed in the experimental part or exhibits at least the ecto-nucleotidase activity of a mammalian ecto-nucleotidase and/or human ecto-nucleotidase and/or soluble CD73 protein derived from a mammalian ecto-nucleotidase and/or human ecto-nucleotidase and/or SEQ ID NO: 3 or SEQ ID NO: 7 or SEQ ID NO: 13 or SEQ ID NO: 15 to at least some extent. "To at least some extent" preferably means that at least 20%, 30%, 40%, 50%, 60%, 70%, 80%, 90% or 100%. Exhibiting an ecto-nucleotidase activity has already been defined herein.

Accordingly, a preferred source of a CD73 protein comprises an amino acid sequence that has at least 60% sequence identity or similarity with amino acid sequence of a soluble CD73 protein derived from the mammalian ecto-nucleotidase protein and/or of human ecto-nucleotidase protein and/or of SEQ ID NO: 13 and/or SEQ ID NO: 15 or a part thereof and/or it has or exhibits a ecto-nucleotidase activity. Identity or similarity with SEQ ID NO: 13 and/or SEQ ID NO: 15 means identity or similarity with SEQ ID NO:13 and/or SEQ ID NO: 15 over its whole length or as a whole. Identity or similarity with amino acid sequence of soluble CD73 protein derived from the mammalian ecto-nucleotidase protein and/or human ecto-nucleotidase protein and/or SEQ ID NO: 13 and/or SEQ ID NO: 15 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 10%, 20%, 30%, 40%, 50%, 60%, 70%, 80%, 80%, 90% or 100% of the length of SEQ ID NO:13 and/or SEQ ID NO: 15.

Accordingly a source of a CD73 protein may also be a nucleic acid molecule as follows:

i. a nucleotide sequence comprising a nucleotide sequence that has at least 60% sequence identity or similarity with a nucleotide sequence encoding a soluble CD73 protein derived from a mammalian ecto-nucleotidase protein and/or with a human ecto-nucleotidase protein, preferably with SEQ ID NO: 14 and/or SEQ ID NO: 16 or a part thereof;

ii. a nucleotide sequences the complementary strand of which hybridizes to a nucleic acid molecule of sequence of (i);

iii. a nucleotide sequence the sequence of which differs from the sequence of a nucleic acid molecule of (iii) due to the degeneracy of the genetic code; or, iv. a nucleotide sequence that encodes an amino acid sequence that has at least 60% amino acid identity or similarity with a soluble CD73 protein derived from a mammalian ecto-nucleotidase protein and/or with a human ecto-nucleotidase protein, preferably with an amino acid sequence encoded by a nucleotide sequence SEQ ID NO: 14 and/or SEQ ID NO: 16 or a part thereof.

Preferably said amino acid sequence being a CD73 source represents a polypeptide that exhibits an ecto-nucleotidase activity. Assessing an ecto-nucleotidase activity has already been defined herein.

Identity or similarity with a nucleotide sequence encoding a soluble CD73 protein derived from a mammalian ecto-nucleotidase protein and/or a human ecto-nucleotidase protein, preferably with SEQ ID NO: 14 and/or SEQ ID NO: 16 or a part thereof and/or with an amino acid sequence of a soluble CD73 protein derived from a mammalian ecto-nucleotidase protein and/or a human ecto-nucleotidase protein, preferably an amino acid sequence encoded by a nucleotide sequence SEQ ID NO: 14 and/or SEQ ID NO: 16 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

"A part thereof" in this context means at least 10%, 20%, 30%, 40%, 50%, 60%, 70%, 80%, 80%, 90% or 100% of the length of SEQ ID NO: 13 or SEQ ID NO: 15 or SEQ ID NO: 14 or SEQ ID NO: 16.

An advantage of the use of a combination of a CD39 source and a CD73 source is the possibility to adjust the ratio of CD39 to CD73 expression to optimize the consumption of ATP and/or the production of adenosine. The ratio of a CD39 source and CD73 source in a combination according to the present invention (i.e. CD39:CD73) preferably is from 5:1 to 1:39, more preferably from 3:1 to 1:39, or from 2:1 to 1:20, most preferably from 1:1 to 1:10. Preferably the ratio of a CD39 source and CD73 source in a combination according to the present invention is 1:10, 1:9, 1:8, 1:7, 1:6, 1:5, 1:4, 1:3, 1:2 or 1:1. Preferably the ratio of a CD39 source and CD73 source in a combination according to the present invention is 1:1.

A source of a CD39 and/or of a source of a CD73 as present or as used in a combination of the invention may be protein-based, i.e. comprising a CD39 protein, protein fragment, polypeptide or peptide or derived peptide and/or a CD73 protein, protein fragment, polypeptide or peptide or derived peptide. Each of these features has already been defined herein.

A source of a CD39 and/or a source of a CD73 as present or as used in a combination of the invention may be nucleic acid-based, i.e. comprising a nucleic acid molecule encoding a CD39 protein, protein fragment, polypeptide or peptide or derived peptide and/or a nucleic acid molecule encoding a CD73 protein, protein fragment, polypeptide or peptide or derived peptide. Each of these features has already been defined herein.

A source of a CD39 protein and/or a source of a CD73 protein as present or as used in a combination of the invention may comprise a soluble CD39 protein, soluble protein fragment, soluble polypeptide or soluble peptide or derived peptide and/or a soluble CD73 protein, soluble protein fragment, soluble polypeptide or soluble peptide or soluble derived peptide. Each of these features has already been defined herein.

A soluble CD39 or a soluble CD73 protein is defined by opposition to a membrane bound form of said protein. A membrane bound form protein is a protein having an amino acid sequence that spans a cell membrane with amino acid on each side of the membrane (integral membrane protein). A membrane bound form of protein can also be one that is anchored to one side of the membrane by a moiety such as glycophosphatidylinositol (GPI) (peripheral membrane protein). Therefore, a protein will be said membrane bound when it is detectable in a cellular fraction which is associated with a cell membrane using a conventional assay known to the skilled person. An example of such a cellular fraction is a cellular extract comprising membrane bound proteins. Such extract may be prepared using Nonidet P40. An example of a conventional assay is an ELISA or a Western Blot. An alternative way of determining if a protein is membrane bound is when it is detectable by FLOW cytometry of intact cells using fluorescently labeled antibodies. The conventional FLOW cytometry based assay is known to a person skilled in the art. A CD39 protein has two membrane spanning segments. In the murine CD39 protein represented by SEQ ID NO: 5, the first membrane spanning segment starts at or around amino acid 17 and ends at or around amino acid 37 and the second membrane spanning segment starts at or around amino acid 480 and ends at or around amino acid 500. In the human CD39 protein represented by SEQ ID NO: 1, the first membrane spanning segment starts at or around amino acid 14 and ends at or around amino acid 37 and the second membrane spanning segment starts at or around amino acid 474 and ends at or around amino acid 501. In this context, "around" means that such a segment may start or end one or two or three amino acids upstream or downstream said identified amino acid. A membrane spanning segment of a CD39 protein may be defined as being represented by an amino acid sequence as identified above or by a sequence having at least 60%, 70%, 80%, 90%, 95% or 99% or 100% identity with one of the amino acid sequences identified above or a part thereof. The CD73 protein does not have any membrane spanning segment, however it has a C-terminal GPI (glycophosphatidylinositol) anchor site. In the CD73 protein derived from the murine CD73 protein represented by SEQ ID NO: 7, said C-terminal GPI anchor site is present at Serine 551. The skilled person will therefore understand that in a preferred embodiment, a soluble CD39 protein does not have a membrane spanning segment and that a soluble CD73 protein does not have a C-terminal GPI anchor site both as identified above.

A source of a CD39 and a source of a CD73 as present or as used in a combination of the invention may be a fusion protein comprising a CD73 protein, protein fragment, peptide or derived peptide or polypeptide as identified herein fused to a CD39 protein, protein fragment, peptide or derived peptide or polypeptide as identified herein and/or a nucleic acid molecule encoding said fusion protein. The invention encompasses a fusion protein wherein a CD73 protein, protein fragment, peptide or derived peptide or polypeptide as identified herein may be fused directly or via a linker to a CD39 protein, protein fragment, peptide or derived peptide or polypeptide as identified herein. Such a linker is known to the skilled person. Said linker may be a flexible linker, a rigid linker and/or a cleavable linker, said cleavable linker preferably being an in vivo cleavable linker. Preferably said linker is an amino acid linker.

In a preferred embodiment, said linker is a flexible linker allowing the adjacent protein domains to move relative freely to one another. Preferably said flexible linker is composed of amino residues like glycine, serine and/or alanine. A flexible linker preferably comprises or consists of 3 to 59 amino acid residues. Preferably said flexible linker is a longer linker to ensure that two adjacent domains do not sterically interfere with one another, preferably said longer linker comprises or consists of at least 11, 12, 13, 14, 15, 16, 17, 18, 19, 20 or 21 amino acid residues. Preferably said longer linker comprises or consists of 11 to 59 amino acids, or 11 to 25 amino acids, or 12 to 23 or 15 to 23 or 17 to 22 or 19 to 21 or 20 amino acid residues. Said linker may comprise or consist of 11, 12, 13, 14, 15, 16, 17, 18, 19, 20, 21, 22, 23, 24, 25 amino acids. A preferred linker comprises or consists of 21 amino acids, more preferably said linker comprises or consists of SEQ ID NO: 21

Preferably, a fusion protein of the invention comprises a linker that is present in between a soluble CD39 protein as defined herein and a soluble CD73 as defined herein, wherein preferably said linker is a flexible linker as defined above in terms of length and/or flexibility. More preferred, said linker is a flexible linker that comprises or consists of 19 or 21 amino acids, more preferably, 21 amino acids. Most preferably said linker comprises or consists of SEQ ID NO: 21. Preferably, said fusion protein of the invention comprises or consists of an amino acid sequence that has at least 60% sequence identity or similarity with the amino acid sequence of any of SEQ ID NO: 17 and/or 19, preferably with SEQ ID NO: 19.

Preferably, a fusion protein of the invention further comprises a tag for ease of purification as defined herein. Preferably, said tag being an Fc-tag as is known in the art. Preferably, said fusion protein of the invention comprises or consists of an amino acid sequence that has at least 60% sequence identity or similarity with the amino acid sequence of SEQ ID NO: 53.

Preferably said nucleic acid molecule encoding said fusion protein codes for a fusion protein that exhibits a nucleoside triphosphate diphosphohydrolase activity and an ecto-nucleotidase activity. Exhibiting a nucleoside triphosphate diphosphohydrolase activity and exhibiting an ecto-nucleotidase activity have already been defined herein. A preferred fusion protein is represented by SEQ ID NO: 17 and/or SEQ ID NO: 53 (i.e. fusion protein based on the fusion of a protein derived from a murine CD73 and CD39 protein fragments) or SEQ ID NO: 19 (i.e. fusion protein based on the fusion of a protein derived from a human CD73 and CD39 protein fragments). Such a preferred fusion protein represented by SEQ ID NO: 17 is encoded by SEQ ID NO: 18, SEQ ID NO: 19 is encoded by SEQ ID NO: 20 and SEQ ID NO: 53 is encoded by SEQ ID NO: 52.

Accordingly, a preferred fusion protein comprises an amino acid sequence that has at least 60% sequence identity or similarity with amino acid sequence SEQ ID NO: 17, SEQ ID NO: 53 and/or SEQ ID NO: 19 or a part thereof and/or it has or exhibits a nucleoside triphosphate diphosphohydrolase and an ecto-nucleotidase activity. Identity or similarity with an amino acid sequence SEQ ID NO: 17, SEQ ID NO: 53 and/or SEQ ID NO: 19 means identity or similarity with amino acid sequence SEQ ID NO:17, SEQ ID NO: 53 and/or SEQ ID NO:19 over its whole length or as a whole. Identity or similarity with an amino acid sequence SEQ ID NO: 17, SEQ ID NO: 53 and/or SEQ ID NO: 19 or part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 10%, 20%, 30%, 40%, 50%, 60%, 70%, 80%, 80%, 90% or 100% of the length of SEQ ID NO: 17, SEQ ID NO: 53 and/or SEQ ID NO: 19.

Accordingly a source of a CD39 protein and/or a source of a CD73 protein may also be a nucleic acid molecule encoding said preferred fusion protein and being as follows:
 i. a nucleotide sequence comprising a nucleotide sequence that has at least 60% sequence identity or similarity with SEQ ID NO: 18, SEQ ID NO: 52 and/or SEQ ID NO: 20 or a part thereof
 ii. a nucleotide sequences the complementary strand of which hybridizes to a nucleic acid molecule of sequence of (i);
 iii. a nucleotide sequence the sequence of which differs from the sequence of a nucleic acid molecule of (iii) due to the degeneracy of the genetic code or
 iv. a nucleotide sequence that encodes an amino acid sequence that has at least 60% amino acid identity or similarity with an amino acid sequence encoded by a nucleotide sequence SEQ ID NO: 18, SEQ ID NO: 52 and/or SEQ ID NO: 20 or a part thereof.

A linker and/or signal sequences are already included in above-identified nucleic acid molecule (i.e. a linker as defined herein is present in SEQ ID NO: 18, 52 or 20) encoding a fusion protein. However no promoter sequence is included in these sequences yet. Any promoter may be used. A preferred promoter is identified herein as comprising SEQ ID NO: 23. Preferably said amino acid sequence being a CD73 source and/or a CD39 source represents a polypeptide that exhibits a nucleoside triphosphate diphosphohydrolase and an ecto-nucleotidase activity. Assessing a nucleoside triphosphate diphosphohydrolase and an ecto-nucleotidase activity has already been defined herein.

Identity or similarity with SEQ ID NO: 18, SEQ ID NO: 52 and/or SEQ ID NO: 20 means identity or similarity with SEQ ID NO:18, SEQ ID NO: 52 and/or SEQ ID NO:20 over its whole length or as a whole. Identity or similarity with SEQ ID NO: 18, SEQ ID NO: 52 and/or SEQ ID NO: 20 or a part thereof and/or an amino acid sequence encoded by a nucleotide sequence SEQ ID NO: 18, SEQ ID NO: 52 and/or SEQ ID NO: 20 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

"A part thereof" in this context means at least 10%, 20%, 30%, 40%, 50%, 60%, 70%, 80%, 80%, 90% or 100% of the length of SEQ ID NO: 17, SEQ ID NO: 53 or SEQ ID NO: 19 or SEQ ID NO: 18, SEQ ID NO: 52 or SEQ ID NO: 20.

A signal sequence may also be present in said nucleic acid molecule encoding said fusion protein. A preferred signal sequence from human alpha 1 anti-trypsin is represented by SEQ ID NO: 22. The inventors surprisingly found a novel fusion protein as defined herein, more preferably a fusion protein of SEQ ID NO: 17, encoded by a nucleotide sequence of SEQ ID NO: 18 to be fully active, i.e. showing both nucleoside triphosphate diphosphohydrolase activity and ecto-nucleotidase activity as defined herein (Examples, FIG. 7). In fact, the fusion protein of SEQ ID NO: 17 was found to show a higher CD73 activity as compared to the one of the soluble CD73 of SEQ ID NO: 13, which is surprising as usually when two proteins are fused together, the activity of either protein decreases.

Also encompassed by the present invention is a fusion protein comprising a membrane bound CD39 protein as defined herein, preferably having at least 60% identity with SEQ ID NO: 1 and/or 5 and/or encoded by a sequence having at least 60% identity with SEQ ID NO: 2, 6 and/or 55, and a membrane bound CD73 protein, preferably having at least 60% identity with SEQ ID NO: 3 and/or 7 and/or encoded by a sequence having at least 60% identity with SEQ ID NO: 4, 8 and/or 56, linked via a linker as defined herein, preferably said linker comprises or consists of SEQ ID NO: 21.

Also encompassed by the present invention is a fusion protein comprising a membrane bound CD39 protein as defined herein, preferably having at least 60% identity with SEQ ID NO: 1 and/or 5 and/or encoded by a sequence having at least 60% identity with SEQ ID NO: 2, 6 and/or 55, and a soluble CD73 protein, preferably having at least 60% identity with SEQ ID NO: 13 and/or 15 and/or encoded by a sequence having at least 60% identity with SEQ ID NO: 14 and/or 16, linked via a linker as defined herein, preferably said linker comprises or consists of SEQ ID NO: 21.

Also encompassed by the present invention is a fusion protein comprising a soluble CD39 protein as defined herein, preferably having at least 60% identity with SEQ ID NO: 9 and/or 11 and/or encoded by a sequence having at least 60% identity with SEQ ID NO: 10 and/or 12, and a membrane bound CD73 protein, preferably having at least 60% identity with SEQ ID NO: 3 and/or 7 and/or encoded by a sequence having at least 60% identity with SEQ ID NO: 4, 8 and/or 56, linked via a linker as defined herein, preferably said linker comprises or consists of SEQ ID NO: 21.

Identity or similarity with nucleotide sequence SEQ ID NO: 2, 4, 6, 8, 10, 12, 14, 16, 55 and/or 56 means identity or similarity with SEQ ID NO: 2, 4, 6, 8, 10, 12, 14, 16, 55 and/or 56 over its whole length or as a whole. Identity or similarity with nucleotide sequence SEQ ID NO: 2, 4, 6, 8, 10, 12, 14, 16, 55 and/or 56 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 10%, 20%, 30%, 40%, 50%, 60%, 70%, 80%, 80%, 90% or 100% of the length of SEQ ID NO: 2, 4, 6, 8, 10, 12, 14, 16, 55 and/or 56.

Identity or similarity with amino acid sequence SEQ ID NO: 1, 3, 5, 7, 9, 11, 13 and/or SEQ ID NO: 15 means identity or similarity with SEQ ID NO: 1, 3, 5, 7, 9, 11, 13 and/or SEQ ID NO: 15 over its whole length or as a whole. Identity or similarity with amino acid sequence SEQ ID NO: SEQ ID NO: 1, 3, 5, 7, 9, 11, 13 and/or SEQ ID NO: 15 or a part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions". "A part thereof" in this context means at least 10%, 20%, 30%, 40%, 50%, 60%, 70%, 80%, 80%, 90% or 100% of the length of SEQ ID NO: 1, 3, 5, 7, 9, 11, 13 and/or SEQ ID NO: 15.

In a further preferred embodiment, a source of a CD39 and a source of a CD73 of the present invention are located on a single nucleic acid construct or fusion construct, such as a plasmid or expression vector, to allow for the simultaneous expression of both CD39 and CD73, wherein the resulting CD39 and CD73 are expressed as separate proteins or expressed as a single protein wherein the CD39 and CD73 are separated after expression, to act independently. Options to reach simultaneous expression of both CD39 and CD73, wherein the resulting protein or polypeptide products are not fused together, are known by the person skilled in the art and comprise, but are not limit to, the strategy of (i) multiple promoters operably linked to each of the CD39 and CD73 encoding sequences; (ii) a fusion of the CD39 encoding sequence and CD73 encoding sequence linked via an inserted splicing signal between the CD39 and CD73 encoding sequences, allowing for the expression of both CD39 and CD73 to be driven by a single promoter; (iii) a fusion of the CD39 encoding sequence and CD73 encoding sequence linked via an inserted sequence encoding for a sequence that comprises a proteolytic cleavage between the CD39 and CD73 encoding sequences, allowing for the expression of both CD39 and CD73 to be driven by a single promoter, but requiring proteolytic cleavage after expression; (iv) a fusion of the CD39 encoding sequence and CD73 encoding sequence linked via an internal ribosomal entry site (IRES) between the CD39 and CD73 encoding sequences; and (v) a fusion of the CD39 encoding sequence and CD73 encoding sequence linked via a 2A peptide defined herein below, allowing for the expression of both CD39 and CD73 to be driven by a single promoter, while giving rise to separate CD39 and CD37 proteins or polypeptide products. A 2A sequence is a so called self-cleaving linker. During expression of a 2A sequence, a ribosome skipping event takes place wherein the ribosome skips the synthesis of the glycyl-prolyl peptide bond at the C-terminus of a 2A peptide, leading to the cleavage between the 2A peptide and its immediate downstream peptide, resulting in two separate proteins or polypeptide products flanking the 2A peptide sequence, i.e. CD39 and CD73.

Encompassed by the invention is a fusion protein comprising a CD39 and a CD73 linked via a cleavable linker and a nucleic acid construct encoding such a fusion protein. Cleavable linkers are well known in the art and can be defined as linkers which are engineered with one or more cleavage sites for proteases or chemical agents which enable the liberation of the two separate proteins flanked by such a linker. Preferably a cleavable linker of the present invention is an in vivo cleavable linker, such as a peptide with the following amino acid sequence RKRRK, which can be cleaved by furin. Cleavable linkers allow for the efficient, stoichiometric production of discrete protein products within a fusion protein through a cleavage event within the linker sequence. Preferably a cleavable linker of the present invention is an in vivo cleavable linker. Preferably, an in vivo cleavable linker encompassed by the present invention is a linker that comprises a protease cleavage site.

In a further preferred embodiment, a source of a CD39 and a source of a CD73 are encoded on a single nucleic acid construct or fusion construct wherein the CD39 encoding sequence and CD73 encoding sequence are linked via a 2A peptide. A 2A peptide is used in the art, as indicated above, to express multiple proteins flanking the 2A peptide from a single open reading frame. A 2A peptide linker allows for the efficient, stoichiometric production of discrete protein products within a single vector through a cleavage event (i.e. ribosome skipping) within the 2A peptide sequence. A 2A peptide linker encompassed by the present invention may be, but is not limited to, FMDV 2A (abbreviated herein as F2A); equine rhinitis A virus (ERAV) 2A (E2A); porcine teschovirus-1 2A (P2A) and Thoseaasigna virus 2A (T2A), more preferable porcine teschovirus-1 2A (P2A).

In a preferred embodiment, a fusion construct of the present invention comprises or consists of a CD39 encoding sequence fused to a CD73 encoding sequence via a 2A sequence as defined herein. Preferably, a fusion construct of the invention comprises or consists of a nucleotide sequence that has at least 60% sequence identity or similarity with the nucleotide sequence of nucleotides 853-4182 of SEQ ID NO: 42 (referred here is to Table 2), i.e. to SEQ ID NO: 54, or has at least 60% sequence identity or similarity with SEQ ID NO: 57.

Accordingly, a source of a CD39 protein and/or a source of a CD73 protein may also be a nucleic acid molecule comprising a fusion construct as follows:
i. a nucleotide sequence comprising a nucleotide sequence that has at least 60% sequence identity or similarity with nucleotides 853-4182 of SEQ ID NO: 42 and/or with SEQ ID NO: 54 and/or SEQ ID NO: 57 or a part thereof
ii. a nucleotide sequences the complementary strand of which hybridizes to a nucleic acid molecule of sequence of (i); or,
iii. a nucleotide sequence the sequence of which differs from the sequence of a nucleic acid molecule of (iii) due to the degeneracy of the genetic code.
iv. a nucleotide sequence comprising a 2A sequence flanked by a nucleotide sequence that encodes an amino acid sequence that has at least 60% sequence identity or similarity with an amino acid sequence of a CD39 of the invention and by a nucleotide sequence that encodes amino acid sequence that has at least 60% sequence identity or similarity with an amino acid sequence of a CD73 of the invention.

Identity or similarity with nucleotides 853-4182 of SEQ ID NO: 42 or with SEQ ID NO: 54 or with SEQ ID NO: 57 means identity or similarity with nucleotides 853-4182 of SEQ ID NO: 42 or with SEQ ID NO: 54 or with SEQ ID NO: 57 over its whole length or as a whole. Identity or similarity with nucleotides 853-4182 of SEQ ID NO: 42 or with SEQ ID NO: 54 or with SEQ ID NO: 57 or a part thereof is preferably at least 65%, 70%, 75%, 80%, 85%, 90%, 95%, 97%, 98%, 99% or 100% sequence identity. "A part thereof" in this context means at least 10%, 20%, 30%, 40%, 50%, 60%, 70%, 80%, 80%, 90% or 100% of the length of SEQ ID NO: 54 or 57 or with the sequence of nucleotides 853-4182 of SEQ ID NO: 42. The assessment of sequence identity may be carried out as explained in the general part dedicated to "general definitions". Preferably, a fusion construct of the present invention comprising or consisting of a CD39 encoding sequence fused to a CD73 encoding sequence via a 2A sequence as defined herein result after expression in a CD39 exhibiting nucleosidase triphosphate diphosphohydrolase activity as defined herein and a CD73 exhibiting ecto-nucleotidase activity as defined herein.

A fusion construct or protein as defined herein has the advantage of comprising the combination of the present invention on a single nucleic acid or protein molecule in a predetermined stoichiometric ratio within a fusion protein of the invention. Furthermore, a fusion construct or protein of the invention, requires the development of a single protein and/or a single nucleic acid molecule, construct or vector encoding both a CD39 and CD73 and/or the administration of a single protein and/or nucleic acid molecule, construct or vector encoding said fusion protein to an individual in the need thereof, as further defined herein.

Furthermore, in case of an fusion protein of the invention which does not comprise a cleavable linker as identified herein, or nucleic acid molecule encoding such a fusion protein, both NTPDase and ecto-nucleotidase activity are present in a single protein or encoded protein, respectively, with functional and practical benefits; as both NTPDase and ecto-nucleotidase activities are required for the conversion of ATP and/or ADP in adenosine it is a functional advantage of such a fusion protein that both activities are co-localized both in space and in time.

A benefit of a cleavable or self-cleaving fusion protein or a construct encoding such a cleavable or self-cleaving fusion protein as encompassed by the invention, which result after cleavage, or expression, or expression and cleavage into a separate CD39 and CD73, is that only a single compound (fusion construct or protein) needs to be developed, while after administration, and/or expression and cleavage, both proteins flanked by the linker are released which allows them to move freely, thereby preventing any steric hindrance, while being present in a predetermined stoichiometric ratio. Such cleavable or self-cleaving fusion proteins and constructs encoding such a cleavable or self-cleaving fusion protein are preferred where administration or application of membrane bound CD39 and/or membrane bound CD73, as defined herein, is desired.

In a preferred embodiment, a CD39 and/or CD73 protein, polypeptide, peptide, derived peptide, protein fragment or fusion protein according to present invention comprises a sequence encoding a tag for ease of purification. In a further preferred embodiment, a nucleic acid sequence of the present invention encodes for a CD39 and/or CD73 protein, polypeptide, peptide, derived peptide, protein fragment or fusion protein according to present invention comprising a sequence encoding a tag for ease of purification. Preferably, said tag is selected from, but is not limited to, the group consisting of an Fc-tag, FLAG-tag, poly(His)-tag, HA-tag and Myc-tag. More preferably said tag is an N-terminal Fc-tag. Even more preferably, said tag is an N-terminal human IgG1 Fc-tag identical or similar to amino acid sequence 20-246 of SEQ ID NO: 53 and encoded by a nucleotide sequence identical or similar to 60-738 of SEQ ID NO: 52, as a whole or as part thereof (referred here is to Table 4). Identity or similarity with the amino acid sequence 20-246 of SEQ ID NO: 53 or with the nucleotide sequence 60-738 of SEQ ID NO: 52 as a whole or as part thereof is preferably at least 65%, 70%, 75%, 80%, 85%, 90%, 95%, 97%, 98%, 99% or 100% sequence identity. The assessment of sequence identity may be carried out as explained in the general part dedicated to "general definitions".

A promoter may be present in said nucleic acid molecule. A preferred promoter is active or functional in a synoviocyte, such as, but not limited to, a CMV promoter or a NF-κB responsive promoter, both well known in the art[20]. A preferred promoter is a NF-κB responsive promoter as represented by SEQ ID NO: 23. Preferably said fusion protein is soluble and exhibits a nucleoside triphosphate diphosphohydrolase activity and an ecto-nucleotidase activity. Surprisingly, the inventors demonstrated that such a fusion protein exhibits both CD39 and CD73 activities (see for example FIGS. 6 and 7).

If a source of a CD39 and/or a source of a CD73 as present or as used in a combination of the invention is a nucleic acid molecule, each or both of said nucleic acid molecules may be present in a nucleic acid construct. A nucleic acid construct has been extensively defined in the general part dedicated to general definitions. In an embodiment, each or both of said nucleic acid construct is or comprises an expression construct. A preferred expression construct as present or as used in a combination of the invention is a viral expression construct. Each or both of said viral expression constructs may be a retrovirus vector, an adenovirus vector, an adeno-associated virus (AAV) vector, a herpesvirus vector, a polyoma virus vector or a vaccinia virus vector. Several of these viral vector expression constructs as present or as used in a combination of the invention have been further defined in the general part dedicated to general definitions.

If an adeno-associated virus vector is used as comprising a source of a CD39 and/or a source of a CD73, such adeno-associated virus vector preferably comprises a rAAV2 and/or a rAAV5 based genome (ITR) or a part thereof and AAV2 and/or AAV5 and/or rAAV8 capsid protein shell or a part thereof. A more preferred embodiment relates to an adeno-associated virus comprises a rAAV2 or rAAV5 genome and AAV2 or AAV5 or AAV8 capsid protein shell and a nucleic acid molecule encoding a fusion protein as earlier defined herein.

Several types of sources are encompassed by the present invention and as present or as used in a combination of the invention are listed below. A combination of the invention may be or may comprise or may consist of a source of a CD39 and a source of a CD73 as listed below:

A CD39 protein, protein fragment, polypeptide, peptide, derived peptide and/or a CD73 protein, protein fragment, polypeptide, peptide, derived peptide (protein-based source)

A soluble CD39 protein and/or a soluble CD73 protein (protein-based source)

A fusion protein (protein-based source) comprising a CD73 protein, protein fragment, polypeptide, peptide, derived peptide fused to a CD39 protein, protein fragment, polypeptide, peptide, derived peptide, e.g. a fusion protein comprising both soluble CD39 and soluble CD73, or soluble CD39 and membrane bound CD73, or membrane bound CD39 and soluble CD73, or membrane bound CD39 and membrane bound CD73.

A nucleic acid molecule (nucleic acid-based source) encoding such a CD39 protein, protein fragment, polypeptide, peptide, derived peptide, soluble protein, fusion protein and/or encoding such a CD73 protein, protein fragment, polypeptide, peptide, derived peptide, soluble protein, fusion protein A fusion construct (nucleic acid-based source) comprising a sequence encoding a fusion protein as indicated above, or comprising a sequence encoding a membrane bound CD39 and a sequence encoding a membrane bound CD73 linked via a 2A sequence or a cleavable linker as identified herein.

An expression construct (nucleic acid-based source) comprising a nucleic acid molecule as identified above, A viral vector expression construct comprising an expression construct as identified above.

A liposome or an exosome as further defined herein comprising a CD39 protein, protein fragment, polypeptide, peptide, derived peptide and/or a CD73 protein, protein fragment, polypeptide, peptide, derived peptide and/or a nucleic acid molecule encoding such a CD39 protein, protein fragment, polypeptide, peptide, derived peptide, soluble protein, fusion protein and/or e a nucleic acid molecule encoding such a CD73 protein, protein fragment, polypeptide, peptide, derived peptide, soluble protein, fusion protein.

Each of these sources of a CD39 may be used in combination with each of these sources of a CD73 as identified herein.

We anticipate that depending on the type of inflammatory disease or condition, the type of preferred source of CD39 and of CD73 is different. For example, for chronic inflammation, it is preferred to use a nucleic acid-based source of a CD39 and/or of a CD73. For acute inflammation, it is preferred to use a protein-based source of a CD39 and/or of a CD73. In a preferred embodiment an advantage of using a source of a soluble CD39 and/or a source of a soluble CD73 (i.e. a soluble CD39 and/or a soluble CD73 and/or a fusion protein comprising both soluble CD39 and soluble CD73 as defined herein and/or a nucleic acid-based source encoding said soluble CD39 and/or said soluble CD73 and/or a fusion protein comprising both soluble CD39 and soluble CD73 as defined herein) is that it may affect more cells and/or tissues and/or organs than a source of a CD39 and/or a source of a CD73, each of these sources being not soluble (i.e. membrane bound CD39 and/or membrane bound CD73 and/or a nucleic acid-based source encoding said membrane bound CD39 and/or said membrane bound CD73). A liposome and/or exosomes as further defined herein comprising a source of a CD39 and/or a source of a CD73, each of these sources being soluble (i.e. a soluble CD39 and/or a soluble CD73 and/or a fusion protein comprising both soluble CD39 and soluble CD73 as defined herein and/or a nucleic acid-based source encoding said soluble CD39 and/or said soluble CD73 and/or a fusion protein comprising both soluble CD39 and soluble CD73 as defined herein) or not soluble (i.e. membrane bound CD39 and/or membrane bound CD73 and/or a nucleic acid-based source encoding said membrane bound CD39 and/or said membrane bound CD73) is preferred to be used in acute inflammation as such liposome and/or exosome will have the same advantages as soluble CD39 and/or soluble CD73, i.e. being able to diffuse and affect a wide range of cells. In a preferred embodiment an advantage of using a source of a CD39 and/or a source of a CD73 wherein each said CD39 and CD73 are fused either as a nucleic acid- or as a protein-based source (e.g. a fusion protein comprising both soluble CD39 and soluble CD73 as represented by SEQ ID NO: 17, 19 or 52 or a construct comprising a sequence represented by SEQ ID NO: 18, 20 or 52 encoding such a such a fusion protein, or a fusion construct as represented by SEQ ID NO: 54 or SEQ ID NO: 57 comprising a sequence encoding a membrane bound CD39 and a sequence encoding a membrane bound CD73 linked via a P2A sequence) is that both enzymes are present at the same place and at the same time and could act synergistically compared to the use of a source of a CD39 and a source of a CD73 not being fused (i.e. as a nucleic acid- or as a protein-based source). A fused protein-based source of a CD39 and CD73 of the invention preferably is a fusion protein as defined earlier herein. A fused nucleic acid-based source of a CD39 and CD73 of the invention preferably is a nucleic acid molecule, construct and/or vector encoding said fused protein. A fused nucleic acid-based source of a CD39 and CD73 of the invention may also be a single nucleic acid molecule, construct and/or vector comprising both a sequence encoding a CD39 and a sequence encoding a CD37 in a non-operably linked fashion, i.e. wherein said CD39 said CD37 are expressed by separate expression regulating sequence.

A preferred source comprises a viral expression construct as identified herein. A preferred source of a CD39 protein and of a CD73 protein is an adeno-associated virus vector comprises a rAAV2 or rAAV5 genome ITRs and AAV2 or AAV5 or AAV8 capsid protein shell and a nucleic acid molecule encoding a fusion protein as earlier defined herein. Encompassed within the present invention is a vesicle composed of a lipid-bilayer, such as a liposome or an exosome comprising a source of a CD39 and/or a source of a CD73. In a preferred embodiment, said vesicle is a liposome, preferably an artificial liposome, comprising a source of a CD39 and/or a source of a CD73. In a further preferred embodiment, said vesicle is an exosome comprising a source of a CD39 and/or a source of a CD73. An exosome of the present invention may be referred to as a microvesicle, an epididimosome, an argosome, an exosome-like vesicle, a microparticle, a promininosome, a prostasome, a dexosome, a texosome, a dex, a tex, an archeosome and/or an oncosome. An exosome in the sense of the invention is meant any small vesicle of a cell as defined in the general part dedicated to general definitions under "Exosome".

A source of a CD39 and/or a source of a CD73 as present or as used in a combination of the invention may be present in a liposome or an exosome of the present invention in the form of a protein fragment, polypeptide, peptide, derived peptide, soluble protein, fusion protein as defined herein and/or as a nucleic acid molecule encoding such a protein fragment, polypeptide, peptide, derived peptide, soluble protein, fusion protein as defined herein. Preferably, a source of a CD39 and/or a source of a CD73 as present or as used in a combination of the invention is present in a liposome or an exosome as a CD39 protein and/or a CD73 protein as defined herein. Encompasses within the present invention is a liposome or an exosome comprising a source of a CD39 and/or a source of a CD73 as defined herein, more preferably a CD39 protein and/or a CD73 protein as defined herein, even more preferably a membrane bound CD39 protein and/or a membrane bound CD73 protein as defined herein.

A liposome or an exosome comprising both a source of a CD39 and a CD73, preferably a CD39 protein and CD73 protein, more preferably a membrane bound CD39 and a membrane bound CD73 as defined herein has the advantage of having both enzymes present at the same place and at the same time, preferably close to each other on the liposome or the exosome membrane, allowing these enzymes to act synergistically compared to the use of a source of a CD39 and a source of a CD73 not being present in a liposome or an exosome.

In a preferred embodiment, an advantage of using a source of a CD39 present in a liposome or an exosome and/or a source of a CD73 present in a liposome or an exosome, is that the CD39 and/or CD73 may be more active than corresponding source not present in a liposome or an exosome and could act synergistically compared to the use of a source of a CD39 and a source of a CD73 not being present in a liposome or an exosome.

The benefit of using liposomes or exosomes as carrier for a source of CD39 and/or a source of CD73 of the present invention is the possibility to characterize and/or engineer liposomes or exosomes to a further extent and/or in a pre-defined way as further detailed herein in the section entitled "Composition".

The further benefit of using liposomes or exosomes as carrier for the combination of the present invention, more preferably as a carrier of a CD39 protein, a CD39 polypeptide, a CD39 protein fragment, a CD39 peptide, a CD39 derived peptide, a CD73 protein, a CD73 polypeptide, a CD73 protein fragment, a CD73 peptide and/or a CD73 derived peptide, even more preferably as a carrier of a membrane bound CD39 protein, a membrane bound CD39 polypeptide, a membrane bound CD39 protein fragment, a membrane bound CD39 peptide, a membrane bound CD39 derived peptide, a membrane bound CD73 protein, a membrane bound CD73 polypeptide, a membrane bound CD73 protein fragment, a membrane bound CD73 peptide and/or a membrane bound CD73 derived peptide, is the increased stability and/or NTPDase and/or ecto-nucleotidase activity of a CD39 and/or a CD73, preferably of a membrane bound CD39 protein and/or a membrane bound CD73 protein as defined herein within the liposome or exosome as compared to said soluble or membrane bound CD39 and/or soluble or membrane bound CD73, preferably of said membrane bound CD39 protein and/or said membrane bound CD73 protein. The inventors surprisingly found an approximately 10 fold higher CD39 activity when comparing membrane bound CD39 to soluble CD39 (Examples, FIG. 15). Furthermore, a source of a CD39 and/or a source of a CD73 may exhibit improved pharmacokinetics if localized in a liposome or an exosome as compared to a similar source of a CD39 and/or CD73 in aqueous solution.

A further benefit of using a liposome or an exosome as carrier for the combination of the invention comprising a source of CD39 and a source of CD73, is the co-localization in both time and space of both a CD39 and a CD73 protein as defined herein, which both serve in the same pathway in the conversion of ATP to adenosine.

In an embodiment, each of the sources of a CD39 and/or of a CD73 may be expressed or introduced or targeted into a synoviocyte cell.

Composition

The invention further provides a composition comprising a source of a CD39 and/or a source of a CD73. Each of these features has been extensively defined in the previous section entitled "combination". In an embodiment, said composition is a pharmaceutical composition. A pharmaceutical composition may comprise a pharmaceutically acceptable carrier, diluents, adjuvant, filler, preservative, solubilizer and/or excipient. Such pharmaceutically acceptable carrier, filler, preservative, solubilizer, diluent and/or excipient may for instance be found in Remington: The Science and Practice of Pharmacy, 20th Edition. Baltimore, Md.: Lippincott Williams & Wilkins, 2000.

An excipient may protect each of the constituents of a combination and/or of a composition as defined herein to a cell and/or into a cell, preferably a synovial cell and/or a fibroblast-like synovial cell. A preferred excipient is a buffered surfactant solution. A preferred buffer is phosphate buffer saline (PBS) to protect against pH changes. A preferred surfactant is Pluronic F-68 $((C_3H_6O.C_2H_4O)_x)$ (Sigma) which is known to the skilled person.

Dose ranges of a combination or a composition according to the invention are preferably designed on the basis of rising dose studies in clinical trials (in vivo use) for which rigorous protocol requirements exist. The ranges of concentration or dose of as given above are preferred concentrations or doses for in vitro or ex vivo uses. The skilled person will understand that depending on the CD39 source and/or the CD73 source used, the concentration or dose of a CD39 source and/or CD73 source used may further vary and may need to be optimised any further.

If a source of a CD39 and a source of a CD73 is present or used in a single or in one composition, concentration or dose defined herein may refer to the total concentration or dose of both source of a CD39 and source of a CD73 used or the concentration or dose of each used source of a CD39 and source of a CD73.

A combination or a composition as defined herein is preferably for use as a medicament. Said medicament is preferably for preventing, delaying, reverting, curing and/or treating an inflammatory condition or disease.

An inflammatory condition or disease may be any condition or disease wherein inflammation may be detected. Inflammation may be detected by the assessment of the concentration of a C-reactive protein and/or of an inflammatory cytokine/chemokine as IL-6, IL-8 or CCL2 in a sample from a subject. The assessment of the concentration of a C-reactive protein and/or of an inflammatory cytokine/chemokine as IL-6, IL-8 or CCL2 may be carried out at the protein level using an ELISA or Western Blotting. The assessment of the concentration of a C-reactive protein and/or of an inflammatory cytokine/chemokine as IL-6, IL-8 or CCL2 may be carried out at the nucleic acid level using PCR. All these assays are known to the skilled person. Assays for the assessment of the presence of an inflammatory cytokine/chemokine as IL-6, IL-8 or CCL2 have been described in the experimental part. A detectable C-reactive protein and/or of an inflammatory cytokine/chemokine as IL-6, IL-8 or CCL2 may be present as a first or early parameter of such an inflammatory disease or condition. A detectable C-reactive protein and/or of an inflammatory cytokine/chemokine as IL-6, IL-8 or CCL2 may be present later on during the course of said inflammatory disease or condition.

An inflammatory disease or condition may be defined as any disease or condition wherein an increased level of ATP and/or an increased level of AMP and/or a decreased (or a reduction of the) level of adenosine and/or a decreased (or a reduction of the) ATPase activity level could be assessed in a sample or in a tissue from a subject. An inflammatory disease or condition may be defined as any disease or condition wherein an increased level of adenosine is expected to alleviate a parameter or symptom associated with such inflammatory disease or condition. The increase or decrease as identified in the previous sentence is preferably assessed as explained herein.

An inflammatory condition or disease may be selected from: rheumatoid arthritis (RA), juvenile rheumatoid arthritis, osteoarthritis (OA), gout, spondlyarthritis (SpA), psoriasis, psoriatic arthritis, ankylosing spondylitis, inflammatory bowel disease including Crohn's disease or ulcerative colitis, hepatitis, sepsis, alcoholic liver disease, and non-alcoholic steatosis. An inflammatory condition or disease may further be selected from, but is not limited to, pain, ischemic disorder, glaucoma, asthma, arthritis, cancer, neurodegenerative disorders, chronic disorders, acute inflammation, blood clotting disorders, heart failure, disorder of platelet function and other disorders where inflammation could be detected 21-23, preferably, further selected from but no limited to, pain, ischemic disorder, glaucoma, arthritis, cancer, neurodegenerative disorders, chronic disorders, acute inflammation, blood clotting disorders, heart failure, disorder of platelet function and other disorders where inflammation could be detected.

In an embodiment, an inflammatory condition or disease does not involve or is not detectable in the lung or in lung tissue or lung cells.

As used herein, the term "hepatitis" refers to a gastroenterological disease, condition, or disorder that is characterized, at least in part, by inflammation of the liver. Examples of hepatitis include, but are not limited to, hepatitis associated with hepatitis A virus, hepatitis B virus, hepatitis C virus, or liver inflammation associated with ischemia/reperfusion.

In a preferred embodiment, a source of a CD39 and a source of a CD73 when not fused or when not fused with a cleavable linker or self-cleaving linker are used for RA.

In a preferred embodiment, a source of a CD39 and a source of a CD73 when fused (e.g. a fusion protein of the invention represented by SEQ ID NO: 17, 19 or 53 or encoded by SEQ ID NO: 18, 20 or 52) or when fused with a cleavable linker or self-cleaving linker (e.g. a fusion construct of the invention as represented by SEQ ID NO: 54 or SEQ ID NO: 57 comprising a sequence encoding a membrane bound CD39 and a sequence encoding a membrane bound CD73 linked via a P2A sequence) are used for any inflammatory condition or disease as identified herein.

A medicament may be used in a subject. "Subjects" means any member of the class mammalia, including without limitation humans, non-human primates, farm animals, domestic animals and laboratory animals.

A combination or a composition as encompassed by the present invention is preferably for use as a medicament. Said combination or composition is preferably said to be able to be used for preventing, delaying, reverting, curing and/or treating an inflammatory condition or disease, when said combination or composition is able to exhibit an anti-inflammatory effect. An anti-inflammatory effect may be reached when at least one of the following effect is achieved:

molecular level: exhibit a nucleoside triphosphate diphosphohydrolase activity or the induction or the promotion or the increase of such activity and exhibit an ecto-nucleotidase activity or the induction or the promotion or the increase of such activity molecular level: exhibit an increase of cAMP amount or concentration molecular level: exhibit a decrease in the amount or concentration or an activity of C-reactive protein and/or of an inflammatory cytokine/chemokine such as IL-6, IL-8 or CCL2 molecular level: exhibit an increase in the amount or concentration or an activity of an anti-inflammatory cytokine as IL1-RA and/or IL-10.

cellular/tissue level: a decrease in a symptom, such as a decrease in inflammation in the inflamed tissue.

patient level: an improvement in a disease symptom as measured by self-reported questionnaires such as RAPID3 and RADA15[5] or a DAS or DAS28 as later explained herein.

In the case of RA, an inflamed tissue may be a synovial tissue. In the case of RA, a typical symptom may be the cartilage that may be reduced and/or the bone that may be destructed. A decrease in a symptom of RA may therefore be a decrease in cartilage and/or bone destruction of the joint.

The assessment of a nucleoside triphosphate diphosphohydrolase activity or the induction or the promotion or the increase of such activity and the assessment of an ecto-nucleotidase activity or the induction or the promotion or the increase of such activity have already been explained earlier herein.

Increasing the amount or concentration of cAMP in a sample from a patient preferably means that the amount or concentration of cAMP is increased of at least 1%, 2%, 5%, 10%, 15%, 20%, 25%, 30%, 35%, 45%, 55%, 65%, 75%, 85%, 95%, 100% or more by comparison to the initial amount or concentration of cAMP before treatment. A sample from a patient may be a tissue biopsy, preferably synovium or synovial fluid, or serum/plasma or peripheral blood mononuclear cells (PBMCs) from blood. cAMP levels can be measured by commercially available assays (ELISA or luminescence based) that are known to one skilled in the art.

Increasing the amount or concentration or activity of an anti-inflammatory cytokine as IL1-RA and/or IL-10 in a sample from a patient may be assessed has already explained herein and preferably means that the amount or concentration or activity of an anti-inflammatory cytokine as IL1-RA and/or IL-10 is increased of at least 1%, 2%, 5%, 10%, 15%, 20%, 25%, 30%, 35%, 45%, 55%, 65%, 75%, 85%, 95%, 100% or more by comparison to the initial amount or concentration or activity of said anti-inflammatory cytokine as IL1-RA and/or IL-10 before treatment. A sample from a patient may be a tissue biopsy (synovium or synovial fluid), or serum/plasma or PBMCs from blood. The assessment of the amount or concentration of IL1-RA or IL-10 may be carried out using commercially available assays (ELISA or fluorescence based) that are known to one skilled in the art.

A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of rheumatoid arthritis, including clinical examination and routine laboratory tests. Such methods include both macroscopic and microscopic methods, as well as molecular methods, X-rays, biochemical, immunohistochemical and others. The methods may involve analysis of the whole joint (e.g. X-ray, MRI), or of parts thereof, such as extracted synovial fluid or biopsies of synovial tissue analysis of patient blood serum and/or plasma and/or PBMCs. Rheumatoid synovial fluid, which is in direct contact with the synovium and the articular cartilage, has a high diagnostic value and is easily accessible for aspiration[6].

A decrease or increase as defined herein is preferably assessed in a tissue or in a cell or in a sample of an individual or a patient by comparison to the amount present in said individual or patient before treatment with said combination or composition of the invention. A sample is preferably a tissue biopsy (synovium and/or synovial fluid) or blood serum and/or plasma and/or PBMCs. Alternatively, the comparison can be made with a tissue or cell or sample of said individual or patient which has not yet been treated with said combination or composition in case the treatment is local. The comparison is preferably carried out everywhere where a CD39 source and/or a CD73 source is expressed or produced or administered. A preferred cell in this context is a synovial cell or a fibroblast-like synoviocyte (FLS). A preferred tissue or tissue biopsy is or is derived from or comprises or consists of a cartilage and/or joint and/or a synovium and/or synovial fluid. A FLS may be defined as a mesenchymal cell present in the joint and that displays characteristics of fibroblasts such as the expression of collagen IV, collagen V, vimentin, CD90, cadherin-11 and/or CD55[7].

In a more preferred embodiment, said medicament is able to alleviate one or more symptom(s) from a treated patient and/or one or more characteristic(s) or parameter(s) of a cell or tissue from a treated patient is/are improved using a combination or a composition of the invention. For each inflammatory disease, the skilled person knows at least one symptom, parameter or characteristic, values of said parameter or characteristic associated with said disease and how to assess each of them. Below, we give a parameter specific for Rheumatoid arthritis. Rheumatoid arthritis is a disease that is preferably diagnosed after having assessed the index of Disease Activity Score (DAS) or the related DAS28[8] including the measurements of several parameters and symptoms on a subject. The assessment of said indexes may be carried out by a clinician examining a subject. In a more preferred embodiment, said medicament is able to alleviate one or more symptom(s) from a treated patient and/or one or more characteristic(s) or parameter(s) of a cell or tissue from a treated patient is/are improved using a combination or a composition of the invention when said medicament is able to induce a significant change in DAS or DAS28. Other ways of assessing rheumatoid arthritis are also described in (van Riel P. L. C. M., 2001 and in Gester A. M., 1999,). A medicament as defined herein is able to improve one parameter if after at least one week, one month, six month, one year or more of treatment using a combination and/or a composition of the invention, the value of said parameter has been improved of at least 1%, 2%, 5%, 10% or more by comparison of the value of said parameter before the onset of the treatment.

A medicament as defined herein is able to alleviate one symptom or one characteristic of a patient or of a cell, tissue or organ or said patient if after at least one week, one month, six month, one year or more of treatment using a combination and/or a composition of the invention, said symptom or characteristic is no longer detectable.

A combination and/or a composition as defined herein for use according to the invention may be suitable for administration to a cell, tissue and/or an organ in vivo of individuals affected by or at risk of developing an inflammatory disorder, and may be administered in vivo, ex vivo or in vitro. Said combination and/or composition may be directly or indirectly administrated to a cell, tissue and/or an organ in vivo of an individual affected by or at risk of developing an inflammatory disorder, and may be administered directly or indirectly in vivo, ex vivo or in vitro. A combination and/or a composition of the invention should be able to be delivered everywhere where inflammation is supposed to occur.

In the case of RA, and other types of arthritis (OA, psoriatic arthritis, spondyloarthritis (SpA), gout), inflammation is supposed to occur in a joint and/or in a cartilage and/or in a synovial tissue and/or in a synovial cell and/or in fibroblast-like synoviocyte cell and/or in immune cells as macrophage, neutrophil, T and/or B cells. Each of these tissues and/or cell types is involved, contribute and/or is associated with inflammation. It is therefore encompassed for RA and other types of arthritis (OA, psoriatic arthritis, SpA, gout), that a combination and/or a composition of the invention is able to be delivered to a joint and/or in a cartilage and/or in a synovial tissue and/or in a synovial cell and/or in fibroblast-like synoviocyte cell and/or to immune cells as macrophage, neutrophil, T and/or B cells. Preferably said joint, cartilage, synovial tissue and/or synovial cell and/or in fibroblast-like synoviocyte cell and/or immune cells as macrophage, neutrophil, T and/or B cells are of an individual suffering from said inflammatory disorder. In a preferred embodiment, the administration of a combination and/or a composition of the invention is local or systemic, preferably targeted to any of the types of cells identified above. More preferably the administration is intra-articular.

The term "intra-articular" refers to the interior of a joint, e.g., knee, elbow, shoulder, ankle, wrist, etc. Thus, an intra-articular injection is an injection into the space between the bones of a joint. In the knee, "intra-articular" refers to the space between the femur and the tibia, behind and surrounding the patella.

For IBD and Crohn's disease, inflammation primarily occurs in the stomach and intestine (gut). It is therefore encompassed for IBD and Crohn's disease, that a combination and/or a composition of the invention is able to be delivered to the stomach and/or the intestine. Preferably said stomach and/or intestine are of an individual suffering from such inflammatory disorder. In a preferred embodiment, the administration of a combination and/or a composition of the invention is local or systemic. More preferably the administration is local or systemic and targeted to the stomach and/or the intestine.

For Hepatitis and liver disease, inflammation is primarily occurs in the liver. It is therefore encompassed for hepatitis and liver diseases, that a combination and/or a composition of the invention is able to be delivered to the liver. Preferably said liver is of an individual suffering from such inflammatory disorder. In a preferred embodiment, the administration of a combination and/or a composition of the invention is local or systemic. More preferably the administration is local or systemic and targeted to the liver.

For sepsis, inflammation may be systemic. It is therefore encompass for such disease that the administration of a combination and/or a composition of the invention is systemic, preferably targeting the liver of such patients.

A combination and/or a composition of the invention may be directly or indirectly administrated using suitable means known in the art. Improvements in means for providing an individual or a cell, tissue, organ of said individual with a combination and/or a composition of the invention, are anticipated considering the progress that has already thus far been achieved. Such future improvements may of course be incorporated to achieve the mentioned effect of the invention. A combination and/or a composition can be delivered as is to an individual, a cell, tissue or organ of said individual. Depending on the disease or condition, a cell, tissue or organ of said individual may be as earlier defined herein. When administering a combination and/or a composition of the invention, it is preferred that such combination and/or composition is dissolved in a solution that is compatible with the delivery method. For intravenous, subcutaneous, intramuscular, intrathecal, intraarticular and/or intraventricular administration it is preferred that the solution is a physiological salt solution.

A combination and/or a composition of the invention if in the form of a nucleic acid molecule as earlier defined herein may use naked plasmid DNA to be delivered to a cell, tissue of an individual. It means that it is delivered or administered in the absence of any type of carrier. Preferably it is delivered under high pressure[10] (hydrodynamic delivery).

Alternatively, an additional compound may be present in a combination and/or a composition of the invention. Said compound may help in delivery of each of the constituents of said combination and/or composition. Below is provided a list of suitable compounds: compounds capable of forming complexes, nanoparticles, micelles, vesicles such as exosomes as identified herein and/or liposomes that deliver each constituent as defined herein, complexed or trapped in a vesicle or liposome through a cell membrane. Many of these compounds are known in the art. Suitable compounds comprise polyethylenimine (PEI), or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent of a combination and/or of a composition as defined herein to a cell, preferably a synovial cell.

Lipofectamine represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent of a combination and/or of a composition as defined herein, across cell membranes into cells.

In addition to these common nanoparticle materials, the cationic peptide protamine offers an alternative approach to formulate a combination and/or a composition with colloids. This colloidal nanoparticle system can form so called proticles, which can be prepared by a simple self-assembly process to package and mediate intracellular release of an oligonucleotide. The skilled person may select and adapt any of the above or other commercially available alternative delivery systems to package and deliver a combination and/or a composition for use in the current invention to deliver it for the treatment of an inflammatory disorder in humans.

A source of the present invention may be present in an liposome or exosome as identified herein, in other words, a liposome or an exosome may be used as carrier for a source of a CD39 and/or a source of a CD73 as defined herein, preferably a liposome or an exosome is used as carrier for a source of a CD39 protein and/or a source of a CD73 protein as defined herein, even more preferably, a liposome or an exosome is used as carrier for a source of a membrane bound CD39 protein and/or a source of a membrane bound CD73 protein as defined herein.

The benefit of using liposomes or exosomes as carrier for a source of CD39 and/or a source of CD73 of the present invention is the possibility to characterize and/or engineer exosomes to a further extent and/or in a pre-defined way. "Engineered to a further extent" is understood herein as to be engineered to carry other additional functional molecules next to a source of CD39 and/or a source of CD73. Using a liposome or an exosome as carrier for the combination of the invention allows for adding and/or loading other functional molecules to said liposome or exosome, for instance to target the liposome or exosome to a preferred location in the body, such as a particular organ and/or tissue and/or a particular diseased or affected organ and/or tissue such as, but not limited to, a site of inflammation, more specific to a joint and/or an affected joint in a individual suffering from Rheumatoid Arthritis, and/or a tumor. In addition to a source of CD39 and/or a source of CD73, a liposomes or exosomes extracted from cells and/or engineered may further comprise and/or be loaded with additional function proteins such as target proteins like antibodies and/or receptor binding molecules or ligands and/or immunomodulatory proteins, and/or miRNA, mRNA or siRNA for either inducing or increasing the expression a specific encoding sequence or the inhibition of expression of a specific encoding sequence targeted with the miRNA or siRNA[24,25], preferably, said specific encoding sequence is a sequence encoding for an additional functional protein as defined herein. Such further additional functional proteins may be added to the liposomes or exosomes of the present invention via co-expression of the additional functional protein together with the CD39 and/or CD73 protein, and/or via co-culturing of cells expressing the additional functional protein with cells expressing the CD39 and/or CD73 protein, and/or via exposure of the liposomes or exosomes of the invention with additional functional protein, possibly under conditions promoting the uptake additional functional proteins such as a shift in pH, for instance a shift from neutral pH of about 7 to a pH of at least 5, preferably of 5.2. Liposomes or exosomes of the present invention may also be engineered to comprise additional functional proteins or protein domains for instance via chemical (cross-)linkers such as BS3, DSS, BSG.

Other functional molecules present within the liposome or exosome of the invention may also be active compounds other than a source of CD39 and/or a source of CD73 working together additionally or synergistically with a source of CD39 and/or a source of CD73 in preventing and/or treating and/or curing and/or delaying and/or reverting a diseased and/or disordered state in an individual as indicated herein before, preferably Rheumatoid Arthritis.

Further benefits of an exosome as carrier for a source of CD39 and/or a source of CD73 of the present invention are detailed in the previous section entitled "Combination".

In another embodiment, a CD39 source and/or a CD73 source as used or as present in a combination and/or in a composition of the invention could be covalently or non-convalently linked to another molecule. A preferred molecule is a ligand as defined below and/or a molecule that alters stability and/or pharmacokinetics and/or pharmacodynamics of said CD39 source and/or CD73 source as used or as present in a combination and/or in a composition of the invention. Each of these parameters (i.e. stability and/or pharmacokinetics and/or pharmacodynamics) could be assessed using assays known to the skilled person.

A CD39 source and/or a CD73 source as used or as present in a combination and/or in a composition of the invention could be covalently or non-covalently linked to a ligand specifically designed to facilitate the uptake in to the cell, cytoplasm and/or its nucleus. Such ligand could comprise (i) a compound (including but not limited to peptide (-like) structures) recognising cell, tissue or organ specific elements facilitating cellular uptake and/or (ii) a chemical compound able to facilitate the uptake in to cells and/or the intracellular release of a CD39 source and/or a CD73 source as used or as present in a combination and/or in a composition of the invention from vesicles, e.g. endosomes or lysosomes.

Therefore, in a preferred embodiment, a CD39 source and/or a CD73 source as used or as present in a combination and/or in a composition of the invention is formulated in a medicament which is provided with at least an excipient, with at least a compound and/or a ligand for delivery and/or a delivery device thereof to a cell and/or enhancing its intracellular delivery. Accordingly, the invention also encompasses a pharmaceutically acceptable composition comprising a CD39 source and/or a CD73 source as used or as present in a combination and/or in a composition of the invention and further comprising at least one excipient and/or a ligand for delivery and/or a delivery device of said CD39 source and/or a CD73 source to a cell and/or enhancing its intracellular delivery.

Depending on their identity, the skilled person will know which type of formulation is the most appropriate for each constituent as defined herein. In a preferred embodiment, the invention provides a combination and/or a composition and/or a preparation which is in the form of a kit of parts comprising a CD39 source and/or a CD73 source and a further adjunct compound as later defined herein.

A preferred combination and/or composition as defined herein is for preventing and/or treating and/or delaying and/or reverting and/or curing an inflammatory disorder in an individual. An individual which may be treated using a combination and/or a composition of the invention may already have been diagnosed as having an inflammatory disorder. Alternatively an individual which may be treated using a combination and/or a composition of the invention may not have yet been diagnosed as having an inflammatory disorder but may be an individual having an increased risk of developing an inflammatory disorder in the future given his or her genetic background. A preferred individual is a human being.

Use

In a further aspect, there is provided the use of a combination and/or a composition of the invention as defined herein for the manufacture of a medicament for preventing and/or treating and/or curing and/or delaying and/or reverting an inflammatory disorder in an individual. Each feature of said use has earlier been defined herein.

A treatment in a use or in a method according to the invention may be repeated multiple times a week, month or year, or each 1, 2, 3, 4, 5, 6 years. Preferably, a protein based treatment in a use or in a method according to the invention may be repeated multiple times a week or month. Preferably, a nucleic acid based treatment, preferably gene therapy, in a use or in a method according to the invention may be repeated each year or each 2, 3, 4, 5, 6 years. Each CD39 source and/or each CD73 source and/or each combination and/or each composition or equivalent thereof as defined herein for use according to the invention may be suitable for direct administration to a cell, tissue and/or an organ in vivo of individuals affected by or at risk of developing an inflammatory disorder, and may be administered directly in vivo, ex vivo or in vitro. The frequency of administration of a combination and/or a composition of the invention may depend on several parameters such as the age of the patient, the nature of the patient's disease, the number of molecules (i.e. dose), the formulation of said molecule. The frequency may be daily, weekly or ranged between at least once in two weeks, or three weeks or four weeks or five weeks or a longer time period.

Method

In a further aspect, there is provided a method for alleviating one or more symptom(s) of an inflammatory disorder in an individual, in a cell, tissue or organ of said individual or alleviate one or more characteristic(s) or symptom(s) of a cell, tissue or organ of said individual, the method comprising administering to said individual a combination and/or a composition as defined herein.

In one embodiment said method is performed in vitro, for instance using a cell culture. Preferably, said method is in vivo. Each feature of these methods has already been defined herein. In a method of the invention, a combination and/or a composition may be combined with an additional compound known to be used for treating an inflammatory disorder in an individual. Such compound may be an antibody, a DMARD (disease-modifying anti-rheumatic drugs), a NSAID (Non-steroidal Anti-inflammatory Agents), an ADORA1 antagonist, or a Biologic. An ADORA1 antagonist may be Dipropylcyclopentyl (DPCPX). A Biologic may be at least one of the following compounds: etanercept, adalimumab, infliximab, certolizumab pegol, golimumab. Actemra, Cimzia, Enbrel, Humira, Kineret, Orencia, Remicade, Rituxan, Simponi. Each of these additional compound may be administered simultaneously or sequentially with a combination and/or a composition of the invention.

General Definitions

Identity/Similarity

In the context of the invention, a protein or a protein fragment is represented by an amino acid sequence.

In the context of the invention, a nucleic acid molecule is represented by a nucleic acid or nucleotide sequence which encodes a protein or a polypeptide or a protein fragment or a peptide or a derived peptide. A nucleic acid molecule may comprise a regulatory region.

It is to be understood that each nucleic acid molecule or protein or protein fragment or peptide or derived peptide or polypeptide as identified herein by a given Sequence Identity Number (SEQ ID NO) is not limited to this specific sequence as disclosed. Each gene sequence or nucleotide sequence as identified herein encodes a given protein or polypeptide or protein fragment or peptide or derived peptide or is it self a protein or a protein fragment or polypeptide or peptide or derived peptide. Throughout this application, each time one refers to a specific nucleotide sequence SEQ ID NO (take SEQ ID NO: 2 as example), one may replace it by:

i. a nucleotide sequence comprising a nucleotide sequence that has at least 60% sequence identity or similarity with SEQ ID NO: 2;
ii. a nucleotide sequences the complementary strand of which hybridizes to a nucleic acid molecule of sequence of (i);
iii. a nucleotide sequence the sequence of which differs from the sequence of a nucleic acid molecule of (iii) due to the degeneracy of the genetic code; or,
iv. a nucleotide sequence that encodes an amino acid sequence that has at least 60% amino acid identity or similarity with an amino acid sequence encoded by a nucleotide sequence SEQ ID NO: 2.

Throughout this application, each time one refers to a specific amino acid sequence SEQ ID NO (take SEQ ID NO: 1 as example), one may replace it by: a polypeptide comprising an amino acid sequence that has at least 60% sequence identity or similarity with amino acid sequence SEQ ID NO: 1.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10%, 20%, 30%, 40%, 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Gene or Coding Sequence

"Gene" or "coding sequence" refers to a DNA or RNA region (the transcribed region, i.e. a CD39 source and/or a CD73 source) which "encodes" a particular protein. A coding sequence is transcribed (DNA) and translated (RNA) into a polypeptide when placed under the control of an appropriate regulatory region, such as a promoter. A gene may comprise several operably linked fragments, such as a promoter, a 5'leader sequence, an intron, a coding sequence and a 3'nontranslated sequence, comprising a polyadenylation site or a signal sequence. A chimeric or recombinant gene is a gene not normally found in nature, such as a gene in which for example the promoter is not associated in nature with part or all of the transcribed DNA region. "Expression of a gene" refers to the process wherein a gene is transcribed into an RNA and/or translated into an active protein.

Nucleic Acid Construct

If a source of a CD39 and/or a source of a CD73 is or comprises a nucleic acid molecule, it may be present in a nucleic acid construct or a vector. Preferably, a vector carries a genome that is able to stabilize and remain episomal in a host cell. Within the context of the invention, a host cell may mean to encompass a cell used to make the vector or a cell wherein the vector will be administered. Alternatively a vector is capable of integrating into a host cell's genome, e.g. through homologous recombination or otherwise. A particularly preferred vector is an expression vector or expression construct wherein a nucleotide sequence encoding a CD39 source and/or a CD73 source as defined herein, is operably linked to a promoter capable of directing expression of said nucleotide sequence (i.e. a coding sequence) in a host cell for the vector.

As used herein, the term "promoter" refers to a nucleic acid fragment that functions to control the transcription of one or more genes (or coding sequence), located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A preferred inducible promoter is an NF-Kb responsive promoter which is inducible upon inflammation. A more preferred NF-Kb responsive promoter comprises SEQ ID NO: 23. A "tissue specific" promoter is preferentially active in specific types of differentiated cells/tissues, such as preferably a synovial cell or tissue derived therefrom.

Expression vectors allow a CD39 source and/or a CD73 source as defined herein to be prepared using recombinant techniques in which a nucleotide sequence encoding said CD39 and/or CD73 source is expressed in a suitable cell, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34: 315 (describing cassette mutagenesis).

Typically, a nucleic acid or nucleotide sequence encoding a CD39 source and/or a CD73 source is used in an expression vector. The phrase "expression vector" generally refers to a nucleotide sequence that is capable of effecting expression of a gene in a host compatible with such sequences. These expression vectors typically include at least suitable promoter sequences and optionally, transcription termination signals. An additional factor necessary or helpful in effecting expression can also be used as described herein. A nucleic acid or DNA or nucleotide sequence encoding a CD39 source and/or a CD73 source is incorporated into a DNA construct capable of introduction into and expression in an in vitro cell culture. Specifically, a DNA construct is suitable for replication in a prokaryotic host, such as bacteria, e.g., E. coli, or can be introduced into a cultured mammalian, plant, insect, (e.g., SD), yeast, fungi or other eukaryotic cell lines.

A DNA construct prepared for introduction into a particular host may include a replication system recognized by the host, an intended DNA segment encoding a desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis. A preferred signal sequence is a human alpha 1 anti-trypsin signal sequence. A more preferred human alpha 1 anti-trypsin signal sequence comprises SEQ ID NO: 22.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression vectors includes the replication system and transcriptional and translational regulatory sequences together with the insertion site for the polypeptide encoding segment can be employed. In most cases, the replication system is only functional in the cell that is used to make the vector (bacterial cell as E. Coli). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. S. cerevisiae, e.g., insect cells, e.g., SD cells, mammalian cells, e.g., CHO cells and bacterial cells, e.g., E. coli. A host cell may thus be a prokaryotic or eukaryotic host cell. A host cell may be a host cell that is suitable for culture in liquid or on solid media. A host cell is preferably used in a method for producing a CD39 source and/or a CD73 source as defined herein. A method comprises the step of culturing a host cell under conditions conducive to the expression of a CD39 source and/or a CD73 source. Optionally the method may comprise recovery of a CD39 source and/or a CD73 source. A CD39 source and/or a CD73 source may e.g. be recovered from the culture medium by standard protein purification techniques, including a variety of chromatography methods known in the art per se.

Alternatively, a host cell is a cell that is part of a multicellular organism such as a transgenic plant or animal, preferably a non-human animal. A transgenic plant comprises in at least a part of its cells a vector as defined above. Methods for generating transgenic plants are e.g. described in U.S. Pat. No. 6,359,196 and in the references cited therein. Such transgenic plant or animal may be used in a method for producing a CD39 source and/or a CD73 source as defined herein. For transgenic plant, a method comprises the step of recovering a part of a transgenic plant comprising in its cells the vector or a part of a descendant of such transgenic plant, whereby the plant part contains a CD39 source and/or a CD73 source, and, optionally recovery of a CD39 source and/or a CD73 source from the plant part. Such methods are also described in U.S. Pat. No. 6,359,196 and in the references cited therein. Similarly, a transgenic animal comprises in its somatic and germ cells a vector as defined above. A transgenic animal preferably is a non-human animal. Methods for generating transgenic animals are e.g. described in WO 01/57079 and in the references cited therein. Such transgenic animals may be used in a method for producing a polypeptide of the invention as defined above, the method comprising the step of recovering a body fluid from a transgenic animal comprising the vector or a female descendant thereof, wherein the body fluid contains a CD39 source and/or a CD73 source, and, optionally recovery of a CD39 source and/or a CD73 source from the body fluid. Such methods are also described in WO 01/57079 and in the references cited therein. A body fluid containing a CD39 source and/or a CD73 source preferably is blood or more preferably milk.

Another method for preparing a CD39 source and/or a CD73 source is to employ an in vitro transcription/translation system. A DNA encoding a polypeptide is cloned into an expression vector as described supra. An expression vector is then transcribed and translated in vitro. A translation product can be used directly or first purified. A polypeptide resulting from in vitro translation typically do not contain the post-translation modifications present on a polypeptide synthesised in vivo, although due to the inherent presence of microsomes some post-translational modification may occur. A method for synthesis of a polypeptide by in vitro translation is described by, for example, Berger & Kimmel, Methods in Enzymology, Volume 152, Guide to Molecular Cloning Techniques, Academic Press, Inc., San Diego, Calif., 1987.

Gene Therapy

Some aspects of the invention concern a source of a CD39 and/or a source of a CD73 wherein said source is present in a nucleic acid construct or expression vector, wherein the vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an Adenoviral and Adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications. (Russell, 2000, J. Gen. Virol. 81: 2573-2604; Goncalves, 2005, Virol J. 2(1):43) as indicated above. AAV vectors are even more preferred since they are known to result in very stable long term expression of transgene expression (up to 9 years in dog (Niemeyer et al, Blood. 2009 Jan. 22; 113(4):797-806) and ~2 years in human (Nathwani et al, N Engl J Med. 2011 Dec. 22; 365(25): 2357-65, Simonelli et al, Mol Ther. 2010 March; 18(3):643-50. Epub 2009 Dec. 1.)). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, N Engl J Med. 2011 Dec. 22; 365(25): 2357-65, Apparailly et al, Hum Gene Ther. 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and Vigna et al. (2000, J Gene Med 2000; 2: 308-16).

Other suitable gene therapy vectors include a herpes virus vector, a polyoma virus vector or a vaccinia virus vector.

Generally, gene therapy vectors will be as the expression vectors described above in the sense that they comprise a nucleotide sequence encoding a source of a CD39 and/or of a CD73 to be expressed, whereby a nucleotide sequence is operably linked to the appropriate regulatory sequences as indicated above. Such regulatory sequence will at least comprise a promoter sequence. Suitable promoters for expression of a nucleotide sequence encoding a CD39 source and/or a CD73 source from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Suitable promoters are described below.

Several inducible promoter systems have been described that may be induced by the administration of small organic or inorganic compounds. Such inducible promoters include those controlled by heavy metals, such as the metallothionine promoter (Brinster et al. 1982 Nature 296: 39-42; Mayo et al. 1982 Cell 29: 99-108), RU-486 (a progesterone antagonist) (Wang et al. 1994 Proc. Natl. Acad. Sci. USA 91: 8180-8184), steroids (Mader and White, 1993 Proc. Natl. Acad. Sci. USA 90: 5603-5607), tetracycline (Gossen and Bujard 1992 Proc. Natl. Acad. Sci. USA 89: 5547-5551; U.S. Pat. No. 5,464,758; Furth et al. 1994 Proc. Natl. Acad. Sci. USA 91: 9302-9306; Howe et al. 1995 J. Biol. Chem. 270: 14168-14174; Resnitzky et al. 1994 Mol. Cell. Biol. 14: 1669-1679; Shockett et al. 1995 Proc. Natl. Acad. Sci. USA 92: 6522-6526) and the tTAER system that is based on the multi-chimeric transactivator composed of a tetR polypeptide, as activation domain of VP16, and a ligand binding domain of an estrogen receptor (Yee et al., 2002, U.S. Pat. No. 6,432,705). Another preferred inducible promoter is an NF-κB inducible promoter (Khoury et al, J Gen Virol (2007) 88:1717-1721). This promoter is attractive to be used in the context of the invention since it is induced by inflammatory conditions.

A gene therapy vector may optionally comprise a second or one or more further nucleotide sequence coding for a second or further polypeptide. A second or further polypeptide may be a (selectable) marker polypeptide that allows for the identification, selection and/or screening for cells containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York.

Alternatively, a second or further nucleotide sequence may encode a polypeptide that provides for fail-safe mechanism that allows to cure a subject from the transgenic cells, if deemed necessary. Such a nucleotide sequence, often referred to as a suicide gene, encodes a polypeptide that is capable of converting a prodrug into a toxic substance that is capable of killing the transgenic cells in which a CD39 source and/or a CD73 source is expressed. Suitable examples of such suicide genes include e.g. the E. coli cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see e.g. Clair et al., 1987, Antimicrob. Agents Chemother. 31: 844-849).

A gene therapy vector is preferably formulated in a pharmaceutical composition as defined herein. In this context, a pharmaceutical composition may comprise a suitable pharmaceutical carrier as earlier defined herein.

Adeno-Associated Virus Vector (AAV Vector)

An AAV vector as used herein preferably comprises a recombinant AAV vector (rAAV). A "rAAV vector" as used herein refers to a recombinant vector comprising part of an AAV genome encapsidated in a protein shell of capsid protein derived from an AAV serotype as explained herein. Part of an AAV genome may contain the inverted terminal repeats (ITR) derived from an adeno-associated virus serotype, such as AAV1, AAV2, AAV3, AAV4, AAV5 and others. Protein shell comprised of capsid protein may be derived from an AAV serotype such as AAV1, 2, 3, 4, 5 and others. A protein shell may also be named a capsid protein shell. rAAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. Preferred ITR sequences are represented by the SEQ ID NO as indicated Table 1. In the context of the present invention a capsid protein shell may be of a different serotype than the rAAV vector genome ITR. An AAV vector of the invention may thus be composed of a capsid protein shell, i.e. the icosahedral capsid, which comprises capsid proteins (VP1, VP2, and/or VP3) of one AAV serotype, e.g. AAV serotype 5, whereas the ITRs sequences contained in that AAV5 vector may be any of the rAAV serotypes described above, including a rAAV5 vector. An "rAAV5 vector" thus comprises a capsid protein shell of AAV serotype 5, while e.g. a rAAV2 vector comprises a capsid protein shell of AAV serotype 2, whereby either may encapsidate any rAAV vector genome ITR of the invention. Preferred wild type capsid protein shell sequences are represented by the SEQ ID NO as indicated in the table. In an embodiment, a recombinant AAV vector (rAAV) comprises a capsid protein shell of AAV serotype 5 or AAV serotype 2 or AAV serotype 8 wherein the rAAV genome or ITRs present in said rAAV vector are derived from AAV serotype 2 or AAV serotype 5 (encoded by SEQ ID NO: 28 and 29) or AAV serotype 8. In this embodiment, it is further preferred that a rAAV vector comprises a capsid protein shell of the AAV serotype 5 (more preferably SEQ ID: 35, 36, 37 encoded by SEQ ID NO: 34) and the rAAV genome or ITRs present in said rAAV vector are derived from AAV serotype 2 (more preferably single stranded as SEQ ID NO: 24, 25, or double stranded as SEQ ID NO: 26, 27). This embodiment is preferred for local delivery of a gene to a joint.

In another embodiment it is preferred that a rAAV vector comprises a capsid protein shell of the AAV serotype 8 (more preferably SEQ ID NO: 39, 40, 41 encoded by SEQ ID NO: 38) and the rAAV genome or ITRs present in said vector are derived from AAV serotype 2 (more preferably single stranded as SEQ ID NO: 24, 25, or double stranded as SEQ ID NO: 26, 27). This embodiment is preferred for systemic delivery.

In yet another embodiment, it is preferred that a rAAV vector comprises a capsid protein shell of the AAV serotype 2 (more preferably SEQ ID: 31, 32, 33 encoded by SEQ ID NO: 30) and the rAAV genome or ITRs present in said vector is derived from AAV serotype 2 (more preferably single stranded as SEQ ID NO: 24, 25, or double stranded as SEQ ID NO: 26, 27).

A recombinant AAV genome can comprise of single stranded or double stranded (self-complementary) DNA. The single stranded nucleic acid molecule is either sense or antisense strand, as both polarities are equally capable of gene expression.

A nucleic acid molecule represented by a nucleic acid sequence of choice is preferably inserted between the rAAV genome or ITR sequences as identified above, for example an expression construct comprising an expression regulatory element operably linked to a coding sequence and a 3' termination sequence. Said nucleic acid molecule may also be called a transgene. Within the context of the invention, a nucleic acid molecule inserted between the rAAV genome may be called a source of a CD39 and/or a source of a CD73 as earlier defined herein. Most preferred rAAV genome ITR present in a rAAV vector is a rAAV2 genome ITR. Most preferably, this rAAV2 genome ITR is represented by SEQ ID NO: 24 or 25 as single stranded or by SEQ ID NO: 26 or 27 as double stranded.

"AAV helper functions" generally refers to the corresponding AAV functions required for rAAV replication and packaging supplied to the rAAV vector in trans. AAV helper functions complement the AAV functions which are missing in the rAAV vector, but they lack AAV ITRs (which are provided by the rAAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct. Introduction of the helper construct into the host cell can occur e.g. by transformation, transfection, or transduction prior to or concurrently with the introduction of the rAAV genome present in the rAAV vector as identified herein. The AAV helper constructs of the invention may thus be chosen such that they produce the desired combination of serotypes for the rAAV vector's capsid protein shell on the one hand and for the rAAV genome present in said rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

A "transgene" is herein defined as a gene or a nucleic acid molecule (i.e. a CD39 source and/or a CD73 source) that has been newly introduced into a cell, i.e. a gene that may be present but may normally not be expressed or expressed at an insufficient level in the cell. In this context, "insufficient" means that although said CD39 and/or CD73 is expressed in a cell, an inflammatory condition and/or disease as defined herein could still be developed. In this case, the invention allows the over-expression of a CD39 source and of a CD73 source. The transgene may comprise sequences that are native to the cell, sequences that naturally do not occur in the cell and it may comprise combinations of both. A transgene may contain sequences coding for a CD39 source and/or a CD73 source and/or additional proteins as earlier identified herein that may be operably linked to appropriate regulatory sequences for expression of the sequences coding for a CD39 source and/or a CD73 source in the cell. Preferably, the transgene is not integrated into the host cell's genome.

"Transduction" refers to the delivery of a CD39 source and/or of a CD73 source into a recipient host cell by a viral vector. For example, transduction of a target cell by a rAAV vector of the invention leads to transfer of the rAAV genome contained in that vector into the transduced cell. "Host cell" or "target cell" refers to the cell into which the DNA delivery takes place, such as the synoviocytes or synovial cells of a subject. AAV vectors are able to transduce both dividing and non-dividing cells.

Production of an AAV Vector

The recombinant AAV vector, including all combinations of AAV serotype capsid and AAV genome ITRs, is produced using methods known in the art, as described in Pan et al. (J. of Virology 1999, Vol 73(4):3410-3417) and Clark et al. (Human Gene Therapy, 1999, 10:1031-1039), incorporated herein by reference. In short, the methods generally involve (a) the introduction of the rAAV genome into a host cell, (b) the introduction of an AAV helper construct into the host cell, wherein the helper construct comprises the viral functions missing from the rAAV genome and (c) introducing a helper virus into the host cell. All functions for rAAV vector replication and packaging need to be present, to achieve replication and packaging of the rAAV genome into rAAV vectors. The introduction into the host cell can be carried out using standard virological techniques and can be simultaneously or sequentially. Finally, the host cells are cultured to produce rAAV vectors and are purified using standard techniques such as CsCl gradients (Xiao et al. 1996, J. Virol. 70: 8098-8108). Residual helper virus activity can be inactivated using known methods, such as for example heat inactivation. The purified rAAV vector is then ready for use in the methods. High titers of more than $10^{12}$ particles per ml and high purity (free of detectable helper and wild type viruses) can be achieved (Clark et al. supra and Flotte et al. 1995, Gene Ther. 2: 29-37).

The rAAV genome present in a rAAV vector comprises at least the nucleotide sequences of the inverted terminal repeat regions (ITR) of one of the AAV serotypes, or nucleotide sequences substantially identical thereto, and at least one nucleotide sequence encoding a therapeutic protein (under control of a suitable regulatory element) inserted between the two ITRs. The majority of currently used rAAV vectors use the ITR sequences from AAV serotype 2. A vector genome requires the use of flanking 5' and a 3' ITR sequences to allow for efficient packaging of the vector genome into the rAAV capsid. Single stranded rAAV vectors utilize the wild-type AAV serotype 2 ITR sequences (SEQ ID: 24, 25), and double stranded (self-complementary) rAAV vectors utilize a modified version of the ITRs (SEQ ID: 26, 27).

The complete genome of AAV5 and other AAV serotypes has been sequenced (Chiorini et al. 1999, J. of Virology Vol. 73, No. 2, p 1309-1319) and the nucleotide sequence is available in GenBank (Accession No. AF085716). The ITR nucleotide sequences of AAV5 are thus readily available to a skilled person. The complete genome of AAV2 is available in NCBI (NCBI Reference Sequence NC_001401.2). They can be either cloned or made by chemical synthesis as known in the art, using for example an oligonucleotide synthesizer as supplied e.g. by Applied Biosystems Inc. (Fosters, Calif., USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the wild type AAV sequence between the ITRs can be replaced with the desired nucleotide sequence. Preferred ITRs and capsid proteins sequences are identified in table 1 by their SEQ ID NO.

Preferably, the rAAV genome as present in a rAAV vector does not comprise any nucleotide sequences encoding viral proteins, such as the rep (replication) or cap (capsid) genes of AAV. This rAAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV genome as present in said rAAV vector further comprises a promoter sequence operably linked to the nucleotide sequence encoding a CD39 source and/or a CD73 source. Suitable promoter sequences are promoters which confer expression in cells of the rheumatoid synovium, such as in intimal macrophages and/or in fibroblast-like synoviocytes and/or other synovial cells such as, but not limited to, T-cells. Suitable promoters are for example the promoters of genes known to be expressed in synovial cells, such as the CMV promoter (cytomegalovirus), the promoter of the IL-6 gene or the SV40 promoter, or an NF-κB inducible promoter as earlier identified herein and others, as readily determined by a skilled person. Alternatively a source of a CD39 and/or a source of a CD73 will be operably linked to a promoter/enhancer that will allow for efficient systemic expression. Suitable promoter sequences are CMV promoter, CBA (chicken beta actin), or liver specific promoters such as human alpha-1 anti-trypsin (hAAT) or TBG (thyroxine binding globulin).

A suitable 3' untranslated sequence may also be operably linked to the nucleotide sequence encoding a CD39 source and/or a CD73 source. Suitable 3' untranslated regions may be those naturally associated with the nucleotide sequence or may be derived from different genes, such as for example the bovine growth hormone 3' untranslated region (BGH polyA) sequence or a WPRE (woodchuck hepatitis post-translational regulatory element).

The total size of the DNA molecule inserted into the rAAV vector between the ITR regions is generally smaller than 5 kilobases (kb) in size. It is also envisaged that the rAAV genome as present in said rAAV vector comprises nucleotide sequences encoding a CD39 source and a CD73 source. These may either comprise a suitable promoter and suitable 3'untranslated region each, or they may be linked by an IRES (internal ribosome entry sites) element, providing a bicistronic transcript under control of a single promoter. Suitable IRES elements are described in e.g. Hsieh et al. (1995, Biochemical Biophys. Res. Commun. 214:910-917). Alternately, a source encoding a CD39 and a source encoding a CD73 may be linked by a viral 2A sequence to allow for efficient expression of both transgenes from a single promoter. Examples of 2A sequences include foot and mouth disease virus, equine rhinitis A virus, Those asigna virus and porcine teschovirus-1 (17).).

Optionally, additional nucleotide sequences may be operably linked to the nucleotide sequence(s) encoding a CD39 source and/or a CD73 source, such as nucleotide sequences encoding signal sequences (e.g. for targeting transport of a source of a CD39 and/or of a CD73 to the extracellular space), nuclear localization signals, expression enhancers, and the like. A preferred signal sequence has already been defined herein: a human alpha 1 anti-trypsin signal sequence (SEQ ID NO: 22).

Synovium/Synovial Cell or Tissue

The "synovium" or "synovial tissue" or "synovial cells" as used herein refers to the cellular lining covering the non-cartilaginous surfaces of the synovial joints, as further described in Tak (2000, Examination of the synovium and synovial fluid. In: Firestein G S, Panyani G S, Wollheim F A editors. Rheumatoid Arthritis. New York: Oxford Univ. Press, Inc. 55-68) and incorporated herein by reference. The synovium consists of the intimal lining layer (or synovial lining layer) and the synovial sublining (subsynovium), which merges with the joint capsule. The intimal lining layer comprises intimal macrophages (or macrophage-like synoviocytes or type A synoviocytes) and fibroblast-like synoviocytes (FLS or type B synoviocytes). "Synovium" may therefore be replaced by or is synonymous with "synovial tissue". "A synovial cell can include any cell present in the synovium including FLS and macrophage-like synoviocyte. A synoviocyte cell may also be a neutrophil, T, B cells and/or connective tissue cells, which may all be present in the synovium.

The term "rheumatoid synovium" or "rheumatoid synovial cells" or "rheumatoid synovial tissue" refers to the inflamed synovium of the joints of a subject suffering from rheumatoid arthritis. The rheumatoid synovium is characterized by intimal lining hyperplasia and by accumulation of T-cells, plasma cells, macrophages, B-cells, natural killer cells and dendritic cells in the synovial sublining. These accumulated cells are comprised in the definition of rheumatoid synovial cells.

Exosome

"Exosome" as used herein refers to any vesicle or membrane bound structure of 20-250 nm in size, for example of 20-100 nm, or 30-120 nm in size but may also be 100 nm-3 µM in size. Exosomes are released by many cell types during normal growth. Exosomes have been shown to carry bioactive cargo, including protein, mRNA, and miRNA (19). It is currently unclear how cargo is sorted into exosomes, however a number of proteins and nucleic acid molecules have been shown to be selectively sorted into exosomes. Examples of proteins enriched on exosomes may include, but are not limited to: CD63, Transferrin receptor, sialic acid, mucins, Tsg101 (Tumor susceptibility gene 101), Alix, annexin II, EF1a (Translation elongation factor 1a), CD82 (Cluster of Differentiation 82), ceramide, sphingomyelin, lipid raft markers, PRNP (PRioN Protein).

Exosomes may be purified by means known to the man skilled in the art, for example from blood, urine, saliva and/or other bodily fluids. For example, it is possible to purify exosomes from blood, urine, saliva and/or other bodily fluids by elimination of cells, usually by centrifugation, for example at 200 g, thus obtaining a supernatant containing vesicles or exosomes. Another way to obtain vesicles or exosomes is by performing further centrifugation steps to purify exosomes or vesicles and possibly including steps at 1000 g, and 10,000-16,000 g to further eliminate bigger vesicles. Subsequent centrifugation at 70,000-120,000 g is commonly used to purify exosomes.

The pelleted exosomes may be washed with a suitable medium such as PBS and optionally thereafter resuspended in a suitable medium where after the whole cycle of centrifugation, pelleting of the exosomes and washing with for example PBS may be repeated until an acceptable purity of the exosomes is reached.

Another way to obtain exosomes or vesicles include using combinations of filters that exclude different sizes of particles, for example 0.45 µM or 0.22 µM filters can be used to eliminate vesicles or particles bigger than the vesicles of interest. Exosomes or vesicles may be purified by several means, including antibodies, lectins, or other molecules that specifically bind vesicles of interest, eventually in combination with beads (e.g. agarose/sepharose beads, magnetic beads, or other beads that facilitate purification) to enrich for exosomes. A marker derived from the cell type of interest may also be used for purifying exosomes. For example, if a treatment is aimed at liver tissues, vesicles may be purified from cell-free fluids using a liver-specific marker, to distinguish liver derived vesicles from vesicles derived from other cells or tissues. Other techniques to purify exosomes include density gradient centrifugation (e.g. sucrose or optiprep gradients), electric charge separation. All these enrichment and purification techniques may be combined with other methods or used by themselves. A further way to purify exosomes is by selective precipitation using commercially available reagents such as ExoQuick™ (System Biosciences, Inc.) or Total Exosome Isolation kit (Invitrogen™, Life Technologies Corporation).

Exosomes may be derived from exosome-secreting cells and/or engineered as is known in the art. Preferably, exosomes of the present invention are isolated from cells expressing a CD39 protein and/or a CD73 protein as defined herein. Even more preferably, said cells are transduced to express said CD39 protein and/or said CD73 protein as defined herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a combination, a source of a CD39, a source of a CD73, a composition, as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

BRIEF DESCRIPTION OF THE DRAWINGS

FIG. 2A) expression of ADORA1, P2RX4, AMPD3, AMPD1, ADORA2A. FIG. 2B) expression of 5NTE (CD73). FIG. 2C) Schematic diagram representing the primary genes involved in the conversion of ATP to adenosine. Gray arrows indicate the change in expression comparing high inflammation tissue vs. low inflammation tissue FIG. 3: Plasmid/gene diagram: A) An representative diagram of a plasmid expressing CD39 and CD73 (separated by a 2A sequence) under control of the CMV promoter and human growth hormone polyA. B) diagrams of membrane bound, soluble, and fusion proteins used in these studies

FIG. 5A) CD39 activity: 293 cells were transfected with pCMV-CD39-2A-CD73 (SEQ ID NO: 54), pCMV-CD39 (SEQ ID NO: 6), or with an irrelevant control plasmid (GFP). ATP was added to the media of transfected cells and the amount of ATP remaining over time was measured by ATPlite luciferase assay. FIG. 5B) CD73 activity: 293 cells were transfected with pCMV-CD39-2A-CD73 (SEQ ID NO: 54), pCMV-CD73 (SEQ ID NO: 8), or an irrelevant control plasmid (GFP). AMP was added to the media and adenosine levels were measured at 2 min post ATP addition.

FIG. 7A) CD39 activity: 293 cells were transfected with pCMV-sCD39 (SEQ ID NO: 10), pCMV-CD73-CD39 fusion (SEQ ID NO: 18), or with an irrelevant control plasmid (GFP). ATP was added to the media of transfected cells and the amount of ATP remaining over time was measured by ATPlite luciferase assay. FIG. 7B) CD73 activity: 293 cells were transfected with pCMV-sCD73 (SEQ ID NO: 14), pCMV-CD73-CD39 fusion (SEQ ID NO: 18), or an irrelevant control plasmid (GFP). AMP was added to the media and adenosine levels were measured at 2 min post ATP addition.

FIG. 10: CD39 and CD73 act synergistically to reduce CCL2 production in in vitro inflammation assay. A) Diagram of in vitro inflammation assay. ATP (1 mM) is added to CD39 and/or CD73 expressing cells (293T or FLS) before the addition of LPS activated cells. Conditioned media is harvested 24 hours later and cytokine (IL-6) or chemokine (CCL2) levels are measured by ELISA. B-E) 293T cells were transfected with CD39 and/or CD73 expressing plasmids (or GFP control) and used in an in vitro inflammation assay 24 hours post transfection (cells+media B, D). Duplicate 293T transfections were performed and cell free-conditioned media (cells media alone D,E) was transferred to a fresh plate before addition of ATP and LPS activated THP1 cells. Data shown is the SEM of 4 (media only) or 5 (cells+media) independent experiments. Note that IL-6 levels for many samples were undetectable (<10 pg/ML). The following plasmids were used for transfection: SEQ ID NO: 6 for CD39, SEQ ID NO: 8 for CD73, SEQ ID NO: 6 and 8 for CD39 and CD73, SEQ ID NO: 54 for CD39-2A-CD73, SEQ ID NO: 10 for sCD39, SEQ ID NO: 14 for sCD73, SEQ ID NO: 10 and 14 for sCD39+sCD73 and SEQ ID NO: 18 for CD73-39 fusion.

FIG. 13: Air pouch synovial inflammation model: Total white blood cells (WBC) were counted in the air pouch fluid collected at 24 and 48 hours post LPS administration. A significant decrease in WBC infiltrate was observed with AAV-CD39-2A-CD73 (SEQ ID NO: 54) animals when compared with AAV-control animals at 24 hr, and a trend towards significance was observed after 48 hr.

EXAMPLES

Materials and Methods

Figure 1:
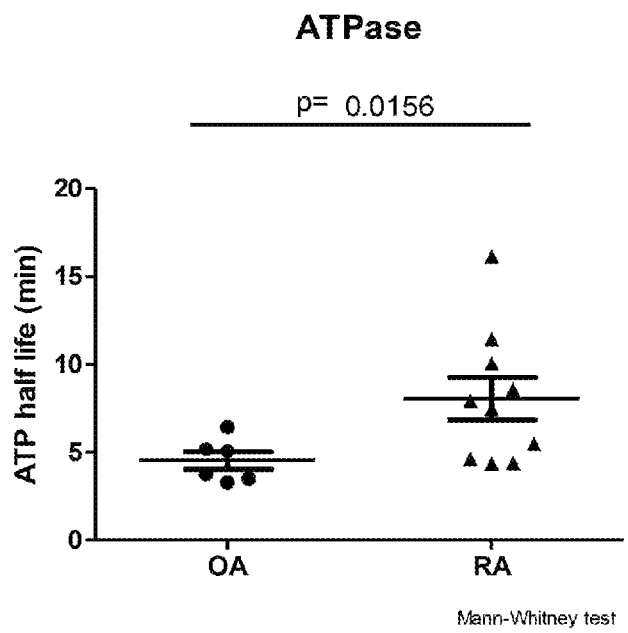
FIG. 1: ATPase activity assay. The half-life of ATP was assayed in synovial fluid from patients with osteoarthritis (OA) (n=6), or rheumatoid arthritis (RA) (n=10).

Plasmid Cloning and Characterization:

Codon optimized versions of murine CD39 and CD73 separated by a porcine teschovirus-1 2A (P2A) sequence (17) were synthesized (GenScript, Piscataway, N.J.) and cloned into a. CMV expression vector containing the AAV2 inverted terminal repeat (ITR) sequences to give pAAV-CMV-CD39-2A-CD73 (SEQ ID NO: 42). Plasmids expressing CD39 or CD73 separately were constructed using PCR to amplify' CD39 or CD73 from pAAV-CMV-CD39-2A-CD73 and add a 5' HindIII site and 3' BO site for cloning into the same CMV vector. A soluble CD39 protein was designed based on previous published literature[11]. Briefly, the signal sequence (SS) of the endogenous CD39 was replaced with the highly efficient SS from the human alpha-1 anti-trypsin (hAAT) gene and the N and C terminal transmembrane domains of CD39 were removed. A codon optimized version of the sCD39 gene was synthesized and cloned into the same CMV expression vector (see above). To generate soluble CD73 we used the GPI Lipid Anchor Project prediction program (http://mendel.imp.ac.at/gpi/gpi_server.html) to determine that the probable GPI anchor site was at S551. We then used PCR to generate a truncated version of CD73 (M1 to F550) that lacks the GPI anchor site.

TABLE 3 primer sequences

| Primer name | Sequence |
|---|---|
| CD39-FWD | GCGAAGCTTACCATGAGCCGCATGGAGGAC |
| CD39-REV | GCGAGATCTTTATCACACTGCCTCTTTCCAAAAATAAC |
| CD73-FWD | GCGAAGCTTACCATG AGGCCTGCAGCCGCTAA |
| CD73-REV | GCGAGATCTTTATCAGAGAATCAGAATCATAGCCC |
| CD73-REV-noGPI SEQ ID NO: 43-47 | GCGAGATCTTTATCAGAACTTGATCCTGCCTTCCAC |

All protein coding regions were verified by sequencing.

A schematic diagram of the plasmids used is found in FIG. 3.

Surface expression of CD39/CD73

293T cells were transfected with pAAV-CMV-CD39-2A-CD73, pAAV-CMV-CD39, pAAV-CMV-CD73, or an irrelevant CMV control plasmid. Expression of CD39 and CD73 was assayed by FLOW cytometry using anti-CD39-PE and anti-CD73-PE-Cy7 labelled antibodies and a Canto flow cytometer (BD, Breda, Netherlands). Data was analyzed using FloJo v7.6.5 (Treestar Inc, Ashland, Oreg.)

CD39 Activity:

CD39 activity was assayed by measuring the half-life of ATP spiked into the medium of transfected 293T cells. Briefly, 293T cells were transfected with CD39 or sCD39 expressing plasmids using lipofectamine 2000. An irrelevant control plasmid (GFP) was also transfected as a control. 24 hrs later ATP (1 µM final concentration) was added to the media and aliquots (5 µL) were removed and mixed with 45 µL, ATPlite lysis buffer to inhibit ATPase activity at time points indicated. Residual ATP levels were assayed by luminescence using the ATPlite quantification kit according to manufacturer's instructions (Perkin-Elmer, Netherlands).

CD73 Activity:

CD73 activity was measured by a modified version of the cell based adenosine assay described by Hausler et al[12]. 293T cells were co-transfected with a cAMP inducible firefly reporter plasmid[13] (pRIP1-CRE-Luc, a kind gift from Dr. George Holz) and a renilla luciferase control plasmid (pSV40-RenLuc). 24 hours later the transfected 293 cells were trypsinized and plated out in 96 well plates. These cells were used as adenosine sensor reporter cells. In a separate plate, 293T cells were transfected with CD73 expressing plasmids (or irrelevant control plasmid). 48 hours post transfection AMP (Sigma) was added to the media (1 µM final concentration). At various time points aliquots of the media were removed from the CD73 expressing cells and was added to the adenosine sensor cells. 4 hours after media addition the cells were washed and assayed for firefly and renilla luciferase using the Promega Dual Luciferase assay system. Firefly luciferase expression levels were normalized to renilla luciferase levels (transfection control) and were used to estimate adenosine levels in the samples. A standard curve was generated by adding known amounts of adenosine to sensor cells and this standard was used to quantify the level of adenosine production.

In Vitro Inflammation Assay:

293 cells were transfected (Lipofectamine 2000, Invitrogen) with plasmids expressing CD39 or CD73 alone (human or murine), or co-expressing CD39 and CD73 (either by transfecting two plasmids, or both enzymes present on a single plasmid separated by a P2A sequence (see FIG. 3). After 24 hours the media was removed and was replaced with media containing 1000 μM ATP. Activated THP-1 cells (human monocyte/macrophage cell line stimulated with ITS (1 μg/mL)) were added immediately following ATP addition. Cells were co-cultured for 24 hours and media was then harvested and CM levels were measured by standard ELISA.

Gene Expression Analysis:

Previously published gene expression microarray data[14] was used to analyze the expression of genes involved in the extracellular ATP catabolism pathway in high and low inflammation tissue from patients with rheumatoid arthritis.

Ethical Approval

This study was conducted with the approval of the Medical Ethical Committee of the Academic Medical Center/University of Amsterdam and all patients gave their written informed consent.

ATPase Levels:

Synovial fluid from rheumatoid arthritis (n=10) or osteoarthritis (n=6) patients were collected during therapeutic arthrocentesis and transferred to heparin containing tubes. The samples were centrifuged and the supernatants stored at −80° C. Before testing, thawed synovial fluid samples were centrifuged at 13,000 g for 5 min to pellet any residual cells and debris. Supernatants were transferred to a fresh microcentrifuge tube prior to ATPase analysis. Synovial fluid samples were spiked with ATP (Sigma) (1 μM) and aliquots were removed and added to lysis buffer (ATPlite) at time points indicated to inhibit ATPase activity. Residual ATP levels were quantified using the ATPlite ATP quantification kit (Perkin Elmer, The Netherlands).

Vector Construction and Production

Production of rAAV5 (type 2 ITR recombinant AAV genome packaged in AAV5 capsid, SEQ ID NO: 24, 25, 34-37) was performed the Center for Cellular and Molecular Therapeutics at The Children's Hospital of Philadelphia. AAV vectors were produced using previously described triple transfection methods into human embryonic kidney-293 cells and subsequent CsCl density gradient purification[15].

Air Pouch model of Inflammation

Animals

Male DBA/1 mice (8-10 weeks of age) were purchased from Harlan (Horst, The Netherlands). They were housed in IVC cages in the AB SLIII unit at the animal facility of the Academic Medical Center, University of Amsterdam. Animals were fed ad libitum. The Institutional Animal Care and Use Committee of Academic Medical Center approved all experiments.

Air Pouch Synovial Inflammation Model.

Subcutaneous air pouches were generated by standard protocol. Briefly, after anaesthesia (isoflurane) a single air pouch was induced per animal by injecting 3 mL of air subcutaneously onto the back of each animal, followed by re-inflation of the air pouch with 1-2 mL of air every 2 or 3 days as needed to keep the pouch inflated. At day 6, AAV (1e12 vg of CD39-2A-CD73 or AAV-control (not expressing protein) or saline was administered into the air pouch. On day 11, inflammation was induced by intra-air pouch injection of LPS (500 ng). On day 12 fluid was collected (~100 ul) and mice were sacrificed on day 13, followed by an air pouch lavage to collect the remaining fluid.

Study Design

Air pouches were induced in 5 groups of 5 mice/group. The groups were as follows: saline alone, saline+LPS, AAV-control alone, AAV-control+LPS, AAV-CD39-2A-CD73+LPS WBC Count and Synovial Membrane Analysis:

The total number of white blood cells (WBCs) was measured in the air pouch fluid collected at 24 hr and 48 hr using a coulter counter (Beckman coulter/Coulter Ac·T diff2). Air pouch membranes were enzymatically digested and analyzed by FLOW cytometry after staining for antibodies against immune cell markers (CD11b, Ly6G, CD4). Stained cells were analyzed by FLOW cytometry BD Canto2).

CD39 and CD73 Sample Preparations:

Preparations of exosomal CD39, CD73, CD39+CD73, soluble CD39, soluble CD73, or CD73-29 fusion were prepared by transfecting 293 cells with plasmids expressing the respective transgenes (SEQ ID NO 6, 8, 54, 10, 14, 18), or CMV-GFP as a control. After 48 hours, the conditioned media was harvested and used for concentration. The exosome samples were precipitated with ExoQuick TC and were dialyzed into HBS (Hepes buffered saline, pH 7.5) overnight. The soluble proteins were concentrated using a 10K MWCO filter (Amicon, Millipore) and this filter was also used to change the buffer to HBS. Glycerol was added to a final concentration of 45% and samples were aliquoted and stored at −20 degrees C.

Malachite Green Assay:

CD39 and CD73 activity in the CD39 and CD73 sample preparations were assayed using a Malachite Green Phosphate Detection kit (R&D Systems, Minneapolis). Briefly, dilutions of CD39 and CD73 samples were prepared in HBS and 100 μM ATP (CD39 activity) or 100 μM AMP (CD73 activity) was used a substrate. A phosphate standard was prepared and the assay was run as per the manufactures instructions. CD39 and CD73 activity was determined by measuring the release of phosphate over time (pmol phosphate released/min). Only sample dilutions that fell on the standard curve were used for determining the CD39 or CD73 activity of the samples.

Quantitative Western Blot:

Western blot analysis was used to quantify the amount of CD39 and CD73 in the sample preparations. Murine soluble CD73 or soluble CD39 were purchased from R&D systems and were used to generate a standard, ranging from 50 ng to 1.28 ng/well. Appropriately diluted samples were loaded along side the standard and a standard western blot protocol was performed. CD73 was detected using a sheep anti-mouse CD73 polyclonal antibody (R&D systems) and CD39 was detected using a sheep anti-mouse CD39 polyclonal antibody (R&D Systems). Western blots were scanned using a Licor Odyssey imaging system and quantified using Odyssey V.3.0 software.

Whole Blood Inflammasome Activation:

Fresh whole blood from a healthy donor was diluted 1:1 with RPMI media and LPS (100 ng/mL) was added and incubated for 2 hr at RT. Following incubation, samples containing CD39 and/or CD73 were added (exosome, soluble, fusion) (or appropriate controls) followed by ATP (1 mM) and allowed to incubate at 37 degrees C. for another 1 hour. Supernatants were then harvested and IL-1b levels were measured by ELISA (R&D systems). For CD73 containing samples, the same units of activity (20000 pmol phosphate/min/mL) were used. For CD39 containing samples, the same units of activity (300000 pmol phosphate/min/mL) were added. For samples containing CD39 and CD73 (CD39-P2A-CD73, fusion), the amount of sample added was normalized to the CD39 activity (300000 pmol phosphate/min/mL).

Statistical Analysis

Differences between groups were analyzed for statistical difference with the Mann-Whitney U-test (GraphPad Prism Version 5.0; GraphPad Software, San Diego, Calif.). P values <0.05 were considered statistically significant. Incidence was compared using Kaplan-Meier survival analysis (GraphPad Prism Version 5.0; GraphPad Software, San Diego, Calif.).

Results:

Synovial Fluid ATPase Levels:

As previous studies have indicated that synovial fluid from RA patients may have decreased ATPase activity[16], we measured the ATPase activity in synovial fluid from RA (n=10) or OA (n=6) patients. OA patient synovial fluid was used as a comparison as it is very difficult to obtain synovial fluid from healthy donors, and the etiology of OA is different than RA, with inflammation playing a much smaller role. As seen in FIG. 1, synovial fluid from RA patients had a significant reduction in ATPase activity, as measured by the ~2 fold increase in the ATP half-life when compared with synovial fluid from OA patients. These data indicate that the synovial fluid from RA patients has a defect in ATPase activity, and thus it is probable that the synovium will have increased extraceullar ATP levels, perhaps leading to a skewed ATP:adenosine ratio.

Figure 2B:
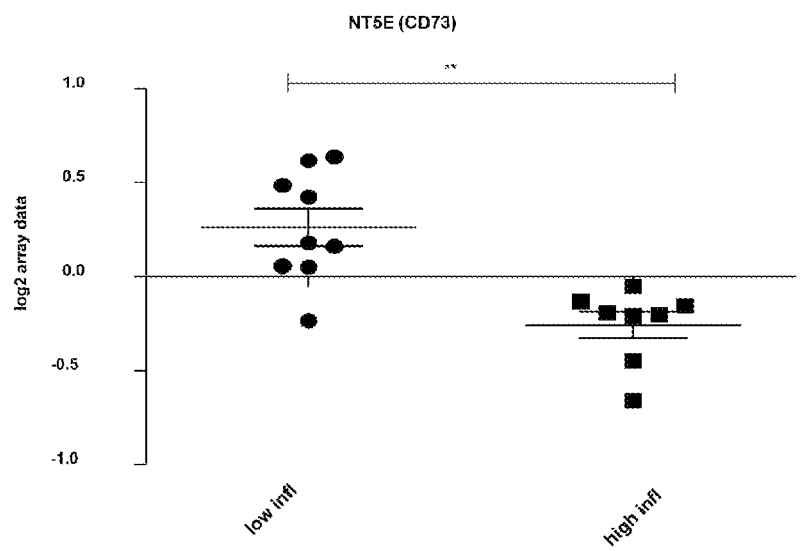
FIGS. 2A-2C: mRNA expression array data comparing gene expression in synovial tissue from low inflammation vs high inflammation tissue.
Figure 2A:
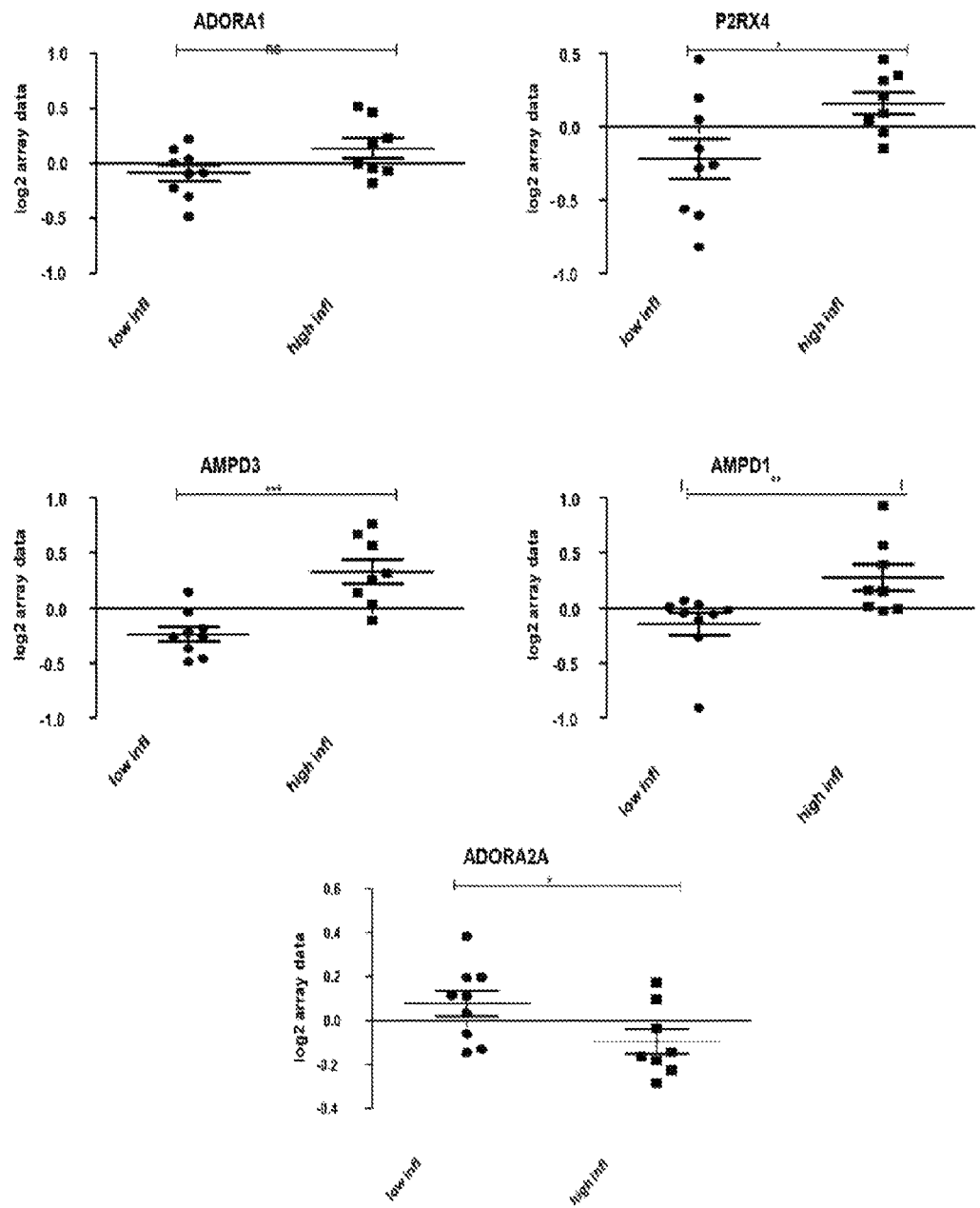
Figure 2C:
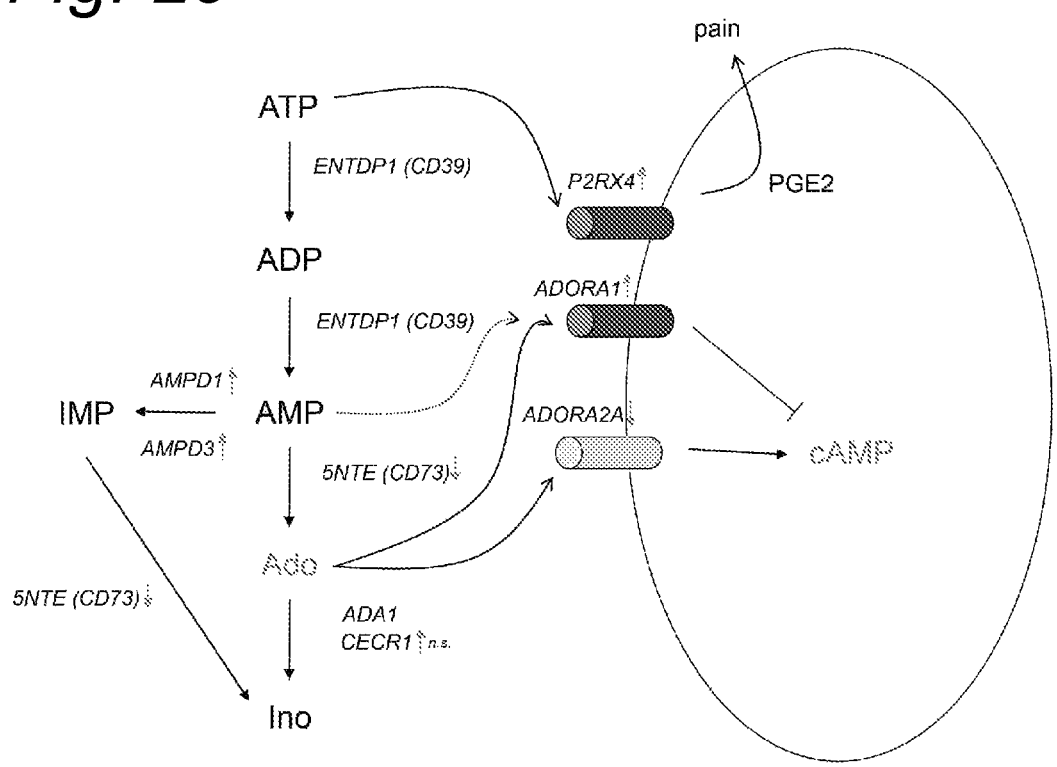

Gene Expression Study:

Previously published gene expression microarray data[14] was used to analyze expression levels of genes involved in the extracellular ATP catabolism pathway in high and low inflammation tissue from patients with rheumatoid arthritis. As seen in FIG. 2AB, there were significant changes in the expression level of many genes in the ATP:adenosine pathway, including ADORA1, ADORA2A, AMPD3, AMDP1, P2RX4, and CD73. When analyzed together the gene expression data indicates that in high inflammation tissue there is a distinct gene expression profile that is predicted to result in decreased adenosine levels and increased pro-inflammatory effects of ATP (FIG. 2C). Of note, expression of the ecto-nucleotidase CD73 was significantly decreased in high inflammation tissue (FIG. 2B), suggesting that restoring CD73 activity may lead to increased adenosine levels and thus decrease inflammation.

CD39 CD73 Expression and Activity

Figure 4:
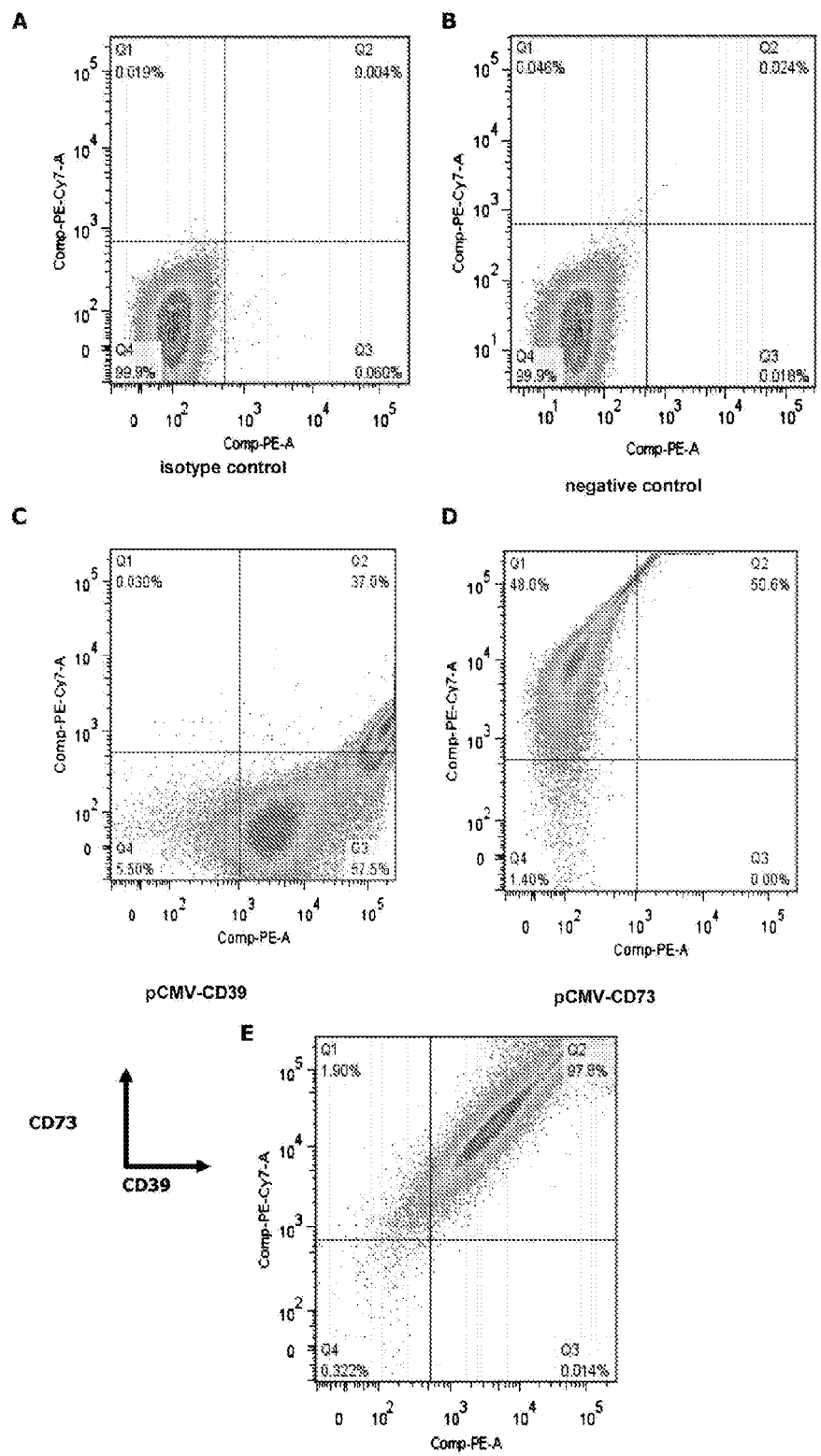
FIG. 4: Expression of CD39 and CD73 on 293 cells. A) isotype control (untransfected) B) negative control, C) pCMV-CD39 (SEQ ID NO: 6), D) pCMV-CD73 (SEQ ID NO: 8) or E) pCMV-CD39-2A-CD73 (SEQ ID NO:54) transfected 293 cells were stained with anti-CD73 (PE-Cy7 labelled) and anti-CD39 (PE labelled) and were analyzed by FLOW cytometry.
Figure 5A:
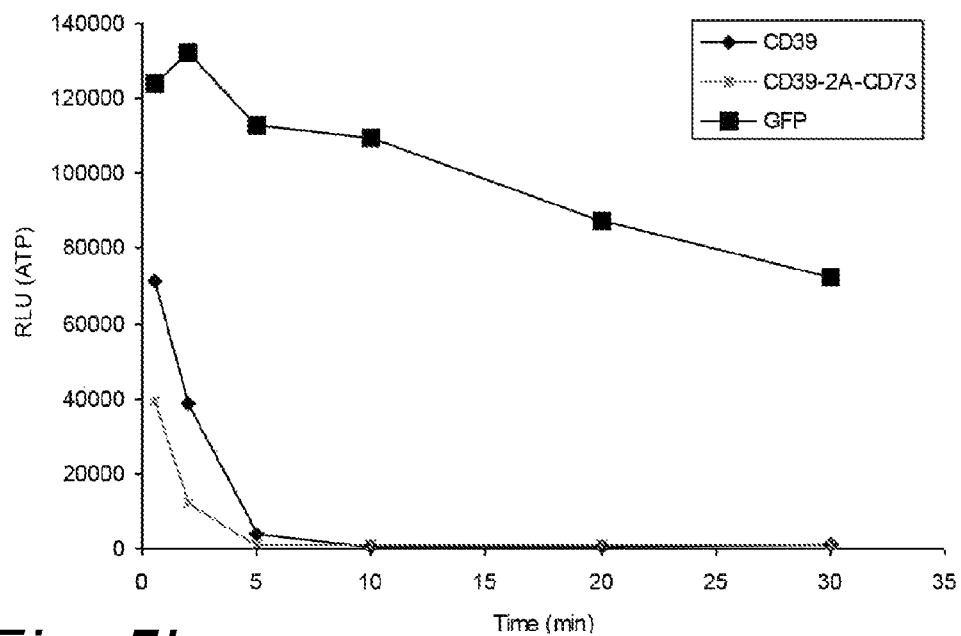
FIGS. 5A and 5B: Activity of CD39 and CD73.
Figure 5B:
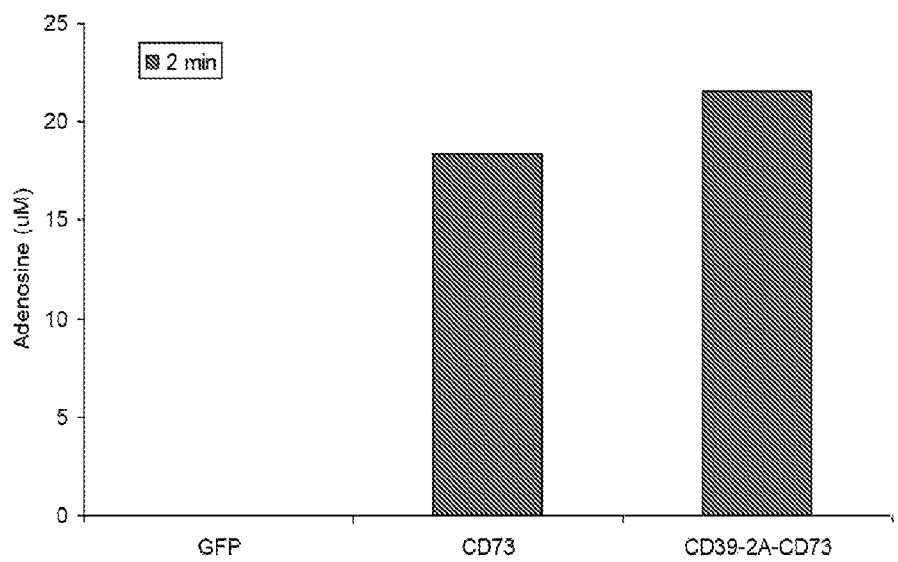

As our biochemical data and gene expression analysis have indicated that inflamed synovial tissue/fluid have a defect in the conversion of ATP to adenosine, we decided to test the hypothesis that expression of the ATPase CD39 and the ecto-nucleotidase CD73 will correct this defect, Plasmids expressing CD39 and/or CD73 were constructed and used for in vitro and in vivo analysis. To test the expression and activity of CD39 and CD73, 293T cells were transiently transfected with plasmids expressing CD39 and/or CD73. After 24 hours cells were harvested and CD39 and CD73 expression was assayed by FLOW cytometry using fluorescent labelled antibodies. As seen in FIG. 4, 293T cells expressed high levels of both CD39 and CD73 on the cell surface. In order to test the activity of CD39, 293T cells were transfected with CD39 expressing plasmids or an irrelevant plasmid (pCMV-GFP). After 24 hours media of transfected cells was spiked with ATP and the half-life of the ATP was measured. ATP levels were relatively stable in control or untransfected cell media, however ATP levels decreased quickly in media from CD39 expressing cells, indicating that this enzyme was functional (FIG. 5A). CD73 activity was tested using a similar experimental setup, Briefly, CD73 transfected cells were spiked with AMP and the generation of adenosine was assayed by measuring luciferase levels from 293T cells transfected with a cAMP responsive luciferase plasmid[12]. Adenosine production was rapid in media from cells expressing CD73 (FIG. 5B), while control cells did not generate any adenosine, indicating that CD73 was functional.

Figure 8:
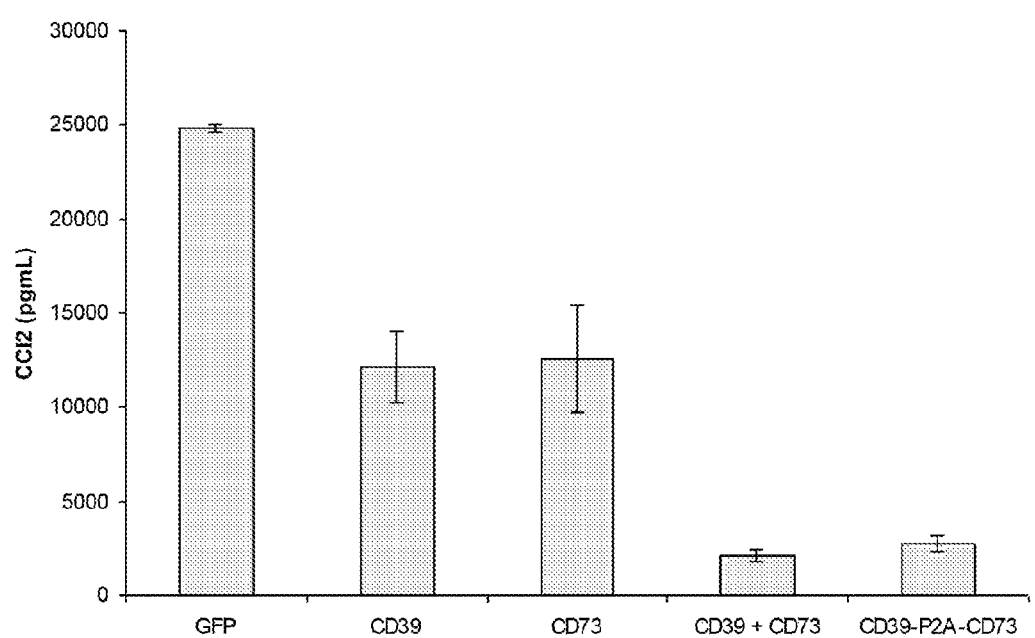
FIG. 8: Co-expression of CD39 and CD73 is required for optimal anti-inflammatory effect. 293 cells were transfected with plasmids expressing CD39 or CD73 alone (SEQ ID NO: 6 or 8, respectively), or co-expressing CD39 and CD73 either by transfecting two plasmids (SEQ ID NO: 6 and 8), or both enzymes present on a single plasmid separated by a P2A sequence (SEQ ID NO: 54). After 24 hours the media was removed and was replaced with media containing 1000 µM ATP. Activated THP-1 cells (human monocyte/macrophage cell line stimulated with LPS (1 ug/mL)) were added immediately following ATP addition. Cells were co-cultured for 24 hours and media was then harvested and CCL2 levels were measured by ELISA.
Figure 17:
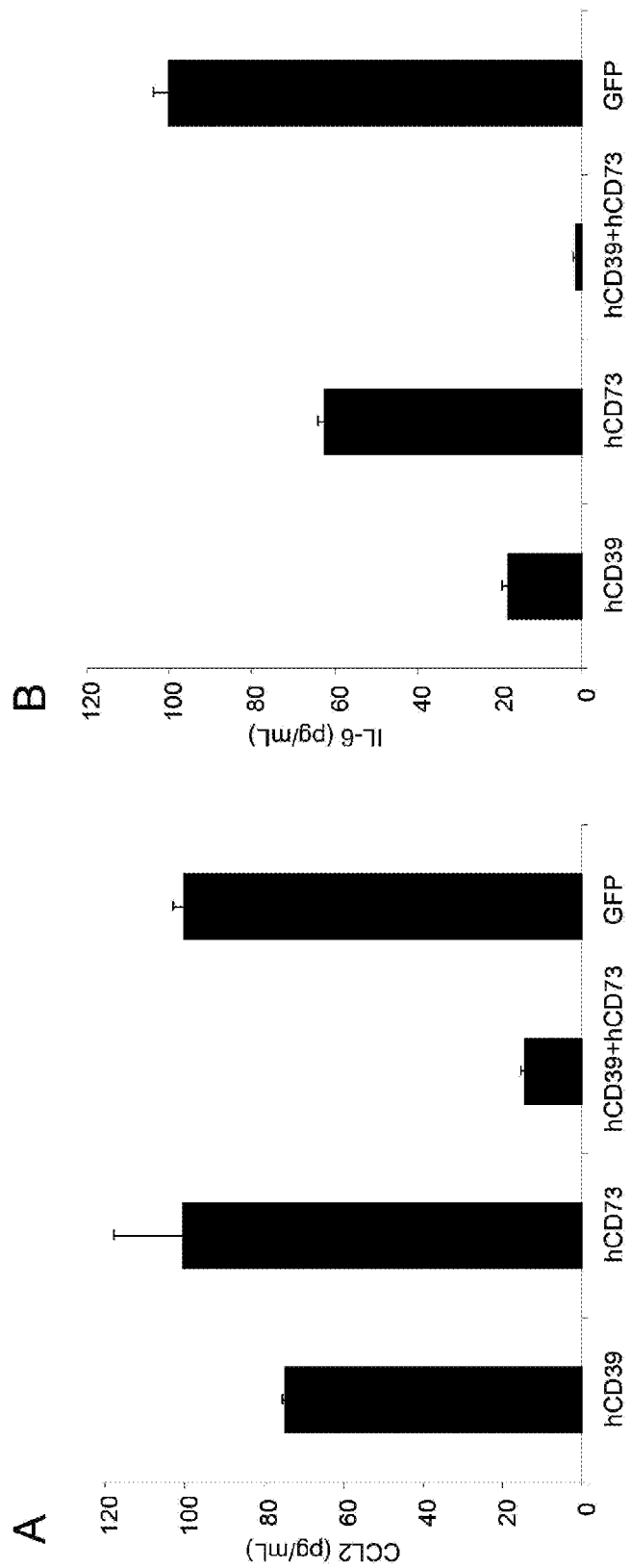
FIG. 17: Human CD39 and human CD73 act synergistically to reduce CCL2 production in in vitro inflammation assay. 293T cells were transfected with hCD39 (SEQ ID NO: 55) and/or hCD73 (SEQ ID NO: 56) expressing plasmids (or GFP control) and used in an in vitro inflammation assay 24 hours post transfection. CCL2 (A) or IL-6 (B) levels in the media were assayed by ELISA. Mean+standard deviation is shown.

In Vitro Studies:

LPS activated human monocyte/macrophage cell line (THP1) was used as an in vitro inflammation model to allow us to determine the effect of CD39 and CD73 expression on inflammatory cytokine/chemokine production. As THP1 cells are very difficult to transfect, we used transfected 293 cells as a source of CD39 and/or CD73. 293 cells were transfected with plasmids expressing CD39 or CD73 alone, or co-expressing CD39 and CD73 (either by transfecting two plasmids, or both enzymes present on a single plasmid separated by a P A sequence (see FIG. 3). After 24 hours the media was removed and was replaced with media containing 1000 μM ATP. Activated THP-1 cells (human monocyte/macrophage cell line stimulated with LPS (1 μg/mL)) were added immediately following ATP addition. Cells were co-cultured for 24 hours and media were then harvested and CCL2 levels were measured by standard ELISA. We have previously shown that adenosine is able to inhibit the production of CCL2 from LPS stimulated THP1 (data, not shown). We observed a partial decrease ('-50%) in CCL2 expression when CD39 or CD73 was expressed alone, however when both CD39 and CD73 were co-expressed we observed a synergistic effect (~92% decrease) (FIG. 8). This indicates that co-expression of both CD39 and CD73 is required for efficient reduction of inflammatory chemokine production from LPS stimulated THP1 cells. We observed a similar effect when co-expressing human CD39 and human CD73 (FIG. 17).

In Vitro Expression of Soluble CD39 and CD73

Figure 6:
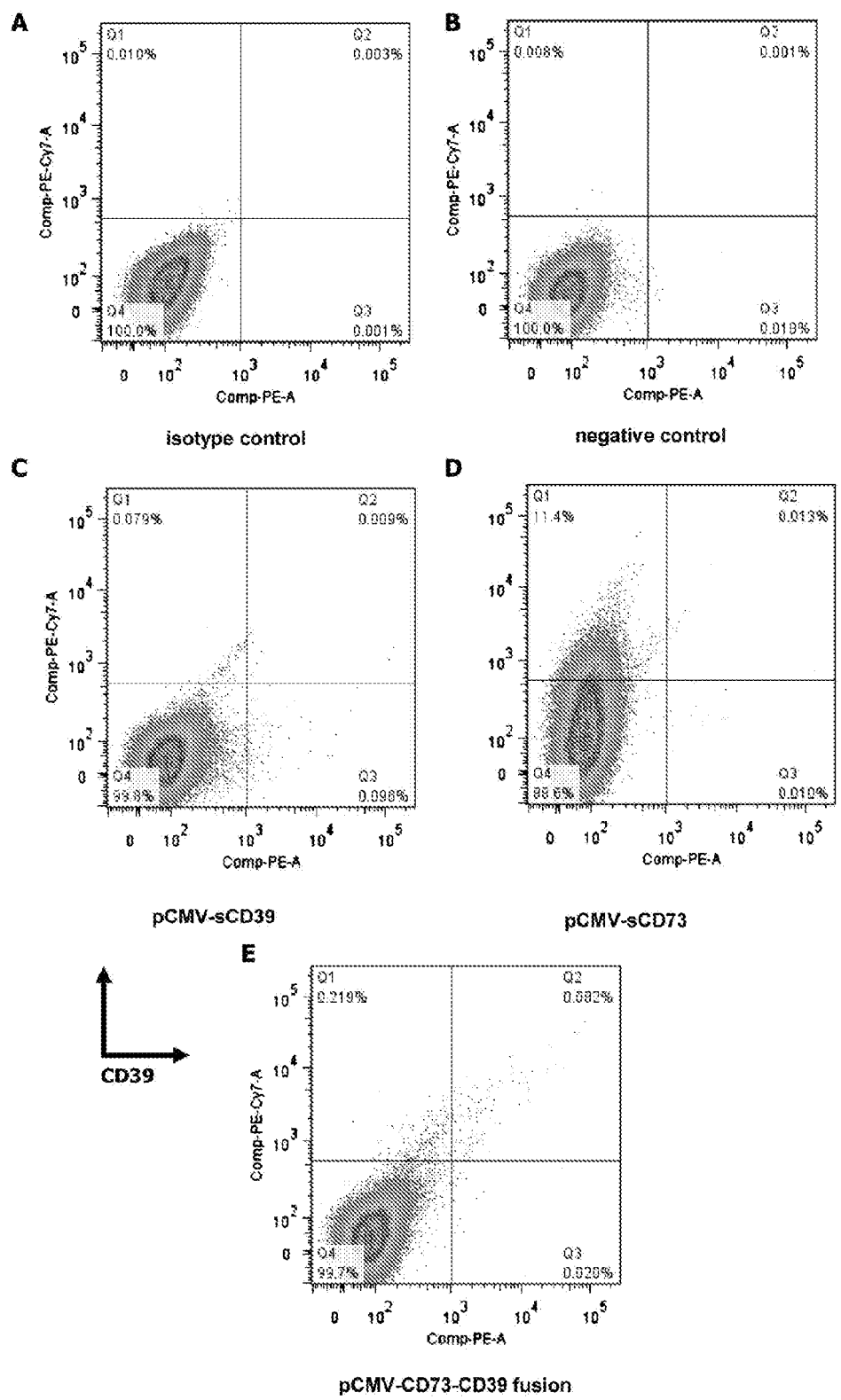
FIG. 6: Expression of soluble CD39 (sCD39) (SEQ ID NO: 10) and soluble CD73 (sCD73) (SEQ ID NO: 14) and CD73-CD39 fusion protein (SEQ ID NO: 18) on the surface of 293 cells. Cells were transfected with the indicated plasmid and stained with anti-CD73 (PE-Cy7 labelled) and anti-CD39 (PE labelled) and were analyzed by FLOW cytometry.
A) isotype control (rat-PE); B) negative control (irrelvant plasmid); C) pCMV-sCD39 (SEQ ID NO: 10); D) pCMV-sCD73 (SEQ ID NO: 14); E) pCMV-CD73-CD39 fusion (SEQ ID NO: 18).
Figure 7A:
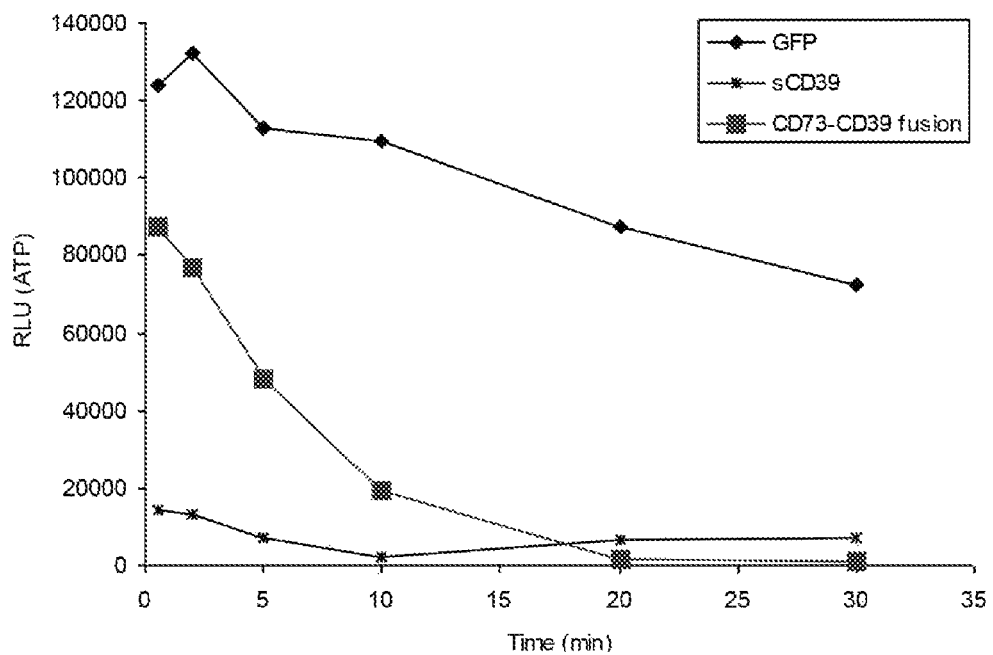
FIGS. 7A and 7B: Activity of soluble CD39 and soluble CD73.
Figure 7B:
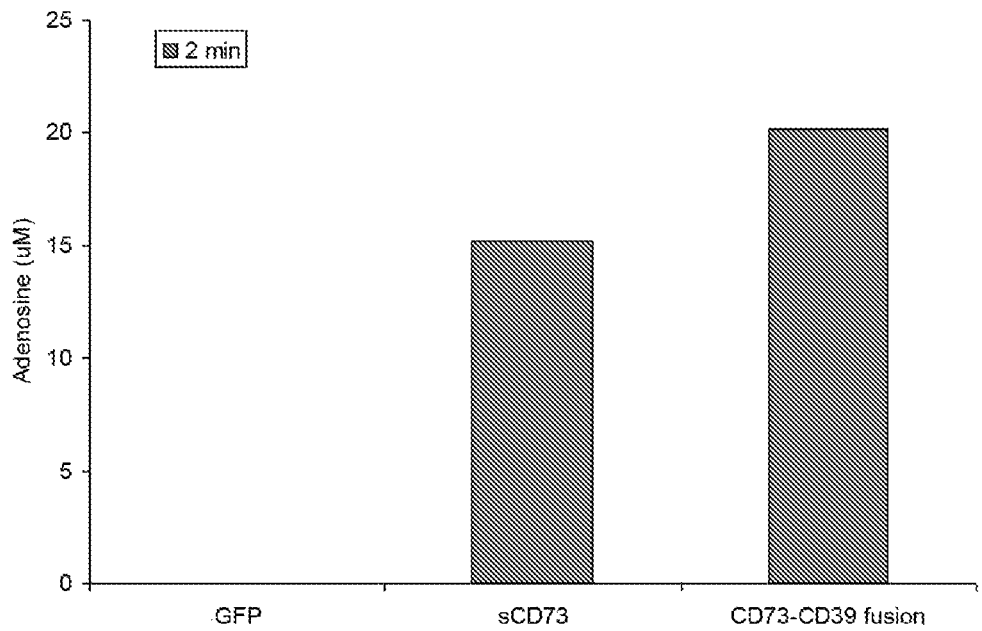

As CD39 and CD73 are normally membrane bound proteins that are attached to the extracellular surface of expressing cells, we were interested in expanding the therapeutic range of these enzymes by engineering soluble versions of both CD39 and CD73. Similar to previously published work using a soluble CD39 protein[11] to inhibit platelet activation, we designed a codon optimized CD39 protein that lacks the N and C terminal transmembrane domains and is directed to the ER for secretion by highly efficient signal sequence from the human alpha 1 anti-trypsin protein. CD73 does not contain a transmembrane domain, however is anchored into the membrane by a glycophosphatidylinosital (GPI) anchor. Using the GPI Lipid Anchor Project prediction program we determined that the probable GPI anchor site was at S551 of CD73. Therefore we used PCR to generate a truncated version of CD73 (M1 to F550) that lacks the GPI anchor site. Expression and activity of both proteins was verified the same way as for the membrane bound versions (see materials and methods) (FIGS. 6 and 7).

Anti-Inflammatory Effect of AAV Mediated Expression of CD39 and CD73 in RA-FLS

Figure 9B:
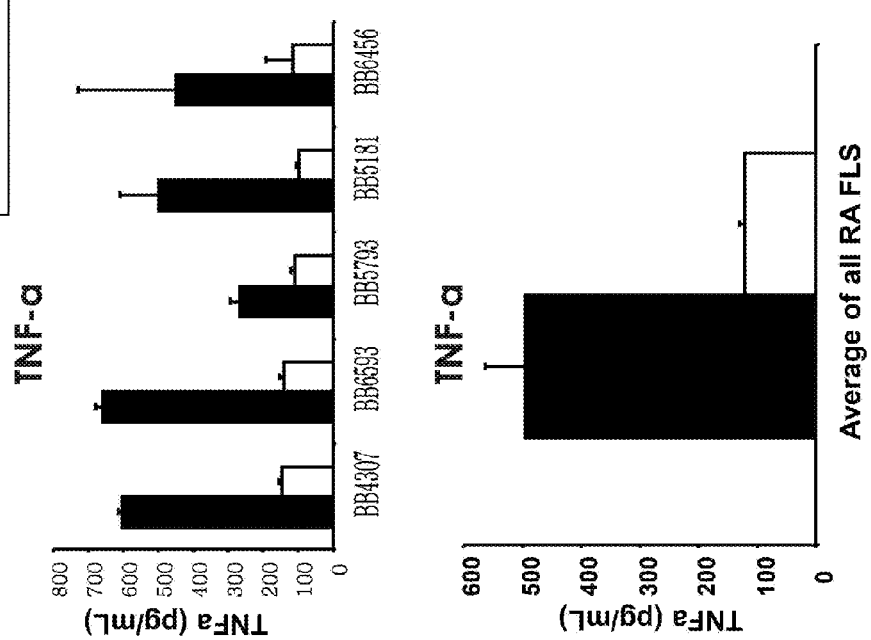
FIGS. 9A and 9B: AAV mediated expression of CD39 and CD73 is anti-inflammatory in RA-FLS based in vitro inflammation model. Five RA-FLS primary cell lines were transduced with AAV5 vectors expressing CD39 and CD73 separated by a 2A sequence (SEQ ID NO: 54) or GFP control. 48 hours post transduction, media was removed and ATP (1000 µM) was added. Activated THP1 cells were immediately added and cells were co-cultured overnight. Pro-inflammatory (FIG. 9A) chemokine levels (CCL2) or (FIG. 9B) cytokine (TNF-α) were measured by ELISA.
Figure 9A:
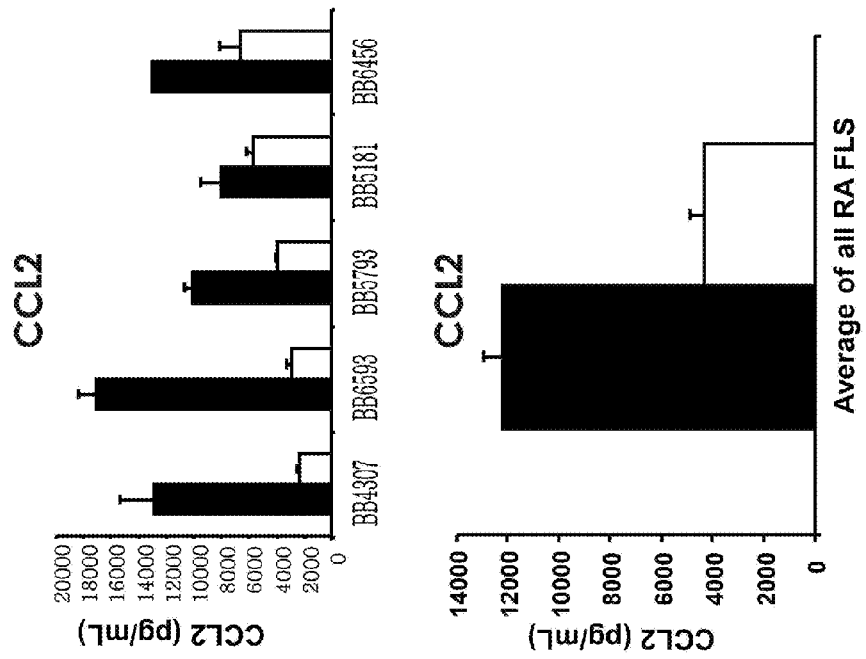

FIG. 9 shows that expression of CD39 and CD73 (not fusion) by rAAV5 mediated transduction of fibroblast like synoviocytes isolated from Rheumatoid Arthritis patients (RA-FLS) is effective in reducing inflammation in an in vitro inflammation model. Briefly, 5 days following AAV transduction of RA FLS, media was changed and ATP (1000 uM) was added to each well LPS activated THP-1 cells were immediately added and allowed to incubate overnight before harvesting the supernatant and assaying pro-inflammatory cytokine (TNF-α) or chemokine (CCL2) levels. These data are important because they demonstrate that AAV5 mediated expression of CD39 and CD73 is effective in reducing inflammation using primary cells derived from RA patients.
Exosomes The inventors were comparing the efficacy of membrane bound, soluble, and fusion protein expression of CD39 and/or CD73 in an in vitro inflammation assay (FIG. 10A). It was predicted that the soluble proteins and fusion protein would have the highest activity in the absence of cells, as the membrane bound CD39 and CD73 would not be present in the conditioned media. To test this hypothesis. HEK 293 cells were transfected with plasmids expressing CD39 and/or CD73 (membrane bound, soluble, fusion) and after 24 hours LPS activated THP1 cells were added (in the presence of 1000 μM ATP) either to the cells+conditioned media (FIGS. 10B and 10D) or to the conditioned media alone (FIGS. 10C and 10E). After a further 24 hour incubation, the media was harvested and chemokine (CCL2) or cytokine (IL-6) levels were analyzed by ELISA. It was found that the combination of the two membrane bound enzymes had a synergistic effect, resulting in 85% inhibition of CCL2 and 97% inhibition of IL-16 production (FIGS. 10B and 10D). Surprising, they found that the conditioned media (no cells) (FIGS. 10C and 10E) had very high anti-inflammatory effect when membrane bound CD39 and CD73 were expressed, comparable to the activity found in conditioned media plus cells (FIGS. 10B and 10D). These results were quite unexpected as CD39 and CD73 are attached to the membrane, and thus it was expected that the majority of CD39 and CD73 activity would be associated with the cells, and not with the cell-free conditioned media.

Given this surprising and unusual finding, the inventors hypothesized that perhaps CD39 and CD73 were being sorted into exosomes and released from the cells, able to float free in the conditioned media, and this would explain the high enzyme activity in the cell-free conditioned media.

To test this hypothesis, HEK 293 cells were transfected with plasmids expressing CD39 and/or CD73 or (FP as a control. After 48 hrs, the conditioned media was harvested and residual cells and debris were removed by centrifugation (3000×g, 15 min). The conditioned media was used to isolate exosomes (Exoquick TC). Thus each original sample gave rise to three conditions, total conditioned media, exosome enriched fraction, and exosome depleted fraction. CD39 (ATPase) and CD73 (AMPase) activity was measured in all fractions.

Figure 11:
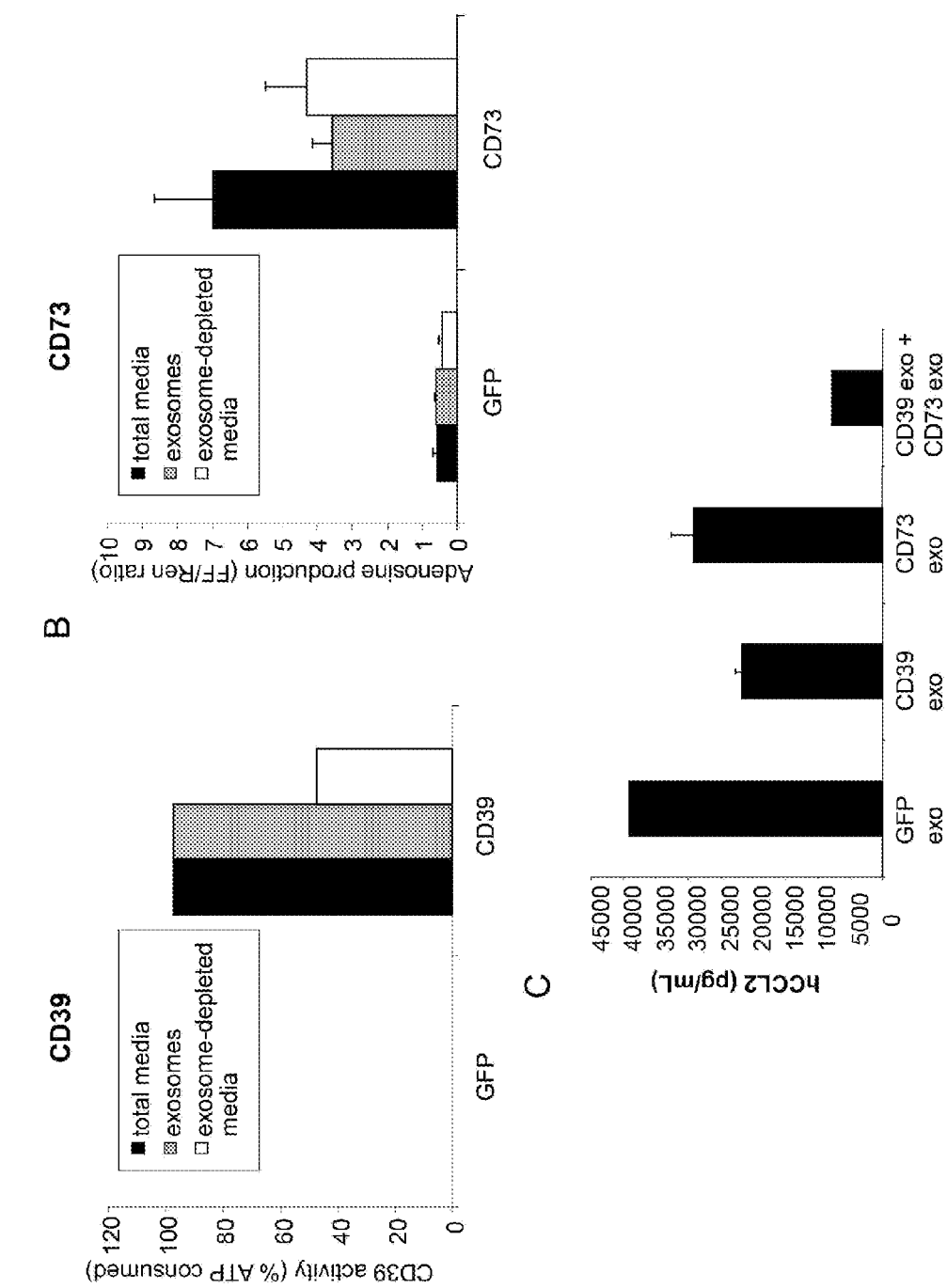
FIG. 11: Exosomes from CD39 or CD73 expressing HEK 293 cells demonstrate high enzymatic activity. HEK 293 cells were transfected with CD39 or CD73 expressing plasmids (SEQ ID NO: 6 or 8, respectively) and the conditioned media was harvested after 48 hrs. Exosomes were purified from media to give an exosome enriched fraction (exosomes) and exosome-depleted media. CD39 (A) or CD73 (B) activity was assayed on total media, exosomes, or exosome depleted media from CD39, CD73, or GFP expressing cells. C) CD39 and/or CD73 containing exosomes were used in a THP1 based in vitro inflammation assay. The combination of CD39 and CD73 exosomes (harvested from HEK 293 cells transfected with plasmids expressing CD39 (SEQ ID NO: 6) or CD73 (SEQ ID NO: 8) resulted in the highest decrease in pro-inflammatory chemokine (CCL2) production.

As can be seen in FIG. 11, the total media from HEK 293 cells expressing CD39 or CD73 had very high levels of both CD39 (FIG. 11a) and CD73 (FIG. 11b) activity. In contrast, media from HEK 293 cells transfected with a control plasmid (GFP) had very little CD39 or CD73 activity. Interestingly, the majority of the CD39 activity was associated with the exosome enriched fraction, with much less activity in the exosome depleted fraction (FIG. 11a). These data clearly show that exosomes from CD39 expressing HEK 293 cells have high CD39 activity. It was also found that exosomes from CD73 expressing cells contain CD73 activity (FIG. 11b). These data indicate that exosome mediated delivery of CD39 and CD73 may be an effective strategy for the conversion of pro-inflammatory ATP to anti-inflammatory adenosine.

The inventors then used these exosomes containing CD39 and CD73 in an in vitro inflammation assay using LPS activated THP1 cells. As can be seen in FIG. 11C, while a small anti-inflammatory effect of CD39 or CD73 containing exosomes was found, the combination of CD39 and CD73 exosomes gave the highest anti-inflammatory effect. This is consistent with our previously generated data using CD39 or CD73 expressing 293 cells, and gives evidence that the use of CD39/CD73 containing exosomes can decrease inflammation in an in vitro inflammation model.

Note that some cancer types have been shown to produce exosomes that contain CD39 and CD73 (18), and that these exosomes have been shown to suppress tumor specific T cells through generation of immune suppressive adenosine. Thus the production of CD39-CD73 containing exosomes is a mechanism that tumors can exploit to reduce local immune responses. We propose to exploit this natural immune modulatory pathway by using gene expression technology to generate exosomes that contain high levels of CD39 and CD73.

CD39/CD73 Ratio Study

CD39 and CD73 are both necessary for the full conversion of ATP to adenosine, however the optimal ratio of CD39 to CD73 is currently unknown. The inventors used exosome preparations containing known amounts of CD39 and CD73 to determine the optimal ratio of CD39 and CD73 necessary for conversion of pro-inflammatory ATP to anti-inflammatory adenosine.

Figure 12:
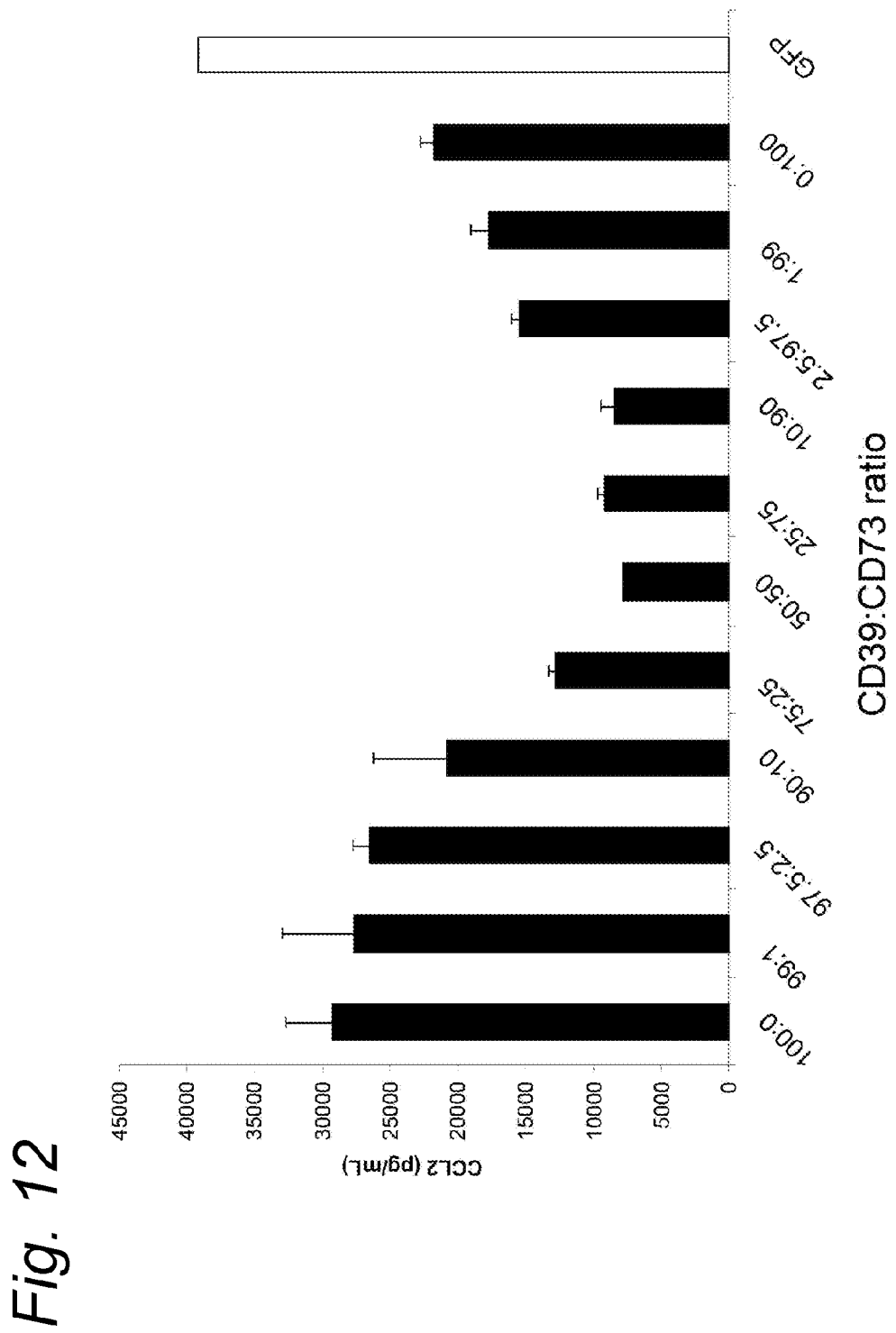
FIG. 12: Ratio of CD39 and CD73 influences efficacy. Exosomes containing CD39 or CD73 activity (or GFP control), harvested from HEK293 cells transfected with plasmids expressing CD39 (SEQ ID NO: 6) or CD73 (SEQ ID NO:8) were mixed in different amounts to generate a broad range of CD39:CD73 ratios. ATP was added to these exosomes and then LPS activated THP1 cells were added and incubated for a further 24 hours. Supernatants were harvested and pro-inflammatory chemokine (CCL2) production was assayed by ELISA.

Briefly, aliquots of exosomes (CD39 or CD73) were mixed in different amounts to generate a broad range of CD39:CD73 ratios. ATP was added to these exosome containing solutions and then LPS activated THP1 (human monocyte cell line) cells were added. After overnight incubation, the conditioned media was harvested and pro-inflammatory chemokine (CCL2) levels were measured. As can been seen in FIG. 12, while there was some reduction in CCL2 levels when CD39 or CD73 alone was present, the combination of the two gave rise to the maximal anti-inflammatory effect, consistent with our data expressing CD39 and CD73 from transfected HEK 293 cells. Interestingly, the inventors found that in this in vitro inflammation assay the optimal ratio of CD39 to CD73 fell between 50:50 to 10:90 (CD39:CD73).

It is expected that the optimal ratio of CD39 and CD73 may have to be determined for each application, however based on these preliminary studies, it appears as if adjusting the ratio of CD39 and CD73 to between 50:50 to 10:90 may allow for maximal conversion of ATP to adenosine.

Figure 14:
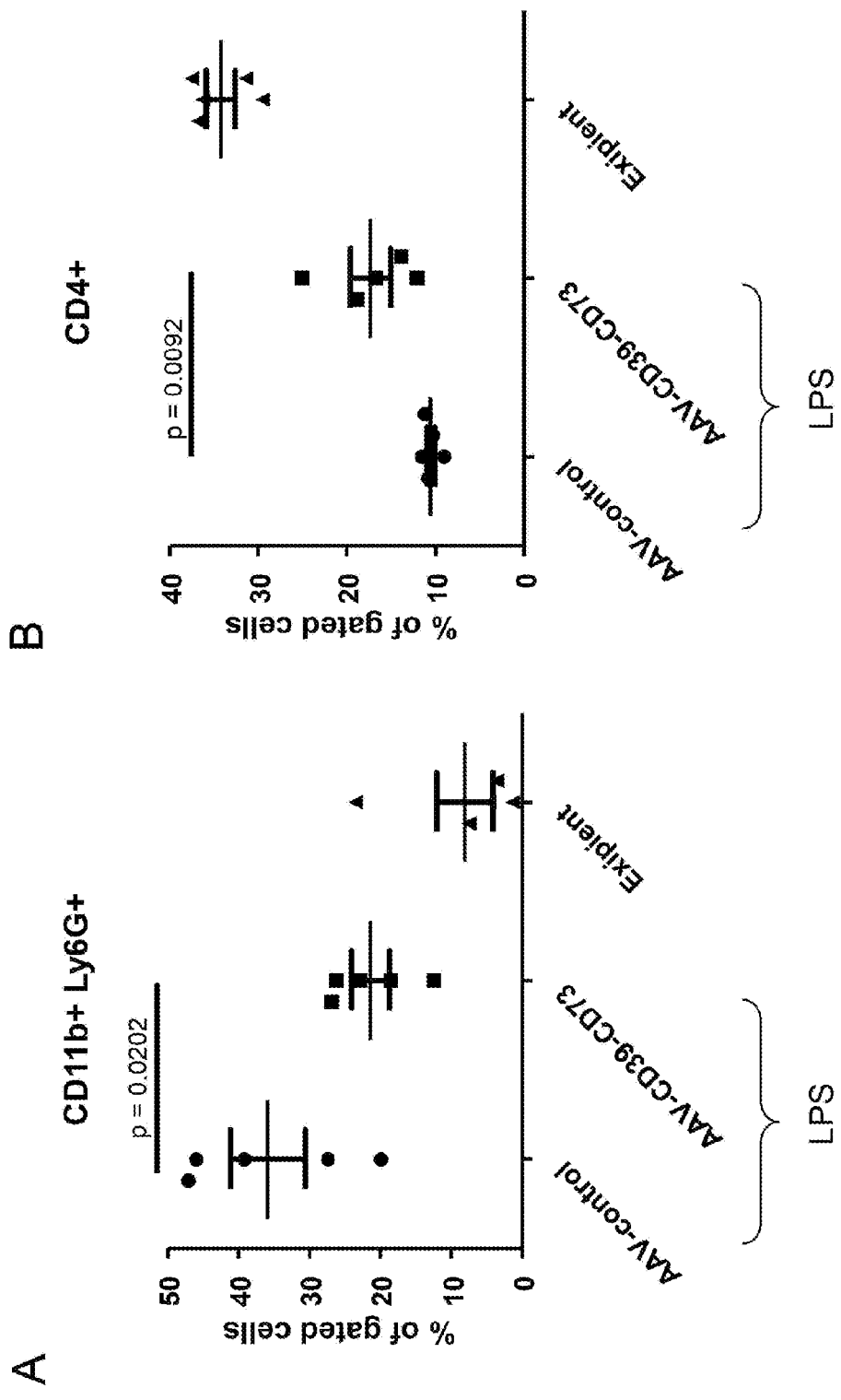
FIG. 14: Air pouch membrane immune cell composition. Air pouch membrane was isolated 48 hours after LPS administration and membrane immune cells were released by enzymatic digestion and cells were analyzed by FLOW cytometry. Air pouch membranes (APM) isolated from animals expressing CD39 and CD73 (SEQ ID NO: 54) have decreased CD11b+ Ly6G+ cells when compared with AAV-control animals (p=0.0202), and show increased CD4+ve cells when compared with AAV-control animals (p=0.0092). These data indicate that APM isolated from LPS treated CD39-CD73 expressing animals appear more like APM isolated from non-inflamed animals (Excipient, no LPS). Significance was calculated using a one-tailed t-test

In Vivo Air Pouch Model of Inflammation:

The inventors used a modified version of the standard air pouch inflammation model[26] to determine if expression of CD39 and CD73 was able to affect inflammation in a mouse model. In this pilot study it was found that expression of CD39 and CD73 was associated with a reduced white blood cell (WBC) influx into the air pouch fluid when compared with an AAV control (p=0.036 24 hr, p=0.1626 48 hr) (FIG. 13). This reduction in immune cell infiltration is evidence of an anti-inflammatory effect. Additionally, when the air pouch membranes were analyzed for immune cell composition, it was found that expression of CD39 and CD73 was associated with a decrease in CD11b+ Ly6G+ (neutrophil like) p=0.0202 and an increase in CD4+ (p=0.0092) (FIG. 14). These changes indicate that expression of CD39 and CD73 resulted in air pouch membrane immune cell compositions that look more like healthy, non-inflamed membrane (Excipient—no LPS).

Figure 15:
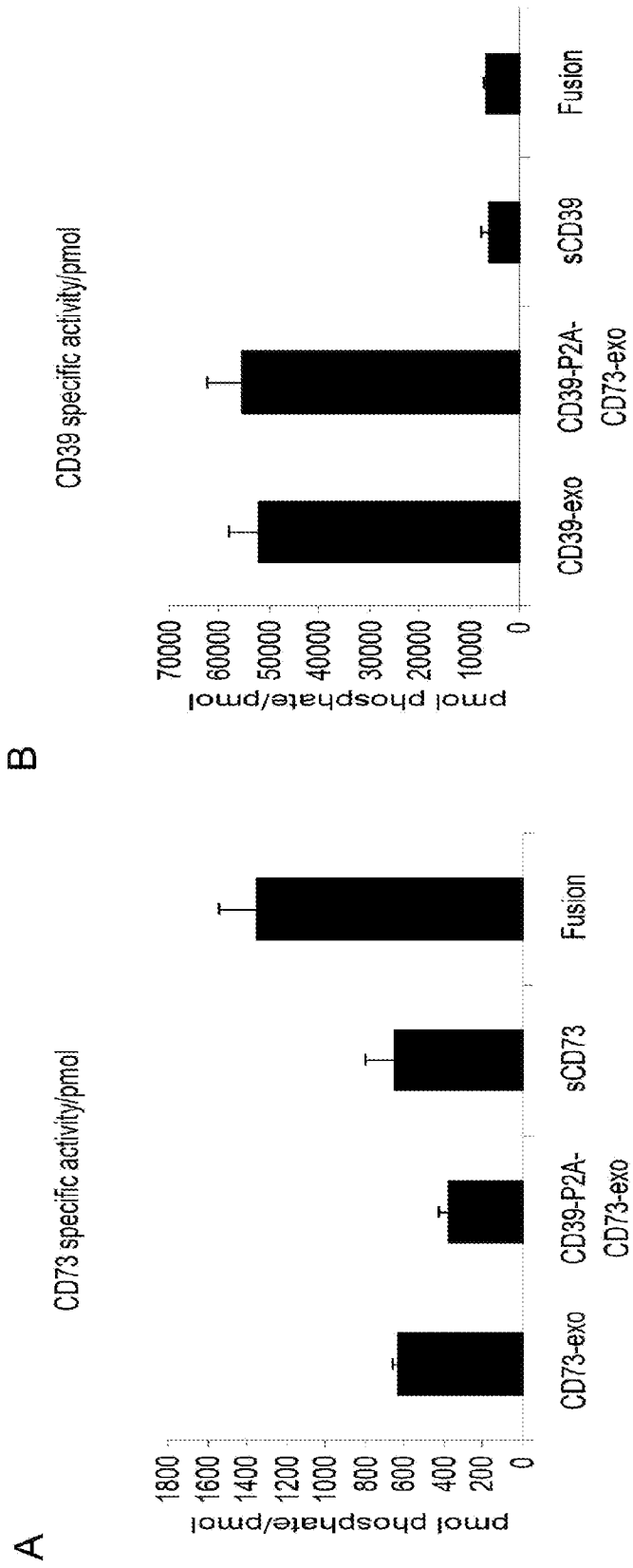
FIG. 15: Specific activity of CD39 and CD73 configurations: Samples containing CD39 or CD73 (exosome, soluble, fusion), harvested from HEK 293 cells transfected with plasmids expressing CD39 (SEQ ID NO: 6) or CD73 (SEQ ID NO: 8) or CD39-2A-CD73 (SEQ ID NO: 54) or soluble CD39 (SEQ ID NO: 10) or soluble CD73 (SEQ ID NO:14) or CD73-39 (SEQ ID NO:18) were analyzed for both activity and for antigen levels. Specific activity of CD73 (A) or CD39 (B) was determined by dividing the total activity by the estimated number of molecules (pmol).

CD39 and CD73 Specific Activity:

The inventors wanted to determine the specific activity of the various CD39 and CD73 configurations (exosome, soluble, fusion, in order to determine the properties of each configuration. Standardized preparations of exosomes containing CD39, CD73, or CD39+CD73 (or CUT control) were prepared, as well as standardized preparations of soluble CD39, soluble CD73, or CD73-39 fusion. CD39 and CD73 activity was assayed by measuring the release of free phosphate upon incubation with either ATP (CD39 activity) or AMP (CD73 activity. Levels of CD39 and CD73 in each sample were estimated by quantitative western blot. Specific activity of CD73 (FIG. 15A) or CD39 (FIG. 15B) was determined by dividing the activity (pmol phosphate released/min) by the number of molecules (pmol) of protein in each assay. As seen in FIG. 15AB, it was found that all CD73 configurations had similar specific activity. This is surprising as it was expected that the CD73-39 fusion protein would have decreased activity as usually fusing two proteins together can have a detrimental effect on the enzyme activity, however in this case it appears as if fusing CD73 and CD39 may even have enhanced the activity of CD73, especially when compared with sCD73 on a per molecule basis (FIG. 15A). It was also found that the soluble CD73 had similar activity to the membrane bound CD73 (exosome). This is not surprising given that CD73 is only attached to the membrane by a single GPI anchor, and thus the majority of the protein is extracellular, with no transmembrane sequences. In contrast, it was found that membrane bound CD39 (exosome) had much higher (~10 fold) activity when compared with soluble CD39 (FIG. 15 CD), This is the first time to our knowledge that the activity of membrane bound CD39 has been compared with soluble CD39. Given that CD39 is attached to the membrane by two transmembrane domains, it is not surprising that removing these large segments of the protein has a detrimental effect on the enzyme activity. This demonstrates a clear advantage of delivering CD39 via exosome, given the 10 fold increase in specific activity. It was found that fusing CD39 to CD73 did not have a detrimental effect on CD39 activity, which was unexpected as previously mentioned for CD73, usually fusing two proteins together can cause steric hindrance and decrease activity.

Figure 16:
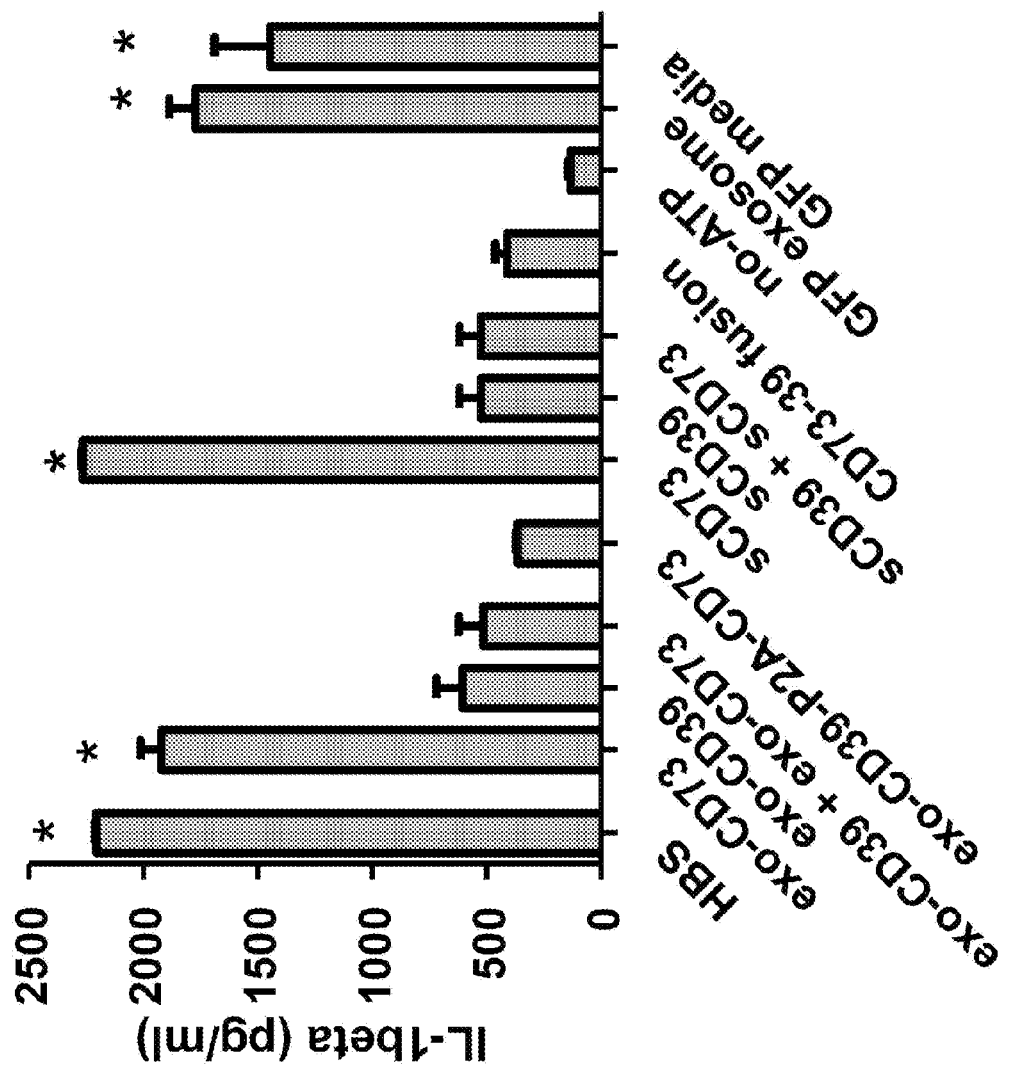
FIG. 16: Effect of CD39 and/or CD73 on whole blood inflammasome activation: Whole blood from a healthy donor was diluted with RPMI and incubated with LPS (100 ng/mL) for 2 hr at RT. Following incubation, samples containing CD39 and/or CD73 (exosome, soluble, fusion) harvested from HEK 293 cells transfected with plasmids expressing CD39 (SEQ ID NO: 6) or CD73 (SEQ ID NO: 8) or CD39-2A-CD73 (SEQ ID NO: 54) or soluble CD39 (SEQ ID NO: 10) or soluble CD73 (SEQ ID NO:14) or CD73-39 (SEQ ID NO:18, or GFP control were added followed by inflammasome activation by addition of ATP (1 mM). Supernatants were harvested 1 hr later and IL-1b levels were analyzed by ELISA. * indicates values are estimated as they are higher than standard curve.

Whole Blood Inflammasome Activation:

IL-1b is an essential cytokine in the generation of a potent inflammatory response. Mature IL-1b is generated by an inflammasome dependent processing reaction. Inflammasomes are multiprotein oligomers consisting of a number of caspases and is an essential component of the innate immune system. Inflammasomes can be activated by a two-step process, where the first signal can be an inflammatory stimulus, such as LPS, and the second signal can be a danger associated molecular pattern (DAMP), such as extracellular ATP[27]. Given the essential role of ATP in inflammasome activation, the inventors wanted to test the efficacy of CD39 and/or CD73 samples in reducing inflammasome activation using whole blood isolated from a healthy donor. As can be seen in FIG. 16, the combination of CD39 and CD73 had the greatest effect on inhibiting IL-1b production, while CD73 alone was not effective in reducing IL-1b production. It should be noted that ATP levels are the primary determinant of inflammasome activation, and this is why CD39 alone gives similar results to CD39 CD73, as the anti-inflammatory adenosine generated by CD73 activity will not be functional given the short incubation time (1 hr).

TABLE 1 list of most sequences identified in the application

| Name of the sequence | SEQ ID NO |
|---|---|
| CD39 protein, derived from *homo sapiens* | 1 |
| CD39 cDNA, derived from *homo sapiens* | 2 |
| CD73 protein, derived from *homo sapiens* | 3 |
| CD73 cDNA, derived from *homo sapiens* | 4 |
| CD39 protein, derived from *mus musculus* | 5 |
| CD39 cDNA, derived from *mus musculus* | 6 |
| CD73 protein, derived from *mus musculus* | 7 |
| CD73 cDNA, derived from *mus musculus* | 8 |
| soluble CD39 protein derived from *mus musculus* | 9 |
| soluble CD39 cDNA derived from *mus musculus* | 10 |
| soluble CD39 protein derived from *homo sapiens* | 11 |
| soluble CD39 cDNA derived from *homo sapiens* | 12 |
| soluble CD73 protein derived from *mus musculus* | 13 |
| soluble CD73 cDNA derived from *mus musculus* | 14 |
| soluble CD73 protein derived from *homo sapiens* | 15 |
| soluble CD73 cDNA derived from *homo sapiens* | 16 |
| soluble CD73-CD39 fusion protein derived from *mus musculus* | 17 |
| soluble CD73-CD39 fusion cDNA derived from *mus musculus* | 18 |
| soluble CD73-CD39 fusion protein derived from *homo sapiens* | 19 |
| soluble CD73-CD39 fusion cDNA derived from *homo sapiens* | 20 |
| Linker used in the fusion protein CD73-CD39 | 21 |
| Signal sequence human alpha 1 anti-trypsin | 22 |
| NF-κb inducible promoter | 23 |
| Single stranded AAV2 ITR 5' | 24 |
| Single stranded AAV2 ITR 3' | 25 |
| Double stranded AAV2 ITR 5' | 26 |
| Double stranded AAV2 ITR 3' | 27 |
| AAV5 ITR 5' | 28 |
| AAV5 ITR 3' | 29 |
| AAV2 Capsid DNA | 30 |
| AAV2 Capsid VP1 | 31 |
| AAV2 Capsid VP2 | 32 |
| AAV2 Capsid VP3 | 33 |
| AAV5 Capsid DNA | 34 |
| AAV5 Capsid VP1 | 35 |
| AAV5 Capsid VP2 | 36 |
| AAV5 Capsid VP3 | 37 |
| AAV8 Capsid DNA | 38 |
| AAV8 Capsid VP1 | 39 |
| AAV8 Capsid VP2 | 40 |
| AAV8 Capsid VP3 | 41 |
| pAAV-CMV-CD39-2ACD73 | 42 |
| primer sequence CD39-FWD | 43 |
| primer sequence CD39-REV | 44 |
| primer sequence CD73-FWD | 45 |
| primer sequence CD73-REV | 46 |
| primer sequence CD73-REV-noGPI | 47 |
| *Homo sapiens* CD39L1 cDNA | 48 |
| *Homo sapiens* CD39L1 protein | 49 |
| *Homo sapiens* NTPDase 8 cDNA | 50 |
| *Homo sapiens* NTPDase 8 protein | 51 |
| Fc-tagged CD73-39 fusion cDNA derived from *mus musculus* | 52 |
| Fc-tagged CD73-39 fusion protein derived from *mus musculus* | 53 |
| membrane bound CD39-2A-CD73 derived from *mus musculus* | 54 |
| CD39 cDNA derived from *homo sapiens*, codon optimized | 55 |
| CD73 cDNA derived from *homo sapiens*, codon optimized | 56 |
| membrane bound CD39-2A-CD73 derived from *homo sapiens* | 57 |

TABLE 2

Features of PAAVCMVCD39-2ACD73 (SEQ ID NO: 42)

| Feature | Start | End |
|---|---|---|
| ITR | 1 | 140 |
| CMV promoter | 161 | 735 |
| Murine CD39 | 853 | 2391 |
| Murine CD73 | 2458 | 4182 |
| P2A | 2392 | 2457 |
| CD39-2A-CD73 ORF | 853 | 4182 |
| HGH poly A | 4240 | 4707 |
| ITR | 4757 | 4897 |
| Amp | 5814 | 6674 |

TABLE 4

Features of Fc-tagged murine CD73-39 fusion protein (SEQ ID NO: 53)

| Feature | Start | End |
| --- | --- | --- |
| Artificial signal sequence (SS) | 1 | 19 |
| human IgG1 Fc Tag | 20 | 246 |
| linker | 247 | 280 |
| FLAG tag/EK cleavage site | 281 | 288 |
| murine CD73-39 fusion protein | 289 | 1273 |

REFERENCE LIST

1. McInnes I B, Schett G. The pathogenesis of rheumatoid arthritis. N. Engl. J. Med. 2011; 365:2205-2219.
2. Segal R, Yaron M, Tartakovsky B. Methotrexate: mechanism of action in rheumatoid arthritis. Semin. Arthritis Rheum. 1990; 20:190-200.
3. Schnabel et al. Tolerability of methotrexate starting with 15 or 25 mg/week for rheumatoid arthritis. Rheumatol Int. 1994; 14(1):33-8
4. Horton et al. Established rheumatoid arthritis: rationale for best practice: physicians' perspective of how to realise tight control in clinical practice. Best Pract Res Clin Rheumatol. 2011 August; 25(4):509-21
5. Bossert et al. Evaluation of self-report questionnaires for assessing rheumatoid arthritis activity: a cross-sectional study of RAPID3 and RADAI5 and flare detection in 200 patients. Joint Bone Spine, January 2012 p. 57-62
6. Tak P. P. AAV vectors for in vivo gene therapy of rheumatoid arthritis. Rheumatoid Arthritis 2000:55-68, supra.
7. Bartok and Firestein. Fibroblast-like synoviocytes: key effector cells in rheumatoid arthritis. Immunol. Rev, 2010; 233: 233-255
8. van Riel P. L. C. M. How does one assess early rheumatoid arthritis in daily clinical practice? Best Practice & Research Clinical Rheumatology, 2001; 15: 67-76
9. Gester A. M. et al. Evaluation of established rheumatoid arthritis. Bailliere's Clinical Immunology, 1999; 13: 629-644
10. Herweijer et al Gene therapy progress and prospects: hydrodynamic gene delivery. Gene Ther. 2007 January: 14(2): 99-107
11. Gayle R B, III, Maliszewski C R, Gimpel S D et al. Inhibition of platelet function by recombinant soluble ecto-ADPase/CD39. J. Clin. Invest 1998; 101:1851-1859.
12. Hausler S F, Ossadnik M, Horn E et al. A cell-based luciferase-dependent assay for the quantitative determination of free extracellular adenosine with paracrine signaling activity. J. Immunol. Methods 2010; 361:51-56.
13. Chepurny O G, Holz G G. A novel cyclic adenosine monophosphate responsive luciferase reporter incorporating a nonpalindromic cyclic adenosine monophosphate response element provides optimal performance for use in G protein coupled receptor drug discovery efforts. J. Biomol. Screen. 2007; 12:740-746.
14. van Baarsen L G, Bos W H, Rustenburg F et al. Gene expression profiling in autoantibody-positive patients with arthralgia predicts development of arthritis. Arthritis Rheum. 2010; 62:694-704.
15. Grimm D, Zhou S. Nakai H et al. Preclinical in vivo evaluation of pseudotyped adeno-associated virus vectors for liver gene therapy, Blood 2003; 102:2412-2419.
16. Park W, Masuda I, Cardenal-Escarcena A, Palmer D L, McCarty D J. Inorganic pyrophosphate generation from adenosine triphosphate by cell-free human synovial fluid. J. Rheumatol. 1996; 23:665-671.
17. Kim et al, PLoS One. 2011; 6(4):e18556. Epub 2011 Apr. 29
18. Clayton, A., et al. "Cancer exosomes express CD39 and CD73, which suppress T cells through adenosine production." J. Immunol. 187.2 (2011): 676-83.
19. Vlassov, A. V., et al. "Exosomes: current knowledge of their composition, biological functions, and diagnostic and therapeutic potentials." Biochim. Biophys. Acta 1820.7 (2012): 940-948.
20. Adriaansen et al. Local delivery of beta interferon using an adeno-associated virus type 5 effectively inhibits adjuvant arthritis in rats. Journal of General Virology (2007) 88:1717-1721.
21. Libby. Inflammation in atherosclerosis. Arteriscler Thromb Vasc Biol, 2012 32(9), 20145-20151)
22. Bending et al., Inflammation and type one diabetes. Int Immunol 2012, June 24(6):339-346
23. Calle and Fernandez. Inflammation and type 2 diabetes. Diabetes Metab 2012 June 38(3):183-191.
24. Alvarez-Erviti et al. Delivery of siRNA to the mouse brain by systemic injection of targeted exosomes. Nature Biotechnology, 2011 29: 341-345.
25. El-Andaloussi et al. Exosome-mediated delivery of siRNA in vitro and in vivo. Nat Protoc, 2012 7(12) 2112-2126.
26. Edwards et al. The formation of a structure with features of synovial lining by subcutaneous injection of air: an in vivo tissue culture system. Journal of Pathology. 1981, June. Volume 134, Issue 2, p. 147-156.
27. Martinon et al. (2002). The inflammasome: a molecular platform triggering activation of inflammatory caspases and processing of proIL-beta. Mol Cell 2002 10 (2): 417-426.

The invention claimed is:

1. A method for treating an inflammatory condition or disease selected from: rheumatoid arthritis (RA), juvenile rheumatoid arthritis, osteoarthritis (OA), gout, spondylyarthritis (SpA), psoriasis, psoriatic arthritis, ankylosing spondylitis, inflammatory bowel disease including Crohn's disease or ulcerative colitis, hepatitis, sepsis, alcoholic liver disease, and non-alcoholic steatosis, pain, ischemic disorder, glaucoma, asthma, arthritis, cancer, neurodegenerative disorders, chronic disorders, acute inflammation, blood clotting disorders, heart failure, and disorder of platelet function, the method comprising administering to a person in need thereof a combination of:

(a) a source of a CD39 comprising a nucleic acid molecule encoding the CD39 and (b) a source of a CD73 comprising a nucleic acid molecule encoding the CD73, wherein the nucleic acid molecules encoding the CD39 and the CD73 are present in a nucleic acid construct comprising a viral expression construct selected from a retrovirus vector, an adenovirus vector, an adeno-associated virus vector, a herpesvirus vector, a polyoma virus vector or a vaccinia virus vector.

2. The method according to claim 1, wherein the inflammatory condition or disease is selected from: rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, and non-alcoholic steatosis.

3. The method according to claim 1, wherein the source of a CD39 is administered sequentially or simultaneously with the source of a CD73.

4. The method according to claim 1, wherein the source of a CD39 and the source of a CD73 are present in one single composition or wherein the source of a CD39 is present in one composition and the source of a CD73 is present in distinct compositions.

5. The method according to claim 1, wherein the source of a CD39 encodes a soluble CD39 and/or the source of a CD73 encodes a soluble CD73.

6. The method according to claim 1, wherein the source of a CD39 and the source of a CD73 encodes a fusion protein comprising a CD39 protein or part thereof and a CD73 protein or part thereof.

7. The method according to claim 6, wherein the fusion protein comprises an amino acid sequence that has at least 60% sequence identity or similarity with the amino acid sequence of SEQ ID NO: 17 and/or 19.

8. The method according to claim 1, wherein the nucleic acid construct is a fusion construct comprising a nucleic acid molecule encoding CD39 fused to a nucleic acid molecule encoding CD73 via a 2A sequence.

9. The method according to claim 8, wherein the fusion construct has at least 60% sequence identity or similarity with the nucleotide sequence of SEQ ID NO: 54 or SEQ ID NO: 57.

10. The method according to claim 1, wherein the adeno-associated virus vector comprising a source of a CD39 and/or the adeno-associated virus vector comprising a source of a CD73 comprises a rAAV2 or rAAV5 or a rAAV8 vector comprising rAAV2 or rAAV5 ITR.

11. The method according to claim 1, wherein the combination is administrated as a pharmaceutical composition comprising the combination and a pharmaceutically acceptable carrier, adjuvant, diluents, solubilizer, filler, preservative and/or excipient.

12. The method according to claim 1, wherein the inflammatory condition or disease is selected from the group consisting of: rheumatoid arthritis (RA), juvenile rheumatoid arthritis, osteoarthritis (OA), gout, spondlyarthritis (SpA), psoriatic arthritis and ankylosing spondylitis.

* * * * *

SEQUENCE LISTING

```
<160> NUMBER OF SEQ ID NOS: 57

<210> SEQ ID NO 1
<211> LENGTH: 510
<212> TYPE: PRT
<213> ORGANISM: Artificial
<220> FEATURE:
<223> OTHER INFORMATION: CD39 derived from homo sapiens

<400> SEQUENCE: 1

Met Glu Asp Thr Lys Glu Ser Asn Val Lys Thr Phe Cys Ser Lys Asn
1               5                   10                  15
```

-continued

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
            35                  40                  45

Tyr Gly Ile Val Leu Asp Ala Gly Ser Ser His Thr Ser Leu Tyr Ile
50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
            115                 120                 125

Gly Ala Thr Ala Gly Met Arg Leu Leu Arg Met Glu Ser Glu Glu Leu
130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
            195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
            275                 280                 285

Lys Val Val Asn Val Ser Asp Leu Tyr Lys Thr Pro Cys Thr Lys Arg
290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
            355                 360                 365

Phe Leu Asn Leu Thr Ser Glu Lys Val Ser Gln Glu Lys Val Thr Glu
370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

```
Ser Trp Glu His Ile His Phe Ile Gly Lys Ile Gln Gly Ser Asp Ala
            435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 2
<211> LENGTH: 1533
<212> TYPE: DNA
<213> ORGANISM: Artificial
<220> FEATURE:
<223> OTHER INFORMATION: CD39 derived from homo sapiens

<400> SEQUENCE: 2
atggaggaca ccaaggagag caacgtgaag accttctgca gcaagaacat cctggccatc      60
ctgggcttca gcagcatcat cgccgtgatc gccctgctgg ccgtgggcct gacccagaac     120
aaggccctgc ccgagaacgt gaagtacggc atcgtgctgg acgccggcag cagccacacc     180
agcctgtaca tctacaagtg gcccgccgag aaggagaacg acaccggcgt ggtgcaccag     240
gtggaggagt gcagagtgaa gggccccggc atcagcaagt tcgtgcagaa ggtgaacgag     300
atcggcatct acctgaccga ctgcatggag agagccagag aggtgatccc agaagccag      360
caccaggaga ccccgtgta cctgggcgcc accgccggca tgagactgct gagaatggag      420
agcgaggagc tggccgacag agtgctggac gtggtggaga aagcctgag caactacccc      480
ttcgacttcc agggcgccag aatcatcacc ggccaggagg agggcgccta cggctggatc     540
accatcaact acctgctggg caagttcagc agaagaccca tggttcag catcgtgccc      600
tacgagacca caaccagga gaccttcggc gccctggacc tgggcggcgc cagcacccag     660
gtgaccttcg tgccccagaa ccagaccatc gagagcccg acaacgccct gcagttcaga      720
ctgtacggca aggactacaa cgtgtacacc cacagcttcc tgtgctacgg caaggaccag     780
gccctgtggc agaagctggc caaggacatc caggtggcca gcaacgagat cctgagagac    840
ccctgcttcc accccggcta caagaaggtg gtgaacgtga cgacctgta caagaccccc    900
tgcaccaaga gattcgagat gacccctgccc ttccagcagt tcgagatcca gggcatcggc    960
aactaccagc agtgccacca gagcatcctg agctgttca acaccagcta ctgcccctac    1020
agccagtgcg ccttcaacgg catcttcctg ccccccctgc agggcgactt cggcgccttc    1080
agcgccttct acttcgtgat gaagttcctg aacctgacca gcgagaaggt gagccaggag    1140
aaggtgaccg agatgatgaa gaagttctgc gcccagccct gggaggagat caagaccagc    1200
tacgccggcg tgaaggagaa gtacctgagc gagtactgct tcagcggcac ctacatcctg    1260
agcctgctgc tgcagggcta ccacttcacc gccgacagct gggagcacat ccacttcatc    1320
ggcaagatcc agggcagcga cgccggctgg accctgggct acatgctgaa cctgaccaac    1380
atgatccccg ccgagcagcc cctgagcacc cccctgagcc acagcaccta cgtgttcctg    1440
atggtgctgt tcagcctggt gctgttcacc gtggccatca tcggcctgct gatcttccac    1500
aagcccagct acttctggaa ggacatggtg tga                                1533

<210> SEQ ID NO 3
```

```
<211> LENGTH: 574
<212> TYPE: PRT
<213> ORGANISM: Artificial
<220> FEATURE:
<223> OTHER INFORMATION: CD73 derived from homo sapiens

<400> SEQUENCE: 3

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Ala Asp Glu Thr Phe Trp Asn His Val
    370                 375                 380
```

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
            565                 570

```
<210> SEQ ID NO 4
<211> LENGTH: 1725
<212> TYPE: DNA
<213> ORGANISM: Artificial
<220> FEATURE:
<223> OTHER INFORMATION: CD73 derived from homo sapiens

<400> SEQUENCE: 4
atgtgcccca gagccgccag agcccccgcc accctgctgc tggccctggg cgccgtgctg      60
tggcccgccg ccggcgcctg ggagctgacc atcctgcaca ccaacgacgt gcacagcaga     120
ctggagcaga ccagcgagga cagcagcaag tgcgtgaacg ccagcagatg catgggcggc     180
gtggccagac tgttcaccaa ggtgcagcag atcagaagag ccgagcccaa cgtgctgctg     240
ctggacgccg cgaccagta ccagggcacc atctggttca ccgtgtacaa gggcgccgag     300
gtggcccact tcatgaacgc cctgagatac gacgccatgg ccctgggcaa ccacgagttc     360
gacaacggcg tggagggcct gatcgagccc ctgctgaagg aggccaagtt ccccatcctg     420
agcgccaaca tcaaggccaa ggccccccctg ccagccaga tcagcggcct gtacctgccc     480
tacaaggtgc tgcccgtggg cgacgaggtg gtgggcatcg tgggctacac cagcaaggag     540 accccccttcc tgagcaaccc cggcaccaac ctggtgttcg aggacgagat caccgccctg     600
cagcccgagg tggacaagct gaagaccctg aacgtgaaca agatcatcgc cctgggccac     660
agcggcttcg agatggacaa gctgatcgcc cagaaggtga gaggcgtgga cgtggtggtg     720
ggcggccaca gcaacacctt cctgtacacc ggcaacccc ccagcaagga ggtgcccgcc     780
ggcaagtacc ccttcatcgt gaccagcgac gacggcagaa aggtgcccgt ggtgcaggcc     840
tacgccttcg gcaagtacct gggctacctg aagatcgagt cgacgagag aggcaacgtg     900 atcagcagcc acggcaaccc catcctgctg aacagcagca tccccgagga ccccagcatc     960
```

-continued

```
aaggccgaca tcaacaagtg agaatcaag ctggacaact acagcaccca ggagctgggc    1020
aagaccatcg tgtacctgga cggcagcagc cagagctgca gattcagaga gtgcaacatg    1080
ggcaacctga tctgcgacgc catgatcaac aacaacctga cacgccga cgagaccttc     1140 tggaaccacg tgagcatgtg catcctgaac ggcggcggca tcagaagccc catcgacgag    1200
agaaacaacg gcaccatcac ctgggagaac ctggccgccg tgctgccctt cggcggcacc    1260
ttcgacctgg tgcagctgaa gggcagcacc ctgaagaagg ccttcgagca cagcgtgcac    1320
agatacggcc agagcaccgg cgagttcctg caggtgggcg catccacgt ggtgtacgac     1380 ctgagcagaa agcccggcga cagagtggtg aagctggacg tgctgtgcac caagtgcaga    1440
gtgcccagct acgacccct gaagatggac gaggtgtaca aggtgatcct gcccaacttc    1500
ctggccaacg cggcgacgg cttccagatg atcaaggacg agctgctgag acacgacagc    1560
ggcgaccagg acatcaacgt ggtgagcacc tacatcagca agatgaaggt gatctacccc    1620
gccgtggagg cagaatcaa gttcagcacc ggcagccact gccacggcag cttcagcctg     1680
atcttcctga gcctgtgggc cgtgatcttc gtgctgtacc agtga                    1725
```

<210> SEQ ID NO 5
<211> LENGTH: 513
<212> TYPE: PRT
<213> ORGANISM: Artificial
<220> FEATURE:
<223> OTHER INFORMATION: CD39 derived from mus musculus

<400> SEQUENCE: 5

```
Met Ser Arg Met Glu Asp Ile Lys Asp Ser Lys Val Lys Arg Phe Cys
1               5                   10                  15

Ser Lys Asn Ile Leu Ile Ile Leu Gly Phe Thr Ser Ile Leu Ala Val
            20                  25                  30

Ile Ala Leu Ile Ala Val Gly Leu Thr Gln Asn Lys Pro Leu Pro Glu
        35                  40                  45

Asn Val Lys Tyr Gly Ile Val Leu Asp Ala Gly Ser Ser His Thr Asn
    50                  55                  60

Leu Tyr Ile Tyr Lys Trp Pro Ala Glu Lys Glu Asn Asp Thr Gly Val
65                  70                  75                  80

Val Gln Gln Leu Glu Glu Cys Gln Val Lys Gly Pro Gly Ile Ser Lys
                85                  90                  95

Tyr Ala Gln Lys Thr Asp Glu Ile Gly Ala Tyr Leu Ala Glu Cys Met
            100                 105                 110

Glu Leu Ser Thr Glu Leu Ile Pro Thr Ser Lys His His Gln Thr Pro
        115                 120                 125

Val Tyr Leu Gly Ala Thr Ala Gly Met Arg Leu Leu Arg Met Glu Ser
    130                 135                 140

Glu Gln Ser Ala Asp Glu Val Leu Ala Ala Val Ser Thr Ser Leu Lys
145                 150                 155                 160

Ser Tyr Pro Phe Asp Phe Gln Gly Ala Lys Ile Ile Thr Gly Gln Glu
                165                 170                 175

Glu Gly Ala Tyr Gly Trp Ile Thr Ile Asn Tyr Leu Leu Gly Arg Phe
            180                 185                 190

Thr Gln Glu Gln Ser Trp Leu Ser Leu Ile Ser Asp Ser Gln Lys Gln
        195                 200                 205

Glu Thr Phe Gly Ala Leu Asp Leu Gly Gly Ala Ser Thr Gln Ile Thr
    210                 215                 220

Phe Val Pro Gln Asn Ser Thr Ile Glu Ser Pro Glu Asn Ser Leu Gln
```

-continued

```
            225                 230                 235                 240
        Phe Arg Leu Tyr Gly Glu Asp Tyr Thr Val Tyr Thr His Ser Phe Leu
                        245                 250                 255
        Cys Tyr Gly Lys Asp Gln Ala Leu Trp Gln Lys Leu Ala Lys Asp Ile
                        260                 265                 270
        Gln Val Ser Ser Gly Val Leu Lys Asp Pro Cys Phe Asn Pro Gly
                    275                 280                 285
        Tyr Glu Lys Val Val Asn Val Ser Glu Leu Tyr Gly Thr Pro Cys Thr
            290                 295                 300
        Lys Arg Phe Glu Lys Lys Leu Pro Phe Asp Gln Phe Arg Ile Gln Gly
        305                 310                 315                 320
        Thr Gly Asp Tyr Glu Gln Cys His Gln Ser Ile Leu Glu Leu Phe Asn
                        325                 330                 335
        Asn Ser His Cys Pro Tyr Ser Gln Cys Ala Phe Asn Gly Val Phe Leu
                        340                 345                 350
        Pro Pro Leu His Gly Ser Phe Gly Ala Phe Ser Ala Phe Tyr Phe Val
                    355                 360                 365
        Met Asp Phe Phe Lys Lys Val Ala Lys Asn Ser Val Ile Ser Gln Glu
            370                 375                 380
        Lys Met Thr Glu Ile Thr Lys Asn Phe Cys Ser Lys Ser Trp Glu
        385                 390                 395                 400
        Thr Lys Thr Ser Tyr Pro Ser Val Lys Glu Lys Tyr Leu Ser Glu Tyr
                        405                 410                 415
        Cys Phe Ser Gly Ala Tyr Ile Leu Ser Leu Leu Gln Gly Tyr Asn Phe
                        420                 425                 430
        Thr Asp Ser Ser Trp Glu Gln Ile His Phe Met Gly Lys Ile Lys Asp
                    435                 440                 445
        Ser Asn Ala Gly Trp Thr Leu Gly Tyr Met Leu Asn Leu Thr Asn Met
                    450                 455                 460
        Ile Pro Ala Glu Gln Pro Leu Ser Pro Pro Leu Pro His Ser Thr Tyr
        465                 470                 475                 480
        Ile Gly Leu Met Val Leu Phe Ser Leu Leu Leu Val Ala Val Ala Ile
                        485                 490                 495
        Thr Gly Leu Phe Ile Tyr Ser Lys Pro Ser Tyr Phe Trp Lys Glu Ala
                    500                 505                 510
        Val

<210> SEQ ID NO 6
<211> LENGTH: 1542
<212> TYPE: DNA
<213> ORGANISM: Artificial
<220> FEATURE:
<223> OTHER INFORMATION: CD39 derived from mus musculus, codon optimized

<400> SEQUENCE: 6
atgagccgca tggaggacat caaagactca aaagtgaaaa gattctgctc aaaaaacatt      60
ctcatcattc tggggtttac atcaattctc gctgtgatcg cactgattgc cgtcggcctc     120
actcagaaca gcccctgcc tgagaacgtg aagtacggaa tcgtcctgga cgctgggagc      180
tcccacacca atctgtacat ctacaagtgg ccagcagaga agaaaacga tacaggcgtg      240 gtccagcagc tggaggaatg ccaggtgaag ggtcccggca tctccaagta cgcccagaaa     300
acagacgaga ttggagctta tctggcagag tgtatggaac tgagcacaga actcatcccc     360
acttccaagc accatcagac accgtgtac ctgggtgcaa ctgcaggaat gcgactgctc     420
```

```
cgcatggagt cagaacagag cgccgacgag gtgctggcag ctgtcagtac ttcactcaaa    480
tcttatccat tcgatttca gggtgccaag atcattaccg gccaggagga aggagcttac    540
gggtggatca ctattaacta tctgctcggg cggttcaccc aggagcagtc ctggctgtct    600
ctcatcagcg actcccagaa gcaggaaacc ttcggcgctc tggatctcgg cggagcaagc    660
acccagatca catttgtgcc acagaatagc acaattgagt cccccgaaaa ctctctgcag    720
ttccgcctct acggggagga ctacaccgtg tacacccact cctttctgtg ctatggcaag    780
gaccaggccc tgtggcagaa gctcgctaaa gatatccagg tgtctagtgg gggtgtcctg    840
aaagatccct gcttcaatcc tggttacgag aaggtggtca cgtgtctga actgtatgga    900 acaccatgta ctaagaggtt cgagaagaaa ctgcccttcg accagtttcg aatccaggga    960
accggggatt acgagcagtg tcaccagagc attctggaac tcttcaacaa tagccattgc   1020
ccatattccc agtgtgcctt caacggagtg tttctgcccc ctctccacgg ttctttcggc   1080
gcctttagtg cttctactt tgtgatggac ttctttaaga aagtggctaa gaatagtgtc   1140
atctcacagg agaagatgac cgaaatcaca agaacttct gctctaagag ttgggaggaa   1200
accaagacaa gctacccctc cgtgaaggag aaatacctgt cagaatattg ttttagcggt   1260
gcctacatcc tgtccctgct ccagggctat aatttcaccg actcaagctg ggagcagatc   1320
cactttatgg gcaagatcaa ggattctaac gccggatgga ccctggggta catgctgaat   1380
ctcacaaaca tgatcccagc tgagcagcca ctgtccccac cactccctca ttctacctat   1440
attggcctga tggtgctctt ctccctgctc ctggtggctg tcgcaatcac aggactgttc   1500
atctactcta agccaagtta tttttggaaa gaggcagtgt ga                      1542
```

<210> SEQ ID NO 7
<211> LENGTH: 574
<212> TYPE: PRT
<213> ORGANISM: Artificial
<220> FEATURE:
<223> OTHER INFORMATION: CD73 derived from mus musculus

<400> SEQUENCE: 7

Met Arg Pro Ala Ala Lys Val Pro Lys Trp Leu Leu Ala Leu
1               5                   10                  15

Ser Ala Leu Leu Pro Gln Trp Pro Ala Ala Ser Ala Trp Glu Leu Thr
            20                  25                  30

Ile Leu His Thr Asn Asp Val His Ser Arg Leu Glu Gln Thr Ser Asp
        35                  40                  45

Asp Ser Thr Lys Cys Leu Asn Ala Ser Leu Cys Val Gly Gly Val Ala
    50                  55                  60

Arg Leu Phe Thr Lys Val Gln Gln Ile Arg Lys Glu Glu Pro Asn Val
65                  70                  75                  80

Leu Phe Leu Asp Ala Gly Asp Gln Tyr Gln Gly Thr Ile Trp Phe Thr
                85                  90                  95

Val Tyr Lys Gly Leu Glu Val Ala His Phe Met Asn Ile Leu Gly Tyr
            100                 105                 110

Asp Ala Met Ala Leu Gly Asn His Glu Phe Asp Asn Val Glu Gly
        115                 120                 125

Leu Ile Asp Pro Leu Leu Arg Asn Val Lys Phe Pro Ile Leu Ser Ala
    130                 135                 140

Asn Ile Lys Ala Arg Gly Pro Leu Ala His Gln Ile Ser Gly Leu Phe
145                 150                 155                 160

Leu Pro Ser Lys Val Leu Ser Val Gly Gly Glu Val Val Gly Ile Val

```
                    165                 170                 175
Gly Tyr Thr Ser Lys Glu Thr Pro Phe Leu Ser Asn Pro Gly Thr Asn
                180                 185                 190

Leu Val Phe Glu Asp Glu Ile Ser Ala Leu Gln Pro Glu Val Asp Lys
            195                 200                 205

Leu Lys Thr Leu Asn Val Asn Lys Ile Ile Ala Leu Gly His Ser Gly
        210                 215                 220

Phe Glu Met Asp Lys Leu Ile Ala Gln Lys Val Arg Gly Val Asp Ile
225                 230                 235                 240

Val Val Gly Gly His Ser Asn Thr Phe Leu Tyr Thr Gly Asn Pro Pro
                245                 250                 255

Ser Lys Glu Val Pro Ala Gly Lys Tyr Pro Phe Ile Val Thr Ala Asp
                260                 265                 270

Asp Gly Arg Gln Val Pro Val Val Gln Ala Tyr Ala Phe Gly Lys Tyr
                275                 280                 285

Leu Gly Tyr Leu Lys Val Glu Phe Asp Asp Lys Gly Asn Val Ile Thr
            290                 295                 300

Ser Tyr Gly Asn Pro Ile Leu Leu Asn Ser Ser Ile Pro Glu Asp Ala
305                 310                 315                 320

Thr Ile Lys Ala Asp Ile Asn Gln Trp Arg Ile Lys Leu Asp Asn Tyr
                325                 330                 335

Ser Thr Gln Glu Leu Gly Arg Thr Ile Val Tyr Leu Asp Gly Ser Thr
            340                 345                 350

Gln Thr Cys Arg Phe Arg Glu Cys Asn Met Gly Asn Leu Ile Cys Asp
        355                 360                 365

Ala Met Ile Asn Asn Asn Leu Arg His Pro Asp Glu Met Phe Trp Asn
370                 375                 380

His Val Ser Met Cys Ile Val Asn Gly Gly Ile Arg Ser Pro Ile
385                 390                 395                 400

Asp Glu Lys Asn Asn Gly Thr Ile Thr Trp Glu Asn Leu Ala Ala Val
                405                 410                 415

Leu Pro Phe Gly Gly Thr Phe Asp Leu Val Gln Leu Lys Gly Ser Thr
            420                 425                 430

Leu Lys Lys Ala Phe Glu His Ser Val His Arg Tyr Gly Gln Ser Thr
        435                 440                 445

Gly Glu Phe Leu Gln Val Gly Gly Ile His Val Val Tyr Asp Ile Asn
    450                 455                 460

Arg Lys Pro Trp Asn Arg Val Val Gln Leu Glu Val Leu Cys Thr Lys
465                 470                 475                 480

Cys Arg Val Pro Ile Tyr Glu Pro Leu Glu Met Asp Lys Val Tyr Lys
                485                 490                 495

Val Thr Leu Pro Ser Tyr Leu Ala Asn Gly Gly Asp Gly Phe Gln Met
            500                 505                 510

Ile Lys Asp Glu Leu Leu Lys His Asp Ser Gly Asp Gln Asp Ile Ser
        515                 520                 525

Val Val Ser Glu Tyr Ile Ser Lys Met Lys Val Val Tyr Pro Ala Val
    530                 535                 540

Glu Gly Arg Ile Lys Phe Ser Ala Ala Ser His Tyr Gln Gly Ser Phe
545                 550                 555                 560

Pro Leu Val Ile Leu Ser Phe Trp Ala Met Ile Leu Ile Leu
                565                 570

<210> SEQ ID NO 8
```

<211> LENGTH: 1725
<212> TYPE: DNA
<213> ORGANISM: Artificial
<220> FEATURE:
<223> OTHER INFORMATION: CD73 derived from mus musculus, codon optimized

<400> SEQUENCE: 8

```
atgaggcctg cagccgctaa ggtgccaaaa tggctcctgc tcgcactgtc cgccctgctc      60
cctcagtggc cagcagcctc tgcttgggag ctgactatcc tccacaccaa tgatgtgcat     120
agtagactgg aacagacctc agacgatagc acaaagtgcc tgaacgccag cctgtgcgtg     180
ggaggagtcg caagactgtt caccaaggtg cagcagatcc ggaaagagga acctaatgtc     240
ctgtttctcg acgcaggcga ccagtaccag ggcacaatct ggttcaccgt gtacaaggga     300
ctggaggtcg ctcactttat gaacattctg ggttacgacg ccatggctct cggcaatcat     360
gagttcgaca acggagtgga agggctgatc gatcctctgc tccggaatgt gaaatttcca     420
atcctgtcag ctaacattaa ggcacgaggt cctctggcac accagatcag cggactgttc     480
ctcccaagta aagtgctgtc agtcggggggc gaggtggtcg gtattgtggg ctacacctct     540
aaggaaacac ccttcctgag taatcctggc acaaacctcg tgtttgagga cgaaatctct     600
gccctgcagc tgaggtgga taagctgaaa actctcaatg tcaacaagat cattgcactg     660
ggacacagcg ggttcgaaat ggacaagctg atcgcccaga agtgagaggg gtcgatatt     720
gtggtcggcg gacatagtaa actttcctg tacaccggaa accctccatc aaaggaggtg     780
ccagctggga aatatccctt tatcgtgacc gcagacgatg ccggcaggt cccagtggtc     840
caggcatacg ccttcggcaa gtacctgggc tatctcaaag tggagtttga cgataaggga     900
aacgtcatca aagctatgg gaatcccatc ctgctcaact cctctattcc tgaagacgcc     960
actatcaaag ctgatattaa tcagtggagg atcaagctgg acaactactc cactcaggag    1020
ctgggaagaa ccatcgtgta cctggatggg tctactcaga cctgcaggtt cagagaatgt    1080
aatatgggca acctgatctg cgacgccatg attaacaata acctgcgaca ccccgatgag    1140
atgttttgga atcatgtgag catgtgcatc gtcaacgggg gtggcatcag gtcccccatt    1200
gacgagaaga ataacggaac aattacttgg gaaaacctgg ctgcagtgct cccttttcgga    1260
gggacatttg atctggtcca gctcaagggg tccactctga gaaagccttt cgagcactca    1320
gtgcatcgct acggacagag caccggggaa ttttctgcaag tgggtggcat ccacgtggtc    1380
tatgacatta atcgaaaacc ctggaacagg gtggtccagc tggaggtgct ctgcactaag    1440
tgtcgagtcc ctatctacga gccactgaaa atggacaagg tgtacaaagt cacccctgcct    1500
agctatctcg ccaacggagg ggatggattc cagatgatta aggacgagct gctcaaacat    1560
gattctgggg accaggatat ctccgtggtc tctgagtaca ttagtaagat gaaagtggtc    1620
tatcctgctg tggaaggcag gatcaagttc agtgccgctt cacattacca gggttctttt    1680
ccactcgtga ttctctcttt ttgggctatg attctgattc tctga                    1725
```

<210> SEQ ID NO 9
<211> LENGTH: 464
<212> TYPE: PRT
<213> ORGANISM: Artificial
<220> FEATURE:
<223> OTHER INFORMATION: soluble CD39 derived from mus musculus

<400> SEQUENCE: 9

Met Pro Ser Ser Val Ser Trp Gly Ile Leu Leu Leu Ala Gly Leu Cys
1               5                   10                  15

-continued

Cys Leu Val Pro Val Ser Leu Ala Glu Thr Gln Asn Lys Pro Leu Pro
               20                  25                  30

Glu Asn Val Lys Tyr Gly Ile Val Leu Asp Ala Gly Ser Ser His Thr
           35                  40                  45

Asn Leu Tyr Ile Tyr Lys Trp Pro Ala Glu Lys Glu Asn Asp Thr Gly
        50                  55                  60

Val Val Gln Gln Leu Glu Cys Gln Val Lys Gly Pro Gly Ile Ser
65              70                  75                  80

Lys Tyr Ala Gln Lys Thr Asp Glu Ile Gly Ala Tyr Leu Ala Glu Cys
                85                  90                  95

Met Glu Leu Ser Thr Glu Leu Ile Pro Thr Ser Lys His His Gln Thr
            100                 105                 110

Pro Val Tyr Leu Gly Ala Thr Ala Gly Met Arg Leu Leu Arg Met Glu
            115                 120                 125

Ser Glu Gln Ser Ala Asp Glu Val Leu Ala Ala Val Ser Thr Ser Leu
            130                 135                 140

Lys Ser Tyr Pro Phe Asp Phe Gln Gly Ala Lys Ile Ile Thr Gly Gln
145                 150                 155                 160

Glu Glu Gly Ala Tyr Gly Trp Ile Thr Ile Asn Tyr Leu Leu Gly Arg
                165                 170                 175

Phe Thr Gln Glu Gln Ser Trp Leu Ser Leu Ile Ser Asp Ser Gln Lys
            180                 185                 190

Gln Glu Thr Phe Gly Ala Leu Asp Leu Gly Gly Ala Ser Thr Gln Ile
            195                 200                 205

Thr Phe Val Pro Gln Asn Ser Thr Ile Glu Ser Pro Glu Asn Ser Leu
            210                 215                 220

Gln Phe Arg Leu Tyr Gly Glu Asp Tyr Thr Val Tyr Thr His Ser Phe
225                 230                 235                 240

Leu Cys Tyr Gly Lys Asp Gln Ala Leu Trp Gln Lys Leu Ala Lys Asp
                245                 250                 255

Ile Gln Val Ser Ser Gly Gly Val Leu Lys Asp Pro Cys Phe Asn Pro
            260                 265                 270

Gly Tyr Glu Lys Val Val Asn Val Ser Glu Leu Tyr Gly Thr Pro Cys
            275                 280                 285

Thr Lys Arg Phe Glu Lys Lys Leu Pro Phe Asp Gln Phe Arg Ile Gln
290                 295                 300

Gly Thr Gly Asp Tyr Glu Gln Cys His Gln Ser Ile Leu Glu Leu Phe
305                 310                 315                 320

Asn Asn Ser His Cys Pro Tyr Ser Gln Cys Ala Phe Asn Gly Val Phe
                325                 330                 335

Leu Pro Pro Leu His Gly Ser Phe Gly Ala Phe Ser Ala Phe Tyr Phe
            340                 345                 350

Val Met Asp Phe Phe Lys Lys Val Ala Lys Asn Ser Val Ile Ser Gln
            355                 360                 365

Glu Lys Met Thr Glu Ile Thr Lys Asn Phe Cys Ser Lys Ser Trp Glu
            370                 375                 380

Glu Thr Lys Thr Ser Tyr Pro Ser Val Lys Glu Lys Tyr Leu Ser Glu
385                 390                 395                 400

Tyr Cys Phe Ser Gly Ala Tyr Ile Leu Ser Leu Leu Gln Gly Tyr Asn
                405                 410                 415

Phe Thr Asp Ser Ser Trp Glu Gln Ile His Phe Met Gly Lys Ile Lys
            420                 425                 430

Asp Ser Asn Ala Gly Trp Thr Leu Gly Tyr Met Leu Asn Leu Thr Asn

```
            435                 440                 445
Met Ile Pro Ala Glu Gln Pro Leu Ser Pro Pro Leu Pro His Ser Thr
            450                 455                 460
```

<210> SEQ ID NO 10
<211> LENGTH: 1395
<212> TYPE: DNA
<213> ORGANISM: Artificial
<220> FEATURE:
<223> OTHER INFORMATION: soluble CD39 derived from mus musculus, codon
      optimized

<400> SEQUENCE: 10

```
atgccttcct ccgtctcatg gggtatcctc ctgctcgctg gctgtgctg cctggtgcct      60
gtctcactcg ccgaaactca gaacaagcca ctgcccgaga cgtgaagta cggcatcgtc     120
ctggacgcag aagctcccca cacaaaccctc tacatctaca gtggcccgc cgagaaagaa     180
aatgatactg gagtggtcca gcagctggag gaatgccagg tgaagggccc tggaatctcc    240
aagtacgccc agaaaaccga cgagattggg gcttatctgg cagagtgtat ggaactgtca    300
acagaactca tccccacttc taaacaccat cagacccccg tgtacctggg agcaacagca    360
ggaatgaggc tgctcagaat ggagtctgaa cagagtgctg acgaggtgct ggccgctgtc    420
tccacctctc tcaagagcta tccccttcgat tttcagggggg ccaaaatcat taccggtcag    480
gaggaaggcg cttacggatg gatcactatt aactatctgc tcgggcgatt cacccaggag    540
cagtcatggc tgagcctcat cagtgactca cagaagcagg aaactttcgg cgcactggat    600
ctcggaggag caagcactca gatcacccttt gtgccacaga cagcaccat tgagtccccc    660
gaaaattctc tgcagttcag actctacggc gaggactaca agtctatac tcattccttt    720
ctgtgctatg gaaaggacca ggctctgtgg cagaagctcg caaagatat tcaggtgtct    780
agtggggtg tcctgaagga tccttgcttc aacccagggt acgagaaagt ggtcaacgtg    840
agcgaactgt atggtacccc ttgtacaaag cggtttgaga gaaaactgcc attcgaccag    900
tttcgcatcc agggggacag cgactacgag cagtgtcacc agagcattct ggaactcttc    960
aacaatagtc attgcccata ttcacagtgt gctttcaacg cgtgtttct gccacctctc   1020
cacgggagct tcggtgcctt ttccgctttc tacttcgtca tggatttctt taagaaagtg   1080
gcaaagaact ccgtcatctc tcaggagaag atgactgaaa tcaccaagaa cttctgcagc   1140
aaatcctggg aggaaaccaa gacaagttat ccctcagtga aggagaaata cctgtctgaa   1200
tattgtttta gtggcgccta catcctgagt ctgctccagg gatataattt tcacagactca   1260
agctgggagc agatccactt catgggcaag atcaaggatt ctaacgctgg gtggactctg   1320
ggttacatgc tcaatctcac caatatgatt ccagccgaac agccactcag cccccccactc   1380
ccacactcaa cctga                                                    1395
```

<210> SEQ ID NO 11
<211> LENGTH: 464
<212> TYPE: PRT
<213> ORGANISM: Artificial
<220> FEATURE:
<223> OTHER INFORMATION: soluble CD39 derived from homo sapiens

<400> SEQUENCE: 11

```
Met Pro Ser Ser Val Ser Trp Gly Ile Leu Leu Leu Ala Gly Leu Cys
1               5                   10                  15

Cys Leu Val Pro Val Ser Leu Ala Glu Thr Gln Asn Lys Ala Leu Pro
            20                  25                  30
```

```
Glu Asn Val Lys Tyr Gly Ile Val Leu Asp Ala Gly Ser Ser His Thr
            35                  40                  45

Ser Leu Tyr Ile Tyr Lys Trp Pro Ala Glu Lys Glu Asn Asp Thr Gly
 50                      55                  60

Val Val His Gln Val Glu Glu Cys Arg Val Lys Gly Pro Gly Ile Ser
 65              70                  75                      80

Lys Phe Val Gln Lys Val Asn Glu Ile Gly Ile Tyr Leu Thr Asp Cys
                85                  90                  95

Met Glu Arg Ala Arg Glu Val Ile Pro Arg Ser Gln His Gln Glu Thr
                100                 105                 110

Pro Val Tyr Leu Gly Ala Thr Ala Gly Met Arg Leu Leu Arg Met Glu
                115                 120                 125

Ser Glu Glu Leu Ala Asp Arg Val Leu Asp Val Val Glu Arg Ser Leu
130                 135                 140

Ser Asn Tyr Pro Phe Asp Phe Gln Gly Ala Arg Ile Ile Thr Gly Gln
145                 150                 155                 160

Glu Glu Gly Ala Tyr Gly Trp Ile Thr Ile Asn Tyr Leu Leu Gly Lys
                165                 170                 175

Phe Ser Gln Lys Thr Arg Trp Phe Ser Ile Val Pro Tyr Glu Thr Asn
                180                 185                 190

Asn Gln Glu Thr Phe Gly Ala Leu Asp Leu Gly Gly Ala Ser Thr Gln
                195                 200                 205

Val Thr Phe Val Pro Gln Asn Gln Thr Ile Glu Ser Pro Asp Asn Ala
210                 215                 220

Leu Gln Phe Arg Leu Tyr Gly Lys Asp Tyr Asn Val Tyr Thr His Ser
225                 230                 235                 240

Phe Leu Cys Tyr Gly Lys Asp Gln Ala Leu Trp Gln Lys Leu Ala Lys
                245                 250                 255

Asp Ile Gln Val Ala Ser Asn Glu Ile Leu Arg Asp Pro Cys Phe His
                260                 265                 270

Pro Gly Tyr Lys Lys Val Val Asn Val Ser Asp Leu Tyr Lys Thr Pro
                275                 280                 285

Cys Thr Lys Arg Phe Glu Met Thr Leu Pro Phe Gln Gln Phe Glu Ile
                290                 295                 300

Gln Gly Ile Gly Asn Tyr Gln Gln Cys His Gln Ser Ile Leu Glu Leu
305                 310                 315                 320

Phe Asn Thr Ser Tyr Cys Pro Tyr Ser Gln Cys Ala Phe Asn Gly Ile
                325                 330                 335

Phe Leu Pro Pro Leu Gln Gly Asp Phe Gly Ala Phe Ser Ala Phe Tyr
                340                 345                 350

Phe Val Met Lys Phe Leu Asn Leu Thr Ser Glu Lys Val Ser Gln Glu
                355                 360                 365

Lys Val Thr Glu Met Met Lys Lys Phe Cys Ala Gln Pro Trp Glu Glu
                370                 375                 380

Ile Lys Thr Ser Tyr Ala Gly Val Lys Glu Lys Tyr Leu Ser Glu Tyr
385                 390                 395                 400

Cys Phe Ser Gly Thr Tyr Ile Leu Ser Leu Leu Leu Gln Gly Tyr His
                405                 410                 415

Phe Thr Ala Asp Ser Trp Glu His Ile His Phe Ile Gly Lys Ile Gln
                420                 425                 430

Gly Ser Asp Ala Gly Trp Thr Leu Gly Tyr Met Leu Asn Leu Thr Asn
                435                 440                 445
```

Met Ile Pro Ala Glu Gln Pro Leu Ser Thr Pro Leu Ser His Ser Thr
    450                 455                 460

<210> SEQ ID NO 12
<211> LENGTH: 1395
<212> TYPE: DNA
<213> ORGANISM: Artificial
<220> FEATURE:
<223> OTHER INFORMATION: soluble CD39 derived from homo sapiens, codon
      optimized

<400> SEQUENCE: 12

| | |
|---|---|
| atgcccagca gcgtgagctg gggcatcctg ctgctggccg cctgtgctg cctggtgccc | 60 |
| gtgagcctgg ccgagaccca gaacaaggcc ctgcccgaga cgtgaagta cggcatcgtg | 120 |
| ctggacgccg gcagcagcca caccagcctg tacatctaca gtggcccgc cgagaaggag | 180 |
| aacgacaccg gcgtggtgca ccaggtggag gagtgcagag tgaagggccc cggcatcagc | 240 |
| aagttcgtgc agaaggtgaa cgagatcggc atctacctga ccgactgcat ggagagagcc | 300 |
| agagaggtga tccccagaag ccagcaccag agaccccccg tgtacctggg cgccaccgcc | 360 |
| ggcatgagac tgctgagaat ggagagcgag gagctggccg acagagtgct ggacgtggtg | 420 |
| gagagaagcc tgagcaacta ccccttcgac ttccagggcg ccagaatcat caccggccag | 480 |
| gaggagggcg cctacggctg gatcaccatc aactacctgc tgggcaagtt cagccagaag | 540 |
| accagatggt tcagcatcgt gcctacgag accaacaacc aggagacctt cggcgccctg | 600 |
| gacctgggcg cgccagcac ccaggtgacc ttcgtgcccc agaaccagac catcgagagc | 660 |
| cccgacaacg ccctgcagtt cagactgtac ggcaaggact acaacgtgta cccacacagc | 720 |
| ttcctgtgct acggcaagga ccaggccctg tggcagaagc tggccaagga catccaggtg | 780 |
| gccagcaacg agatcctgag agacccctgc ttccaccccg gctacaagaa ggtggtgaac | 840 |
| gtgagcgacc tgtacaagac ccctgcacc aagagattcg agatgaccct gcccttccag | 900 |
| cagttcgaga tccagggcat cggcaactac agcagtgcc accagagcat cctggagctg | 960 |
| ttcaacacca gctactgccc ctacagccag tgcgccttca cggcatctt cctgccccc | 1020 |
| ctgcagggcg acttcggcgc cttcagcgcc ttctacttcg tgatgaagtt cctgaacctg | 1080 |
| accagcgaga aggtgagcca ggagaaggtg accgagatga tgaagaagtt ctgcgcccag | 1140 |
| ccctgggagg agatcaagac cagctacgcc ggcgtgaagg agaagtacct gagcgagtac | 1200 |
| tgcttcagcg gcacctacat cctgagcctg ctgctgcagg gctaccactt caccgccgac | 1260 |
| agctgggagc acatccactt catcggcaag atccagggca cgacgccgg ctggaccctg | 1320 |
| ggctacatgc tgaacctgac caacatgatc cccgccgagc agcccctgag cacccccctg | 1380 |
| agccacagca cctga | 1395 |

<210> SEQ ID NO 13
<211> LENGTH: 550
<212> TYPE: PRT
<213> ORGANISM: Artificial
<220> FEATURE:
<223> OTHER INFORMATION: soluble CD73 derived from mus musculus

<400> SEQUENCE: 13

Met Arg Pro Ala Ala Ala Lys Val Pro Lys Trp Leu Leu Ala Leu
1               5                   10                  15

Ser Ala Leu Leu Pro Gln Trp Pro Ala Ala Ser Ala Trp Glu Leu Thr
                20                  25                  30

Ile Leu His Thr Asn Asp Val His Ser Arg Leu Glu Gln Thr Ser Asp

-continued

```
                35                  40                  45
Asp Ser Thr Lys Cys Leu Asn Ala Ser Leu Cys Val Gly Gly Val Ala
 50                  55                  60
Arg Leu Phe Thr Lys Val Gln Gln Ile Arg Lys Glu Glu Pro Asn Val
 65                  70                  75                  80
Leu Phe Leu Asp Ala Gly Asp Gln Tyr Gln Gly Thr Ile Trp Phe Thr
                     85                  90                  95
Val Tyr Lys Gly Leu Glu Val Ala His Phe Met Asn Ile Leu Gly Tyr
                100                 105                 110
Asp Ala Met Ala Leu Gly Asn His Glu Phe Asp Asn Gly Val Glu Gly
                115                 120                 125
Leu Ile Asp Pro Leu Leu Arg Asn Val Lys Phe Pro Ile Leu Ser Ala
130                 135                 140
Asn Ile Lys Ala Arg Gly Pro Leu Ala His Gln Ile Ser Gly Leu Phe
145                 150                 155                 160
Leu Pro Ser Lys Val Leu Ser Val Gly Gly Glu Val Val Gly Ile Val
                165                 170                 175
Gly Tyr Thr Ser Lys Glu Thr Pro Phe Leu Ser Asn Pro Gly Thr Asn
                180                 185                 190
Leu Val Phe Glu Asp Glu Ile Ser Ala Leu Gln Pro Glu Val Asp Lys
                195                 200                 205
Leu Lys Thr Leu Asn Val Asn Lys Ile Ile Ala Leu Gly His Ser Gly
210                 215                 220
Phe Glu Met Asp Lys Leu Ile Ala Gln Lys Val Arg Gly Val Asp Ile
225                 230                 235                 240
Val Val Gly Gly His Ser Asn Thr Phe Leu Tyr Thr Gly Asn Pro Pro
                245                 250                 255
Ser Lys Glu Val Pro Ala Gly Lys Tyr Pro Phe Ile Val Thr Ala Asp
                260                 265                 270
Asp Gly Arg Gln Val Pro Val Val Gln Ala Tyr Ala Phe Gly Lys Tyr
                275                 280                 285
Leu Gly Tyr Leu Lys Val Glu Phe Asp Asp Lys Gly Asn Val Ile Thr
290                 295                 300
Ser Tyr Gly Asn Pro Ile Leu Leu Asn Ser Ser Ile Pro Glu Asp Ala
305                 310                 315                 320
Thr Ile Lys Ala Asp Ile Asn Gln Trp Arg Ile Lys Leu Asp Asn Tyr
                325                 330                 335
Ser Thr Gln Glu Leu Gly Arg Thr Ile Val Tyr Leu Asp Gly Ser Thr
                340                 345                 350
Gln Thr Cys Arg Phe Arg Glu Cys Asn Met Gly Asn Leu Ile Cys Asp
                355                 360                 365
Ala Met Ile Asn Asn Asn Leu Arg His Pro Asp Glu Met Phe Trp Asn
                370                 375                 380
His Val Ser Met Cys Ile Val Asn Gly Gly Ile Arg Ser Pro Ile
385                 390                 395                 400
Asp Glu Lys Asn Asn Gly Thr Ile Thr Trp Glu Asn Leu Ala Ala Val
                405                 410                 415
Leu Pro Phe Gly Gly Thr Phe Asp Leu Val Gln Leu Lys Gly Ser Thr
                420                 425                 430
Leu Lys Lys Ala Phe Glu His Ser Val His Arg Tyr Gly Gln Ser Thr
                435                 440                 445
Gly Glu Phe Leu Gln Val Gly Gly Ile His Val Val Tyr Asp Ile Asn
450                 455                 460
```

```
Arg Lys Pro Trp Asn Arg Val Val Gln Leu Glu Val Leu Cys Thr Lys
465                 470                 475                 480

Cys Arg Val Pro Ile Tyr Glu Pro Leu Glu Met Asp Lys Val Tyr Lys
                485                 490                 495

Val Thr Leu Pro Ser Tyr Leu Ala Asn Gly Gly Asp Gly Phe Gln Met
            500                 505                 510

Ile Lys Asp Glu Leu Leu Lys His Asp Ser Gly Asp Gln Asp Ile Ser
        515                 520                 525

Val Val Ser Glu Tyr Ile Ser Lys Met Lys Val Tyr Pro Ala Val
    530                 535                 540

Glu Gly Arg Ile Lys Phe
545                 550

<210> SEQ ID NO 14
<211> LENGTH: 1653
<212> TYPE: DNA
<213> ORGANISM: Artificial
<220> FEATURE:
<223> OTHER INFORMATION: soluble CD73 derived from mus musculus, codon
      optimized

<400> SEQUENCE: 14
atgaggcctg cagccgctaa ggtgccaaaa tggctcctgc tcgcactgtc cgccctgctc      60
cctcagtggc cagcagcctc tgcttgggag ctgactatcc tccacaccaa tgatgtgcat     120
agtagactgg aacagacctc agacgatagc acaaagtgcc tgaacgccag cctgtgcgtg     180
ggaggagtcg caagactgtt caccaaggtg cagcagatcc ggaaagagga acctaatgtc     240
ctgtttctcg acgcaggcga ccagtaccag ggcacaatct ggttcaccgt gtacaaggga     300
ctggaggtcg ctcactttat gaacattctg ggttacgacg ccatggctct cggcaatcat     360
gagttcgaca acggagtgga agggctgatc gatcctctgc tccggaatgt gaaatttcca     420
atcctgtcag ctaacattaa ggcacgaggt cctctggcac accagatcag cggactgttc     480
ctcccaagta agtgctgtc agtcggggc gaggtggtcg gtattgtggg ctacacctct     540
aaggaaacac ccttcctgag taatcctggc acaaacctcg tgtttgagga cgaaatctct     600
gccctgcagc ctgaggtgga taagctgaaa actctcaatg tcaacaagat cattgcactg     660
ggacacagcg ggttcgaaat ggacaagctg atcgcccaga agtgagagg ggtcgatatt     720 gtggtcggcg gacatagtaa actttcctg tacaccggaa accctccatc aaaggaggtg     780
ccagctggga aatatccctt tatcgtgacc gcagacgatg gccggcaggt cccagtggtc     840
caggcatacg ccttcggcaa gtacctgggc tatctcaaag tggagtttga cgataaggga     900
aacgtcatca aagctatgg gaatcccatc ctgctcaact cctctattcc tgaagacgcc     960
actatcaaag ctgatattaa tcagtggagg atcaagctgg acaactactc cactcaggag    1020
ctgggaagaa ccatcgtgta cctggatggg tctactcaga cctgcaggtt cagagaatgt    1080
aatatgggca acctgatctg cgacgccatg attaacaata acctgcgaca ccccgatgag    1140
atgttttgga tcatgtgag catgtgcatc gtcaacgggg gtggcatcag gtcccccatt    1200
gacgagaaga taacggaac aattacttgg gaaaacctgg ctgcagtgct ccctttcgga    1260
gggacatttg atctggtcca gctcaagggg tccactctga gaaagccctt cgagcactca    1320
gtgcatcgct acggacagag caccggggaa tttctgcaag tgggtggcat ccacgtggtc    1380
tatgacatta atcgaaaacc ctggaacagg gtggtccagc tggaggtgct ctgcactaag    1440
tgtcgagtcc ctatctacga gccactggaa atggacaagg tgtacaaagt caccctgcct    1500
```
agctatctcg ccaacggagg ggatggattc cagatgatta aggacgagct gctcaaacat    1560
gattctgggg accaggatat ctccgtggtc tctgagtaca ttagtaagat gaaagtggtc    1620
tatcctgctg tggaaggcag gatcaagttc tga    1653

<210> SEQ ID NO 15
<211> LENGTH: 548
<212> TYPE: PRT
<213> ORGANISM: Artificial
<220> FEATURE:
<223> OTHER INFORMATION: soluble CD73 derived from homo sapiens

<400> SEQUENCE: 15

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335
```

Gln Glu Leu Gly Lys Thr Ile Val Tyr Leu Asp Gly Ser Gln Ser
            340                 345                 350

Cys Arg Phe Arg Glu Cys Asn Met Gly Asn Leu Ile Cys Asp Ala Met
            355                 360                 365

Ile Asn Asn Leu Arg His Ala Asp Glu Thr Phe Trp Asn His Val
370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
            450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
            530                 535                 540

Arg Ile Lys Phe
545

<210> SEQ ID NO 16
<211> LENGTH: 1647
<212> TYPE: DNA
<213> ORGANISM: Artificial
<220> FEATURE:
<223> OTHER INFORMATION: soluble CD73 derived from homo sapiens, codon
      optimized

<400> SEQUENCE: 16
atgtgcccca gagccgccag agcccccgcc accctgctgc tggccctggg cgccgtgctg      60
tggcccgccg ccggcgcctg ggagctgacc atcctgcaca ccaacgacgt gcacagcaga     120
ctggagcaga ccagcgagga cagcagcaag tgcgtgaacg ccagcagatg catgggcggc     180
gtggccagac tgttcaccaa ggtgcagcag atcagaagag ccgagcccaa cgtgctgctg     240
ctggacgccg gcgaccagta ccagggcacc atctggttca ccgtgtacaa gggcgccgag     300
gtggcccact tcatgaacgc cctgagatac gacgccatgg ccctgggcaa ccacgagttc     360
gacaacggcg tggagggcct gatcgagccc tgctgaagg aggccaagtt ccccatcctg     420
agcgccaaca tcaaggccaa gggccccctg gccagccaga tcagcggcct gtacctgccc     480
tacaaggtgc tgcccgtggg cgacgagtg gtgggcatcg tgggctacac cagcaaggag     540
acccccttcc tgagcaaccc cggcaccaac ctggtgttcg aggacgagat caccgccctg     600
cagcccgagg tggacaagct gaagaccctg aacgtgaaca agatcatcgc cctgggccac     660
agcggcttcg agatggacaa gctgatcgcc cagaaggtga aggcgtgga cgtggtggtg     720 ggcggccaca gcaacacctt cctgtacacc ggcaaccccc ccagcaagga ggtgcccgcc     780

-continued

```
ggcaagtacc ccttcatcgt gaccagcgac gacggcagaa aggtgcccgt ggtgcaggcc    840
tacgccttcg gcaagtacct gggctacctg aagatcgagt tcgacgagag aggcaacgtg    900
atcagcagcc acggcaaccc catcctgctg aacagcagca tccccgagga ccccagcatc    960
aaggccgaca tcaacaagtg gagaatcaag ctggacaact acagcaccca ggagctgggc   1020
aagaccatcg tgtacctgga cggcagcagc cagagctgca gattcagaga gtgcaacatg   1080
ggcaacctga tctgcgacgc catgatcaac aacaacctga cacgccga cgagaccttc    1140
tggaaccacg tgagcatgtg catcctgaac ggcggcggca tcagaagccc catcgacgag   1200
agaaacaacg gcaccatcac ctgggagaac ctggccgccg tgctgccctt cggcggcacc   1260
ttcgacctgg tgcagctgaa gggcagcacc ctgaagaagg ccttcgagca gcgtgcac    1320
agatacggcc agagcaccgg cgagttcctg caggtgggcg catccacgt ggtgtacgac   1380
ctgagcagaa agcccggcga cagagtggtg aagctggacg tgctgtgcac caagtgcaga   1440
gtgcccagct acgaccccct gaagatggac gaggtgtaca aggtgatcct gcccaacttc   1500
ctggccaacg gcggcgacgg cttccagatg atcaaggacg agctgctgag cacgacagc    1560
ggcgaccagg acatcaacgt ggtgagcacc tacatcagca agatgaaggt gatctacccc   1620
gccgtggagg gcagaatcaa gttctga                                       1647
```

<210> SEQ ID NO 17
<211> LENGTH: 1009
<212> TYPE: PRT
<213> ORGANISM: Artificial
<220> FEATURE:
<223> OTHER INFORMATION: soluble CD73-CD39 fusion derived from mus musculus

<400> SEQUENCE: 17

```
Met Pro Ser Ser Val Ser Trp Gly Ile Leu Leu Ala Gly Leu Cys
1               5                   10                  15

Cys Leu Val Pro Val Ser Leu Ala Glu Trp Glu Leu Thr Ile Leu His
            20                  25                  30

Thr Asn Asp Val His Ser Arg Leu Glu Gln Thr Ser Asp Asp Ser Thr
        35                  40                  45

Lys Cys Leu Asn Ala Ser Leu Cys Val Gly Gly Val Ala Arg Leu Phe
    50                  55                  60

Thr Lys Val Gln Gln Ile Arg Lys Glu Glu Pro Asn Val Leu Phe Leu
65                  70                  75                  80

Asp Ala Gly Asp Gln Tyr Gln Gly Thr Ile Trp Phe Thr Val Tyr Lys
                85                  90                  95

Gly Leu Glu Val Ala His Phe Met Asn Ile Leu Gly Tyr Asp Ala Met
            100                 105                 110

Ala Leu Gly Asn His Glu Phe Asp Asn Gly Val Glu Gly Leu Ile Asp
        115                 120                 125

Pro Leu Leu Arg Asn Val Lys Phe Pro Ile Leu Ser Ala Asn Ile Lys
    130                 135                 140

Ala Arg Gly Pro Leu Ala His Gln Ile Ser Gly Leu Phe Leu Pro Ser
145                 150                 155                 160

Lys Val Leu Ser Val Gly Gly Glu Val Gly Ile Val Gly Tyr Thr
                165                 170                 175

Ser Lys Glu Thr Pro Phe Leu Ser Asn Pro Gly Thr Asn Leu Val Phe
            180                 185                 190

Glu Asp Glu Ile Ser Ala Leu Gln Pro Glu Val Asp Lys Leu Lys Thr
```

```
            195                 200                 205
Leu Asn Val Asn Lys Ile Ile Ala Leu Gly His Ser Gly Phe Glu Met
210                 215                 220
Asp Lys Leu Ile Ala Gln Lys Val Arg Gly Val Asp Ile Val Val Gly
225                 230                 235                 240
Gly His Ser Asn Thr Phe Leu Tyr Thr Gly Asn Pro Pro Ser Lys Glu
                245                 250                 255
Val Pro Ala Gly Lys Tyr Pro Phe Ile Val Thr Ala Asp Asp Gly Arg
                260                 265                 270
Gln Val Pro Val Val Gln Ala Tyr Ala Phe Gly Lys Tyr Leu Gly Tyr
                275                 280                 285
Leu Lys Val Glu Phe Asp Asp Lys Gly Asn Val Ile Thr Ser Tyr Gly
290                 295                 300
Asn Pro Ile Leu Leu Asn Ser Ser Ile Pro Glu Asp Ala Thr Ile Lys
305                 310                 315                 320
Ala Asp Ile Asn Gln Trp Arg Ile Lys Leu Asp Asn Tyr Ser Thr Gln
                325                 330                 335
Glu Leu Gly Arg Thr Ile Val Tyr Leu Asp Gly Ser Thr Gln Thr Cys
                340                 345                 350
Arg Phe Arg Glu Cys Asn Met Gly Asn Leu Ile Cys Asp Ala Met Ile
                355                 360                 365
Asn Asn Asn Leu Arg His Pro Asp Glu Met Phe Trp Asn His Val Ser
370                 375                 380
Met Cys Ile Val Asn Gly Gly Ile Arg Ser Pro Ile Asp Glu Lys
385                 390                 395                 400
Asn Asn Gly Thr Ile Thr Trp Glu Asn Leu Ala Ala Val Leu Pro Phe
                405                 410                 415
Gly Gly Thr Phe Asp Leu Val Gln Leu Lys Gly Ser Thr Leu Lys Lys
                420                 425                 430
Ala Phe Glu His Ser Val His Arg Tyr Gly Gln Ser Thr Gly Glu Phe
                435                 440                 445
Leu Gln Val Gly Gly Ile His Val Val Tyr Asp Ile Asn Arg Lys Pro
450                 455                 460
Trp Asn Arg Val Val Gln Leu Glu Val Leu Cys Thr Lys Cys Arg Val
465                 470                 475                 480
Pro Ile Tyr Glu Pro Leu Glu Met Asp Lys Val Tyr Lys Val Thr Leu
                485                 490                 495
Pro Ser Tyr Leu Ala Asn Gly Gly Asp Gly Phe Gln Met Ile Lys Asp
                500                 505                 510
Glu Leu Leu Lys His Asp Ser Gly Asp Gln Asp Ile Ser Val Val Ser
                515                 520                 525
Glu Tyr Ile Ser Lys Met Lys Val Val Tyr Pro Ala Val Glu Gly Arg
                530                 535                 540
Ile Lys Phe Ala Ser Gly Gly Ala Gly Gly Ala Gly Gly Gly
545                 550                 555                 560
Ala Gly Gly Gly Ala Gly Gly Thr Gly Thr Gln Asn Lys Pro Leu
                565                 570                 575
Pro Glu Asn Val Lys Tyr Gly Ile Val Leu Asp Ala Gly Ser Ser His
                580                 585                 590
Thr Asn Leu Tyr Ile Tyr Lys Trp Pro Ala Glu Lys Glu Asn Asp Thr
                595                 600                 605
Gly Val Val Gln Gln Leu Glu Glu Cys Gln Val Lys Gly Pro Gly Ile
                610                 615                 620
```

Ser Lys Tyr Ala Gln Lys Thr Asp Glu Ile Gly Ala Tyr Leu Ala Glu
625                 630                 635                 640

Cys Met Glu Leu Ser Thr Glu Leu Ile Pro Thr Ser Lys His His Gln
            645                 650                 655

Thr Pro Val Tyr Leu Gly Ala Thr Ala Gly Met Arg Leu Leu Arg Met
        660                 665                 670

Glu Ser Glu Gln Ser Ala Asp Glu Val Leu Ala Ala Val Ser Thr Ser
            675                 680                 685

Leu Lys Ser Tyr Pro Phe Asp Phe Gln Gly Ala Lys Ile Ile Thr Gly
        690                 695                 700

Gln Glu Gly Ala Tyr Gly Trp Ile Thr Ile Asn Tyr Leu Leu Gly
705                 710                 715                 720

Arg Phe Thr Gln Glu Gln Ser Trp Leu Ser Leu Ile Ser Asp Ser Gln
                725                 730                 735

Lys Gln Glu Thr Phe Gly Ala Leu Asp Leu Gly Gly Ala Ser Thr Gln
            740                 745                 750

Ile Thr Phe Val Pro Gln Asn Ser Thr Ile Glu Ser Pro Glu Asn Ser
        755                 760                 765

Leu Gln Phe Arg Leu Tyr Gly Glu Asp Tyr Thr Val Tyr Thr His Ser
770                 775                 780

Phe Leu Cys Tyr Gly Lys Asp Gln Ala Leu Trp Gln Lys Leu Ala Lys
785                 790                 795                 800

Asp Ile Gln Val Ser Ser Gly Gly Val Leu Lys Asp Pro Cys Phe Asn
                805                 810                 815

Pro Gly Tyr Glu Lys Val Val Asn Val Ser Glu Leu Tyr Gly Thr Pro
            820                 825                 830

Cys Thr Lys Arg Phe Glu Lys Lys Leu Pro Phe Asp Gln Phe Arg Ile
        835                 840                 845

Gln Gly Thr Gly Asp Tyr Glu Gln Cys His Gln Ser Ile Leu Glu Leu
850                 855                 860

Phe Asn Asn Ser His Cys Pro Tyr Ser Gln Cys Ala Phe Asn Gly Val
865                 870                 875                 880

Phe Leu Pro Pro Leu His Gly Ser Phe Gly Ala Phe Ser Ala Phe Tyr
                885                 890                 895

Phe Val Met Asp Phe Lys Lys Val Ala Lys Asn Ser Val Ile Ser
            900                 905                 910

Gln Glu Lys Met Thr Glu Ile Thr Lys Asn Phe Cys Ser Lys Ser Trp
        915                 920                 925

Glu Glu Thr Lys Thr Ser Tyr Pro Ser Val Lys Glu Lys Tyr Leu Ser
930                 935                 940

Glu Tyr Cys Phe Ser Gly Ala Tyr Ile Leu Ser Leu Leu Gln Gly Tyr
945                 950                 955                 960

Asn Phe Thr Asp Ser Ser Trp Glu Gln Ile His Phe Met Gly Lys Ile
                965                 970                 975

Lys Asp Ser Asn Ala Gly Trp Thr Leu Gly Tyr Met Leu Asn Leu Thr
            980                 985                 990

Asn Met Ile Pro Ala Glu Gln Pro  Leu Ser Pro Leu  Pro His Ser
        995                 1000                1005

Thr

<210> SEQ ID NO 18
<211> LENGTH: 3030
<212> TYPE: DNA

<213> ORGANISM: Artificial
<220> FEATURE:
<223> OTHER INFORMATION: soluble CD73-CD39 fusion derived from mus musculus, codon optimized

<400> SEQUENCE: 18

```
atgcctagta gcgtgagttg ggggattctg ctgctggctg gtctctgctg cctggtgccc      60
gtgagtctcg ccgagtggga actgacaatc ctgcacacca atgacgtgca tagtcggctc     120
gagcagacat cagacgatag cactaagtgc ctgaacgcca gcctgtgcgt gggaggagtc     180
gcaagactgt tcacaaaggt gcagcagatc cggaagagg  aacctaatgt cctgtttctc     240
gacgctggcg atcagtacca gggaacaatc tggttcaccg tgtacaaggg cctggaggtc     300
gcacacttta tgaacattct ggggtacgac gctatggcac tcggtaatca tgagttcgac     360
aacggggtgg aaggtctgat cgatcctctg ctccggaatg tgaaatttcc aatcctgtca     420
gcaaacatta aggcacgagg accactggca caccagatca gcggtctgtt cctcccctcc     480
aaagtgctgt ctgtcggggg cgaggtggtc ggcattgtgg atacacctc  taaggaaaca     540
cccttcctga gtaatcctgg cactaacctc gtgtttgagg acgaaatcag tgctctgcag     600
cccgaggtgg ataagctgaa aaccctcaat gtcaacaaga tcattgctct ggggcactct     660
ggtttcgaaa tggacaagct gatcgcacag aaagtgagag gcgtcgatat tgtggtcggc     720
ggacatagta tactttcct  gtacaccggc aaccccctt  caaggaggt  gccagccgga     780
aaatatccct ttatcgtgac cgctgacgat ggacggcagg tccctgtggt ccaggcctac     840
gctttcggca gtacctggg  atatctcaaa gtggagtttg acgataaggg caacgtcatt     900
acatcctatg aaatcccat  cctgctcaac agctccattc ctgaagacgc tactatcaaa     960
gcagatatta tcagtggag  gatcaagctg acaactact  ccactcagga gctggggaga    1020
accatcgtgt acctggatgg ctctacccag acatgcaggt tcagagaatg taatatgggc    1080
aacctgatct gcgacgccat gattaacaat aacctgcgac acccagatga gatgttttgg    1140
aatcatgtga gcatgtgcat cgtcaacggg ggtggcatca ggtcccctat tgacgagaag    1200
aataacggaa ctattacctg gaaaaacctg gccgctgtgc tcccattcgg agggacattt    1260
gatctggtgc agctcaaggg gagcactctg aagaaagcct cgagcactc  agtgcatcgc    1320
tacgggcaga gcacaggtga atttctgcaa gtgggtggca tccacgtggt ctatgacatt    1380
aatcgaaaac catggaacag ggtggtccag ctggaggtgc tctgcaccaa gtgtcgagtc    1440
ccaatctacg agcccctgga atggacaag  gtgtacaaag tcacactgcc cagctatctc    1500
gccaacggag gggatggatt ccagatgatt aaggacagc  tgctcaaaca tgattctggg    1560
gaccaggata tctccgtggt ctctgagtac attagtaaga tgaaagtggt ctatccagct    1620
gtggaaggca ggatcaagtt cgctagcggt ggaggagcag gaggtggagc tggaggggt     1680
gcaggcggag gggccggtgg cggaaccggt actcagaaca gcctctgcc  agagaacgtg    1740
aagtacggga tcgtcctgga cgccggttct agtcacacca atctctacat ctacaagtgg    1800
cccgctgaga agaaaacga  tacaggcgtg gtccagcagc tggaggaatg ccaggtgaag    1860
gggcctggta tctctaagta cgcccagaaa accgacgaga ttggagctta tctggcagag    1920
tgtatggaac tgtccaccga actcatccca acatctaagc caccatcagac acccgtgtac    1980
ctgggagcaa ctgcaggaat gcgactgctc cgcatggaga gtgaacagtc agctgacgag    2040
gtgctggcag ccgtcagtac ttcactcaaa agctatccct cgatttttca gggcgcaaag    2100
atcattaccg gacaggagga aggcgcctac ggatggatca ctattaacta tctgctcggg    2160
```

```
aggttcaccc aggagcagag ctggctgtcc ctcatcagcg actcccagaa gcaggaaaca    2220
ttcggcgctc tggatctcgg gggtgcatct actcagatca cctttgtgcc tcagaatagt    2280
actattgagt caccagaaaa cagcctgcag ttcagactct acggcgagga ctacacagtg    2340
tatactcaca gctttctgtg ctatggaaag gaccaggccc tgtggcagaa gctcgctaaa    2400
gatatccagg tgtcaagcgg cggagtcctg aaagatcctt gcttcaatcc agggtacgag    2460
aaggtggtca acgtgtccga actgtatggc accccctgta caaagaggtt cgagaagaaa    2520 ctgccttttcg accagtttcg aatccagggc accggagatt acgagcagtg tcaccagtct    2580
attctggaac tcttcaataa ctcccattgc ccctattctc agtgtgcctt caacggcgtg    2640
tttctgccac ccctccacgg gagtttcggt gccttttcag ctttctactt tgtgatggac    2700
ttctttaaga agtggctaa gaattctgtc atcagtcagg agaagatgac tgaaattacc    2760
aagaacttct gctctaaaag ttgggaggaa accaagacat catatcctag cgtgaaggag    2820
aaatacctga gcgaatattg ttttttccgga gcctacatcc tgtccctgct ccagggtat    2880 aatttcacag actcctcttg ggagcagatc cacttcatgg gcaagatcaa ggatagcaac    2940
gcagggtgga ccctgggtta catgctgaat ctcacaaaca tgatcccagc cgaacagccc    3000
ctgtcccctc cactgcctca ctccacctaa                                     3030
```

<210> SEQ ID NO 19
<211> LENGTH: 1009
<212> TYPE: PRT
<213> ORGANISM: Artificial
<220> FEATURE:
<223> OTHER INFORMATION: soluble CD73-CD39 fusion derived from homo sapiens

<400> SEQUENCE: 19

```
Met Pro Ser Ser Val Ser Trp Gly Ile Leu Leu Leu Ala Gly Leu Cys
1               5                   10                  15

Cys Leu Val Pro Val Ser Leu Ala Glu Trp Glu Leu Thr Ile Leu His
            20                  25                  30

Thr Asn Asp Val His Ser Arg Leu Glu Gln Thr Ser Glu Asp Ser Ser
        35                  40                  45

Lys Cys Val Asn Ala Ser Arg Cys Met Gly Gly Val Ala Arg Leu Phe
    50                  55                  60

Thr Lys Val Gln Gln Ile Arg Arg Ala Glu Pro Asn Val Leu Leu Leu
65                  70                  75                  80

Asp Ala Gly Asp Gln Tyr Gln Gly Thr Ile Trp Phe Thr Val Tyr Lys
                85                  90                  95

Gly Ala Glu Val Ala His Phe Met Asn Ala Leu Arg Tyr Asp Ala Met
            100                 105                 110

Ala Leu Gly Asn His Glu Phe Asp Asn Gly Val Glu Gly Leu Ile Glu
        115                 120                 125

Pro Leu Leu Lys Glu Ala Lys Phe Pro Ile Leu Ser Ala Asn Ile Lys
    130                 135                 140

Ala Lys Gly Pro Leu Ala Ser Gln Ile Ser Gly Leu Tyr Leu Pro Tyr
145                 150                 155                 160

Lys Val Leu Pro Val Gly Asp Glu Val Val Gly Ile Val Gly Tyr Thr
                165                 170                 175

Ser Lys Glu Thr Pro Phe Leu Ser Asn Pro Gly Thr Asn Leu Val Phe
            180                 185                 190

Glu Asp Glu Ile Thr Ala Leu Gln Pro Glu Val Asp Lys Leu Lys Thr
        195                 200                 205
```

```
Leu Asn Val Asn Lys Ile Ile Ala Leu Gly His Ser Gly Phe Glu Met
        210                 215                 220

Asp Lys Leu Ile Ala Gln Lys Val Arg Gly Val Asp Val Val Gly
225                 230                 235                 240

Gly His Ser Asn Thr Phe Leu Tyr Thr Gly Asn Pro Pro Ser Lys Glu
                245                 250                 255

Val Pro Ala Gly Lys Tyr Pro Phe Ile Val Thr Ser Asp Asp Gly Arg
            260                 265                 270

Lys Val Pro Val Val Gln Ala Tyr Ala Phe Gly Lys Tyr Leu Gly Tyr
        275                 280                 285

Leu Lys Ile Glu Phe Asp Glu Arg Gly Asn Val Ile Ser Ser His Gly
    290                 295                 300

Asn Pro Ile Leu Leu Asn Ser Ser Ile Pro Glu Asp Pro Ser Ile Lys
305                 310                 315                 320

Ala Asp Ile Asn Lys Trp Arg Ile Lys Leu Asp Asn Tyr Ser Thr Gln
                325                 330                 335

Glu Leu Gly Lys Thr Ile Val Tyr Leu Asp Gly Ser Ser Gln Ser Cys
            340                 345                 350

Arg Phe Arg Glu Cys Asn Met Gly Asn Leu Ile Cys Asp Ala Met Ile
        355                 360                 365

Asn Asn Asn Leu Arg His Ala Asp Glu Thr Phe Trp Asn His Val Ser
370                 375                 380

Met Cys Ile Leu Asn Gly Gly Ile Arg Ser Pro Ile Asp Glu Arg
385                 390                 395                 400

Asn Asn Gly Thr Ile Thr Trp Glu Asn Leu Ala Ala Val Leu Pro Phe
                405                 410                 415

Gly Gly Thr Phe Asp Leu Val Gln Leu Lys Gly Ser Thr Leu Lys Lys
            420                 425                 430

Ala Phe Glu His Ser Val His Arg Tyr Gly Gln Ser Thr Gly Glu Phe
        435                 440                 445

Leu Gln Val Gly Gly Ile His Val Val Tyr Asp Leu Ser Arg Lys Pro
    450                 455                 460

Gly Asp Arg Val Val Lys Leu Asp Val Leu Cys Thr Lys Cys Arg Val
465                 470                 475                 480

Pro Ser Tyr Asp Pro Leu Lys Met Asp Glu Val Tyr Lys Val Ile Leu
                485                 490                 495

Pro Asn Phe Leu Ala Asn Gly Asp Gly Phe Gln Met Ile Lys Asp
            500                 505                 510

Glu Leu Leu Arg His Asp Ser Gly Asp Gln Asp Ile Asn Val Val Ser
        515                 520                 525

Thr Tyr Ile Ser Lys Met Lys Val Ile Tyr Pro Ala Val Glu Gly Arg
    530                 535                 540

Ile Lys Phe Ala Ser Gly Gly Ala Gly Gly Ala Gly Gly
545                 550                 555                 560

Ala Gly Gly Gly Ala Gly Gly Thr Gly Thr Gln Asn Lys Ala Leu
                565                 570                 575

Pro Glu Asn Val Lys Tyr Gly Ile Val Leu Asp Ala Gly Ser Ser His
            580                 585                 590

Thr Ser Leu Tyr Ile Tyr Lys Trp Pro Ala Glu Lys Glu Asn Asp Thr
        595                 600                 605

Gly Val Val His Gln Val Glu Glu Cys Arg Val Lys Gly Pro Gly Ile
    610                 615                 620
```

```
Ser Lys Phe Val Gln Lys Val Asn Glu Ile Gly Ile Tyr Leu Thr Asp
625                 630                 635                 640

Cys Met Glu Arg Ala Arg Glu Val Ile Pro Arg Ser Gln His Gln Glu
            645                 650                 655

Thr Pro Val Tyr Leu Gly Ala Thr Ala Gly Met Arg Leu Leu Arg Met
        660                 665                 670

Glu Ser Glu Glu Leu Ala Asp Arg Val Leu Asp Val Val Glu Arg Ser
    675                 680                 685

Leu Ser Asn Tyr Pro Phe Asp Phe Gln Gly Ala Arg Ile Ile Thr Gly
690                 695                 700

Gln Glu Glu Gly Ala Tyr Gly Trp Ile Thr Ile Asn Tyr Leu Leu Gly
705                 710                 715                 720

Lys Phe Ser Gln Lys Thr Arg Trp Phe Ser Ile Val Pro Tyr Glu Thr
            725                 730                 735

Asn Asn Gln Glu Thr Phe Gly Ala Leu Asp Leu Gly Gly Ala Ser Thr
            740                 745                 750

Gln Val Thr Phe Val Pro Gln Asn Gln Thr Ile Glu Ser Pro Asp Asn
    755                 760                 765

Ala Leu Gln Phe Arg Leu Tyr Gly Lys Asp Tyr Asn Val Tyr Thr His
770                 775                 780

Ser Phe Leu Cys Tyr Gly Lys Asp Gln Ala Leu Trp Gln Lys Leu Ala
785                 790                 795                 800

Lys Asp Ile Gln Val Ala Ser Asn Glu Ile Leu Arg Asp Pro Cys Phe
            805                 810                 815

His Pro Gly Tyr Lys Lys Val Val Asn Val Ser Asp Leu Tyr Lys Thr
            820                 825                 830

Pro Cys Thr Lys Arg Phe Glu Met Thr Leu Pro Phe Gln Gln Phe Glu
    835                 840                 845

Ile Gln Gly Ile Gly Asn Tyr Gln Gln Cys His Gln Ser Ile Leu Glu
850                 855                 860

Leu Phe Asn Thr Ser Tyr Cys Pro Tyr Ser Gln Cys Ala Phe Asn Gly
865                 870                 875                 880

Ile Phe Leu Pro Pro Leu Gln Gly Asp Phe Gly Ala Phe Ser Ala Phe
            885                 890                 895

Tyr Phe Val Met Lys Phe Leu Asn Leu Thr Ser Glu Lys Val Ser Gln
            900                 905                 910

Glu Lys Val Thr Glu Met Met Lys Lys Phe Cys Ala Gln Pro Trp Glu
    915                 920                 925

Glu Ile Lys Thr Ser Tyr Ala Gly Val Lys Glu Lys Tyr Leu Ser Glu
930                 935                 940

Tyr Cys Phe Ser Gly Thr Tyr Ile Leu Ser Leu Leu Leu Gln Gly Tyr
945                 950                 955                 960

His Phe Thr Ala Asp Ser Trp Glu His Ile His Phe Ile Gly Lys Ile
            965                 970                 975

Gln Gly Ser Asp Ala Gly Trp Thr Leu Gly Tyr Met Leu Asn Leu Thr
            980                 985                 990

Asn Met Ile Pro Ala Glu Gln Pro Leu Ser Thr Pro Leu Ser His Ser
    995                 1000                1005

Thr

<210> SEQ ID NO 20
<211> LENGTH: 3030
<212> TYPE: DNA
<213> ORGANISM: Artificial
```

<220> FEATURE:
<223> OTHER INFORMATION: soluble CD73-CD39 fusion derived from homo sapiens, codon optimized

<400> SEQUENCE: 20

```
atgcccagca gcgtgagctg gggcatcctg ctgctggccg gcctgtgctg cctggtgccc      60
gtgagcctgg ccgagtggga gctgaccatc ctgcacacca cgacgtgca cagcagactg     120
gagcagacca gcgaggacag cagcaagtgc gtgaacgcca gcagatgcat gggcggcgtg     180
gccagactgt tcaccaaggt gcagcagatc agaagagccg agcccaacgt gctgctgctg     240
gacgccggcg accagtacca gggcaccatc tggttcaccg tgtacaaggg cgccgaggtg     300
gcccacttca tgaacgccct gagatacgac gccatggccc tgggcaacca cgagttcgac     360
aacggcgtgg agggcctgat cgagcccctg ctgaaggagg ccaagttccc catcctgagc     420
gccaacatca aggccaaggg ccccctggcc agccagatca gcggcctgta cctgccctac     480
aaggtgctgc ccgtgggcga cgaggtggtg ggcatcgtgg gctacaccag caaggagacc     540
cccttcctga gcaaccccgg caccaacctg gtgttcgagg acgagatcac cgccctgcag     600
cccgaggtgg acaagctgaa gaccctgaac gtgaacaaga tcatcgccct gggccacagc     660
ggcttcgaga tggacaagct gatcgcccag aaggtgagag gcgtggacgt ggtggtgggc     720
ggccacagca acaccttcct gtacaccggc aaccccccca gcaaggaggt gcccgccggc     780
aagtacccct tcatcgtgac cagcgacgac ggcagaaagg tgcccgtggt gcaggcctac     840
gccttcggca gtacctgggc tacctgaag atcgagttcg acgagagagg caacgtgatc     900
agcagccacg gcaaccccat cctgctgaac agcagcatcc ccgaggaccc cagcatcaag     960
gccgacatca caagtggag aatcaagctg gacaactaca gcacccagga gctgggcaag    1020
accatcgtgt acctggacgg cagcagccag agctgcagat tcagagagtg caacatgggc    1080
aacctgatct gcgacgccat gatcaacaac aacctgagac acgccgacga ccttctgg     1140
aaccacgtga catgtgcat cctgaacggc ggcggcatca gaagcccat cgacgagaga    1200
aacaacggca ccatcacctg ggagaacctg gccgccgtgc tgcccttcgg cggcaccttc    1260
gacctggtgc agctgaaggg cagcacctg aagaaggcct cgagcacag cgtgcacaga    1320
tacggccaga gcaccggcga gttcctgcag gtgggcggca tccacgtggt gtacgacctg    1380
agcagaaagc ccggcgacag agtggtgaag ctggacgtgc tgtgcaccaa gtgcagagtg    1440
cccagctacg accccctgaa gatggacgag gtgtacaagg tgatcctgcc caacttcctg    1500
gccaacggcg cgacggctt ccagatgatc aaggacgagc tgctgagaca cgacagcggc    1560
gaccaggaca tcaacgtggt gagcacctac atcagcaaga tgaaggtgat ctaccccgcc    1620
gtggagggca gaatcaagtt cgccagcggc ggcggcccg cggcggcgc cggcggcggc    1680
gccggcggcg cgccggcgg cggcaccggc acccagaaca aggccctgcc cgagaacgtg    1740
aagtacggca tcgtgctgga cgccggcagc agccacacca gcctgtacat ctacaagtgg    1800
cccgccgaga aggagaacga caccggcgtg gtgcaccagt ggaggagtg cagagtgaag    1860
ggccccggca tcagcaagtt cgtgcagaag gtgaacgaga tcggcatcta cctgaccgac    1920
tgcatggaga gagccagaga ggtgatcccc agaagccagc accaggagac ccccgtgtac    1980
ctgggcgcca ccgccggcat gagactgctg agaatggaga gcgaggagct ggccgacaga    2040
gtgctggacg tggtggagag aagcctgagc aactacccct tcgacttcca gggcgccaga    2100
atcatcaccg gccaggagga gggcgcctac ggctggatca ccatcaacta cctgctgggc    2160
aagttcagcc agaagaccag atggttcagc atcgtgccct acgagaccaa caaccaggag    2220
```

-continued

```
accttcggcg ccctggacct gggcggcgcc agcacccagg tgaccttcgt gccccagaac    2280
cagaccatcg agagccccga caacgccctg cagttcagac tgtacggcaa ggactacaac    2340
gtgtacaccc acagcttcct gtgctacggc aaggaccagg ccctgtggca gaagctggcc    2400
aaggacatcc aggtggccag caacgagatc ctgagagacc cctgcttcca ccccggctac    2460
aagaaggtgg tgaacgtgag cgacctgtac aagacccccct gcaccaagag attcgagatg    2520
accctgccct tccagcagtt cgagatccag ggcatcggca actaccagca gtgccaccag    2580
agcatcctgg agctgttcaa caccagctac tgccctaca gccagtgcgc cttcaacggc    2640
atcttcctgc ccccctgca gggcgacttc ggcgccttca cgccttcta cttcgtgatg    2700 aagttcctga acctgaccag cgagaaggtg agccaggaga aggtgaccga gatgatgaag    2760
aagttctgcg cccagccctg ggaggagatc aagaccagct acgccggcgt gaaggagaag    2820
tacctgagcg agtactgctt cagcggcacc tacatcctga gcctgctgct gcagggctac    2880
cacttcaccg ccgacagctg ggagcacatc cacttcatcg gcaagatcca gggcagcgac    2940
gccggctgga ccctgggcta catgctgaac ctgaccaaca tgatccccgc cgagcagccc    3000
ctgagcaccc ccctgagcca cagcacctga                                       3030

<210> SEQ ID NO 21
<211> LENGTH: 21
<212> TYPE: PRT
<213> ORGANISM: Artificial
<220> FEATURE:
<223> OTHER INFORMATION: linker

<400> SEQUENCE: 21

Ala Ser Gly Gly Gly Ala Gly Gly Ala Gly Gly Ala Gly Gly
1               5                   10                  15

Gly Ala Gly Gly Gly
            20

<210> SEQ ID NO 22
<211> LENGTH: 24
<212> TYPE: PRT
<213> ORGANISM: Artificial
<220> FEATURE:
<223> OTHER INFORMATION: hAAT signal sequence

<400> SEQUENCE: 22

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 23
<211> LENGTH: 166
<212> TYPE: DNA
<213> ORGANISM: Artificial
<220> FEATURE:
<223> OTHER INFORMATION: promoter

<400> SEQUENCE: 23
ctagcaggcc tcgagggac tttccacaag gggactttcc gtcgagggga ctttccacaa      60
ggggactttc cgtcgagggg actttccaca aggggacttt ccgtcgaggc ctgtaggcgt    120
gtacggtggg aggcttatat aagcagagct caagcttggt accgag                   166

<210> SEQ ID NO 24
```

```
<211> LENGTH: 130
<212> TYPE: DNA
<213> ORGANISM: Artificial
<220> FEATURE:
<223> OTHER INFORMATION: single stranded AAV2 ITR, 5' ITR

<400> SEQUENCE: 24
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 25
<211> LENGTH: 142
<212> TYPE: DNA
<213> ORGANISM: Artificial
<220> FEATURE:
<223> OTHER INFORMATION: single stranded AAV2 ITR, 3'ITR

<400> SEQUENCE: 25
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc     120 gagcgcgcag ctgcctgcag gg                                              142

<210> SEQ ID NO 26
<211> LENGTH: 95
<212> TYPE: DNA
<213> ORGANISM: Artificial
<220> FEATURE:
<223> OTHER INFORMATION: double stranded AAV2 ITR, 5'ITR

<400> SEQUENCE: 26
ctgcgcgctc gctcgctcac tgaggccgcc cgggcgtcgg gcgacctttg gtcgcccggc      60
ctcagtgagc gagcgagcgc gcagagaggg agtgg                                95

<210> SEQ ID NO 27
<211> LENGTH: 142
<212> TYPE: DNA
<213> ORGANISM: Artificial
<220> FEATURE:
<223> OTHER INFORMATION: double stranded AAV2 ITR, 3' ITR

<400> SEQUENCE: 27
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc     120 gagcgcgcag ctgcctgcag gg                                              142

<210> SEQ ID NO 28
<211> LENGTH: 167
<212> TYPE: DNA
<213> ORGANISM: Artificial
<220> FEATURE:
<223> OTHER INFORMATION: AAV5 ITR: 5'ITR

<400> SEQUENCE: 28 ctctccccc tgtcgcgttc gctcgctcgc tggctcgttt ggggggggtgg cagctcaaag     60 agctgccaga cgacggccct ctggccgtcg ccccccaaa cgagccagcg agcgagcgaa     120
cgcgacaggg gggagagtgc cacactctca agcaaggggg ttttgta                  167

<210> SEQ ID NO 29
<211> LENGTH: 167
```

```
<212> TYPE: DNA
<213> ORGANISM: Artificial
<220> FEATURE:
<223> OTHER INFORMATION: AAV5 ITR: 3'ITR

<400> SEQUENCE: 29
tacaaaacct ccttgcttga gagtgtggca ctctccccccc tgtcgcgttc gctcgctcgc    60
tggctcgttt ggggggtgg cagctcaaag agctgccaga cgacggccct ctggccgtcg    120 ccccccaaa cgagccagcg agcgagcgaa cgcgacaggg gggagag                  167

<210> SEQ ID NO 30
<211> LENGTH: 2208
<212> TYPE: DNA
<213> ORGANISM: Artificial
<220> FEATURE:
<223> OTHER INFORMATION: AAV2 Capsid

<400> SEQUENCE: 30
atggctgccg atggttatct tccagattgg ctcgaggaca ctctctctga aggaataaga    60
cagtggtgga agctcaaacc tggcccacca ccaccaaagc ccgcagagcg cataaggac    120 gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt ggggcaacc tcggacgagc agtcttccag    360
gcgaaaaaga gggttcttga acctctgggc ctggttgagg aacctgttaa acgggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600 aatacgatgg ctacaggcag tggcgcacca atggcagaca taacgagggg cgccgacgga    660
gtgggtaatt cctcgggaaa ttggcattgc gattccacat ggatgggcga cagagtcatc    720
accaccagca cccgaaccct ggccctgccc acctacaaca accacctcta caaacaaatt    780
tccagccaat caggagcctc gaacgacaat cactactttg gctacagcac cccttggggg    840
tattttgact tcaacagatt ccactgccac ttttcaccac gtgactggca agactcatc    900 aacaacaact gggggattccg acccaagaga ctcaacttca gctctttaa cattcaagtc    960 aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggga gtcaggcagt aggacgctct tcatttttact gcctggagta ctttcccttct    1200 cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380 cagtttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagcacaa ggacgatgaa gaaaagtttt tcctcagag cggggttctc    1620 atctttggga agcaaggctc agagaaaaca aatgtggaca ttgaaaaggt catgattaca    1680
```

-continued

```
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc agggccccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa               2208
```

<210> SEQ ID NO 31
<211> LENGTH: 735
<212> TYPE: PRT
<213> ORGANISM: Artificial
<220> FEATURE:
<223> OTHER INFORMATION: AAV2 VP1

<400> SEQUENCE: 31

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
```

```
                    690                 695                 700
Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 32
<211> LENGTH: 598
<212> TYPE: PRT
<213> ORGANISM: Artificial
<220> FEATURE:
<223> OTHER INFORMATION: AAV2 VP2

<400> SEQUENCE: 32

Thr Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
                20                  25                  30

Arg Leu Asn Phe Gly Gln Thr Gly Asp Ala Asp Ser Val Pro Asp Pro
            35                  40                  45

Gln Pro Leu Gly Gln Pro Pro Ala Ala Pro Ser Gly Leu Gly Thr Asn
50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
```

-continued

```
                325                 330                 335
Ser Arg Asn Trp Leu Pro Gly Pro Cys Tyr Arg Gln Gln Arg Val Ser
            340                 345                 350

Lys Thr Ser Ala Asp Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
            500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
    530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595
```

```
<210> SEQ ID NO 33
<211> LENGTH: 533
<212> TYPE: PRT
<213> ORGANISM: Artificial
<220> FEATURE:
<223> OTHER INFORMATION: AAV2 VP3

<400> SEQUENCE: 33

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
```

-continued

```
                85                  90                  95
Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
            115                 120                 125

Thr Ile Ala Asn Asn Leu Thr Ser Thr Val Gln Val Phe Thr Asp Ser
            130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
            195                 200                 205

Phe Ser Tyr Thr Phe Glu Asp Val Pro Phe His Ser Ser Tyr Ala His
210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
            275                 280                 285

Thr Ser Ala Asp Asn Asn Asn Ser Glu Tyr Ser Trp Thr Gly Ala Thr
290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
            355                 360                 365

Val Ala Thr Glu Gln Tyr Gly Ser Val Ser Thr Asn Leu Gln Arg Gly
            370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Gln Ile Leu Ile Lys Asn
            435                 440                 445

Thr Pro Val Pro Ala Asn Pro Ser Thr Thr Phe Ser Ala Ala Lys Phe
            450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510
```

Asp Thr Asn Gly Val Tyr Ser Glu Pro Arg Pro Ile Gly Thr Arg Tyr
        515                 520                 525

Leu Thr Arg Asn Leu
    530

<210> SEQ ID NO 34
<211> LENGTH: 2190
<212> TYPE: DNA
<213> ORGANISM: Artificial
<220> FEATURE:
<223> OTHER INFORMATION: AAV5 capsid

<400> SEQUENCE: 34

```
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa ccccctacctc aagtacaacc acgcggacgc cgagtttcag    300
gagaagctcg ccgacgacac atccttcggg ggaaacctcg gaaaggcagt ctttcaggcc     360
aagaaaaggg ttctcgaacc ttttggcctg gttgaagagg gtgctaagac gtttaaacgc     420
gatcgcgccc ctaccggaaa gcggatagac gaccactttc aaaaagaaa gaaggctcgg     480
accgaagagg actccaagcc ttccacctcg tcagacgccg aagctggacc cagcggatcc     540
cagcagctgc aaatcccagc ccaaccagcc tcaagtttgg gagctgatac aatgtctgcg     600
ggaggtggcg gcccattggg cgacaataac caaggtgccg atggagtggg caatgcctcg     660
ggagattggc attgcgattc cacgtggatg ggggacagag tcgtcaccaa gtccacccga     720
acctgggtgc tgcccagcta caacaaccac cagtaccgag agatcaaaag cggctccgtc     780
gacggaagca acgccaacgc ctactttgga tacagcaccc cctgggggta ctttgacttt     840
aaccgcttcc acagccactg gagccccga gactggcaaa gactcatcaa caactactgg     900
ggcttcagac cccggtccct cagagtcaaa atcttcaaca ttcaagtcaa agaggtcacg     960
gtgcaggact ccaccaccac catcgccaac aacctcacct ccaccgtcca agtgtttacg    1020
gacgacgact accagctgcc ctacgtcgtc ggcaacggga ccgagggatg cctgccggcc    1080
ttccctccgc aggtctttac gctgccgcag tacggttacg cgacgctgaa ccgcgacaac    1140
acagaaaatc ccaccgagag gagcagcttc ttctgcctag agtactttcc cagcaagatg    1200
ctgagaacgg gcaacaactt tgagtttacc tacaactttg aggaggtgcc cttccactcc    1260
agcttcgctc ccagtcagaa cctcttcaag ctggccaacc cgctggtgga ccagtacttg    1320
taccgcttcg tgagcacaaa taacactggc ggagtccagt tcaacaagaa cctggccggg    1380
agatacgcca acacctacaa aaactggttc ccggggccca tgggccgaac ccagggctgg    1440
aacctgggct ccgggtcaa cgcgccagt gtcagcgcct cgccacgac caataggatg    1500
gagctcgagg gcgcgagtta ccaggtgccc ccgcagccga cggcatgac caacaacctc    1560
cagggcagca acacctatgc cctggagaac actatgatct tcaacagcca gccggcgaac    1620
ccgggcacca ccgccacgta cctcgagggc aacatgctca tcaccagcga gagcgagacg    1680
cagccggtga accgcgtggc gtacaacgtc ggcgggcaga tggccaccaa caaccagagc    1740
tccaccactg ccccgcgac cggcacgtac aacctccagg aaatcgtgcc cggcagcgtg    1800
tggatggaga gggacgtgta cctccaagga cccatctggg ccaagatccc agagacgggg    1860
```

```
gcgcactttc accoctctcc ggccatgggc ggattcggac tcaaacaccc accgcccatg    1920
atgctcatca agaacacgcc tgtgcccgga aatatcacca gcttctcgga cgtgcccgtc    1980
agcagcttca tcacccagta cagcaccggg caggtcaccg tggagatgga gtgggagctc    2040
aagaaggaaa actccaagag gtggaaccca gagatccagt acacaaacaa ctacaacgac    2100
ccccagtttg tggactttgc cccggacagc accggggaat acagaaccac cagacctatc    2160
ggaacccgat accttacccg acccctttaa                                     2190
```

<210> SEQ ID NO 35
<211> LENGTH: 729
<212> TYPE: PRT
<213> ORGANISM: Artificial
<220> FEATURE:
<223> OTHER INFORMATION: AAV5 VP1

<400> SEQUENCE: 35

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Phe Lys Arg Asp Arg Ala Pro
130                 135                 140

Thr Gly Lys Arg Ile Asp Asp His Phe Pro Lys Arg Lys Lys Ala Arg
145                 150                 155                 160

Thr Glu Glu Asp Ser Lys Pro Ser Thr Ser Ser Asp Ala Glu Ala Gly
                165                 170                 175

Pro Ser Gly Ser Gln Gln Leu Gln Ile Pro Ala Gln Pro Ala Ser Ser
            180                 185                 190

Leu Gly Ala Asp Thr Met Ser Ala Gly Gly Gly Gly Pro Leu Gly Asp
        195                 200                 205

Asn Asn Gln Gly Ala Asp Gly Val Gly Asn Ala Ser Gly Asp Trp His
210                 215                 220

Cys Asp Ser Thr Trp Met Gly Asp Arg Val Val Thr Lys Ser Thr Arg
225                 230                 235                 240

Thr Trp Val Leu Pro Ser Tyr Asn Asn His Gln Tyr Arg Glu Ile Lys
                245                 250                 255

Ser Gly Ser Val Asp Gly Ser Asn Ala Asn Ala Tyr Phe Gly Tyr Ser
            260                 265                 270

Thr Pro Trp Gly Tyr Phe Asp Phe Asn Arg Phe His Ser His Trp Ser
        275                 280                 285

Pro Arg Asp Trp Gln Arg Leu Ile Asn Asn Tyr Trp Gly Phe Arg Pro
290                 295                 300
```

```
Arg Ser Leu Arg Val Lys Ile Phe Asn Ile Gln Val Lys Glu Val Thr
305                 310                 315                 320

Val Gln Asp Ser Thr Thr Thr Ile Ala Asn Asn Leu Thr Ser Thr Val
            325                 330                 335

Gln Val Phe Thr Asp Asp Tyr Gln Leu Pro Tyr Val Val Gly Asn
            340                 345                 350

Gly Thr Glu Gly Cys Leu Pro Ala Phe Pro Pro Gln Val Phe Thr Leu
            355                 360                 365

Pro Gln Tyr Gly Tyr Ala Thr Leu Asn Arg Asp Asn Thr Glu Asn Pro
            370                 375                 380

Thr Glu Arg Ser Ser Phe Phe Cys Leu Glu Tyr Phe Pro Ser Lys Met
385                 390                 395                 400

Leu Arg Thr Gly Asn Asn Phe Glu Phe Thr Tyr Asn Phe Glu Glu Val
                405                 410                 415

Pro Phe His Ser Ser Phe Ala Pro Ser Gln Asn Leu Phe Lys Leu Ala
            420                 425                 430

Asn Pro Leu Val Asp Gln Tyr Leu Tyr Arg Phe Val Ser Thr Asn Asn
            435                 440                 445

Thr Gly Gly Val Gln Phe Asn Lys Asn Leu Ala Gly Arg Tyr Ala Asn
450                 455                 460

Thr Tyr Lys Asn Trp Phe Pro Gly Pro Met Gly Arg Thr Gln Gly Trp
465                 470                 475                 480

Asn Leu Gly Ser Gly Val Asn Arg Ala Ser Val Ser Ala Phe Ala Thr
                485                 490                 495

Thr Asn Arg Met Glu Leu Glu Gly Ala Ser Tyr Gln Val Pro Pro Gln
            500                 505                 510

Pro Asn Gly Met Thr Asn Asn Leu Gln Gly Ser Asn Thr Tyr Ala Leu
            515                 520                 525

Glu Asn Thr Met Ile Phe Asn Ser Gln Pro Ala Asn Pro Gly Thr Thr
            530                 535                 540

Ala Thr Tyr Leu Glu Gly Asn Met Leu Ile Thr Ser Glu Ser Glu Thr
545                 550                 555                 560

Gln Pro Val Asn Arg Val Ala Tyr Asn Val Gly Gly Gln Met Ala Thr
                565                 570                 575

Asn Asn Gln Ser Ser Thr Thr Ala Pro Ala Thr Gly Thr Tyr Asn Leu
            580                 585                 590

Gln Glu Ile Val Pro Gly Ser Val Trp Met Glu Arg Asp Val Tyr Leu
            595                 600                 605

Gln Gly Pro Ile Trp Ala Lys Ile Pro Glu Thr Gly Ala His Phe His
            610                 615                 620

Pro Ser Pro Ala Met Gly Gly Phe Gly Leu Lys His Pro Pro Met
625                 630                 635                 640

Met Leu Ile Lys Asn Thr Pro Val Pro Gly Asn Ile Thr Ser Phe Ser
                645                 650                 655

Asp Val Pro Val Ser Ser Phe Ile Thr Gln Tyr Ser Thr Gly Gln Val
            660                 665                 670

Thr Val Glu Met Glu Trp Glu Leu Lys Lys Glu Asn Ser Lys Arg Trp
            675                 680                 685

Asn Pro Glu Ile Gln Tyr Thr Asn Asn Tyr Asn Asp Pro Gln Phe Val
            690                 695                 700

Asp Phe Ala Pro Asp Ser Thr Gly Glu Tyr Arg Thr Thr Arg Pro Ile
705                 710                 715                 720

Gly Thr Arg Tyr Leu Thr Arg Pro Leu
```

<210> SEQ ID NO 36
<211> LENGTH: 593
<212> TYPE: PRT
<213> ORGANISM: Artificial
<220> FEATURE:
<223> OTHER INFORMATION: AAV5 VP2

<400> SEQUENCE: 36

```
Thr Phe Lys Arg Asp Arg Ala Pro Thr Gly Lys Arg Ile Asp Asp His
1               5                   10                  15

Phe Pro Lys Arg Lys Lys Ala Arg Thr Glu Glu Asp Ser Lys Pro Ser
            20                  25                  30

Thr Ser Ser Asp Ala Glu Ala Gly Pro Ser Gly Ser Gln Gln Leu Gln
        35                  40                  45

Ile Pro Ala Gln Pro Ala Ser Ser Leu Gly Ala Asp Thr Met Ser Ala
    50                  55                  60

Gly Gly Gly Gly Pro Leu Gly Asp Asn Asn Gln Gly Ala Asp Gly Val
65                  70                  75                  80

Gly Asn Ala Ser Gly Asp Trp His Cys Asp Ser Thr Trp Met Gly Asp
                85                  90                  95

Arg Val Val Thr Lys Ser Thr Arg Thr Trp Val Leu Pro Ser Tyr Asn
            100                 105                 110

Asn His Gln Tyr Arg Glu Ile Lys Ser Gly Ser Val Asp Gly Ser Asn
        115                 120                 125

Ala Asn Ala Tyr Phe Gly Tyr Ser Thr Pro Trp Gly Tyr Phe Asp Phe
    130                 135                 140

Asn Arg Phe His Ser His Trp Ser Pro Arg Asp Trp Gln Arg Leu Ile
145                 150                 155                 160

Asn Asn Tyr Trp Gly Phe Arg Pro Arg Ser Leu Arg Val Lys Ile Phe
                165                 170                 175

Asn Ile Gln Val Lys Glu Val Thr Val Gln Asp Ser Thr Thr Thr Ile
            180                 185                 190

Ala Asn Asn Leu Thr Ser Thr Val Gln Val Phe Thr Asp Asp Asp Tyr
        195                 200                 205

Gln Leu Pro Tyr Val Val Gly Asn Gly Thr Glu Gly Cys Leu Pro Ala
    210                 215                 220

Phe Pro Pro Gln Val Phe Thr Leu Pro Gln Tyr Gly Tyr Ala Thr Leu
225                 230                 235                 240

Asn Arg Asp Asn Thr Glu Asn Pro Thr Glu Arg Ser Ser Phe Phe Cys
                245                 250                 255

Leu Glu Tyr Phe Pro Ser Lys Met Leu Arg Thr Gly Asn Asn Phe Glu
            260                 265                 270

Phe Thr Tyr Asn Phe Glu Glu Val Pro Phe His Ser Ser Phe Ala Pro
        275                 280                 285

Ser Gln Asn Leu Phe Lys Leu Ala Asn Pro Leu Val Asp Gln Tyr Leu
    290                 295                 300

Tyr Arg Phe Val Ser Thr Asn Asn Thr Gly Gly Val Gln Phe Asn Lys
305                 310                 315                 320

Asn Leu Ala Gly Arg Tyr Ala Asn Thr Tyr Lys Asn Trp Phe Pro Gly
                325                 330                 335

Pro Met Gly Arg Thr Gln Gly Trp Asn Leu Gly Ser Gly Val Asn Arg
            340                 345                 350

Ala Ser Val Ser Ala Phe Ala Thr Thr Asn Arg Met Glu Leu Glu Gly
```

```
                355                 360                 365
Ala Ser Tyr Gln Val Pro Pro Gln Pro Asn Gly Met Thr Asn Asn Leu
    370                 375                 380

Gln Gly Ser Asn Thr Tyr Ala Leu Glu Asn Thr Met Ile Phe Asn Ser
385                 390                 395                 400

Gln Pro Ala Asn Pro Gly Thr Thr Ala Thr Tyr Leu Glu Gly Asn Met
                405                 410                 415

Leu Ile Thr Ser Glu Ser Glu Thr Gln Pro Val Asn Arg Val Ala Tyr
            420                 425                 430

Asn Val Gly Gly Gln Met Ala Thr Asn Asn Gln Ser Ser Thr Thr Ala
        435                 440                 445

Pro Ala Thr Gly Thr Tyr Asn Leu Gln Glu Ile Val Pro Gly Ser Val
    450                 455                 460

Trp Met Glu Arg Asp Val Tyr Leu Gln Gly Pro Ile Trp Ala Lys Ile
465                 470                 475                 480

Pro Glu Thr Gly Ala His Phe His Pro Ser Pro Ala Met Gly Gly Phe
                485                 490                 495

Gly Leu Lys His Pro Pro Pro Met Met Leu Ile Lys Asn Thr Pro Val
            500                 505                 510

Pro Gly Asn Ile Thr Ser Phe Ser Asp Val Pro Val Ser Ser Phe Ile
        515                 520                 525

Thr Gln Tyr Ser Thr Gly Gln Val Thr Val Glu Met Glu Trp Glu Leu
    530                 535                 540

Lys Lys Glu Asn Ser Lys Arg Trp Asn Pro Glu Ile Gln Tyr Thr Asn
545                 550                 555                 560

Asn Tyr Asn Asp Pro Gln Phe Val Asp Phe Ala Pro Asp Ser Thr Gly
                565                 570                 575

Glu Tyr Arg Thr Thr Arg Pro Ile Gly Thr Arg Tyr Leu Thr Arg Pro
            580                 585                 590

Leu

<210> SEQ ID NO 37
<211> LENGTH: 532
<212> TYPE: PRT
<213> ORGANISM: Artificial
<220> FEATURE:
<223> OTHER INFORMATION: AAV5 VP3

<400> SEQUENCE: 37

Met Ser Ala Gly Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
            20                  25                  30

Met Gly Asp Arg Val Val Thr Lys Ser Thr Arg Thr Trp Val Leu Pro
        35                  40                  45

Ser Tyr Asn Asn His Gln Tyr Arg Glu Ile Lys Ser Gly Ser Val Asp
    50                  55                  60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
            100                 105                 110

Lys Ile Phe Asn Ile Gln Val Lys Glu Val Thr Val Gln Asp Ser Thr
        115                 120                 125
```

-continued

```
Thr Thr Ile Ala Asn Asn Leu Thr Ser Thr Val Gln Val Phe Thr Asp
    130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
    210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu
    290                 295                 300

Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
                325                 330                 335

Phe Asn Ser Gln Pro Ala Asn Pro Gly Thr Thr Ala Thr Tyr Leu Glu
            340                 345                 350

Gly Asn Met Leu Ile Thr Ser Glu Ser Glu Thr Gln Pro Val Asn Arg
        355                 360                 365

Val Ala Tyr Asn Val Gly Gly Gln Met Ala Thr Asn Asn Gln Ser Ser
    370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
            420                 425                 430

Gly Gly Phe Gly Leu Lys His Pro Pro Met Met Leu Ile Lys Asn
        435                 440                 445

Thr Pro Val Pro Gly Asn Ile Thr Ser Phe Ser Asp Val Pro Val Ser
    450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
            500                 505                 510

Ser Thr Gly Glu Tyr Arg Thr Thr Arg Pro Ile Gly Thr Arg Tyr Leu
        515                 520                 525

Thr Arg Pro Leu
    530
```

<210> SEQ ID NO 38
<211> LENGTH: 2217
<212> TYPE: DNA
<213> ORGANISM: Artificial
<220> FEATURE:
<223> OTHER INFORMATION: AAV8 capsid

<400> SEQUENCE: 38

```
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg acccttcaa cggactcgac      180
aagggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag ccaacagcc cgccagaaaa agactcaatt ttggtcagac tggcgactca     540
gagtcagttc cagaccctca acctctcgga gaacctccag cagcgccctc tggtgtggga     600
cctaatacaa tggctgcagg cggtggcgca ccaatggcag acaataacga aggcgccgac     660
ggagtgggta gttcctcggg aaattggcat tgcgattcca catggctggg cgacagagtc     720
atcaccacca gcacccgaac ctgggccctg cccacctaca acaaccacct ctacaagcaa     780
atctccaacg gacatcgggg aggagccacc aacgacaaca cctacttcgg ctacagcacc     840
ccctgggggt attttgactt taacagattc cactgccact tttcaccacg tgactggcag     900
cgactcatca caacaactg gggattccgg cccaagagac tcagcttcaa gctcttcaac     960
atccaggtca aggaggtcac gcagaatgaa ggcaccaaga ccatcgccaa taacctcacc    1020
agcaccatcc aggtgtttac ggactcggag taccagctgc cgtacgttct cggctctgcc    1080
caccagggct gcctgcctcc gttcccggcg gacgtgttca tgattcccca gtacggctac    1140
ctaacactca caacggtag tcaggccgtg gacgctcct ccttctactg cctggaatac    1200
tttccttcgc agatgctgag aaccggcaac aacttccagt ttacttacac cttcgaggac    1260
gtgccttttc acagcagcta cgcccacagc cagagcttgg accggctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgttttt tcccagtaac    1620
gggatcctga tttttggcaa acaaaatgct gccagagaca tgcggattac agcgatgtc    1680
atgctcacca gcgaggaaga aatcaaaaacc actaaccctg tggctacaga ggaatacggt    1740
atcgtggcag ataacttgca gcagcaaaac acggctcctc aaattggaac tgtcaacagc    1800
caggggggct acccggtat ggtctggcag aaccggagac tgtacctgca gggtccatc    1860
tgggccaaga ttcctcacac ggacggcaac ttccacccgt ctccgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
```

```
atccagtaca cctccaacta ctacaaatct acaagtgtgg actttgctgt taatacagaa      2160
ggcgtgtact ctgaaccccg ccccattggc acccgttacc tcacccgtaa tctgtaa        2217
```

<210> SEQ ID NO 39
<211> LENGTH: 782
<212> TYPE: PRT
<213> ORGANISM: Artificial
<220> FEATURE:
<223> OTHER INFORMATION: AAV8 VP1

<400> SEQUENCE: 39

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
```

```
            340               345               350
Leu Pro Tyr Val Leu Gly Ser Ala His Gln Gly Cys Leu Pro Pro Phe
        355               360               365
Pro Ala Asp Val Phe Met Ile Pro Gln Tyr Gly Tyr Leu Thr Leu Asn
        370               375               380
Asn Gly Ser Gln Ala Val Gly Arg Ser Ser Phe Tyr Cys Leu Glu Tyr
385               390               395               400
Phe Pro Ser Gln Met Leu Arg Thr Gly Asn Asn Phe Gln Phe Thr Tyr
            405               410               415
Thr Phe Glu Asp Val Pro Phe His Ser Ser Tyr Ala His Ser Gln Ser
            420               425               430
Leu Asp Arg Leu Met Asn Pro Leu Ile Asp Gln Tyr Leu Tyr Tyr Leu
            435               440               445
Ser Arg Thr Gln Thr Thr Gly Gly Thr Ala Asn Thr Gln Thr Leu Gly
        450               455               460
Phe Ser Gln Gly Gly Pro Asn Thr Met Ala Asn Gln Ala Lys Asn Trp
465               470               475               480
Leu Pro Gly Pro Cys Tyr Arg Gln Gln Arg Val Ser Thr Thr Thr Gly
            485               490               495
Gln Asn Asn Asn Ser Asn Phe Ala Trp Thr Ala Gly Thr Lys Tyr His
            500               505               510
Leu Asn Gly Arg Asn Ser Leu Ala Asn Pro Gly Ile Ala Met Ala Thr
            515               520               525
His Lys Asp Asp Glu Glu Arg Phe Phe Pro Ser Asn Gly Ile Leu Ile
        530               535               540
Phe Gly Lys Gln Asn Ala Ala Arg Asp Asn Ala Asp Tyr Ser Asp Val
545               550               555               560
Met Leu Thr Ser Glu Glu Glu Ile Lys Thr Thr Asn Pro Val Ala Thr
            565               570               575
Glu Glu Tyr Gly Ile Val Ala Asp Asn Leu Gln Gln Gln Asn Thr Ala
            580               585               590
Pro Gln Ile Gly Thr Val Asn Ser Gln Gly Ala Leu Pro Gly Met Val
        595               600               605
Trp Gln Asn Arg Asp Val Tyr Leu Gln Gly Pro Ile Trp Ala Lys Ile
        610               615               620
Pro His Thr Asp Gly Asn Phe His Pro Ser Pro Leu Met Gly Gly Phe
625               630               635               640
Gly Leu Lys His Pro Pro Pro Gln Ile Leu Ile Lys Asn Thr Pro Val
            645               650               655
Pro Ala Asp Pro Pro Thr Thr Phe Asn Gln Ser Lys Leu Asn Ser Phe
            660               665               670
Ile Thr Gln Tyr Ser Thr Gly Gln Val Ser Val Glu Ile Glu Trp Glu
        675               680               685
Leu Gln Lys Glu Asn Ser Lys Arg Trp Asn Pro Glu Ile Gln Tyr Thr
        690               695               700
Ser Asn Tyr Tyr Lys Ser Thr Ser Val Asp Phe Ala Val Asn Thr Glu
705               710               715               720
Gly Val Tyr Ser Glu Pro Arg Pro Ile Gly Thr Arg Tyr Leu Thr Arg
            725               730               735
Asn Leu Met Ala Ala Asp Gly Tyr Leu Pro Asp Trp Leu Glu Asp Asn
            740               745               750
Leu Ser Glu Gly Ile Arg Glu Trp Trp Ala Leu Lys Pro Gly Ala Pro
        755               760               765
```

Lys Pro Lys Ala Asn Gln Gln Lys Gln Asp Asp Gly Arg Gly
            770                 775                 780

<210> SEQ ID NO 40
<211> LENGTH: 601
<212> TYPE: PRT
<213> ORGANISM: Artificial
<220> FEATURE:
<223> OTHER INFORMATION: AAV8 VP2

<400> SEQUENCE: 40

Thr Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Arg
            20                  25                  30

Lys Arg Leu Asn Phe Gly Gln Thr Gly Asp Ser Glu Ser Val Pro Asp
        35                  40                  45

Pro Gln Pro Leu Gly Glu Pro Pro Ala Ala Pro Ser Gly Val Gly Pro
    50                  55                  60

Asn Thr Met Ala Ala Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ala Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Ser Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Gln Phe Thr Tyr Thr Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Thr Thr Gly Gly Thr
305                 310                 315                 320

Ala Asn Thr Gln Thr Leu Gly Phe Ser Gln Gly Gly Pro Asn Thr Met
                325                 330                 335

Ala Asn Gln Ala Lys Asn Trp Leu Pro Gly Pro Cys Tyr Arg Gln Gln
            340                 345                 350

-continued

```
Arg Val Ser Thr Thr Thr Gly Gln Asn Asn Asn Ser Asn Phe Ala Trp
        355                 360                 365

Thr Ala Gly Thr Lys Tyr His Leu Asn Gly Arg Asn Ser Leu Ala Asn
    370                 375                 380

Pro Gly Ile Ala Met Ala Thr His Lys Asp Asp Glu Glu Arg Phe Phe
385                 390                 395                 400

Pro Ser Asn Gly Ile Leu Ile Phe Gly Lys Gln Asn Ala Ala Arg Asp
                405                 410                 415

Asn Ala Asp Tyr Ser Asp Val Met Leu Thr Ser Glu Glu Glu Ile Lys
            420                 425                 430

Thr Thr Asn Pro Val Ala Thr Glu Glu Tyr Gly Ile Val Ala Asp Asn
        435                 440                 445

Leu Gln Gln Gln Asn Thr Ala Pro Gln Ile Gly Thr Val Asn Ser Gln
    450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
            500                 505                 510

Leu Ile Lys Asn Thr Pro Val Pro Ala Asp Pro Pro Thr Thr Phe Asn
    515                 520                 525

Gln Ser Lys Leu Asn Ser Phe Ile Thr Gln Tyr Ser Thr Gly Gln Val
    530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Ser Val
                565                 570                 575

Asp Phe Ala Val Asn Thr Glu Gly Val Tyr Ser Glu Pro Arg Pro Ile
            580                 585                 590

Gly Thr Arg Tyr Leu Thr Arg Asn Leu
        595                 600
```

<210> SEQ ID NO 41
<211> LENGTH: 535
<212> TYPE: PRT
<213> ORGANISM: Artificial
<220> FEATURE:
<223> OTHER INFORMATION: AAV8 VP3

<400> SEQUENCE: 41

```
Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ala Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Ser
            100                 105                 110
```

-continued

```
Phe Lys Leu Phe Asn Ile Gln Val Lys Glu Val Thr Gln Asn Glu Gly
            115                 120                 125

Thr Lys Thr Ile Ala Asn Asn Leu Thr Ser Thr Ile Gln Val Phe Thr
130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
            195                 200                 205

Phe Gln Phe Thr Tyr Thr Phe Glu Asp Val Pro Phe His Ser Ser Tyr
        210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Thr Thr Gly Gly Thr Ala Asn
                245                 250                 255

Thr Gln Thr Leu Gly Phe Ser Gln Gly Gly Pro Asn Thr Met Ala Asn
            260                 265                 270

Gln Ala Lys Asn Trp Leu Pro Gly Pro Cys Tyr Arg Gln Gln Arg Val
            275                 280                 285

Ser Thr Thr Thr Gly Gln Asn Asn Asn Ser Asn Phe Ala Trp Thr Ala
        290                 295                 300

Gly Thr Lys Tyr His Leu Asn Gly Arg Asn Ser Leu Ala Asn Pro Gly
305                 310                 315                 320

Ile Ala Met Ala Thr His Lys Asp Asp Glu Glu Arg Phe Phe Pro Ser
                325                 330                 335

Asn Gly Ile Leu Ile Phe Gly Lys Gln Asn Ala Ala Arg Asp Asn Ala
            340                 345                 350

Asp Tyr Ser Asp Val Met Leu Thr Ser Glu Glu Glu Ile Lys Thr Thr
            355                 360                 365

Asn Pro Val Ala Thr Glu Glu Tyr Gly Ile Val Ala Asp Asn Leu Gln
        370                 375                 380

Gln Gln Asn Thr Ala Pro Gln Ile Gly Thr Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
            435                 440                 445

Lys Asn Thr Pro Val Pro Ala Asp Pro Pro Thr Thr Phe Asn Gln Ser
        450                 455                 460

Lys Leu Asn Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Ser Val Asp Phe
            500                 505                 510

Ala Val Asn Thr Glu Gly Val Tyr Ser Glu Pro Arg Pro Ile Gly Thr
            515                 520                 525
```

Arg Tyr Leu Thr Arg Asn Leu
    530             535

<210> SEQ ID NO 42
<211> LENGTH: 7494
<212> TYPE: DNA
<213> ORGANISM: Artificial
<220> FEATURE:
<223> OTHER INFORMATION: pAAV-CMV-CD39-2A-CD73

<400> SEQUENCE: 42

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggggttcc | tgcggccgca | cgcgtcgaca | ttgattattg | actagttatt | 180 |
| aatagtaatc | aattacgggg | tcattagttc | atagcccata | tatggagttc | cgcgttacat | 240 |
| aacttacggt | aaatggcccg | cctggctgac | cgcccaacga | ccccccgccca | ttgacgtcaa | 300 |
| taatgacgta | tgttcccata | gtaacgccaa | tagggacttt | ccattgacgt | caatgggtgg | 360 |
| actatttacg | gtaaactgcc | cacttggcag | tacatcaagt | gtatcatatg | ccaagtacgc | 420 |
| cccctattga | cgtcaatgac | ggtaaatggc | ccgcctggca | ttatgcccag | tacatgacct | 480 |
| tatgggactt | tcctacttgg | cagtacatct | acgtattagt | catcgctatt | accatggtga | 540 |
| tgcggttttg | gcagtacatc | aatgggcgtg | gatagcggtt | tgactcacgg | ggatttccaa | 600 |
| gtctccaccc | cattgacgtc | aatgggagtt | tgttttggca | ccaaaatcaa | cgggactttc | 660 |
| caaaatgtcg | taacaactcc | gccccattga | cgcaaatggg | cggtaggcgt | gtacggtggg | 720 |
| aggtctatat | aagcagagct | ctctggctaa | ctagagaacc | cactgcttac | tggcttatcg | 780 |
| aaattaatac | gactcactat | agggagaccc | aagctggcta | gttaagcttg | gtaccgagct | 840 |
| cggatcgcca | ccatgagccg | catggaggac | atcaaagact | caaaagtgaa | aagattctgc | 900 |
| tcaaaaaaca | ttctcatcat | tctgggggttt | acatcaattc | tcgctgtgat | cgcactgatt | 960 |
| gccgtcggcc | tcactcagaa | caagcccctg | cctgagaacg | tgaagtacgg | aatcgtcctg | 1020 |
| gacgctggga | gctcccacac | caatctgtac | atctacaagt | ggccagcaga | gaaagaaaac | 1080 |
| gatacaggcg | tggtccagca | gctggaggaa | tgccaggtga | agggtcccgg | catctccaag | 1140 |
| tacgcccaga | aaacagacga | gattggagct | tatctggcag | agtgtatgga | actgagcaca | 1200 |
| gaactcatcc | ccacttccaa | gcaccatcag | acacccgtgt | acctgggtgc | aactgcagga | 1260 |
| atgcgactgc | tccgcatgga | gtcagaacag | agcgccgacg | aggtgctggc | agctgtcagt | 1320 |
| acttcactca | atctctatcc | attcgatttt | cagggtgcca | agatcattac | cggccaggag | 1380 |
| gaaggagctt | acgggtggat | cactattaac | tatctgctcg | gcggttcac | ccaggagcag | 1440 |
| tcctggctgt | ctctcatcag | cgactcccag | aagcaggaaa | ccttcggcgc | tctggatctc | 1500 |
| ggcggagcaa | gcacccagat | cacatttgtg | ccacagaata | gcacaattga | gtccccccgaa | 1560 |
| aactctctgc | agttccgcct | ctacgggag | gactacaccg | tgtacaccca | ctccttttctg | 1620 |
| tgctatggca | aggaccaggc | cctgtggcag | aagctcgcta | agatatccca | ggtgtctagt | 1680 |
| gggggtgtcc | tgaaagatcc | ctgcttcaat | cctggttacg | agaaggtggt | caacgtgtct | 1740 |
| gaactgtatg | gaacaccatg | tactaagagg | ttcgagaaga | actgcccctt | cgaccagttt | 1800 |
| cgaatccagg | gaaccgggga | ttacgagcag | tgtcaccaga | gcattctgga | actcttcaac | 1860 |
| aatagccatt | gccatattc | ccagtgtgcc | ttcaacggag | tgtttctgcc | ccctctccac | 1920 |
| ggttctttcg | gcgcctttag | tgctttctac | tttgtgatgg | acttctttaa | gaaagtggct | 1980 |

```
aagaatagtg tcatctcaca ggagaagatg accgaaatca caaagaactt ctgctctaag    2040
agttgggagg aaaccaagac aagctacccc tccgtgaagg agaaatacct gtcagaatat    2100
tgttttagcg gtgcctacat cctgtccctg ctccagggct ataatttcac cgactcaagc    2160
tgggagcaga tccactttat gggcaagatc aaggattcta acgccggatg gaccctgggg    2220
tacatgctga atctcacaaa catgatccca gctgagcagc cactgtcccc accactccct    2280
cattctacct atattggcct gatggtgctc ttctccctgc tcctggtggc tgtcgcaatc    2340
acaggactgt tcatctactc taagccaagt tattttttgga aagaggcagt gggtagtggc    2400
gccacaaatt tttcactcct gaagcaggcc ggagacgtgg aggaaaaccc agggcccatg    2460
aggcctgcag ccgctaaggt gccaaaatgg ctcctgctcg cactgtccgc cctgctccct    2520
cagtggccag cagcctctgc ttgggagctg actatcctcc acaccaatga tgtgcatagt    2580
agactggaac agacctcaga cgatagcaca aagtgcctga acgccagcct gtgcgtggga    2640
ggagtcgcaa gactgttcac caaggtgcag cagatccgga aagaggaacc taatgtcctg    2700
tttctcgacg caggcgacca gtaccagggc acaatctggt tcaccgtgta caagggactg    2760
gaggtcgctc actttatgaa cattctgggt tacgacgcca tggctctcgg caatcatgag    2820
ttcgacaacg gagtggaagg gctgatcgat cctctgctcc ggaatgtgaa atttccaatc    2880
ctgtcagcta acattaaggc acgaggtcct ctggcacacc agatcagcgg actgttcctc    2940
ccaagtaaag tgctgtcagt cggggggcgag gtggtcggta ttgtgggcta cacctctaag    3000
gaaacaccct tcctgagtaa tcctggcaca aacctcgtgt ttgaggacga aatctctgcc    3060
ctgcagcctg aggtggataa gctgaaaact ctcaatgtca acaagatcat tgcactggga    3120
cacagcgggt tcgaaatgga caagctgatc gcccagaaag tgagagggggt cgatattgtg    3180 gtcggcggac atagtaatac tttcctgtac accggaaacc ctccatcaaa ggaggtgcca    3240
gctgggaaat atccctttat cgtgaccgca gacgatggcc ggcaggtccc agtggtccag    3300
gcatacgcct tcggcaagta cctgggctat ctcaaagtgg agtttgacga taagggaaac    3360
gtcatcacaa gctatgggaa tcccatcctg ctcaactcct ctattcctga agacgccact    3420
atcaaagctg atattaatca gtggaggatc aagctggaca actactccac tcaggagctg    3480
ggaagaacca tcgtgtacct ggatgggtct actcagacct gcaggttcag agaatgtaat    3540
atgggcaacc tgatctgcga cgccatgatt aacaataacc tgcgacaccc cgatgagatg    3600
ttttggaatc atgtgagcat gtgcatcgtc aacgggggtg gcatcaggtc ccccattgac    3660
gagaagaata acgaacaat tacttgggaa aacctggctg cagtgctccc tttcggaggg    3720
acatttgatc tggtccagct caagggggtcc actctgaaga aagccttcga gcactcagtg    3780
catcgctacg gacagagcac cggggaattt ctgcaagtgg gtggcatcca cgtggtctat    3840
gacattaatc gaaaaccctg gaacagggtg gtccagctgg aggtgctctg cactaagtgt    3900
cgagtcccta tctacgagcc actggaaatg gacaaggtgt acaaagtcac cctgcctagc    3960
tatctcgcca acggagggga tggattccag atgattaagg acgagctgct caaacatgat    4020
tctggggacc aggatatctc cgtggtctct gagtacatta gtaagatgaa agtggtctat    4080
cctgctgtgg aaggcaggat caagttcagt gccgcttcac attaccaggg ttcttttcca    4140
ctcgtgattc tctcttttttg ggctatgatt ctgattctct aatatcagtg aggatccact    4200
taagggcgaa ttccagcaca ctggcggccg ttagatctac gggtggcatc cctgtgaccc    4260
ctccccagtg cctctcctgg ccctggaagt tgccactcca gtgcccacca gccttgtcct    4320
aataaaatta agttgcatca ttttgtctga ctaggtgtcc ttctataata ttatgggtg    4380
```

```
gagggggggtg gtatggagca aggggcaagt tgggaagaca acctgtaggg cctgcggggt    4440
ctattgggaa ccaagctgga gtgcagtggc acaatcttgg ctcactgcaa tctccgcctc    4500
ctgggttcaa gcgattctcc tgcctcagcc tcccgagttg ttgggattcc aggcatgcat    4560
gaccaggctc agctaatttt tgtttttttg gtagagacgg ggtttcacca tattggccag    4620
gctggtctcc aactcctaat ctcaggtgat ctacccacct tggcctccca aattgctggg    4680
attacaggcg tgaaccactg ctcccttccc tgtccttctg attttgtagg taaccacgtg    4740
cggaccgagc ggccgcagga acccctagtg atggagttgg ccactccctc tctgcgcgct    4800
cgctcgctca ctgaggccgg gcgaccaaag gtcgcccgac gcccgggctt tgcccgggcg    4860
gcctcagtga gcgagcgagc gcgcagctgc ctgcaggggc gcctgatgcg gtattttctc    4920
cttacgcatc tgtgcggtat ttcacaccgc atacgtcaaa gcaaccatag tacgcgccct    4980
gtagcggcgc attaagcgcg gcgggtgtgg tggttacgcg cagcgtgacc gctacacttg    5040
ccagcgccct agcgcccgct cctttcgctt tcttcccttc ctttctcgcc acgttcgccg    5100
gctttccccg tcaagctcta aatcgggggc tccctttagg gttccgattt agtgctttac    5160
ggcacctcga ccccaaaaaa cttgatttgg gtgatggttc acgtagtggg ccatcgccct    5220
gatagacggt ttttcgccct ttgacgttgg agtccacgtt ctttaatagt ggactcttgt    5280
tccaaactgg aacaacactc aaccctatct cgggctattc ttttgattta agggatttt    5340
tgccgatttc ggcctattgg ttaaaaaatg agctgattta caaaaatttt aacgcgaatt    5400
ttaacaaaat attaacgttt acaatttat ggtgcactct cagtacaatc tgctctgatg    5460
ccgcatagtt aagccagccc cgacacccgc caacacccgc tgacgcgccc tgacgggctt    5520
gtctgctccc ggcatccgct tacagacaag ctgtgaccgt ctccgggagc tgcatgtgtc    5580
agaggttttc accgtcatca ccgaaacgcg cgagacgaaa gggcctcgtg atacgcctat    5640
ttttataggt taatgtcatg ataataatgg tttcttagac gtcaggtggc acttttcggg    5700
gaaatgtgcg cggaacccct atttgtttat ttttctaaat acattcaaat atgtatccgc    5760
tcatgagaca ataaccctga taatgcttc aataatattg aaaaaggaag agtatgagta    5820
ttcaacattt ccgtgtcgcc cttattccct tttttgcggc attttgcctt cctgtttttg    5880
ctcacccaga aacgctggtg aaagtaaaag atgctgaaga tcagttgggt gcacgagtgg    5940
gttacatcga actggatctc aacagcggta agatccttga gagttttcgc cccgaagaac    6000
gttttccaat gatgagcact tttaaagttc tgctatgtgg cgcggtatta tcccgtattg    6060
acgccgggca agagcaactc ggtcgccgca tacactattc tcagaatgac ttggttgagt    6120
actcaccagt cacagaaaag catcttacgg atggcatgac agtaagagaa ttatgcagtg    6180
ctgccataac catgagtgat aacactgcgg ccaacttact tctgacaacg atcggaggac    6240
cgaaggagct aaccgctttt ttgcacaaca tgggggatca tgtaactcgc cttgatcgtt    6300
gggaaccgga gctgaatgaa gccataccaa acgacgagcg tgacaccacg atgcctgtag    6360
caatggcaac aacgttgcgc aaactattaa ctggcgaact acttactcta gcttcccggc    6420
aacaattaat agactggatg gaggcggata aagttgcagg accacttctg cgctcggccc    6480
ttccggctgg ctggtttatt gctgataaat ctggagccgg tgagcgtggg tctcgcggta    6540
tcattgcagc actggggcca gatggtaagc cctcccgtat cgtagttatc tacacgacgg    6600
ggagtcaggc aactatggat gaacgaaata gacagatcgc tgagataggt gcctcactga    6660
ttaagcattg gtaactgtca gaccaagttt actcatatat actttagatt gatttaaaac    6720
```

-continued

```
ttcattttta atttaaaagg atctaggtga agatccttt tgataatctc atgaccaaaa    6780
tcccttaacg tgagttttcg ttccactgag cgtcagaccc cgtagaaaag atcaaaggat    6840
cttcttgaga tccttttttt ctgcgcgtaa tctgctgctt gcaaacaaaa aaaccaccgc    6900
taccagcggt ggtttgtttg ccggatcaag agctaccaac tcttttccg aaggtaactg     6960 gcttcagcag agcgcagata ccaaatactg tccttctagt gtagccgtag ttaggccacc    7020
acttcaagaa ctctgtagca ccgcctacat acctcgctct gctaatcctg ttaccagtgg    7080
ctgctgccag tggcgataag tcgtgtctta ccgggttgga ctcaagacga tagttaccgg    7140
ataaggcgca gcggtcgggc tgaacggggg gttcgtgcac acagcccagc ttggagcgaa    7200
cgacctacac cgaactgaga tacctacagc gtgagctatg agaaagcgcc acgcttcccg    7260
aagggagaaa ggcggacagg tatccggtaa gcggcagggt cggaacagga gagcgcacga    7320
gggagcttcc agggggaaac gcctggtatc tttatagtcc tgtcgggttt cgccacctct    7380
gacttgagcg tcgatttttg tgatgctcgt caggggggcg agcctatgg aaaaacgcca     7440 gcaacgcggc cttttacgg ttcctggcct tttgctggcc ttttgctcac atgt            7494
```

```
<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
gcgaagctta ccatgagccg catggaggac                                      30

<210> SEQ ID NO 44
<211> LENGTH: 38
<212> TYPE: DNA
<213> ORGANISM: Artificial
<220> FEATURE:
<223> OTHER INFORMATION: primer

<400> SEQUENCE: 44
gcgagatctt tatcacactg cctctttcca aaaataac                             38

<210> SEQ ID NO 45
<211> LENGTH: 32
<212> TYPE: DNA
<213> ORGANISM: Artificial
<220> FEATURE:
<223> OTHER INFORMATION: primer

<400> SEQUENCE: 45
gcgaagctta ccatgaggcc tgcagccgct aa                                   32

<210> SEQ ID NO 46
<211> LENGTH: 35
<212> TYPE: DNA
<213> ORGANISM: Artificial
<220> FEATURE:
<223> OTHER INFORMATION: primer

<400> SEQUENCE: 46
gcgagatctt tatcagagaa tcagaatcat agccc                                35

<210> SEQ ID NO 47
<211> LENGTH: 36
<212> TYPE: DNA
<213> ORGANISM: Artificial
```

-continued

```
<220> FEATURE:
<223> OTHER INFORMATION: primer

<400> SEQUENCE: 47
gcgagatctt tatcagaact tgatcctgcc ttccac                               36

<210> SEQ ID NO 48
<211> LENGTH: 1419
<212> TYPE: DNA
<213> ORGANISM: homo sapiens

<400> SEQUENCE: 48
atggccggga aggtgcggtc actgctgccg ccgctgctgc tggccgccgc gggcctcgcc      60
ggcctcctac tgctgtgcgt ccccacccgc gacgtccggg agccgcccgc cctcaagtat     120
ggcatcgtcc tggatgctgg ttcttcacac acgtccatgt ttatctacaa gtggccggca     180
gacaaggaga acgacacagg cattgtgggc cagcacagct cctgtgatgt tccaggtggg     240
ggcatctcca gctatgcaga caaccctcct ggggccagcc agagtcttgt tggatgcctc     300
gaacaggcgc ttcaggatgt gcccaaagag agacacgcgg gcacacccct ctacctggga     360
gccacagcgg gtatgcgcct gctcaacctg accaatccag aggcctcgac cagtgtgctc     420
atggcagtga ctcacacact gacccagtac ccctttgact ccggggtgc acgcatcctc      480 tcgggccaag aagaagggt gtttggctgg gtgactgcca actacctgct ggagaacttc      540
atcaagtacg gctgggtggg ccggtggttc cggccacgga aggggacact gggggccatg     600
gacctggggg tgcctctac ccagatcact tttgagacaa ccagtccagc tgaggacaga      660
gccagcgagg tccagctgca tctctacggc cagcactacc gagtctacac ccacagcttc     720
ctctgctatg ccgtgacca ggtcctccag aggctgctgg ccagcgccct ccagacccac     780
ggcttccacc cctgctggcc gagggggctt tccacccaag tgctgctcgg ggatgtgtac     840
cagtcaccat gcaccatggc ccagcggccc cagaacttca cagcagtgc cagggtcagc      900 ctgtcaggga gcagtgaccc ccacctctgc cgagatctgg tttctgggct cttcagcttc     960
tcctcctgcc cctctcccg atgctctttc aatggggtct ccagccccc agtggctggg      1020 aactttgtgg ccttctctgc cttcttctac actgtggact ttttgcggac ttcgatgggg    1080
ctgcccgtgg ccaccctgca gcagctggag gcagccgcag tgaatgtctg caaccagacc    1140
tgggctcagc agctgctgag tcgcggctac ggcttcgatg agcgcgcctt cggcggcgtg    1200
atcttccaga agaaggccgc ggacactgca gtgggctggg cgctcggcta catgctgaac    1260
ctgaccaacc tgatccccgc cgacccgccg ggctgcgca agggcacaga cttcagctcc    1320
tgggtcgtcc tcctgctgct cttcgcctcc gcgctcctgg ctgcgcttgt cctgctgctg    1380
cgtcaggtgc actccgccaa gctgccaagc accatttag                           1419

<210> SEQ ID NO 49
<211> LENGTH: 472
<212> TYPE: PRT
<213> ORGANISM: homo sapiens

<400> SEQUENCE: 49

Met Ala Gly Lys Val Arg Ser Leu Leu Pro Leu Leu Leu Ala Ala
1               5                   10                  15

Ala Gly Leu Ala Gly Leu Leu Leu Cys Val Pro Thr Arg Asp Val
                20                  25                  30

Arg Glu Pro Pro Ala Leu Lys Tyr Gly Ile Val Leu Asp Ala Gly Ser
            35                  40                  45
```

```
Ser His Thr Ser Met Phe Ile Tyr Lys Trp Pro Ala Asp Lys Glu Asn
    50                  55                  60

Asp Thr Gly Ile Val Gly Gln His Ser Ser Cys Asp Val Pro Gly Gly
65                  70                  75                  80

Gly Ile Ser Ser Tyr Ala Asp Asn Pro Ser Gly Ala Ser Gln Ser Leu
                85                  90                  95

Val Gly Cys Leu Glu Gln Ala Leu Gln Asp Val Pro Lys Glu Arg His
            100                 105                 110

Ala Gly Thr Pro Leu Tyr Leu Gly Ala Thr Ala Gly Met Arg Leu Leu
        115                 120                 125

Asn Leu Thr Asn Pro Glu Ala Ser Thr Ser Val Leu Met Ala Val Thr
    130                 135                 140

His Thr Leu Thr Gln Tyr Pro Phe Asp Phe Arg Gly Ala Arg Ile Leu
145                 150                 155                 160

Ser Gly Gln Glu Glu Gly Val Phe Gly Trp Val Thr Ala Asn Tyr Leu
                165                 170                 175

Leu Glu Asn Phe Ile Lys Tyr Gly Trp Val Gly Arg Trp Phe Arg Pro
            180                 185                 190

Arg Lys Gly Thr Leu Gly Ala Met Asp Leu Gly Ala Ser Thr Gln
        195                 200                 205

Ile Thr Phe Glu Thr Thr Ser Pro Ala Glu Asp Arg Ala Ser Glu Val
    210                 215                 220

Gln Leu His Leu Tyr Gly Gln His Tyr Arg Val Tyr Thr His Ser Phe
225                 230                 235                 240

Leu Cys Tyr Gly Arg Asp Gln Val Leu Gln Arg Leu Leu Ala Ser Ala
                245                 250                 255

Leu Gln Thr His Gly Phe His Pro Cys Trp Pro Arg Gly Phe Ser Thr
            260                 265                 270

Gln Val Leu Leu Gly Asp Val Tyr Gln Ser Pro Cys Thr Met Ala Gln
        275                 280                 285

Arg Pro Gln Asn Phe Asn Ser Ser Ala Arg Val Ser Leu Ser Gly Ser
    290                 295                 300

Ser Asp Pro His Leu Cys Arg Asp Leu Val Ser Gly Leu Phe Ser Phe
305                 310                 315                 320

Ser Ser Cys Pro Phe Ser Arg Cys Ser Phe Asn Gly Val Phe Gln Pro
                325                 330                 335

Pro Val Ala Gly Asn Phe Val Ala Phe Ser Ala Phe Phe Tyr Thr Val
            340                 345                 350

Asp Phe Leu Arg Thr Ser Met Gly Leu Pro Val Ala Thr Leu Gln Gln
        355                 360                 365

Leu Glu Ala Ala Val Asn Val Cys Asn Gln Thr Trp Ala Gln Gln
    370                 375                 380

Leu Leu Ser Arg Gly Tyr Gly Phe Asp Glu Arg Ala Phe Gly Gly Val
385                 390                 395                 400

Ile Phe Gln Lys Lys Ala Ala Asp Thr Ala Val Gly Trp Ala Leu Gly
                405                 410                 415

Tyr Met Leu Asn Leu Thr Asn Leu Ile Pro Ala Asp Pro Pro Gly Leu
            420                 425                 430

Arg Lys Gly Thr Asp Phe Ser Ser Trp Val Val Leu Leu Leu Leu Phe
        435                 440                 445

Ala Ser Ala Leu Leu Ala Ala Leu Val Leu Leu Leu Arg Gln Val His
    450                 455                 460
```

Ser Ala Lys Leu Pro Ser Thr Ile
465                 470

<210> SEQ ID NO 50
<211> LENGTH: 1488
<212> TYPE: DNA
<213> ORGANISM: Homo sapiens

<400> SEQUENCE: 50

| | | | | | |
|---|---|---|---|---|---|
| atggggctgt | cccggaagga | gcaggtcttc | ttggccctgc | tggggcctc | ggggtctca | 60 |
| ggcctcacgg | cactcattct | cctcctggtg | gaggccacca | gcgtgctcct | gcccacagac | 120 |
| atcaagtttg | ggatcgtgtt | tgatgcgggc | tcctcccaca | cgtccctctt | cctgtatcag | 180 |
| tggctggcga | acaaggagaa | tggcacgggt | gtggtcagcc | aggccctggc | ctgccaggtg | 240 |
| gaagggcctg | gaatctcctc | ctacacttct | aatgctgcac | aggctggtga | gagcctgcag | 300 |
| ggctgcttgg | aggaggcgct | ggtgctgatc | ccagaggccc | agcatcggaa | acacccacg | 360 |
| ttcctggggg | ccacggctgg | catgaggttg | ctcagccgga | gaacagctc | tcaggccagg | 420 |
| gacatctttg | cagcagtcac | ccaggtcctg | gccggtctc | ccgtggactt | tggggtgcc | 480 |
| gagctcctgg | ccgggcaggc | cgaaggtgcc | tttggttgga | tcactgtcaa | ctacggcttg | 540 |
| gggacgctgg | tcaagtactc | cttcactgga | gaatggatcc | agcctccgga | ggagatgctg | 600 |
| gtgggtgccc | tggacatggg | aggggcctcc | acccagatca | cgttcgtgcc | tgggggcccc | 660 |
| atcttggaca | gagcacccca | ggccgatttt | cgcctctacg | gctccgacta | cagcgtctac | 720 |
| actcacagct | acctgtgctt | tggacgggac | cagatgctga | gcaggctcct | cgtggggctg | 780 |
| gtacagagcc | gcccggctgc | cctgctccgt | caccgtgct | acctcagcgg | ctaccagacc | 840 |
| acactggccc | tgggcccgct | gtatgagtca | ccctgtgtcc | acgccacgcc | ccgctgagc | 900 |
| ctcccccaga | acctcacagt | tgaagggaca | ggcaaccctg | gagcctgcgt | ctcagccatc | 960 |
| cgggaacttt | tcaacttctc | cagctgccag | ggccaggagg | actgcgcctt | tgacggggtc | 1020 |
| taccagcccc | cgctgcgggg | ccagttctat | gccttctcca | acttctacta | caccttccac | 1080 |
| ttcctgaacc | tcacctccag | gcagccctg | agcacggtca | acgccaccat | ctgggagttt | 1140 |
| tgccagaggc | cctggaaact | ggtggaggcc | agctaccctg | gcaggaccg | ctggctgcgg | 1200 |
| gactactgtg | cctcaggcct | gtacatcctc | accctcctgc | acgagggcta | cgggttcagc | 1260 |
| gaggagacct | ggcccagcct | cgagttccga | aagcaggcgg | gcgtgtgga | cattggctgg | 1320 |
| acactgggct | acatgctgaa | cctgaccggg | atgatcccgg | ccgatgcgcc | ggctcagtgg | 1380 |
| cgggcagaga | gctacggcgt | ctgggtggcc | aaagtggtgt | tcatggtgct | ggccctggtg | 1440 |
| gcggtggtgg | gggctgcctt | ggtccagctc | ttctggttgc | aggactag | | 1488 |

<210> SEQ ID NO 51
<211> LENGTH: 495
<212> TYPE: PRT
<213> ORGANISM: Homo sapiens

<400> SEQUENCE: 51

Met Gly Leu Ser Arg Lys Glu Gln Val Phe Leu Ala Leu Leu Gly Ala
1               5                   10                  15

Ser Gly Val Ser Gly Leu Thr Ala Leu Ile Leu Leu Leu Val Glu Ala
            20                  25                  30

Thr Ser Val Leu Leu Pro Thr Asp Ile Lys Phe Gly Ile Val Phe Asp
        35                  40                  45

Ala Gly Ser Ser His Thr Ser Leu Phe Leu Tyr Gln Trp Leu Ala Asn

-continued

```
            50                  55                  60
Lys Glu Asn Gly Thr Gly Val Ser Gln Ala Leu Ala Cys Gln Val
 65                  70                  75                  80

Glu Gly Pro Gly Ile Ser Ser Tyr Thr Ser Asn Ala Ala Gln Ala Gly
                     85                  90                  95

Glu Ser Leu Gln Gly Cys Leu Glu Ala Leu Val Leu Ile Pro Glu
                100                 105                 110

Ala Gln His Arg Lys Thr Pro Thr Phe Leu Gly Ala Thr Ala Gly Met
                115                 120                 125

Arg Leu Leu Ser Arg Lys Asn Ser Ser Gln Ala Arg Asp Ile Phe Ala
                130                 135                 140

Ala Val Thr Gln Val Leu Gly Arg Ser Pro Val Asp Phe Trp Gly Ala
145                 150                 155                 160

Glu Leu Leu Ala Gly Gln Ala Glu Gly Ala Phe Gly Trp Ile Thr Val
                165                 170                 175

Asn Tyr Gly Leu Gly Thr Leu Val Lys Tyr Ser Phe Thr Gly Glu Trp
                180                 185                 190

Ile Gln Pro Pro Glu Glu Met Leu Val Gly Ala Leu Asp Met Gly Gly
                195                 200                 205

Ala Ser Thr Gln Ile Thr Phe Val Pro Gly Gly Pro Ile Leu Asp Lys
210                 215                 220

Ser Thr Gln Ala Asp Phe Arg Leu Tyr Gly Ser Asp Tyr Ser Val Tyr
225                 230                 235                 240

Thr His Ser Tyr Leu Cys Phe Gly Arg Asp Gln Met Leu Ser Arg Leu
                245                 250                 255

Leu Val Gly Leu Val Gln Ser Arg Pro Ala Ala Leu Leu Arg His Pro
                260                 265                 270

Cys Tyr Leu Ser Gly Tyr Gln Thr Thr Leu Ala Leu Gly Pro Leu Tyr
                275                 280                 285

Glu Ser Pro Cys Val His Ala Thr Pro Pro Leu Ser Leu Pro Gln Asn
                290                 295                 300

Leu Thr Val Glu Gly Thr Gly Asn Pro Gly Ala Cys Val Ser Ala Ile
305                 310                 315                 320

Arg Glu Leu Phe Asn Phe Ser Ser Cys Gln Gly Gln Glu Asp Cys Ala
                325                 330                 335

Phe Asp Gly Val Tyr Gln Pro Pro Leu Arg Gly Gln Phe Tyr Ala Phe
                340                 345                 350

Ser Asn Phe Tyr Tyr Thr Phe His Phe Leu Asn Leu Thr Ser Arg Gln
                355                 360                 365

Pro Leu Ser Thr Val Asn Ala Thr Ile Trp Glu Phe Cys Gln Arg Pro
370                 375                 380

Trp Lys Leu Val Glu Ala Ser Tyr Pro Gly Gln Asp Arg Trp Leu Arg
385                 390                 395                 400

Asp Tyr Cys Ala Ser Gly Leu Tyr Ile Leu Thr Leu Leu His Glu Gly
                405                 410                 415

Tyr Gly Phe Ser Glu Glu Thr Trp Pro Ser Leu Glu Phe Arg Lys Gln
                420                 425                 430

Ala Gly Gly Val Asp Ile Gly Trp Thr Leu Gly Tyr Met Leu Asn Leu
                435                 440                 445

Thr Gly Met Ile Pro Ala Asp Ala Pro Ala Gln Trp Arg Ala Glu Ser
450                 455                 460

Tyr Gly Val Trp Val Ala Lys Val Val Phe Met Val Leu Ala Leu Val
465                 470                 475                 480
```

Ala Val Val Gly Ala Ala Leu Val Gln Leu Phe Trp Leu Gln Asp
            485                 490                 495

<210> SEQ ID NO 52
<211> LENGTH: 3822
<212> TYPE: DNA
<213> ORGANISM: Artificial
<220> FEATURE:
<223> OTHER INFORMATION: Fc-tagged CD73-39 fusion DNA derived from mus
      musculus

<400> SEQUENCE: 52

| | | | | |
|---|---|---|---|---|
| atgggctggt | cctgcatcat | cctgttcctg | gtcgcaaccg | caactggcgt | ccattcagat | 60 |
| aaaactcata | cttgtccacc | ttgtcctgct | cctgagctgc | tgggaggacc | aagcgtgttc | 120 |
| ctgtttcccc | ctaagccaaa | agacaccctg | atgatcagcc | ggactcccga | agtcacctgc | 180 |
| gtggtcgtgg | acgtgagcca | cgaggatccc | gaagtcaagt | tcaactggta | cgtggatggc | 240 |
| gtcgaggtgc | ataatgccaa | gacaaaacct | agggaggaac | agtacaactc | cacctatcgc | 300 |
| gtcgtgtctg | tcctgacagt | gctgcaccag | gactggctga | acggcaaaga | gtataagtgc | 360 |
| aaagtgtcca | ataaggccct | gcccgctcct | atcgagaaaa | ctatttctaa | ggctaaaggg | 420 |
| cagccacgag | aaccacaggt | gtacaccctg | ccaccaagcc | gggaggaaat | gacaaagaac | 480 |
| caggtcagtc | tgacttgtct | ggtgaaagga | ttctatccta | gcgacattgc | agtggagtgg | 540 |
| gaatccaatg | gccagccaga | aaacaattac | aagaccacac | tccagtgct | ggactctgat | 600 |
| gggagtttct | ttctgtatag | taagctgaca | gtggataaat | cacggtggca | gcagggaaac | 660 |
| gtctttctt | gcagtgtgat | gcatgaggca | ctgcacaatc | attacactca | gaagtcactg | 720 |
| agcctgtccc | ccggcaaagc | cgctgcaaat | agctccatcg | acctgatttc | agtcccccgtg | 780 |
| gatagccgga | gacctgcctg | taagattcct | aacgacctga | acagaaagt | gatgaaccac | 840 |
| gactacaaag | acgacgacga | caaagagtgg | gaactgacaa | tcctgcacac | caatgacgtg | 900 |
| catagtcggc | tcgagcagac | atcagacgat | agcactaagt | gcctgaacgc | cagcctgtgc | 960 |
| gtgggaggag | tcgcaagact | gttcacaaag | gtgcagcaga | tccggaaaga | ggaacctaat | 1020 |
| gtcctgtttc | tcgacgctgg | cgatcagtac | cagggaacaa | tctggttcac | cgtgtacaag | 1080 |
| ggcctggagg | tcgcacactt | tatgaacatt | ctggggtacg | acgctatggc | actcggtaat | 1140 |
| catgagttcg | acaacgggt | ggaaggtctg | atcgatcctc | tgctccggaa | tgtgaaattt | 1200 |
| ccaatcctgt | cagcaaacat | taaggcacga | ggaccactgg | cacaccagat | cagcggtctg | 1260 |
| ttcctccct | ccaaagtgct | gtctgtcggg | gcgaggtgg | tcggcattgt | gggatacacc | 1320 |
| tctaaggaaa | caccccttcct | gagtaatcct | ggcactaacc | tcgtgtttga | ggacgaaatc | 1380 |
| agtgctctgc | agcccgagt | ggataagctg | aaaacccctca | atgtcaacaa | gatcattgct | 1440 |
| ctggggcact | ctggtttcga | atggacaag | ctgatcgcac | agaaagtgag | aggcgtcgat | 1500 |
| attgtggtcg | gcggacatag | taatacttc | ctgtacaccg | gcaacccccc | ttcaaaggag | 1560 |
| gtgccagccg | gaaaatatcc | ctttatcgtg | accgctgacg | atggacggca | ggtccctgtg | 1620 |
| gtccaggcct | acgctttcgg | caagtacctg | ggatatctca | agtggagtt | tgacgataag | 1680 |
| ggcaacgtca | ttcatcccta | tggaaatccc | atcctgctca | cagctccat | tcctgaagac | 1740 |
| gctactatca | aagcagatat | taatcagtgg | aggatcaagc | tggacaacta | ctccactcag | 1800 |
| gagctgggga | gaaccatcgt | gtacctggat | ggctctaccc | agacatgcag | gttcagagaa | 1860 |
| tgtaatatgg | gcaacctgat | ctgcgacgcc | atgattaaca | ataacctgcg | cacacccgat | 1920 |

| | |
|---|---|
| gagatgtttt ggaatcatgt gagcatgtgc atcgtcaacg ggggtggcat caggtcccct | 1980 |
| attgacgaga agaataacgg aactattacc tgggaaaacc tggccgctgt gctcccattc | 2040 |
| ggagggacat ttgatctggt gcagctcaag gggagcactc tgaagaaagc cttcgagcac | 2100 |
| tcagtgcatc gctacgggca gagcacaggt gaatttctgc aagtgggtgg catccacgtg | 2160 |
| gtctatgaca ttaatcgaaa accatggaac agggtggtcc agctggaggt gctctgcacc | 2220 |
| aagtgtcgag tcccaatcta cgagcccctg gaaatggaca aggtgtacaa agtcacactg | 2280 |
| cccagctatc tcgccaacgg aggggatgga ttccagatga ttaaggacga gctgctcaaa | 2340 |
| catgattctg ggaccagga tatctccgtg gtctctgagt acattagtaa gatgaaagtg | 2400 |
| gtctatccag ctgtggaagg caggatcaag ttcgctagcg gtggaggagc aggaggtgga | 2460 |
| gctggagggg gtgcaggcgg aggggccggt ggcggaaccg gtactcagaa caagcctctg | 2520 |
| ccagagaacg tgaagtacgg gatcgtcctg gacgccggtt ctagtcacac caatctctac | 2580 |
| atctacaagt ggcccgctga gaaagaaaac gatacaggcg tggtccagca gctggaggaa | 2640 |
| tgccaggtga aggggcctgg tatctctaag tacgcccaga aaaccgacga gattggagct | 2700 |
| tatctggcag agtgtatgga actgtccacc gaactcatcc aacatctaa gcaccatcag | 2760 |
| acacccgtgt acctgggagc aactgcagga atgcgactgc tccgcatgga gagtgaacag | 2820 |
| tcagctgacg aggtgctggc agccgtcagt acttcactca aaagctatcc cttcgatttt | 2880 |
| cagggcgcaa agatcattac cggacaggag gaaggcgcct acggatggat cactattaac | 2940 |
| tatctgctcg ggaggttcac ccaggagcag agctggctgt ccctcatcag cgactcccag | 3000 |
| aagcaggaaa cattcggcgc tctggatctc ggggtgcat ctactcagat caccttttgtg | 3060 |
| cctcagaata gtactattga gtcaccagaa acagcctgc agttcagact ctacggcgag | 3120 |
| gactacacag tgtatactca cagctttctg tgctatggaa aggaccaggc cctgtggcag | 3180 |
| aagctcgcta agatatcca ggtgtcaagc ggcggagtcc tgaaagatcc ttgcttcaat | 3240 |
| ccagggtaca gaaggtggt caacgtgtcc gaactgtatg caccccctg tacaaagagg | 3300 |
| ttcgagaaga aactgccttt cgaccagttt cgaatccagg gcaccggaga ttacgagcag | 3360 |
| tgtcaccagt ctattctgga actcttcaat aactcccatt gccctattc tcagtgtgcc | 3420 |
| ttcaacggcg tgtttctgcc accctccac gggagtttcg gtgcctttc agctttctac | 3480 |
| tttgtgatgg acttctttaa gaaagtggct aagaattctg tcatcagtca ggagaagatg | 3540 |
| actgaaatta ccaagaactt ctgctctaaa agttgggagg aaaccaagac atcatatcct | 3600 |
| agcgtgaagg agaaataccct gagcgaatat tgttttttccg gagcctacat cctgtccctg | 3660 |
| ctccagggt ataatttcac agactcctct tgggagcaga tccacttcat gggcaagatc | 3720 |
| aaggatagca acgcagggtg gaccctgggt tacatgctga atctcacaaa catgatccca | 3780 |
| gccgaacagc ccctgtcccc tccactgcct cactccacct aa | 3822 |

<210> SEQ ID NO 53
<211> LENGTH: 1273
<212> TYPE: PRT
<213> ORGANISM: Artificial
<220> FEATURE:
<223> OTHER INFORMATION: Fc-tagged CD73-39 fusion protein derived from
     mus musculus

<400> SEQUENCE: 53

Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu

-continued

```
                20                  25                  30
Leu Leu Gly Gly Pro Ser Val Phe Leu Phe Pro Lys Pro Lys Asp
                35                  40                  45
Thr Leu Met Ile Ser Arg Thr Pro Glu Val Thr Cys Val Val Asp
        50                  55                  60
Val Ser His Glu Asp Pro Glu Val Lys Phe Asn Trp Tyr Val Asp Gly
65                  70                  75                  80
Val Glu Val His Asn Ala Lys Thr Lys Pro Arg Glu Glu Gln Tyr Asn
                85                  90                  95
Ser Thr Tyr Arg Val Val Ser Val Leu Thr Val Leu His Gln Asp Trp
            100                 105                 110
Leu Asn Gly Lys Glu Tyr Lys Cys Lys Val Ser Asn Lys Ala Leu Pro
            115                 120                 125
Ala Pro Ile Glu Lys Thr Ile Ser Lys Ala Lys Gly Gln Pro Arg Glu
            130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
            195                 200                 205
Leu Thr Val Asp Lys Ser Arg Trp Gln Gln Gly Asn Val Phe Ser Cys
        210                 215                 220
Ser Val Met His Glu Ala Leu His Asn His Tyr Thr Gln Lys Ser Leu
225                 230                 235                 240
Ser Leu Ser Pro Gly Lys Ala Ala Ala Asn Ser Ser Ile Asp Leu Ile
                245                 250                 255
Ser Val Pro Val Asp Ser Arg Arg Pro Ala Cys Lys Ile Pro Asn Asp
            260                 265                 270
Leu Lys Gln Lys Val Met Asn His Asp Tyr Lys Asp Asp Asp Asp Lys
            275                 280                 285
Glu Trp Glu Leu Thr Ile Leu His Thr Asn Asp Val His Ser Arg Leu
            290                 295                 300
Glu Gln Thr Ser Asp Asp Ser Thr Lys Cys Leu Asn Ala Ser Leu Cys
305                 310                 315                 320
Val Gly Gly Val Ala Arg Leu Phe Thr Lys Val Gln Gln Ile Arg Lys
                325                 330                 335
Glu Glu Pro Asn Val Leu Phe Leu Asp Ala Gly Asp Gln Tyr Gln Gly
            340                 345                 350
Thr Ile Trp Phe Thr Val Tyr Lys Gly Leu Glu Val Ala His Phe Met
            355                 360                 365
Asn Ile Leu Gly Tyr Asp Ala Met Ala Leu Gly Asn His Glu Phe Asp
        370                 375                 380
Asn Gly Val Glu Gly Leu Ile Asp Pro Leu Leu Arg Asn Val Lys Phe
385                 390                 395                 400
Pro Ile Leu Ser Ala Asn Ile Lys Ala Arg Gly Pro Leu Ala His Gln
                405                 410                 415
Ile Ser Gly Leu Phe Leu Pro Ser Lys Val Leu Ser Val Gly Gly Glu
            420                 425                 430
Val Val Gly Ile Val Gly Tyr Thr Ser Lys Glu Thr Pro Phe Leu Ser
            435                 440                 445
```

```
Asn Pro Gly Thr Asn Leu Val Phe Glu Asp Glu Ile Ser Ala Leu Gln
    450                 455                 460

Pro Glu Val Asp Lys Leu Lys Thr Leu Asn Val Asn Lys Ile Ile Ala
465                 470                 475                 480

Leu Gly His Ser Gly Phe Glu Met Asp Lys Leu Ile Ala Gln Lys Val
                485                 490                 495

Arg Gly Val Asp Ile Val Val Gly Gly His Ser Asn Thr Phe Leu Tyr
                500                 505                 510

Thr Gly Asn Pro Pro Ser Lys Glu Val Pro Ala Gly Lys Tyr Pro Phe
            515                 520                 525

Ile Val Thr Ala Asp Asp Gly Arg Gln Val Pro Val Val Gln Ala Tyr
        530                 535                 540

Ala Phe Gly Lys Tyr Leu Gly Tyr Leu Lys Val Glu Phe Asp Asp Lys
545                 550                 555                 560

Gly Asn Val Ile Thr Ser Tyr Gly Asn Pro Ile Leu Leu Asn Ser Ser
                565                 570                 575

Ile Pro Glu Asp Ala Thr Ile Lys Ala Asp Ile Asn Gln Trp Arg Ile
            580                 585                 590

Lys Leu Asp Asn Tyr Ser Thr Gln Glu Leu Gly Arg Thr Ile Val Tyr
        595                 600                 605

Leu Asp Gly Ser Thr Gln Thr Cys Arg Phe Arg Glu Cys Asn Met Gly
    610                 615                 620

Asn Leu Ile Cys Asp Ala Met Ile Asn Asn Asn Leu Arg His Pro Asp
625                 630                 635                 640

Glu Met Phe Trp Asn His Val Ser Met Cys Ile Val Asn Gly Gly Gly
                645                 650                 655

Ile Arg Ser Pro Ile Asp Glu Lys Asn Asn Gly Thr Ile Thr Trp Glu
            660                 665                 670

Asn Leu Ala Ala Val Leu Pro Phe Gly Gly Thr Phe Asp Leu Val Gln
        675                 680                 685

Leu Lys Gly Ser Thr Leu Lys Lys Ala Phe Glu His Ser Val His Arg
    690                 695                 700

Tyr Gly Gln Ser Thr Gly Glu Phe Leu Gln Val Gly Gly Ile His Val
705                 710                 715                 720

Val Tyr Asp Ile Asn Arg Lys Pro Trp Asn Arg Val Val Gln Leu Glu
                725                 730                 735

Val Leu Cys Thr Lys Cys Arg Val Pro Ile Tyr Glu Pro Leu Glu Met
            740                 745                 750

Asp Lys Val Tyr Lys Val Thr Leu Pro Ser Tyr Leu Ala Asn Gly Gly
        755                 760                 765

Asp Gly Phe Gln Met Ile Lys Asp Glu Leu Leu Lys His Asp Ser Gly
    770                 775                 780

Asp Gln Asp Ile Ser Val Val Ser Glu Tyr Ile Ser Lys Met Lys Val
785                 790                 795                 800

Val Tyr Pro Ala Val Glu Gly Arg Ile Lys Phe Ala Ser Gly Gly Gly
                805                 810                 815

Ala Gly Gly Gly Ala Gly Gly Gly Ala Gly Gly Gly Ala Gly Gly Gly
            820                 825                 830

Thr Gly Thr Gln Asn Lys Pro Leu Pro Glu Asn Val Lys Tyr Gly Ile
        835                 840                 845

Val Leu Asp Ala Gly Ser Ser His Thr Asn Leu Tyr Ile Tyr Lys Trp
    850                 855                 860
```

```
Pro Ala Glu Lys Glu Asn Asp Thr Gly Val Val Gln Gln Leu Glu Glu
865                 870                 875                 880

Cys Gln Val Lys Gly Pro Gly Ile Ser Lys Tyr Ala Gln Lys Thr Asp
            885                 890                 895

Glu Ile Gly Ala Tyr Leu Ala Glu Cys Met Glu Leu Ser Thr Glu Leu
            900                 905                 910

Ile Pro Thr Ser Lys His His Gln Thr Pro Val Tyr Leu Gly Ala Thr
            915                 920                 925

Ala Gly Met Arg Leu Leu Arg Met Glu Ser Glu Gln Ser Ala Asp Glu
            930                 935                 940

Val Leu Ala Ala Val Ser Thr Ser Leu Lys Ser Tyr Pro Phe Asp Phe
945                 950                 955                 960

Gln Gly Ala Lys Ile Ile Thr Gly Gln Glu Glu Gly Ala Tyr Gly Trp
            965                 970                 975

Ile Thr Ile Asn Tyr Leu Leu Gly Arg Phe Thr Gln Glu Gln Ser Trp
            980                 985                 990

Leu Ser Leu Ile Ser Asp Ser Gln Lys Gln Glu Thr Phe Gly Ala Leu
            995                 1000                1005

Asp Leu Gly Gly Ala Ser Thr Gln Ile Thr Phe Val Pro Gln Asn
    1010                1015                1020

Ser Thr Ile Glu Ser Pro Glu Asn Ser Leu Gln Phe Arg Leu Tyr
    1025                1030                1035

Gly Glu Asp Tyr Thr Val Tyr Thr His Ser Phe Leu Cys Tyr Gly
    1040                1045                1050

Lys Asp Gln Ala Leu Trp Gln Lys Leu Ala Lys Asp Ile Gln Val
    1055                1060                1065

Ser Ser Gly Gly Val Leu Lys Asp Pro Cys Phe Asn Pro Gly Tyr
    1070                1075                1080

Glu Lys Val Val Asn Val Ser Glu Leu Tyr Gly Thr Pro Cys Thr
    1085                1090                1095

Lys Arg Phe Glu Lys Lys Leu Pro Phe Asp Gln Phe Arg Ile Gln
    1100                1105                1110

Gly Thr Gly Asp Tyr Glu Gln Cys His Gln Ser Ile Leu Glu Leu
    1115                1120                1125

Phe Asn Asn Ser His Cys Pro Tyr Ser Gln Cys Ala Phe Asn Gly
    1130                1135                1140

Val Phe Leu Pro Pro Leu His Gly Ser Phe Gly Ala Phe Ser Ala
    1145                1150                1155

Phe Tyr Phe Val Met Asp Phe Phe Lys Lys Val Ala Lys Asn Ser
    1160                1165                1170

Val Ile Ser Gln Glu Lys Met Thr Glu Ile Thr Lys Asn Phe Cys
    1175                1180                1185

Ser Lys Ser Trp Glu Glu Thr Lys Thr Ser Tyr Pro Ser Val Lys
    1190                1195                1200

Glu Lys Tyr Leu Ser Glu Tyr Cys Phe Ser Gly Ala Tyr Ile Leu
    1205                1210                1215

Ser Leu Leu Gln Gly Tyr Asn Phe Thr Asp Ser Ser Trp Glu Gln
    1220                1225                1230

Ile His Phe Met Gly Lys Ile Lys Asp Ser Asn Ala Gly Trp Thr
    1235                1240                1245

Leu Gly Tyr Met Leu Asn Leu Thr Asn Met Ile Pro Ala Glu Gln
    1250                1255                1260

Pro Leu Ser Pro Pro Leu Pro His Ser Thr
```

<210> SEQ ID NO 54
<211> LENGTH: 3330
<212> TYPE: DNA
<213> ORGANISM: Artificial
<220> FEATURE:
<223> OTHER INFORMATION: CD39-2A-CD73 derived from mus musculus, codon optimized

<400> SEQUENCE: 54

```
atgagccgca tggaggacat caaagactca aaagtgaaaa gattctgctc aaaaaacatt     60
ctcatcattc tggggtttac atcaattctc gctgtgatcg cactgattgc cgtcggcctc    120
actcagaaca agcccctgcc tgagaacgtg aagtacggaa tcgtcctgga cgctgggagc    180
tcccacacca atctgtacat ctacaagtgg ccagcagaga agaaaaacga tacaggcgtg    240
gtccagcagc tggaggaatg ccaggtgaag ggtcccggca tctccaagta cgcccagaaa    300
acagacgaga ttggagctta ctggcagag tgtatggaac tgagcacaga actcatcccc    360
acttccaagc accatcagac accgtgtac ctgggtgcaa ctgcaggaat gcgactgctc    420
cgcatggagt cagaacagag cgccgacgag gtgctggcag ctgtcagtac ttcactcaaa    480
tcttatccat tcgattttca gggtgccaag atcattaccg gccaggagga aggagcttac    540
gggtggatca ctattaacta tctgctcggg cggttcaccc aggagcagtc ctggctgtct    600
ctcatcagcg actcccagaa gcaggaaacc ttcgcgctc tggatctcgg cggagcaagc    660
acccagatca catttgtgcc acagaatagc acaattgagt cccccgaaaa ctctctgcag    720
ttccgcctct acggggagga ctacaccgtg tacacccact ccttcctgtg ctatggcaag    780
gaccaggccc tgtggcagaa gctcgctaaa gatatccagg tgtctagtgg gggtgtcctg    840
aaagatccct gcttcaatcc tggttacgag aaggtggtca cgtgtctga actgtatgga    900
acaccatgta ctaagaggtt cgagaagaaa ctgcccttcg accagtttcg aatccaggga    960
accggggatt acgagcagtg tcaccagagc attctggaac tcttcaacaa tagccattgc   1020
ccatattccc agtgtgcctt caacggagtg tttctgcccc ctctccacgg ttctttcggc   1080
gcctttagtg ctttctactt tgtgatggac ttctttaaga agtggctaa gaatagtgtc   1140
atctcacagg agaagatgac cgaaatcaca aagaacttct gctctaagag ttgggaggaa   1200
accaagacaa gctaccccte cgtgaaggag aaataccgt cagaatattg tttagcggt   1260
gcctacatcc tgtccctgct ccagggctat aatttcaccg actcaagctg ggagcagatc   1320
cactttatgg caagatcaa ggattctaac gccggatgga ccctggggta catgctgaat   1380
ctcacaaaca tgatcccagc tgagcagcca ctgtccccac cactccctca ttctacctat   1440
attggcctga tggtgctctt ctccctgctc ctggtggctg tcgcaatcac aggactgttc   1500
atctactcta agccaagtta ttttggaaa gaggcagtgg gtagtggcgc cacaaatttt   1560
tcactcctga gcaggccgg agacgtggag gaaaacccag gccatgag cctgcagcc   1620
gctaaggtgc caaaatggct cctgctcgca ctgtccgccc tgctccctca gtggccagca   1680
gcctctgctt gggagctgac tatcctccac accaatgatg tgcatagtag actggaacag   1740
acctcagacg tagcacaaaa gtgcctgaac gccagcctgt gcgtggggag agtcgcaaga   1800
ctgttcacca aggtgcagca gatccggaaa gaggaaccta atgtcctgtt tctcgacgca   1860
ggcgaccagt accaggcac aatctggttc acccgtgtaca agggactgga ggtcgctcac   1920
tttatgaaca ttctgggtta cgacgccatg gctctcggca atcatgagtt cgacaacgga   1980
```

```
gtggaagggc tgatcgatcc tctgctccgg aatgtgaaat ttccaatcct gtcagctaac   2040
attaaggcac gaggtcctct ggcacaccag atcagcggac tgttcctccc aagtaaagtg   2100
ctgtcagtcg ggggcgaggt ggtcggtatt gtgggctaca cctctaagga acacccttc   2160 ctgagtaatc ctggcacaaa cctcgtgttt gaggacgaaa tctctgccct gcagcctgag   2220
gtggataagc tgaaaactct caatgtcaac aagatcattg cactgggaca cagcgggttc   2280
gaaatggaca agctgatcgc ccagaaagtg agaggggtcg atattgtggt cggcggacat   2340
agtaatactt tcctgtacac cggaaaccct ccatcaaagg aggtgccagc tgggaaatat   2400 cccttatcg tgaccgcaga cgatggccgg caggtcccag tggtccaggc atacgccttc   2460
ggcaagtacc tgggctatct caaagtggag tttgacgata agggaaacgt catcacaagc   2520
tatgggaatc ccatcctgct caactcctct attcctgaag acgccactat caaagctgat   2580
attaatcagt ggaggatcaa gctggacaac tactccactc aggagctggg aagaaccatc   2640
gtgtacctgg atgggtctac tcagacctgc aggttcagag aatgtaatat gggcaacctg   2700
atctgcgacg ccatgattaa caataacctg cgacaccccg atgagatgtt ttggaatcat   2760
gtgagcatgt gcatcgtcaa cggggggtggc atcaggtccc ccattgacga aagaataac   2820 ggaacaatta cttgggaaaa cctggctgca gtgctcccct tcggagggac atttgatctg   2880
gtccagctca agggtccac tctgaagaaa gccttcgagc actcagtgca tcgctacgga   2940
cagagcaccg gggaatttct gcaagtgggt ggcatccacg tggtctatga cattaatcga   3000
aaaccctgga cagggtggt ccagctggag gtgctctgca ctaagtgtcg agtccctatc   3060
tacgagccac tggaaatgga caaggtgtac aaagtcaccc tgcctagcta tctcgccaac   3120 ggagggatg gattccagat gattaaggac gagctgctca acatgattc tggggaccag   3180 gatatctccg tggtctctga gtacattagt aagatgaaag tggtctatcc tgctgtggaa   3240
ggcaggatca gttcagtgc cgcttcacat taccagggtt ctttccact cgtgattctc   3300 tcttttggg ctatgattct gattctctaa                                    3330
```

<210> SEQ ID NO 55
<211> LENGTH: 1533
<212> TYPE: DNA
<213> ORGANISM: Artificial
<220> FEATURE:
<223> OTHER INFORMATION: CD39 cDNA derived from homo sapiens, codon optimized

<400> SEQUENCE: 55

```
atggaagata ccaaagagag caacgtgaag actttctgta gcaagaacat cctcgcaatc     60
ctggggttta gcagcatcat cgccgtcatc gcactgctcg ccgtgggcct cacccagaac    120
aaggccctgc tgagaatgt gaaatacggc attgtcctgg acgctggaag ctcccacacc    180
agcctgtaca tctataagtg gcctgctgag aaagaaaacg atacagggt ggtccatcag    240 gtggaggaat gccgggtcaa ggggccaggt atttccaagt tcgtgcagaa agtcaatgag    300
atcggcatct acctgacaga ctgtatggag agggctagag aagtgatccc taggtctcag    360
caccaggaaa ctccagtcta tctgggagca accgctggta tgcgactgct ccgcatggag    420
agtgaggaac tcgcagaccg agtgctggat gtggtcgaaa ggtctctgag taactacccc    480
ttcgactttc aggggcacg catcattact ggtcaggagg aaggggccta cggttggatc    540
accattaatt atctgctcgg caagtttct cagaaaaccc gatggttcag tattgtgcct    600
tatgagacaa caatcagga aacttttgga gccctcgatc tgggcggagc ttccacccag    660
```

```
gtgacattcg tcccccagaa ccagactatc gagtctcctg acaatgccct ccagtttagg      720
ctgtacggga aggattacaa cgtgtatacc cactctttcc tgtgctatgg taaagaccag      780
gcactctggc agaagctggc caaagatatt caggtggcta gcaacgagat cctgagagac      840
ccatgctttc atcccggata caagaaagtg gtcaatgtct ccgatctgta taagactcca      900
tgtaccaaac ggttcgagat gacactgccc ttccagcagt ttgaaatcca gggcattgga      960
aactaccagc agtgtcatca gtctattctc gagctgttta acactagtta ctgcccatat     1020
tcacagtgtg ctttcaatgg aatctttctc ccccctctgc agggcgattt cggagctttt     1080
agcgcattct actttgtgat gaagtttctc aatctgacct ccgagaaggt gtctcaggag     1140
aaagtcacag aaatgatgaa gaaattctgc gctcagccct gggaggaaat taagactagc     1200
tatgcagggg tgaaggagaa atacctgagc gaatattgtt tctccggcac atacatcctg     1260
tcactgctcc tgcagggata tcactttact gccgacagct gggagcacat ccatttcatt     1320
ggcaagatcc agggatccga tgcagggtgg acactgggtt acatgctcaa cctgactaat     1380
atgatccctg ccgaacagcc actcagtacc ccctgtcac atagcacata cgtgttcctg      1440
atggtcctgt tttcactcgt gctgttcaca gtcgctatca ttggtctgct catttttcac     1500
aagccctctt atttctggaa ggacatggtc tga                                 1533
```

<210> SEQ ID NO 56
<211> LENGTH: 1725
<212> TYPE: DNA
<213> ORGANISM: Artificial
<220> FEATURE:
<223> OTHER INFORMATION: CD73 cDNA derived from homo sapiens, codon
      optimized

<400> SEQUENCE: 56

```
atgtgcccta gagccgctag agcccccgca accctcctcc tcgccctcgg tgctgtcctg       60
tggcccgccg ctggtgcttg gaactgact atcctccaca ccaatgacgt gcattcacgg      120
ctggagcaga ccagcgaaga tagctccaaa tgcgtgaacg ctagccgctg tatgggcgga      180
gtcgcacgac tgttcacaaa ggtgcagcag atcaggagag ccgagcctaa gtgtgctgct      240
ctggacgctg cgaccagta ccagggcaca atttggttca ctgtctataa gggagccgaa      300
gtggctcact ttatgaacgc actccgatac gacgcaatgg cactggggaa tcatgagttc      360
gataacggag tggaggggct gatcgaaccc ctcctgaagg aagccaaatt ccctatcctc      420
tccgcaaaca ttaaggccaa aggaccactg gctagtcaga tcagcgggct ctacctgccc      480
tataaagtcc tgcctgtggg cgacgaggtg gtcggtattg ggctatac ctccaaggaa       540
acaccattcc tctctaatcc cggaaccaac ctggtgtttg aggacgaaat cacagccctg      600
cagcccgagg tcgataagct caaaaccctg aatgtgaaca agatcattgc tctcggacac      660
agtgggtttg aaatggacaa gctgattgca cagaaagtcc ggggagtgga tgtggtcgtg      720
gggggtcata gcaatacttt cctgtacacc ggaaacccc cttccaagga ggtgcctgct       780
gggaaatatc ccttcatcgt cacatccgac gatgggagga aggtgcctgt cgtgcaggct      840
tacgccttcg gcaagtacct cggctatctg aaaatcgagt ttgacgaaag aggaaatgtg      900
atttctagtc acgggaatcc aatcctcctg aactcaagca ttccagagga ccctcaatc      960
aaagccgata ttaataagtg gaggatcaaa ctggacaact acagcacaca ggagctcggc     1020
aagactatcg tgtacctgga tggctcctct cagtcttgcc ggttccgcga atgtaatatg     1080
ggaaacctga tctgcgacgc aatgattaac aataacctga gacacgccga tgagacctt     1140
```

-continued

| | |
|---|---|
| tggaatcacg tgagcatgtg catcctgaac ggcggaggga tcagaagtcc aattgacgag | 1200 |
| cggaataacg ggaccattac atgggaaaac ctcgcagctg tcctgccctt cggtggcact | 1260 |
| tttgatctcg tgcagctgaa gggcagcacc ctgaagaaag ccttcgagca cagtgtgcat | 1320 |
| cgatacggac agtcaactgg ggaatttctg caagtgggag ggatccacgt cgtgtatgac | 1380 |
| ctgtcccgaa agcccggcga cagggtcgtg aaactcgatg tcctgtgcac aaagtgtcgc | 1440 |
| gtgccttctt acgacccact gaagatggat gaggtctata agtgatcct ccctaatttc | 1500 |
| ctggcaaacg gtggcgatgg ttttcagatg atcaaggacg aactcctgcg gcacgattct | 1560 |
| ggcgaccagg atattaacgt cgtgtctaca tacatcagta agatgaaagt gatctaccca | 1620 |
| gctgtggagg gtcgcatcaa gttcagcact ggctcccatt gccacgggtc attttccctc | 1680 |
| attttcctct ccctgtgggc agtcattttt gtcctgtatc agtga | 1725 |

<210> SEQ ID NO 57
<211> LENGTH: 3320
<212> TYPE: DNA
<213> ORGANISM: artificial
<220> FEATURE:
<223> OTHER INFORMATION: CD39-2A-CD73 derived from homo sapiens, codon
      optimized

<400> SEQUENCE: 57

| | |
|---|---|
| atggaggaca ccaaggagag caacgtgaag accttctgca gcaagaacat cctggccatc | 60 |
| ctgggcttca gcagcatcat cgccgtgatc gccctgctgg ccgtgggcct gacccagaac | 120 |
| aaggccctgc ccgagaacgt gaagtacggc atcgtgctgg acgccggcag cagccacacc | 180 |
| agcctgtaca tctacaagtg gcccgccgag aaggagaacg acaccggcgt ggtgcaccag | 240 |
| gtggaggagt gcagagtgaa gggccccggc atcagcaagt tcgtgcagaa ggtgaacgag | 300 |
| atcggcatct acctgaccga ctgcatggag agagccagag aggtgatccc cagaagccag | 360 |
| caccaggaga cccccgtgta cctgggcgcc accgccggca tgagactgct gagaatggag | 420 |
| agcgaggagc tggccgacag agtgctggac gtggtggaga agcctgag caactacccc | 480 |
| ttcgacttcc agggcgccag aatcatcacc ggccaggagg agggcgccta cggctggatc | 540 |
| accatcaact acctgctggg caagttcagc cagaagacca gatggttcag catcgtgccc | 600 |
| tacgagacca caaccagga gaccttcggc gccctggacc tgggcggcgc cagcacccag | 660 |
| gtgaccttcg tgccccagaa ccagaccatc gagagcccg acaacgccct gcagttcaga | 720 |
| ctgtacggca aggactacaa cgtgtacacc cacagcttcc tgtgctacgg caaggaccag | 780 |
| gccctgtggc agaagctggc caaggacatc caggtggcca gcaacgagat cctgagagac | 840 |
| ccctgcttcc accccggcta caagaaggtg gtgaacgtga gcgacctgta caagaccccc | 900 |
| tgcaccaaga gattcgagat gaccctgccc ttccagcagt tcgagatcca gggcatcggc | 960 |
| aactaccagc agtgccacca gagcatcctg gagctgttca caccagcta ctgcccctac | 1020 |
| agccagtgcg ccttcaacgg catcttcctg ccccccctgc agggcgactt cggcgccttc | 1080 |
| agcgccttct acttcgtgat gaagttcctg aacctgacca gcgagaaggt gagccaggag | 1140 |
| aaggtgaccg agatgatgaa gaagttctgc gcccagccct gggaggagat caagaccagc | 1200 |
| tacgccggcg tgaaggagaa gtacctgagc gagtactgct tcagcggcac ctacatcctg | 1260 |
| agcctgctgc tgcagggcta ccacttcacc gccgacagct gggagcacat ccacttcatc | 1320 |
| ggcaagatcc agggcagcga cgccggctgg acctgggct acatgctgaa cctgaccaac | 1380 |
| atgatccccg ccgagcagcc cctgagcacc cccctgagcc acagcaccta cgtgttcctg | 1440 |

-continued

```
atggtgctgt tcagcctggt gctgttcacc gtggccatca tcggcctgct gatcttccac    1500
aagcccagct acttctggaa ggacatggtg ggcagcggcg ccaccaactt cagcctgctg    1560
aagcaggccg gcgacgtgga ggagaacccc ggccccatgt gccccagagc cgccagagcc    1620
cccgccaccc tgctgctggc cctgggcgcc gtgctgtggc ccgccgccgg cgcctgggag    1680
ctgaccatcc tgcacaccaa cgacgtgcac agcagactgg agcagaccag cgaggacagc    1740
agcaagtgcg tgaacgccag cagatgcatg ggcggcgtgg ccagactgtt caccaaggtg    1800
cagcagatca gaagagccga gcccaacgtg ctgctgctgg acgccggcga ccagtaccag    1860
ggcaccatct ggttcaccgt gtacaagggc gccgaggtgg cccacttcat gaacgccctg    1920
agatacgacg ccatggccct gggcaaccac gagttcgaca acggcgtgga gggcctgatc    1980
gagcccctgc tgaaggaggc caagttcccc atcctgagcg ccaacatcaa ggccaagggc    2040
cccctggcca gccagatcag cggcctgtac ctgcccctaca aggtgctgcc cgtgggcgac    2100
gaggtggtgg gcatcgtggg ctacaccagc aaggagaccc ccttcctgag caaccccggc    2160
accaacctgg tgttcgagga cgagatcacc gccctgcagc ccgaggtgga caagctgaag    2220
accctgaacg tgaacaagat catcgccctg ggccacagcg gcttcgagat ggacaagctg    2280
atcgcccaga aggtgagagg cgtggacgtg gtggtgggcg gccacagcaa caccttcctg    2340
tacaccggca accccccccag caaggaggtg cccgccggca agtaccccctt catcgtgacc    2400 gcgacgacgg cagaaaggtg cccgtggtgc aggcctacgc cttcggcaag tacctgggct    2460
acctgaagat cgagttcgac gagagaggca acgtgatcag cagccacggc aaccccatcc    2520
tgctgaacag cagcatcccc gaggacccca gcatcaaggc cgacatcaac aagtggagaa    2580
tcaagctgga caactacagc acccaggagc tgggcaagac catcgtgtac ctggacggca    2640
gcagccagag ctgcagattc agagagtgca acatgggcaa cctgatctgc gacgccatga    2700
tcaacaacaa cctgagacac gccgacgaga ccttctggaa ccacgtgagc atgtgcatcc    2760
tgaacggcgg cggcatcaga agccccatcg acgagagaaa caacggcacc atcacctggg    2820
agaacctggc cgccgtgctg cccttcggcg gcaccttcga cctggtgcag ctgaagggca    2880
gcaccctgaa gaaggccttc gagcacagcg tgcacagata cggccagagc accggcgagt    2940
tcctgcaggt gggcggcatc cacgtggtgt acgacctgag cagaaagccc ggcgacagag    3000
tggtgaagct ggacgtgctg tgcaccaagt gcagagtgcc cagctacgac cccctgaaga    3060
tggacgaggt gtacaaggtg atcctgccca acttcctggc caacggcggc gacggcttcc    3120
agatgatcaa ggacgagctg ctgagacacg acagcggcga ccaggacatc aacgtggtga    3180
gcacctacat cagcaagatg aaggtgatct accccgccgt ggagggcaga atcaagttca    3240
gcaccggcag ccactgccac ggcagcttca gcctgatctt cctgagcctg tgggccgtga    3300
tcttcgtgct gtaccagtag                                                3320
```